(12) United States Patent
Andersen et al.

(10) Patent No.: US 11,919,874 B2
(45) Date of Patent: Mar. 5, 2024

(54) BISPHENOL DERIVATIVES AND THEIR USE AS ANDROGEN RECEPTOR ACTIVITY MODULATORS

(71) Applicants: The University of British Columbia, Vancouver (CA); Provincial Health Services Authority, Vancouver (CA)

(72) Inventors: Raymond J. Andersen, Vancouver (CA); Marianne Dorothy Sadar, West Vancouver (CA); Kunzhong Jian, Surrey (CA); Nasrin R. Mawji, Burnaby (CA); Jun Wang, Surrey (CA); Carmen Adriana Banuelos, Richmond (CA); Yu-Chi Yang, Burnaby (CA)

(73) Assignees: The University of British Columbia, Vancouver (CA); Provincial Health Services Authority, Vancouver (CA)

( * ) Notice: Subject to any disclaimer, the term of this patent is extended or adjusted under 35 U.S.C. 154(b) by 0 days.

(21) Appl. No.: 17/404,589

(22) Filed: Aug. 17, 2021

(65) Prior Publication Data
US 2021/0387957 A1    Dec. 16, 2021

Related U.S. Application Data

(60) Division of application No. 16/848,061, filed on Apr. 14, 2020, now Pat. No. 11,142,508, which is a continuation of application No. 15/489,162, filed on Apr. 17, 2017, now abandoned.

(60) Provisional application No. 62/323,196, filed on Apr. 15, 2016.

(51) Int. Cl.
| | |
|---|---|
| *C07D 295/088* | (2006.01) |
| *A61K 31/09* | (2006.01) |
| *A61K 31/10* | (2006.01) |
| *A61K 31/145* | (2006.01) |
| *A61K 31/4164* | (2006.01) |
| *A61K 31/5375* | (2006.01) |
| *A61K 45/06* | (2006.01) |
| *C07C 43/23* | (2006.01) |
| *C07C 69/28* | (2006.01) |
| *C07C 233/18* | (2006.01) |
| *C07C 311/04* | (2006.01) |
| *C07C 311/51* | (2006.01) |
| *C07C 317/18* | (2006.01) |
| *C07C 317/22* | (2006.01) |
| *C07C 317/28* | (2006.01) |
| *C07D 233/60* | (2006.01) |

(52) U.S. Cl.
CPC .......... *C07D 295/088* (2013.01); *A61K 31/09* (2013.01); *A61K 31/10* (2013.01); *A61K 31/145* (2013.01); *A61K 31/4164* (2013.01); *A61K 31/5375* (2013.01); *A61K 45/06* (2013.01); *C07C 43/23* (2013.01); *C07C 69/28* (2013.01); *C07C 233/18* (2013.01); *C07C 311/04* (2013.01); *C07C 311/51* (2013.01); *C07C 317/18* (2013.01); *C07C 317/22* (2013.01); *C07C 317/28* (2013.01); *C07D 233/60* (2013.01)

(58) Field of Classification Search
CPC ......... A61K 31/09; A61K 31/10; A61P 35/00; A61P 35/04
See application file for complete search history.

(56) References Cited

U.S. PATENT DOCUMENTS

| | | | |
|---|---|---|---|
| 2,571,217 | A | 10/1951 | Davis et al. |
| 2,890,189 | A | 6/1959 | Greenlee |
| 3,074,974 | A | 1/1963 | Gebura |

(Continued)

FOREIGN PATENT DOCUMENTS

| | | |
|---|---|---|
| CA | 2206422 A1 | 6/1996 |
| CA | 2226469 A1 | 1/1997 |

(Continued)

OTHER PUBLICATIONS

Kant-Smits (BMC Neurology 2023, 23:118).*

(Continued)

*Primary Examiner* — Pancham Bakshi
(74) *Attorney, Agent, or Firm* — COOLEY LLP

(57) ABSTRACT

Compounds having a structure of Formula I:

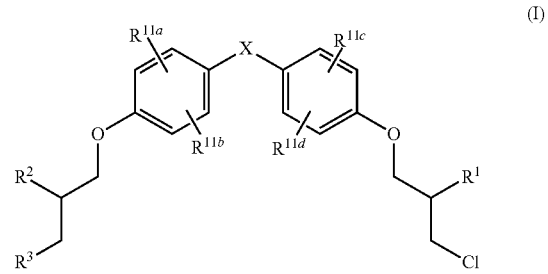

or a pharmaceutically acceptable salt, tautomer or stereoisomer thereof, wherein $R^1$, $R^2$, $R^3$, $R^{11a}$, $R^{11b}$, $R^{11c}$, $R^{11d}$, and X, are as defined herein, are provided. Uses of such compounds for modulating androgen receptor activity, imaging diagnostics in cancer and therapeutics, and methods for treatment of subjects in need thereof, including prostate cancer are also provided.

19 Claims, 6 Drawing Sheets

(56) References Cited

U.S. PATENT DOCUMENTS

| | | |
|---|---|---|
| 3,162,615 A | 12/1964 | Bremmer |
| 4,284,574 A | 8/1981 | Bagga |
| 4,369,298 A | 1/1983 | Kida et al. |
| 4,855,184 A | 8/1989 | Klun et al. |
| 4,904,760 A | 2/1990 | Gaku et al. |
| 5,043,375 A | 8/1991 | Henning et al. |
| 5,155,196 A | 10/1992 | Kolb et al. |
| 5,362,615 A | 11/1994 | Hagemann et al. |
| 5,403,697 A | 4/1995 | Doessel et al. |
| 5,753,730 A | 5/1998 | Nagata et al. |
| 5,807,899 A | 9/1998 | Rolf et al. |
| 5,998,674 A | 12/1999 | Taketani et al. |
| 6,218,430 B1 | 4/2001 | Allegretto et al. |
| 6,245,117 B1 | 6/2001 | Nishikawa et al. |
| 7,183,323 B2 | 2/2007 | Chinn et al. |
| 7,595,345 B2 | 9/2009 | Bunel et al. |
| 7,666,868 B2 | 2/2010 | Maier et al. |
| 7,674,795 B2 | 3/2010 | Mailliet et al. |
| 8,048,888 B2 | 11/2011 | Wosikowski-Buters et al. |
| 8,445,507 B2 | 5/2013 | Jung |
| 8,455,477 B2 | 6/2013 | Katz |
| 8,686,050 B2 | 4/2014 | Sadar et al. |
| 9,173,939 B2 | 11/2015 | Andersen et al. |
| 9,365,510 B2 | 6/2016 | Andersen et al. |
| 9,375,496 B2 | 6/2016 | Andersen et al. |
| 9,388,112 B2 | 7/2016 | Sadar et al. |
| 9,862,667 B2 | 1/2018 | Sadar et al. |
| 10,471,023 B2 | 11/2019 | Andersen et al. |
| 10,654,811 B2 | 5/2020 | Andersen et al. |
| 11,059,795 B2 | 7/2021 | Zhou et al. |
| 11,142,508 B2 | 10/2021 | Andersen et al. |
| 11,242,324 B2 | 2/2022 | Zhou et al. |
| 11,345,670 B2 | 5/2022 | Andersen et al. |
| 11,358,938 B2 | 6/2022 | Zhou et al. |
| 11,485,713 B2 | 11/2022 | Zhou et al. |
| 11,518,747 B2 | 12/2022 | Zhou et al. |
| 2003/0092724 A1 | 5/2003 | Kao et al. |
| 2003/0105268 A1 | 6/2003 | Boriack et al. |
| 2004/0049004 A1 | 3/2004 | Boriack et al. |
| 2004/0243316 A1 | 12/2004 | Weinmann et al. |
| 2008/0153837 A1 | 6/2008 | Mailliet et al. |
| 2008/0193380 A1 | 8/2008 | Dalton et al. |
| 2008/0255395 A1 | 10/2008 | Dai et al. |
| 2009/0105349 A1 | 4/2009 | Barvian et al. |
| 2009/0246158 A1 | 10/2009 | Rudolph et al. |
| 2011/0230556 A1 | 9/2011 | Sadar et al. |
| 2013/0045204 A1 | 2/2013 | Sadar et al. |
| 2013/0109758 A1 | 5/2013 | Sadar et al. |
| 2013/0131167 A1 | 5/2013 | Sadar et al. |
| 2013/0245129 A1 | 9/2013 | Sadar et al. |
| 2013/0336962 A1 | 12/2013 | Andersen et al. |
| 2014/0248263 A1 | 9/2014 | Andersen et al. |
| 2014/0335080 A1 | 11/2014 | Andersen et al. |
| 2015/0010469 A1* | 1/2015 | Andersen ............. C07C 281/14 514/460 |
| 2015/0125389 A1 | 5/2015 | Andersen et al. |
| 2015/0210681 A1 | 7/2015 | Bourque et al. |
| 2016/0068466 A1 | 3/2016 | Andersen et al. |
| 2016/0367707 A1 | 12/2016 | Andersen et al. |
| 2017/0056336 A1 | 3/2017 | Sadar et al. |
| 2017/0081192 A1 | 3/2017 | Schwab et al. |
| 2017/0121261 A1 | 5/2017 | Sadar et al. |
| 2017/0298033 A1 | 10/2017 | Andersen et al. |
| 2017/0368036 A1 | 12/2017 | Hattersley et al. |
| 2018/0064657 A1 | 3/2018 | Andersen et al. |
| 2018/0235925 A1 | 8/2018 | Andersen et al. |
| 2018/0327368 A1 | 11/2018 | Andersen et al. |
| 2019/0022093 A1 | 1/2019 | Wipf et al. |
| 2019/0202800 A1 | 7/2019 | Freeman et al. |
| 2020/0123117 A1 | 4/2020 | Zhou et al. |
| 2020/0247763 A1 | 8/2020 | Zhou et al. |
| 2020/0281949 A1 | 9/2020 | Warner et al. |
| 2020/0325106 A1 | 10/2020 | Andersen et al. |
| 2021/0198213 A1 | 7/2021 | Zhou et al. |
| 2021/0323931 A1 | 10/2021 | Zhou et al. |
| 2021/0332016 A1 | 10/2021 | Zhou et al. |
| 2022/0073472 A1 | 3/2022 | Zhou et al. |
| 2022/0105093 A1 | 4/2022 | Virsik et al. |
| 2022/0202780 A1 | 6/2022 | Virsik et al. |
| 2023/0078913 A1 | 3/2023 | Zhou et al. |

FOREIGN PATENT DOCUMENTS

| | | | |
|---|---|---|---|
| CA | 2339775 A1 | 3/2000 | |
| CA | 2606262 A1 | 11/2006 | |
| CA | 2728219 A1 | 1/2010 | |
| CA | 2786319 A1 | 7/2011 | |
| CN | 102083780 A | 6/2011 | |
| CN | 103342892 A | 10/2013 | |
| EA | 009199 B1 | 12/2007 | |
| EP | 0056175 A1 | 7/1982 | |
| EP | 0155238 A2 | 9/1985 | |
| EP | 0293768 A1 | 12/1988 | |
| EP | 0515128 A1 | 11/1992 | |
| FR | 1389005 | 2/1965 | |
| JP | B-S45-008432 | 3/1970 | |
| JP | S56-5472 A | 1/1981 | |
| JP | 63-196675 | 8/1988 | |
| JP | 63-317539 A | 12/1988 | |
| JP | H01-503541 | 11/1989 | |
| JP | H02-4815 | 1/1990 | |
| JP | 6-049473 A2 | 2/1994 | |
| JP | 7-117349 A | 5/1995 | |
| JP | 09-176240 A | 7/1997 | |
| JP | H10133427 A | 5/1998 | |
| JP | A-H10-316803 | 12/1998 | |
| JP | 11-166087 A2 | 6/1999 | |
| JP | 2000-072705 A2 | 3/2000 | |
| JP | 2001-511170 A | 8/2001 | |
| JP | 2005-325301 A | 11/2005 | |
| JP | 2006-208607 A | 8/2006 | |
| JP | 2006-265351 A2 | 10/2006 | |
| JP | 2007-513089 A | 5/2007 | |
| JP | 2007-290980 | 11/2007 | |
| KR | 10-2011-0044216 A | 4/2011 | |
| PL | 141793 B1 | 8/1987 | |
| RU | 2454394 C2 | 6/2012 | |
| SU | 638596 | 12/1978 | |
| SU | 929630 | 5/1982 | |
| WO | WO 1988/009782 A1 | 12/1988 | |
| WO | WO 1996/16646 A1 | 6/1996 | |
| WO | WO 1998/034930 A1 | 8/1998 | |
| WO | WO 2000/001813 A2 | 1/2000 | |
| WO | WO 2000/010958 A1 | 3/2000 | |
| WO | WO 2001/088013 A2 | 11/2001 | |
| WO | WO 2002/005813 A2 | 1/2002 | |
| WO | WO 2003/004481 A1 | 1/2003 | |
| WO | WO-03106401 A1 | 12/2003 | |
| WO | WO 2005/042464 A1 | 5/2005 | |
| WO | WO 2005/077967 A1 | 8/2005 | |
| WO | WO-2007079078 A1 | 7/2007 | |
| WO | WO 2008/101806 A2 | 8/2008 | |
| WO | WO 2010/000066 A1 | 1/2010 | |
| WO | WO 2011/082487 A1 | 7/2011 | |
| WO | WO 2011/082488 A1 | 7/2011 | |
| WO | WO-2011103202 A2 | 8/2011 | |
| WO | WO 2012/139039 A2 | 10/2012 | |
| WO | WO 2012/145328 A1 | 10/2012 | |
| WO | WO 2012/145330 A1 | 10/2012 | |
| WO | WO 2013/028572 A1 | 2/2013 | |
| WO | WO 2013/028791 A1 | 2/2013 | |
| WO | WO 2014/011220 A2 | 1/2014 | |
| WO | WO 2014/179867 A1 | 11/2014 | |
| WO | WO 2015/031984 A1 | 3/2015 | |
| WO | WO 2016/058080 A1 | 4/2016 | |
| WO | WO 2016/058082 A1 | 4/2016 | |
| WO | WO 2016/112455 A1 | 7/2016 | |
| WO | WO 2016/141458 A1 | 9/2016 | |
| WO | WO 2017/177307 A1 | 10/2017 | |
| WO | WO 2017/210771 A1 | 12/2017 | |
| WO | WO 2018/157232 A1 | 9/2018 | |
| WO | WO 2019/226991 A1 | 11/2019 | |
| WO | WO 2020/081999 A1 | 4/2020 | |

(56) References Cited

FOREIGN PATENT DOCUMENTS

| WO | WO 2020/198710 A1 | 10/2020 |
| WO | WO 2020/198711 A1 | 10/2020 |
| WO | WO 2020/198712 A1 | 10/2020 |

OTHER PUBLICATIONS

Aitipamula, S. et al. "Polymorphs, Salts, and Cocrystals: What's in a Name?", Crystal Growth & Design, 2012, 12(5), p. 2147-2152.
Auberson et al., "Ligand Specific Efficiency (LSE) Index for PET Tracer Optimization," ChemMedChem, vol. 11, No. 13, Jul. 5, 2016, pp. 1415-1427.
Extended European Search Report for European Application No. 19873360.2 dated Jun. 15, 2022, 10 pages.
International Search Report and Written Opinion for International Application No. PCT/US2022/025016, dated Jun. 29, 2022, 9 pages.
International Search Report and Written Opinion for Application No. PCT/US2022/026010, dated Aug. 26, 2022, 10 pages.
Osuka et al., "Synthesis and Photoexcited-State Dynamics of Aromatic Group-Bridged Carotenoid-Porphyrin Dyads and Carotenoid-Porphyrin-Pyromellitimide Triads," J. Am. Chem. Soc. 1993, 115, 9439-9452.
PubChem Compound Summary for CID 145662858, 1-Cyclobutyl-3-cyclopropylcyclobutane, Dec. 12, 2019, 7 pages.
PubChem Compound Summary for CID 146484310, 'N-[4-[[4-[2-[3-chloro-4-(2-chloroethoxy)-5-cyanophenyl]propan-2-yl]phenoxy]methyl]pyrimidin-2yl]methanesulfonamide', U.S. National Library of Medicine, Jun. 27, 2020, 8 pages; retrieved from https://pubchem.ncbi.nlm.nih.gov/compound/146484310.
Alabi, A. et al., "Quick and simple sample treatment for multiresidue analysis of bisphenols, bisphenoldiglycidyl ethers and their derivatives in canned food prior to liquid chromatography and fluorescence detection," J. of Chromatography A, 2014, 1336, 23-33.
Alvarez, C. et al., "Conformational and Experimental Studies on the Dipole Moments of Models of Comblike Polymers", Macromolecules, 30(20): 6369-6375 (1997).
Anderson, R. et al., "Regression of Castrate-Recurrent Prostate Cancer by a Small-Molecule Inhibitor of the Amino-Terminus Domain of the Androgen Receptor", Cancer Cell, 17:535-546 (2010).
Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, Badge), Ref. No. 13510 and 39700 (EFSA-Q-2003-178), The EFSA Journal, 86:1-40 (2004).
Antonarakis et al., "Androgen receptor variant-driven prostate cancer: clinical implications and therapeutic targeting," Prostate Cancer and Prostatic Diseases (2016), 1-11.
Antonarakis et al., "Targeting the N-Terminal Domain of the Androgen Receptor: A New Approach for the Treatment of Advanced Prostate Cancer," The Oncologist 2016;21:1-9.
Auzou et al., European Journal of Medicinal Chemistry, 9(5):548-554 (1974) (with English Abstract).
Balbay, M.D. et al., "Highly Metastatic Human Prostate Cancer Growing within the Prostate of Athymic Mice Overexpresses Vascular Endothelial Growth Factor", Clinical Cancer Research, 5:783-789 (1999).
Banker (ed.) et al., Modern Pharmaceutics, Third Edition, Revised and Expanded, Marcel Dekker, Inc., 1997, pp. 451 and 596.
Banuelos et al., "Sintokamide A is a novel antagonist of androgen receptor that uniquely binds activation function-1 in its amino-terminal domain," The Journal of Biological Chemistry, vol. 291, No. 42, p. 22231-22243, Oct. 14, 2016.
Bao, B. et al., "Androgen signaling is required for the vitamin D-mediated growth inhibition in human prostate cancer cells", Oncogene, 23:3350-3360 (2004).
Berge, S.M. et al., "Pharmaceutical Salts", Pharmaceutical Sciences, 66(1):1-19 (1977).
Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, Food Chemical Contaminants, 83(6):1367-1376 (2000).
Biles, J.E. et al., "Determination of the Diglycidyl Ether of Bisphenol A and its Derivatives in Canned Foods", J. Agric. Food Chem., 47:1965-1969 (1999).
Bisson, W.H. et al., "Discovery of antiandrogen activity of nonsteroidal scaffolds of marketed drugs", PNAS, 104(29):11927-11932 (2007).
Blaszczyk, N. et al., "Osteoblast-Derived factors Induce Androgen-Independent Proliferation and Expression of Prostate-Specific Antigen in Human Prostate Cancer Cells", Clin. Cancer Res., 10:1860-1869 (2004).
Bodei, et al., "Radionuclide Therapy with Iodine-125 and Other Auger-Electron-Emitting Radionuclides: Experimental Models and Clinical Applications." Cancer Biother. & Radiopharm. (2003); 18(6): 861-877.
Bohler, Paul et al., "Identification of Migrants from Coatings of Food Cans and Tubes: Reaction Products of Bisphenol-A-Diglycidyl Ether (BADGE) with Phenols and Solvents", Mitt. Gebiete Lebensm. Hyg., 89:529-547 (1998).
Brand et al., "EPI-001 is a selective peroxisome proliferator-activated receptor-gamma modulator with inhibitory effects on androgen receptor expression and activity in prostate cancer." Oncotarget (2015); 6(6): 3811-3824.
Brzozowski, Z. et al., "Precursors for bisphenolic resins", CAPLUS Database Accession No. 1990:36690, Document No. 112:33690, (1987), 1 page (Abstract).
Bruckheimer, E.M. et al., "Apoptosis in prostate carcinogenesis A growth regulator and a therapeutic target", Cell Tissue Res, 301:153-162 (2000).
Cascini, et al., "Iodine: A Longer-Life Positron Emitter Isotope—New Opportunities in Molecular Imaging." Hindawi Publishing Corp. Biomed. Res. Int. (2014); vol. 2014, Article ID 672094, 7 pages.
Chang, C. et al., "Development of Peptide Antagonists for the Androgen Receptor Using Combinatorial Peptide Phage Display", Molecular Endocrinology, 19(10):2478-2490 (2005).
Choi, K. M. et al., "New Families of Photocurable Oligomeric Fluoromonomers for Use in Dental Composites", Chemistry of Materials, 8(12):2704-2707 (1996).
Clinton, G.M et al., "Estrogen action in human ovarian cancer", Critical Reviews in Oncology/Hematology, 25:1-9 (1997).
Crivello, J. V et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", Journal of Macromolecular Science, Pure and Applied Chemistry, A31(9):1105-1119 (1994).
Cook, W. D., "Fracture and Structure of Highly Crosslinked Polymer Composites", Journal of Applied Polymer Science, 42:1259-1269 (1991).
Culig, Zoran et al., "Androgen Receptor Activation in Prostatic Tumor Cell Lines by Insulin-like Growth Factor-I, Keratinocyte Growth Factor, and Epidermal Growth Factor", Cancer Research, 54:5474-5478 (1994).
Danquah, M. et al., "Micellar Delivery of Bicalutamide and Embelin for Treating Prostate Cancer", Pharmaceutical Research, 26:2081-2092 (2009).
Das, Debabish et al., "Sulfonic acid functionalized mesoporous MCM-41 silica as a convenient catalyst for Bisphenol-A synthesis", Chemical Communications, pp. 2178-2179 (2001).
De Mol et al., "EPI-001, a compound active against castration-resistant prostate cancer, targets transactivation unit 5 of the androgen receptor," ACS Chem. Biol., 2016, 11, 9, 2499-2505.
Dehm, S. et al., "Ligand-independent Androgen Receptor Activity is Activation Function-2-independent and Resistant to Antiandrogens

(56) References Cited

OTHER PUBLICATIONS in Androgen Refractory Prostate Cancer Cells", The Journal of Biological Chemistry, 281(38):27882-27893 (2006).
Dehm, S. et al., "Splicing of a Novel Androgen Receptor Exon Generates a Constitutively Active Androgen Receptor that Mediates Prostate Cancer Therapy Resistance", Cancer Research, 68:5469-5477 (2008).
Edmondson, R.J., et al., "The human ovarian surface epithelium is an androgen responsive tissue", British Journal of Cancer, 86:879-885 (2002).
Estebanez-Perpiñá, E. et al., "A surface on the androgen receptor that allosterically regulates coactivator binding," PNAS, 104(41):16074-16079 (2007).
Estebanez-Perpiñá, E. et al., "The Molecular Mechanisms of Coactivator Utilization in Ligand-dependent Transactivation by the Androgen Receptor," The Journal of Biological Chemistry, 280(9):8060-8068 (2005).
Fehlberg S. et al., "Bisphenol A diglycidyl ether induces apoptosis in tumor cells independently of peroxisome proliferator-activated receptor-y, in caspase-dependent and -independent manners," Biochem. J., 362:573-578 (2002).
Gallart-Ayala, H. et al., "The analysis of bisphenol A-diglycidyl ether (BADGE), bisphenol F-diglycidyl ether (BFDGE) and their derivatives in canned food and beverages by LC-MS/MS", Thermo Fisher Scientific Inc., 4 pages (2011).
Garuti, L., et al., "Irreversible Protein Kinase Inhibitors", Current Medicinal Chemistry, 18:2981-2994 (2011).
Garcia et al., "Determination of compounds from epoxy resins in food simulants by HPLC-fluorescence." Chromatographia, 58(5-6): 337-342 (2003).
Gleave, Martin et al., "Acceleration of Human Prostate Cancer Growth in Vivo by Factors Produced by Prostate and Bone Fibroblasts", Cancer Research, 51:3753-3761 (1991).
Gregory, Christopher et al., "Epidermal Growth Factor Increases Coactivation of the Androgen Receptor in Recurrent Prostate Cancer", The Journal of Biological Chemistry, 279(8):7119-7130 (2004).
Guinan, P.D. et al., "Impotence Therapy and Cancer of the Prostate", The American Journal of Surgery, 131:599-600 (1976).
Guo, Zhiyong et al., "A Novel Androgen Receptor Splice Variant Is Up-regulated during Prostate Cancer Progression and Promotes Androgen Depletion—Resistant Growth", Cancer Research, 69:2305-13 (2009).
Haggstrom, Stina et al., "Testosterone Induces Vascular Endothelial Growth Factor Synthesis in the Ventral Prostate in Castrated Rats", The Journal of Urology, 161:1620-1625 (1999).
Harper et al., "Expression of Androgen Receptor and Growth Factors in Premalignant Lesions of the Prostate", Journal of Pathology, 186:169-177 (1998).
He, B. et al., "Activation Function 2 in the Human Androgen Receptor Ligand Binding Domain Mediates Interdomain Communication with the $NH_2$-terminal Domain", The Journal of Biological Chemistry, 274(52):37219-37225 (1999).
He, B. et al., "Structural Basis for Androgen Receptor Interdomain and Coactivator Interactions Suggests a Transition in Nuclear Receptor Activation Function Dominance", Molecular Cell, 16:425-438 (2004).
Henke, H., "Selektive präparative gelchromatographische Trennung niedermolekularer Verbindungen an Sephadex LH-20", Journal of Chromatography, 254: 296-308 (1983).
Heinlein, Cynthia A., et al., "Androgen Receptor in Prostate Cancer", Endocrine Reviews, 25(2):276-308 (2004).
Helzlsouer, Kathy J., et al., "Serum Gonadotropins and Steroid Hormones and the Development of Ovarian Cancer", JAMA, 274(24):1926-1930 (1995).
Horoszewicz, J.S. et al., "LNCaP Model of Human Prostatic Carcinoma", Cancer Research, 43:1809-1818 (1983).
Hu, R. et al., "Ligand-Independent Androgen Receptor Variants Derived from Splicing of Cryptic Exons Signify Hormone-Refractory Prostate Cancer", Cancer Research, 69:16-22 (2009).

Huber, P.R. et al., "Prostate Specific Antigen. Experimental and Clinical Observations", Scand. J. Urol Nephrol., 104:33-39 (1987).
Hur, E. et al., "Recognition and Accommodation at the Androgen Receptor Coactivator Binding Interface", PLoS Biology, 2(9)(e274): 1303-1312 (2004).
Imamura et al., "An imaging agent to detect androgen receptor and its active splice variants in prostate cancer," JCI Insight. 2016;1(11):e87850 15 pages.
Imamura et al., "Androgen receptor targeted therapies in castration-resistant prostate cancer: Bench to clinic," International Journal of Urology (2016), 23(8):654-65.
Isaacs, J.T., et al., "New Biochemical Methods to Determine Androgen Sensitivity of Prostatic Cancer: The Relative Enzymatic Index (REI)", Prostate Cancer and Hormone Receptors, pp. 133-144 (1979).
Isaacs, J.T., "Antagonistic Effect of Androgen on Prostatic Cell Death", The Prostate, 5:545-557 (1984).
Jackson, J. A. et al., "Prostatic Complications of Testosterone Replacement Therapy", Arch Intern Med., 149:2365-2366 (1989).
Japanese Patent Application No. 2016-512175, Notice of Reasons for Rejection dated Jun. 21, 2016 (and English translation), 12 pages.
Jenster, G. et al., "Domains of the Human Androgen Receptor Involved in Steroid Binding, Transcriptional Activation, and Subcellular Localization", Molecular Endocrinology, 5:1396-1404 (1991).
Jenster, G., et al. "Identification of two transcription activation units in the N-terminal domain of the human androgen receptor." Journal of Biological Chemistry (1995); 270.13: 7341-7346.
Jia, L. et al., "Androgen Receptor Signaling: Mechanism of Interleukin-6 Inhibition", Cancer Research, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", Cancer Research, 65:8003-8008 (2005).
Kaighn, M.E. et al., "Prostate Carcinoma: Tissue Culture Cell Lines", National Cancer Institute Monograph No. 49, pp. 17-21 (1978).
Kemppainen, J. A. et al., "Distinguishing Androgen Receptor Agonists and Antagonists: Distinct Mechanisms of Activation by Medroxyprogesterone Acetate and Dihydrotestosterone", Mol. Endocrinol., 13:440-454 (1999).
Kim, D. et al., "Androgen Receptor Expression and Cellular Proliferation During Transition from Androgen-Dependent to Recurrent Growth after Castration in the CWR22 Prostate Cancer Xenograft", American Journal of Pathology, 160(1):219-226 (2002).
Kolbel, M. et al., "Design of Liquid Crystalline Block Molecules with Nonconventional Mesophase Morphologies: Calamitic Bolaamphiphiles with Lateral Alkyl Chains", J. Am. Chem. Soc., 123:6809-6818 (2001).
Kumar, S. et al., "Synthesis of new crown analogs derived from bisphenol," Indian Journal Chemistry, 36B:656-661 (1997).
L'Heureux, A. et al., "Aminodifluorosulfinium Salts: Selective Fluorination Reagents with Enhanced Thermal Stability and Ease of Handling", J. Org. Chem, 75:3401-3411 (2010).
Langley, E. et al., "Evidence for an Anti-parallel Orientation of the Ligand-activated Human Androgen Receptor Dimer", The Journal of Biological Chemistry, 270(50):29983-29990 (1995).
Lannoye, G.S. et al., "N-Fluoroalkylated and N-alkylated analogs of the dopaminergic D-2 receptor antagonist raclopride", J. Med. Chem., 33(9):2430-2437 (1990).
Leepipatpiboon, N. et al., "Simultaneous determination of bisphenol-A-diglycidyl ether, bisphenol-F-diglycidyl ether, and their derivatives in oil-in-water and aqueous-based canned foods by high-performance liquid chromatography with fluorescence detection." Journal of Chromatography A (2005); 1073.1: 331-339.
Levoin et al., "Determination of the binding mode and interacting amino-acids for dibasic H3 receptor antagonists", Bioorganic & Medicinal Chemistry, 21 (2013) 4526-4529 and Levoin et al., "Supporting Information—Determination of the binding mode and interacting amino-acids for dibasic H3 receptor agonists", Bioorganic & Medicinal Chemistry, vol. 21, Jan. 2013, pp. S1-S3.

(56) References Cited

OTHER PUBLICATIONS

Loren, J.C. et al., "Synthesis of achiral and racemic catenanes based on terpyridine and a directionalized terpyridine mimic, pyridyl-phenanthroline", Org. Biomol. Chem., 3(17):3105-3116 (2005).

Louie, M.C. et al., "Androgen-induced recruitment of RNA polymerase II to a nuclear receptor-p160 coactivator complex", PNAS, 100(5):2226-2230 (2003).

Makary, P., "Principles of salt formation." UK Journal of Pharmaceutical and Biosciences (2014); 2(4): 01-04.

Marriott et al., "Pharmaceutical Compounding and Dispensing," Second Edition, Pharmaceutical Press, 305 pages (2005).

Martin, S.J. et al., "A new precursor for the radiosynthesis of [$^{18}$F]FLT", Nuclear Medicine and Biology, 29:263-273 (2002).

Masiello, D. et al., "Bicalutamide Functions as an Androgen Receptor Antagonist by Assembly of a Transcriptionally Inactive Receptor", The Journal of Biological Chemistry, 277(29):26321-26326 (2002).

Mawji et al., "Preparation of ester derivatives of bisphenol-related compounds as androgen receptor modulators", CAPLUS Database Accession No. 2014:1909735, Document No. 161:737220, Entered on Jan. 6, 2015, 7 pages (Abstract).

Melnyk, O. et al., "Neutralizing Anti-Vascular Endothelial Growth Factor Antibody Inhibits Further Growth of Established Prostate Cancer and Metastases in a Pre-Clinical Model", The Journal of Urology, 161:960-963 (1999).

Miller, J.I. et al., "The Clinical Usefulness of Serum Prostate Specific Antigen After Hormonal Therapy of Metastatic Prostate Cancer", The Journal of Urology, 147:956-961 (1992).

Mitsiades, C.S. et al., "Molecular biology and cellular physiology of refractoriness to androgen ablation therapy in advanced prostate cancer", Expert Opin. Investig. Drugs, 10(6):1099-1115 (2001).

Lima, Lidia M., and Barreiro, Eliezer J. "Bioisosterism: a useful strategy for molecular modification and drug design." Current Medicinal Chemistry (2005); 12.1: 23-49.

Myung, J-K et al., "An androgen receptor N-terminal domain antagonist for treating prostate cancer", The Journal of Clinical Investigation, 123(7):2948-2960 (2013).

Nakazawa, H. et al., "In vitro assay of hydrolysis and chlorohydroxy derivatives of bisphenol A diglycidyl ether for estrogenic activity", Food and Chemical Toxicology, 40:1827-1832 (2002).

Nazareth, L.V. et al., "Activation of the Human Androgen Receptor through a Protein Kinase A Signaling Pathway", The Journal of Biological Chemistry, 271(33):19900-19907 (1996).

Nedolya, N. A. et al., Zhurnal Organicheskoi Khimii, 30(8):1163-1166 (1994) (non English document).

Nishikawa et al., "Epichlorohydrin derivative-based modifier of cellulose fibers and modification method of cellulose fibers," Accession No. 2000:98153 CAPLUS (2009).

Noble, R. L., "The development of prostatic adenocarcinoma in Nb Rats following prolonged sex hormone administration", Cancer Research, 37:1929-1933 (1977).

Noble, R. L., "Sex steroids as a cause of adenocarcinoma of the dorsal prostate in Nb Rats, and their influence on the growth of transplants", Oncology, 34:138-141 (1977).

Ogawa, Y. et al., "Estrogenic activities of chemicals related to food contact plastics and rubbers tested by the yeast two-hybrid assay," Food Additives and Contaminants, 23:4, 422-430 (2006).

Paris, F. et al., "Phenylphenols, biphenols, bisphenol-A and 4-tert-octyphenol exhibit α and β estrogen activities and antiandrogen activity in reporter cell lines," Molecular and Cellular Endocrinology, 193:43-49 (2002).

Patani and LaVoie, "Bioisosterism: A Rational Approach in Drug Design", Chem. Rev., 96: 3147-3176 (1996).

Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.

Penczek, P. et al., "Synthesis and cyclotrimerization of dipropargyl derivatives of diepoxides," Polimery, (Warsaw), 40(5):274-277 (1995).

Petersen, H. et al., "Determination of bisphenol A diglycidyl ether (BADGE) and its derivatives infood: identification and quantification by internal Standard", Eur. Food Res. Technol., 216:355-364 (2003).

Poouthree, K. et al., "Comparison of resolution in microemulsion EKC and MEKC employing suppressed electroosmosis: Application to bisphenol-A-diglycidyl ether and its derivatives", Electrophoresis, 28(20):3705-3711 (2007).

Poustka, J. et al., "Determination and occurrence of bisphenol A, bisphenol A diglycidyl ether, and bisphenol F diglycidyl ether, including their derivatives, in canned foodstuffs' from the Czech retail market," Czech J. Food Sci., 25(4):221-229 (2006).

Poustková et al., "Stability of bisphenol A diglycidyl ether and bisphenol F diglycidyl ether in water-based food simulants." European Food Research and Technology, 219(5): 534-539 (2004).

Quayle, S. et al., "Androgen receptor decoy molecules block the growth of prostate cancer", PNAS, 104(4):1331-1336 (2007).

Rao, B.R. et al., "Endocrine Factors in Common Epithelial Ovarian Cancer", Endocrine Reviews, 12(1):14-26 (1991).

Reader, C. E. L., "Epoxy Resin Derivatives for Stoving Systems", Surface Coatings Australia, 25(10):6-9 (1988).

Reid, J. et al., "Conformational Analysis of the Androgen Receptor Amino-terminal Domain Involved in Transactivation," The Journal of Biological Chemistry, 277:20079-20086 (2002).

Risch, H.A., "Hormonal Etiology of Epithelial Ovarian Cancer, With a Hypothesis Concerning the Role of Androgens and Progesterone", Journal of the National Cancer Institute, 90(23):1774-1786 (1998).

Riu, A. et al., "Characterization of Novel Ligands of ERα, Erβ, and PPARγ: The Case of Halogenated Bisphenol A and Their Conjugated Metabolites", Toxicology Sciences, 122(2): 372-382 (2011).

Roberts, J. T. et al., "Adenocarcinoma of Prostate in 40-Year-Old Body-Builder", Lancet, 2:742 (1986).

Roberts et al., "Emerging drugs for hepatocellular carcinoma," Expert Opin Emerg Drugs, 11(3):469-487 (2006).

Rokicki, G. et al., "Reactions of 4-chloromethyl-1,3-dioxolan-2-one with phenols as a new route to polyols and cyclic carbonates", Journal f. prakt. Chemie., 327:718-722 (1985).

Ross, R.K. et al., "Androgen Metabolism and Prostate Cancer: Establishing a Model of Genetic Susceptibility", European Urology, 35:355-361 (1999).

Roulin et al., "Targeting renal cell carcinoma with NVP-BEZ235, a dual PI3K/mTOR inhibitor, in combination with sorafenib," Mol Cancer, 10:90 (2011).

Rusu, E. et al.: "Photosensitive compounds with chloromethyl groups", Revue Roumaine de Chimie, 45(5):451-456 (2000).

Sadar, M., "Androgen-independent Induction of Prostate-specific Antigen Gene Expression via Cross-talk between the Androgen Receptor and Protein Kinase A signal Transduction Pathways," The Journal of Biological Chemistry, 274(12):7777-7783 (1999).

Sadar, M. et al., "Prostate cancer: molecular biology of early progression to androgen independence", Endocrine-Related Cancer, 6:487-502 (1999).

Sadar, M.D. et al., "Characterization of a New in Vivo Hollow Fiber Model for the Study of Progression of Prostate Cancer to Androgen Independence", Molecular Cancer Therapeutics, 1:629-637 (2002).

Sato, N. et al., "Intermittent Androgen Suppression Delays Progression to Androgen-independent Regulation of Prostate-specific Antigen Gene in the LNCaP Prostate Tumour Model", J. Steroid Biochem. Mol. Biol., 58:139-146 (1996).

Sato, N. et al., "A Metastatic and Androgen-sensitive Human Prostate Cancer Model Using Intraprostatic Inoculation of LNCaP Cells in SCID Mice", Cancer Research, 57:1584-1589 (1997).

Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", Food and Chemical Toxicology, 42:983-993 (2004).

Schaefer, A. et al, "Migration from can coatings: Part 3. Synthesis, identification and quantification of migrating epoxy-based substances below 1000 Da", Food Additives and Contaminants, 21(4):390-405 (2004).

(56) References Cited

OTHER PUBLICATIONS

Schellhammer, "An evaluation of bicalutamide in the treatment of prostate cancer." Expert Opinion on Pharmacotherapy, 3(9): 1313-1328 (2002).
Sharp et al., "Targeting Androgen Receptor Aberrations in Castration-Resistant Prostate Cancer," Clin Cancer Res., Sep. 1, 2016;22(17):4280-4282.
Silverman, R. B., The Organic Chemistry of Drug Design and Drug Action, Academic Press, Inc., Harcourt Brace Jovanovich, pp. 15-20, 9 pages (1992).
Snoek, R. et al., "Induction of Cell-free, In Vitro Transcription by Recombinant Androgen Receptor Peptides", J. Steroid Biochem. Mol. Biol., 59:243-250 (1996).
Stanciuc et al., "Reaction of Pyrylium Salts with Nucleophiles. 23: Triarylethene Derivatives Containing an Oxyalkyleneamino or Oxyalkylene-N-pyridinium Side Chain", Journal of Pharmaceutical Sciences, vol. 82, No. 9, Sep. 1993, pp. 927-933.
Still, W. C. et al., "Rapid Chromatographic Technique for Preparative Separations with Moderate Resolution", J. Org. Chem., 43(14):2923-2925 (1978).
STN Structure Search, dated Oct. 30, 2014 citing PL 135932, 3 pages.
Strub and McKim, "Dimethyl Sulfoxide USP, PhEur in Approved Pharmaceutical Products and Medical Devices", PharmaTech.com, 6 pages (2008). http://www.pharmtech.com/print/224268?page=full&rel=canonical.
Sun, S. et al., "Castration resistance in human prostate cancer is conferred by a frequently occurring androgen receptor splice variant", The Journal of Clinical Investigation, 120(8):2715-30 (2010).
Tanji, N. et al., "Growth Factors: Roles in Andrology", Archives of Andrology, 47:1-7 (2001).
Taplin, M.E et al., "Selection for Androgen Receptor Mutations in Prostate cancers Treated with Androgen Antagonist", Cancer Research, 59:2511-2515 (1999).
Taskeen, A. et al., "Analysis of bisphenol A in canned food: A mini review", Asian Journal of Chemistry, 22(5):4133-4135 (2010).
Thomson, A.A., "Role of androgens and fibroblast growth factors in prostatic development", Reproduction, 121:187-195 (2001).
Ueda, T. et al., "Activation of the Androgen Receptor N-terminal Domain by Interleukin-6 via MAPK and STAT3 Signal Transduction Pathways", The Journal of Biological Chemistry, 277(9):7076-7085 (2002).
Ueda, T. et al., "Ligand-independent Activation of the Androgen Receptor by Interleukin-6 and theRole of Steroid Receptor Coactivator-1 in Prostate cancer Cells", The Journal of Biological Chemistry, 277(41): 38087-38094 (2002).
Uematsu, Y. et al., "Chlorohydrins of bisphenol A diglycidyl ether (BADGE) and bisphenol Fdiglycidyl ether (BFDGE) in canned foods and ready-to-drink coffees from the Japanese market", Food Additives and Contaminants, 18(2):177-185 (2001).
Van Der Kwast, T.H. et al., "Androgen Receptors in Endocrine-Therapy-Resistant Human Prostate Cancer", Inter. J. Cancer, 48:189-193 (1991).
Van Scherpenzeel, M. et al., "Nanomolar affinity, iminosugar-based chemical probes for specific labeling of lysosomal glucocerebrosidase", Bioorganic & Medicinal Chemistry, 18:267-273 (2010).
Venkatesh, Srini, and Lipper, Robert A. "Role of the development scientist in compound lead selection and optimization." Journal of Pharmaceutical Sciences (2000); 89.2: 145-154.
Vippagunta et al., "Crystalline solids," Advanced Drug Delivery Reviews (2001) 48: 3-26.
Walfried et al., "Bisphenol F-Diglycidylether (BFDGE) und Folgeprodukte in Konservenfüllgütern: Synthese und Analytik," Deutsche Lebensmittel-Rundschau, vol. 96, No. 11, 2000, pp. 417-422 (with English abstract).
Wang, G. et al., "Identification of genes targeted by the androgen and PKA signaling pathways in prostate cancer cells", Oncogene, 25:7311-7323 (2006).
Wang, Q. et al., "Spatial and Temporal Recruitment of Androgen Receptor and Its Coactivators Involves Chromosomal Looping and Polymerase Tracking", Molecular Cell, 19:631-642 (2005).
Wetherill, Y. B. et al., "In vitro molecular mechanisms of bisphenol A action," Reproductive Toxicology, 24:178-198 (2007).
Wiedmann and Naqwi, "Pharmaceutical salts: Theory, use in solid dosage forms and in situ preparation in an aerosol." Asian Journal of Pharmaceutical Sciences (2016); 11(6): 722-734.
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
Wilding, G., "The Importance of Steroid Hormones in Prostate Cancer", Cancer Surveys, 14:113-130 (1992).
Wilson, J.D. et al., "Long-Term Consequences of Castration in Men: Lessons from the Skoptzy andthe Eunuchs of the Chinese and Ottoman Courts", The Journal of Clinical Endocrinology & Metabolism, 84:4324-4331 (1999).
Wolff (ed.) et al., Burger's Medicinal Chemistry and Drug Discovery, Fifth Edition, vol. I: Principles and Practice, 1995, pp. 975-977.
Wong, C. et al., "Steroid Requirement for Androgen Receptor Dimerization and DNA Binding", J. Bioi. Chem., 268(25):19004-19012 (1993).
Xu, X. et al, "Synthesis and Stability Study of Dental Monomers Containing Methacrylamidoethyl Phosphonic Acids", Journal of Polymer Science: Part A Polymer Chemistry, 45:99-110 (2007).
Yang et al., "Targeting Androgen Receptor Activation Function-1 with EPI to Overcome Resistance Mechanisms in Castration-Resistant Prostate Cancer," Clin Cancer Res; 22(17) Sep. 1, 2016, 4466-4477.
Ye, Deyong, "An Introduction to Computer-Aided Drug Design", 3 pages, Jan. 31, 2004 (non-English document).
Yonekubo, J. et al., "Concentrations of Bisphenol A, Bisphenol A Diglycidyl Ether, and Their Derivatives in Canned Foods in Japanese Markets," J. Agric. Food Chem., 2008, 56, 2041-2047.
Yong, Eu Leong, et al. "Molecular basis of androgen receptor diseases." Annals of Medicine (2000); 32.1: 15-22.
Zuhayra, M. et al., "New approach for the synthesis of [$^{18}$F]fluoroethyltyrosine for cancer imaging: Simple, fast, and high yielding automated synthesis", Bioorganic & Medicinal Chemistry, 17:7441-7448 (2009).
Extended European Search Report in Application No. EP 12768410.8 dated Sep. 22, 2014, 10 pages.
Extended European Search Report in Application No. EP 14793978.9 dated Sep. 1, 2016, 8 pages.
Supplementary European Search Report in EP Application No. 09771876.1 dated Jun. 20, 2011, 5 pages.
Supplementary European Search Report in EP Application No. 11731645.5 dated Jun. 20, 2013, 11 pages.
Extended European Search Report in Application No. EP 14843037.4 dated Mar. 8, 2017, 5 pages.
Extended European Search Report in Application No. EP 17177010.0 dated Oct. 20, 2017, 10 pages.
Extended European Search Report in Application No. 16736999.0 dated May 24, 2018, 14 pages.
Extended European Search Report for European Application No. 17781660.0 dated Oct. 31, 2019, 8 pages.
Decision of Refusal for Japanese Application No. 2011-515039, dated Dec. 2, 2014, 18 pages (English translation).
International Search Report for International Application No. PCT/CA2009/000902 dated Sep. 1, 2009, 4 pages.
Written Opinion for International Application No. PCT/CA2009/000902 dated Sep. 1, 2009, 6 pages.
International Preliminary Report on Patentability for International Application No. PCT/CA2009/000902 dated Jan. 5, 2011, 7 pages.
International Search Report for International Application No. PCT/US2012/032584 dated Jul. 31, 2012, 3 pages.
Written Opinion for International Application No. PCT/US2012/032584 dated Jul. 31, 2012, 5 pages.
International Preliminary Report on Patentability for PCT/US2012/032584 dated Oct. 8, 2013, 6 pages.
International Search Report for International Application No. PCT/US2012/033959 dated Jul. 18, 2012, 3 pages.

(56) References Cited

OTHER PUBLICATIONS

Written Opinion for International Application No. PCT/US2012/033959 dated Jul. 18, 2012, 7 pages.
International Preliminary Report on Patentability for International Application No. PCT/US2012/033959 dated Oct. 22, 2013, 8 pages.
International Search Report for International Application No. PCT/US2012/033957 dated Jul. 18, 2012, 3 pages.
Written Opinion for International Application No. PCT/US2012/033957 dated Jul. 18, 2012, 5 pages.
International Preliminary Report on Patentability for International Application No. PCT/US2012/033957 dated Oct. 22, 2013, 6 pages.
International Search Report for International Application No. PCT/CA2011/000019 dated Mar. 21, 2011, 7 pages.
Written Opinion for International Application No. PCT/CA2011/000019 dated Mar. 21, 2011, 7 pages.
International Preliminary Report on Patentability for International Application No. PCT/CA2011/000019 dated Jul. 10, 2012, 8 pages.
International Search Report for International Application No. PCT/CA2011/000021 dated Apr. 18, 2011, 8 pages.
Written Opinion for International Application No. PCT/CA2011/000021 dated Apr. 18, 2011, 7 pages.
International Preliminary Report on Patentability for International Application No. PCT/CA2011/000021 dated Jul. 10, 2012, 8 pages.
International Search Report for International Application No. PCT/US2012/051481 dated Nov. 26, 2012, 4 pages.
Written Opinion for International Application No. PCT/US2012/051481 dated Nov. 26, 2012, 7 pages.
International Preliminary Report on Patentability for International Application No. PCT/US2012/051481 dated Feb. 25, 2014, 8 pages.
International Search Report for International Application No. PCT/US2012/051923 dated Jan. 28, 2013, 4 pages.
Written Opinion for International Application No. PCT/US2012/051923 dated Jan. 28, 2013, 8 pages.
International Preliminary Report on Patentability for International Application No. PCT/US2012/051923 dated Feb. 25, 2014, 9 pages.
International Search Report and Written Opinion for International Application No. PCT/CA2014/000414 dated Aug. 5, 2014, 6 pages.
International Preliminary Report on Patentability for International Application No. PCT/CA2014/000414 dated Nov. 10, 2015, 7 pages.
International Search Report and Written Opinion for International Application No. PCT/CA2014/000685 dated Dec. 4, 2014, 13 pages.
International Preliminary Report on Patentability for International Application No. PCT/CA2014/000685 dated Mar. 15, 2016, 7 pages.
International Search Report and Written Opinion for International Application No. PCT/CA2015/000533 dated Dec. 18, 2015, 11 pages.
International Preliminary Report on Patentability for International Application No. PCT/CA2015/000533 dated Apr. 18, 2017, 7 pages.
International Search Report and Written Opinion for International Application No. PCT/CA2015/000535 dated Dec. 23, 2015, 9 pages.
International Preliminary Report on Patentability for International Application No. PCT/CA2015/000535 dated Apr. 18, 2017, 6 pages.
International Search Report and Written Opinion for International Application No. PCT/CA2016/000008 dated Mar. 15, 2016, 13 pages.
International Preliminary Report on Patentability for International Application No. PCT/CA2016/000008 dated Jul. 18, 2017, 7 pages.
International Search Report and Written Opinion for International Application No. PCT/CA2016/000070 dated Jun. 2, 2016, 10 pages.
International Search Report and Written Opinion for International Application No. PCT/CA2017/000083 dated Aug. 3, 2017, 14 pages.
International Preliminary Report on Patentability for International Application No. PCT/CA2016/000070 dated Sep. 12, 2017, 6 pages.
International Search Report and Written Opinion for International Application No. PCT/CA2017/000141 dated Sep. 1, 2017, 11 pages.
International Search Report and Written Opinion for International Application No. PCT/CA2017/000201 dated Dec. 8, 2017, 9 pages.
International Search Report and Written Opinion for International Application No. PCT/US2019/057034 dated Feb. 6, 2020, 10 pages.
International Search Report and Written Opinion for International Application No. PCT/US2021/027771 dated Jul. 9, 2020, 8 pages.
De Santis, M et al., "Practical Guidance on the Role of Corticosteroids in the Treatment of Metastatic Castration-resistant Prostate Cancer," Urology, 2016, vol. 96, pp. 156-164.
Mathur, A et al., "Subverting ER-Stress towards Apoptosis by Nelfinavir and Curcumin Coexposure Augments Docetaxel Efficacy in Castration Resistant Prostate Cancer Cells," PLoS One (2014) 9(8):e103109, 14 pages.
McClurg, UL et al., "The novel anti-androgen candidate galeterone targets deubiquitinating enzymes, USP12 and USP46, to control prostate cancer growth and survival," Oncotarget, 2018, vol. 9, No. 38, pp. 24992-25007.
Qin et al., "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression," J Med Chem. 2018. vol. 61(15), pp. 6665-6704.
Raina et al., "PROTAC-induced BET protein degradation as a therapy for castration-resistant prostate cancer," PNAS, Jun. 28, 2016, vol. 113, No. 26, pp. 7124-7129.
Zurth, "Drug-Drug Interaction Potential of Darolutamide: In Vitro and Clinical Studies," European Journal of Drug Metabolism and Pharmacokinetics (2019) 44:747-759.
Extended European Search Report in Application No. 21212648.6 dated Feb. 21, 2022, 8 pages.
International Search Report and Written Opinion for International Application No. PCT/US2020/025545 dated Jul. 9, 2020, 11 pages.
International Search Report and Written Opinion for International Application No. PCT/US2020/025542 dated Aug. 14, 2020, 10 pages.
International Search Report and Written Opinion for International Application No. PCT/US2020/025539 dated Aug. 18, 2020, 11 pages.
International Search Report and Written Opinion for International Application No. PCT/US2021/050644 dated Feb. 3, 2022, 12 pages.
Comstock et al., "Targeting cell cycle and hormone receptor pathways in cancer," Oncogene, 2013, vol. 32, pp. 5481-5491.
Extended European Search Report for European Application No. 20779267.2 dated Jun. 5, 2023, 10 pages.
Reagan-Shaw S., et al. "Dose translation from animal to human studies revisited," The FASEB Journal, 2007, 22:659-661.

* cited by examiner

BISPHENOL DERIVATIVES AND THEIR USE AS ANDROGEN RECEPTOR ACTIVITY MODULATORS

CROSS-REFERENCE TO RELATED APPLICATION

This application is a division of U.S. application Ser. No. 16/848,061, filed on Apr. 14, 2020, which is a continuation of U.S. application Ser. No. 15/489,162, filed on Apr. 17, 2017, which claims the benefit of priority to U.S. Provisional Application No. 62/323,196, filed on Apr. 15, 2016 and entitled "BISPHENOL DERIVATIVES AND THEIR USE AS ANDROGEN RECEPTOR ACTIVITY MODULATORS," the disclosures of which are hereby incorporated by reference in their entirety for all purposes.

STATEMENT OF GOVERNMENT INTEREST

This invention was made with government support under R01 CA105304 awarded by the National Institutes of Health. The government has certain rights in the invention.

TECHNICAL FIELD

This invention generally relates to bisphenol-related compounds and their use for treatment of various indications. In particular the invention relates to bisphenol ether compounds having halogenated phenyl groups and/or sulfone linking groups and their use for treatment of various cancers, for example prostate cancer, including but not limited to, primary/localized prostate cancer (newly diagnosed), locally advanced prostate cancer, recurrent prostate cancer, metastatic prostate cancer, metastatic castration-resistant prostate cancer (CRPC), and hormone-sensitive prostate cancer. This invention also relates to bisphenol-related compounds and their use for modulating androgen receptor (AR) activity including truncated AR.

DESCRIPTION OF THE RELATED ART

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, Eur Urol 35, 355 361 (1999); A. A. Thomson, Reproduction 121, 187 195 (2001); N. Tanji, K. Aoki & M. Yokoyama, Arch Androl 47, 1 7 (2001)). Several lines of evidence show that androgens are associated with the development of prostate carcinogenesis. Firstly, androgens induce prostatic carcinogenesis in rodent models (R. L. Noble, Cancer Res 37, 1929 1933 (1977); R. L. Noble, Oncology 34, 138 141 (1977)) and men receiving androgens in the form of anabolic steroids have a higher incidence of prostate cancer (J. T. Roberts & D. M. Essenhigh, Lancet 2, 742 (1986); J. A. Jackson, J. Waxman & A. M. Spiekerman, Arch Intern Med 149, 2365 2366 (1989); P. D. Guinan, W. Sadoughi, H. Alsheik, R. J. Ablin, D. Alrenga & I. M. Bush, Am J Surg 131, 599 600 (1976)). Secondly, prostate cancer does not develop if humans or dogs are castrated before puberty (J Clin Endocrinol Metab 84, 4324-4331 (1999); G. Wilding, Cancer Surv 14, 113-130 (1992)). Castration of adult males causes involution of the prostate and apoptosis of prostatic epithelium while eliciting no effect on other male external genitalia (E. M. Bruckheimer & N. Kyprianou, Cell Tissue Res 301, 153-162 (2000); J. T. Isaacs, Prostate 5, 545-557 (1984)). This dependency on androgens provides the underlying rationale for treating prostate cancer with chemical or surgical castration (androgen ablation).

Androgens also play a role in female diseases such as polycystic ovary syndrome as well as cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, JAMA 274, 1926-1930 (1995); R. J. Edmondson, J. M. Monaghan & B. R. Davies, Br J Cancer 86, 879-885 (2002)). The AR has been detected in a majority of ovarian cancers (H. A. Risch, J Natl Cancer Inst 90, 1774-1786 (1998); B. R. Rao & B. J. Slotman, Endocr Rev 12, 14-26 (1991); G. M. Clinton & W. Hua, Crit Rev Oncol Hematol 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate luminal cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 Scand J. Urol Nephrol. 104, 33-39). Castration-resistant prostate cancer that is still driven by AR is biochemically characterized before the onset of symptoms by a rising titre of serum PSA (Miller et al 1992 J. Urol 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains two transcriptional activation units (tau1 and tau5) within activation function-1 (AF-1). Binding of androgen (ligand) to the LBD of the AR results in its activation such that the receptor can effectively bind to its specific DNA consensus site, termed the androgen response element (ARE), on the promoter and enhancer regions of androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig el al 1994 Cancer Res. 54, 5474-5478; Nazareth et al 1996 J. Biol. Chem. 271, 19900-19907; Sadar 1999 J. Biol. Chem. 214, 7777-7783; Ueda et al 2002 A J. Biol. Chem. 277, 7076-7085; and Ueda et al 2002 B J. Biol. Chem. 277, 38087-38094).

Clinically available inhibitors of the AR include non-steroidal antiandrogens such as bicalutamide (Casodex™), nilutamide, flutamide, and enzalutamide. There is also a class of steroidal antiandrogens, such as cyproterone acetate and spironolactone. Both steroidal and non-steroidal antiandrogens target the LBD of the AR and predominantly fail presumably due to poor affinity, mutations that lead to activation of the AR by these same antiandrogens (Taplin, M. E., Bubley, G. J., Kom Y. J., Small E. J., Eiptonm M., Rajeshkumarm B., Balkm S. P., Cancer Res., 59, 2511-2515 (1999)), and constitutively active AR splice variants. Anti-androgens have no effect on the constitutively active AR splice variants that lack the ligand-binding domain (LBD) and are associated with castration-recurrent prostate cancer (Dehm S M, Schmidt L J, Heemers H V, Vessella R L, Tindall D J., Cancer Res 68, 5469-77, 2008; Guo Z, Yang X, Sun F, Jiang R, Linn D E, Chen H, Chen H, Kong X, Melamed J, Tepper C G, Rung H J, Brodie A M, Edwards J, Qiu Y., Cancer Res. 69, 2305-13, 2009; Hu et al 2009 Cancer Res. 69, 16-22; Sun et al 2010 J Clin Invest. 2010 120, 2715-30) and resistant to abiraterone and enzalutamide (Antonarakis et al., N Engl J Med. 2014, 371, 1028-38; Scher et al JAMA Oncol. 2016 doi: 10.1001).

AR antagonists other than the bisphenol ether derivatives previously reported (see, WO 2010/000066, WO 2011/082487; WO 2011/082488; WO 2012/145330; WO 2015/031984; WO 2016/058080; WO 2016/058082, WO 2016/112455, and WO 2016/141458 which are hereby incorporated by reference in their entireties, to the British Columbia Cancer Agency Branch and The University of British Columbia) that bind to full-length AR and/or truncated AR splice variants that are currently being developed include: AR degraders such as niclosamide (Liu C et al 2014), galeterone (Njar et al 2015; Yu Z at al 2014), and ARV-330/Androgen receptor PROTAC (Neklesa et al 201.6 J Clin Oncol 34 suppi 2S; abstr 267); AR DBD inhibitor VPC-14449 (Dalai K et al 2014 J Biol Chem. 289(38): 26417-29; Li H et al 2014 J Med Chem. 57(15):6458-67); antiandrogens apalutamide (Clegg N J et al 2012), ODM-201 (Moilanen A M et al 2015), ODM-204 (Kallio et al J Clin Oncol 2016 vol. 34 no. 2 suppl 230), TAS3681 (Minamiguchi et al 2015 J Clin Oncol 33, suppl 7, abstr 266); and AR NTD inhibitors 3E10-AR441bsAb (Goicochea N L et al 2015), and sintokamide (Sadar et al 2008; Banuelos et al 2016).

The AR-NTD is also a target for drug development (e.g. WO 2000/001813), since the NTD contains Activation-Function-1 (AF-1) which is the essential region required for AR transcriptional activity (Jenster et al 1991. Mol Endocrinol. 5, 1396-404). The AR-NTD importantly plays a role in activation of the AR in the absence of androgens (Sadar, M. D. 1999 J. Biol. Chem. 274, 7777-7783; Sadar M D et al 1999 Endocr Relat Cancer. 6, 487-502; Ueda et al 2002 J. Biol. Chem. 277, 7076-7085; Ueda 2002 J. Biol. Chem. 277, 38087-38094; Blaszczyk et al 2004 Clin Cancer Res. 10, 1860-9; Dehm et al 2006 J Biol Chem. 28, 27882-93; Gregory et al 2004 J Biol Chem. 279, 7119-30). The AR-NTD is important in hormonal progression of prostate cancer as shown by application of decoy molecules (Quayle et al 2007, Proc Natl Acad Sci USA. 104, 1331-1336).

While the crystal structure has been resolved for the AR C-terminus LBD, this has not been the case for the NTD due to its high flexibility and intrinsic disorder in solution (Reid et al 2002 J. Biol. Chem. 277, 20079-20086) thereby hampering virtual docking drug discovery approaches.

While significant advances have been made in this field, there remains a need for improved treatment for prostate cancer, especially metastatic castration-resistant prostate cancer.

BRIEF SUMMARY

The present disclosure is based in part on the surprising discovery that the compounds described herein, can be used to modulate AR activity either in vivo or in vitro for both research and therapeutic uses. In some embodiments, certain compounds disclosed herein are useful for imaging the prostate. The imaging can be for any number of diagnostic purposes. For example, in certain embodiments the compounds are useful for imaging benign prostate cancer diseases. In other embodiments, the compounds find utility for imaging of certain cancers, including prostate cancer since certain embodiments of the compounds localize in prostate tumor sites. Other imaging agents are androgen mimics; however, in one embodiment, the compounds are useful for imaging AR splice variants or any AR species (i.e., those mutated in other domains or regions). The AR can be mammalian. For example, the AR can be human. The prostate cancer can be castration-resistant prostate cancer. The prostate cancer can be androgen-dependent prostate cancer.

In one embodiment, the present disclosure relates to compounds of Formula (I):

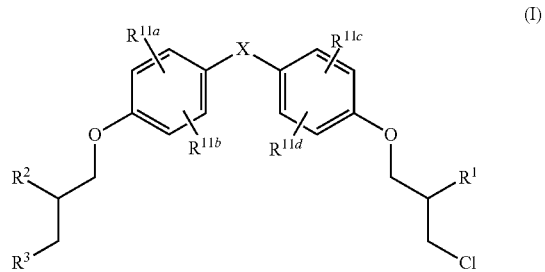

or a pharmaceutically acceptable salt, tautomer or stereoisomer thereof, wherein:
X is —S(O)$_n$— or —C(R$^8$R$^9$)—;
R$^1$ is H, hydroxyl or OC(=O)R$^{13}$;
R$^2$ is hydroxyl or OC(=O)R$^{13}$;
R$^3$ is halo, —OH, —OR$^4$; OC(=O)R$^{13}$, —NH$_2$, —NHS(O)$_n$R$^5$, —N(C$_1$-C$_6$ alkyl)S(O)$_n$R$^5$, —S(O)$_n$R$^5$, —N$_3$, aryl, carbocyclyl, heteroaryl or heterocyclyl which are optionally substituted with one or more R$_6$;
R$^4$ is C$_1$-C$_6$ alkyl, C$_2$-C$_6$ alkenyl, C$_2$-C$_6$ alkynyl, aryl, carbocyclyl, heteroaryl or heterocyclyl which are optionally substituted with one or more R$_6$;
R$^5$ is each independently C$_1$-C$_6$ alkyl or aryl which are optionally substituted with one or more R$^6$;
R$^6$ is each independently selected from the group consisting of H, F, Cl, Br, I, $^{123}$I, hydroxyl, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;
R$^8$ and R$^9$ are each independently H or C$_1$-C$_6$ alkyl;
R$^{11a}$, R$^{11b}$, R$^{11c}$ and R$^{11d}$ are each independently H, methyl, F, Cl, Br, I, or $^{123}$I;
R$^{13}$ is C$_1$-C$_6$ alkyl; and
n is 0, 1, or 2;
wherein at least one of R$^{11a}$, R$^{11b}$, R$^{11c}$ and R$^{11d}$ is methyl F, Cl, Br, I, or $^{123}$I.

In some embodiments, at least two of R$^{11a}$, R$^{11b}$, R$^{11c}$ and R$^{11d}$ in Formula I are independently methyl, F, Cl, Br, I, or $^{123}$I. In other embodiments, any two of R$^{11a}$, R$^{11b}$, R$^{11c}$ and R$^{11d}$ are independently methyl, F, Cl, Br, I, or $^{123}$I and the remaining two of R$^{11a}$, R$^{11b}$, R$^{11c}$ and R$^{11d}$ are each H. In one embodiment, R$^{11a}$ and R$^{11b}$ are each H, and R$^{11c}$ and R$^{11d}$ are each independently methyl, F, Cl, Br, I, or $^{123}$I. In another embodiment, R$^{11a}$ and R$^{11b}$ are each H, and R$^{11c}$ and R$^{11d}$ are each independently methyl, Cl, or Br. In a certain embodiment, R$^{11a}$ and R$^{11b}$ are each H, and R$^{11c}$ and R$^{11d}$ are each Cl.

In one embodiment, R$^{11a}$ and R$^{11c}$ in Formula I are each H, and R$^{11b}$ and R$^{11d}$ in Formula I are each independently methyl, F, Cl, Br, I, or $^{123}$I. In some embodiments, R$^{11a}$ and R$^{11c}$ are each H, and R$^{11b}$ and R$^{11d}$ are each independently methyl, Cl, or Br. In another embodiment, $R^{11a}$ and $R^{11c}$ are each H, and $R^{11b}$ and $R^{11d}$ are each Cl.

In some embodiments, X in Formula I is —S(O)$_2$—. In another embodiment, X in Formula I is —C(R$^8$R$^9$)— and R$_8$ and R$^9$ are each independently C$_1$-C$_3$ alkyl. In one embodiment, X is —C(R$^8$R$^9$)— and R$_8$ and R$^9$ are each methyl.

In some embodiments, R$^1$ in Formula I is hydroxyl or OC(=O)R$^{13}$. In another embodiment R$^1$ is H.

In some embodiments, R$^3$ in Formula I is —OH. In another embodiment, R$^3$ is —OC(=O)R$^{13}$, wherein R$^{13}$ is methyl. In one embodiment, R$^3$ is —OR$^4$ and R$^4$ is C$_1$-C$_6$ alkyl. In other embodiments, R$^3$ is —OR$^4$ and R$^4$ is methyl.

In one embodiment, R$^3$ in Formula I is an optionally substituted 5 or 6 membered heteroaryl or an optionally substituted 3 to 7 membered heterocyclyl, wherein said heteroaryl or said heterocyclyl respectively comprise at least one N atom. In another embodiment, R$^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine.

In one embodiment, each R$^{13}$ in Formula I when present is C$_1$-C$_3$ alkyl. In a further embodiment, each R$^{13}$ when present is methyl.

In one embodiment, R$^1$ and R$^2$ in Formula I are each independently —OH or —OC(=O)R$^{13}$, wherein R$^{13}$ is methyl. In some embodiments, at least one of R$^1$, R$^2$ and R$^3$ is —OC(=O)R$^{13}$, wherein R$^{13}$ is methyl. In another embodiment, any two of R$^1$, R$^2$ and R$^3$ are each —OC(=O)R$^{13}$, wherein R$^{13}$ is methyl. In one embodiment, R$^1$, R$^2$ and R$^3$ are each —OC(=O)R$^{13}$, wherein R$^{13}$ is methyl.

In one embodiment of the present disclosure relates to compounds disclosed in Tables 1, 2, 3, and 4 or a pharmaceutically acceptable salt thereof.

In one embodiment, the present disclosure relates to compounds of Formula (I):

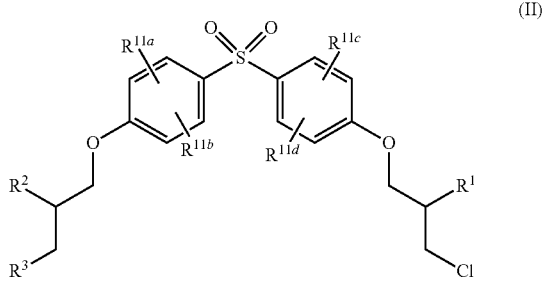

(II)

or a pharmaceutically acceptable salt, tautomer or stereoisomer thereof, wherein:

R$^1$ is H, hydroxyl or —OC(=O)R$^{13}$;
R$^2$ is hydroxyl or —OC(=O)R$^{13}$;
R$^3$ is halo, —OH, —OR$^4$, —OC(=O)R$^{13}$, —NH$_2$, —NHS(O)$_n$R$^5$, —N(C$_1$-C$_6$ alkyl)S(O)$_n$R$^5$, —S(O)$_n$R$^5$, —N$_3$, aryl, carbocyclyl, heteroaryl or heterocyclyl which are optionally substituted with one or more R$^6$;
R$^4$ is C$_1$-C$_6$ alkyl, C$_2$-C$_6$ alkenyl, C$_2$-C$_6$ alkynyl, aryl, carbocyclyl, heteroaryl or heterocyclyl which are optionally substituted with one or more R$^6$;
R$^5$ is each independently C$_1$-C$_6$ alkyl or aryl which are optionally substituted with one or more R$^6$;

R$^6$ is each independently selected from the group consisting of H, F, Cl, Br, I, $^{123}$I, hydroxyl, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;

R$^8$ and R$^9$ are each independently H or C$_1$-C$_6$ alkyl;

n is 0, 1, or 2; and

R$^{11a}$, R$^{11b}$, R$^{11c}$ and R$^{11d}$ are each independently H, methyl, F, Cl, Br, I, or $^{123}$I.

In one embodiment, R$^3$ in Formula II is —OH. In another embodiment, R$^3$ is —OC(=O)R$^{13}$, wherein R$^{13}$ is methyl. In other embodiments, R$^3$ is —OR$^4$, wherein R$^4$ is C$_1$-C$_6$ alkyl. In some embodiments, R$^3$ is —OR$^4$, wherein R$^4$ is methyl.

In some embodiments, R$^1$ in Formula II is hydroxyl or OC(=O)R$^{13}$. In another embodiment R$^1$ in Formula II is H.

In one embodiment, R$^3$ in Formula II is an optionally substituted 5 or 6 membered heteroaryl or an optionally substituted 3 to 7 membered heterocyclyl, wherein said heteroaryl or said heterocyclyl respectively comprise at least one N atom. In some embodiments, R$^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine.

In one embodiment, R$^{11a}$, R$^{11b}$, R$^{11c}$ and R$^{11d}$ in Formula II are each H.

In one embodiment, each R$^{13}$ in Formula II when present is C$_1$-C$_3$ alkyl. In a further embodiment, each R$^{13}$ when present is methyl.

In one embodiment, R$^1$ and R$^2$ in Formula II are each independently —OH or —OC(=O)R$^{13}$, wherein R$^{13}$ is methyl. In some embodiments, at least one of R$^1$, R$^2$ and R$^3$ is —OC(=O)R$^{13}$, wherein R$^{13}$ is methyl. In another embodiment, any two of R$^1$, R$^2$ and R$^3$ are each —OC(=O)R$^{13}$, wherein R$^{13}$ is methyl. In one embodiment, R$^1$, R$^2$ and R3 are each —OC(=O)R$^{13}$, wherein R$^{13}$ is methyl.

In one embodiment of the present disclosure relates to compounds disclosed in Table 5 or a pharmaceutically acceptable salt thereof.

In one embodiment, the present disclosure relates to a pharmaceutical composition comprising a compound of Formula I or Formula II or a pharmaceutically acceptable salt, tautomer or stereoisomer thereof. In one embodiment, the pharmaceutical composition further comprises a pharmaceutically acceptable carrier. In some embodiments, the pharmaceutical composition further comprises a pharmaceutically acceptable carrier and an additional therapeutic agent.

In some embodiments, a pharmaceutical composition comprising a compound of Formula I or Formula II or a pharmaceutically acceptable salt, tautomer or stereoisomer thereof, and an additional therapeutic agent is provided. In one embodiment, the additional therapeutic agent is for treating prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration. In another embodiment, the additional therapeutic agent is enzalutamide, galeterone, abiraterone, bicalutamide, nilutamide, flutamide, cyproterone acetate, docetaxel, bevacizumab (Avastin), OSU-HDAC42, VITAXIN, sunitumib, ZD-4054, cabazitaxel (XRP-6258), MDX-010 (Ipilimumab), OGX 427, OGX Oil, finasteride, dutasteride, turosteride, bexlosteride, izonsteride, FCE 28260, SKF105,111, ODM-201, radium 233, ODM-204, niclosamide, apalutamide, ARV-330, VPC-14449, TAS3681, 3E10-AR441bsAb, sintokamide, or related compounds thereof.

In one embodiment, the present disclosure provides a method for modulating androgen receptor activity, comprising administering a compound of Formula I or Formula II or a pharmaceutically acceptable salt, tautomer or stereoisomer thereof, or a pharmaceutical composition comprising a compound of Formula I or Formula II or a pharmaceutically acceptable salt, tautomer or stereoisomer thereof, to a patient in need thereof. In some embodiments, the method of modulating androgen receptor activity is inhibiting androgen receptor.

In one embodiment, the present disclosure provides a method for treating a condition or disease that is responsive to modulation of androgen receptor activity, comprising: administering a compound of Formula I or Formula II or a pharmaceutically acceptable salt, tautomer or stereoisomer thereof, or a pharmaceutical composition comprising a compound of Formula I or Formula II or a pharmaceutically acceptable salt, tautomer or stereoisomer thereof, to a patient in need thereof. In one embodiment, the condition or disease is selected from the group consisting of: prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, and age related macular degeneration. In one embodiment, the condition is prostate cancer. In another embodiment, the condition or disease is castration-resistant prostate cancer. In some embodiments, the condition or disease is androgen-dependent prostate cancer.

Some embodiments of the compounds described herein can be used for diagnostic purposes to investigate diseases of the prostate, including cancer. In particular embodiments, the compounds are useful for imaging diagnostics in cancer. In some embodiments, such imaging allows for the detection and/or location of cancer sites (e.g., tumor sites). Furthermore, these compounds can be used individually or as part of a kit for such purposes.

BRIEF DESCRIPTION OF THE FIGURES

FIG. 1 shows a $^{13}$C NMR spectrum of Compound 3a.

DETAILED DESCRIPTION

Definitions

Figure 1:
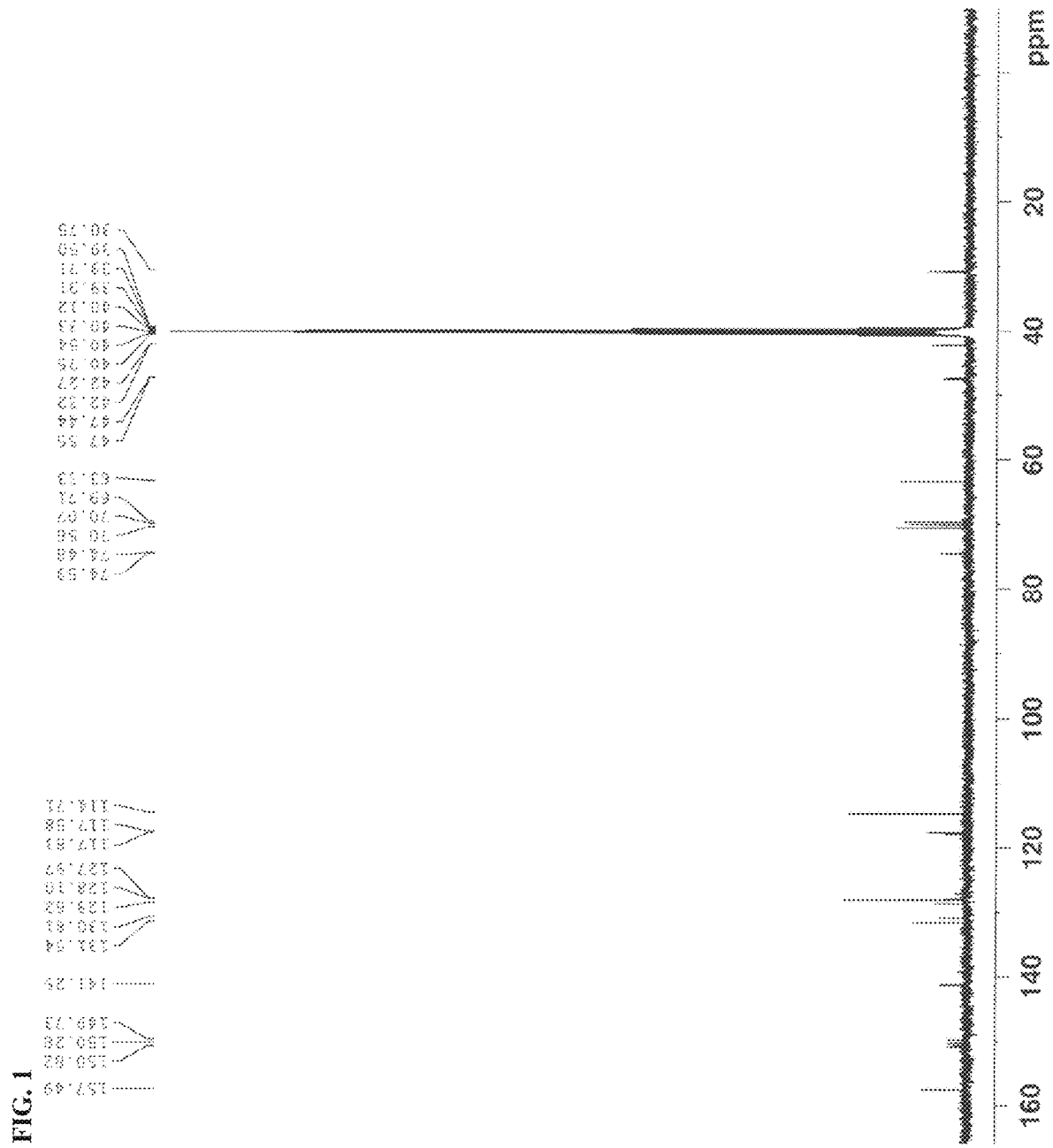

In the following description, certain specific details are set forth in order to provide a thorough understanding of various embodiments. However, one skilled in the art will understand that the invention can be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH$_2$ radical.

"Cyano" refers to the —CN radical.

"Halo" or "halogen" refers to bromo, chloro, fluoro or iodo radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Acetyl" or "Ac" refers to —C(=O)CH$_3$ substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes Cn and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes Cn and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Examples of $C_1$-$C_3$ alkyl includes methyl, ethyl, n-propyl, and t-propyl. Examples of $C_1$-$C_4$ alkyl includes methyl, ethyl, n-propyl, i-propyl, n-butyl, i-butyl, and sec-butyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for C2-C5 alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes Cn and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —OR$_a$ where R$_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —NHR$_a$ or —NR$_a$R$_a$ where each R$_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)R$_a$ moiety, wherein R$_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in R$_a$, above. For example, "$C_1$-$C_{10}$ acyl" refers to alkylcarbonyl group as defined above, where R$_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" refers to a radical of the formula —R$_b$—R$_c$ where R$_b$ is an alkylene, alkenylene or alkynylene group as defined above and R$_c$ is one or more aryl radicals as defined above, for example, benzyl, diphenylmethyl and the like.

Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic ring radical which consists of two to twelve carbon atoms and from one to six heteroatoms selected from the group consisting of nitrogen, oxygen and sulfur. Heterocyclcl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heterocyclylalkyl" refers to a radical of the formula —$R_b$—$R_e$ where $R_b$ is an alkylene, alkenylene, or alkynylene chain as defined above and $R_e$ is a heterocyclyl radical as defined above, and if the heterocyclyl is a nitrogen-containing heterocyclyl, the heterocyclyl can be attached to the alkyl, alkenyl, alkynyl radical at the nitrogen atom. Unless stated otherwise specifically in the specification, a heterocyclylalkyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene, alkenylene, or alkynylene chain as defined above and $R_f$ is a heteroaryl radical as defined above. Unless stated otherwise specifically in the specification, a heteroarylalkyl group can be optionally substituted.

"$^{123}$I" refers to the radioactive isotope of iodine having atomic mass 123. The compounds of Formula I can comprise at least one $^{123}$I moiety. Throughout the present application, where structures depict a $^{123}$I moiety at a certain position it is meant that the I moiety at this position is enriched for $^{123}$I. In other words, the compounds contain more than the natural abundance of $^{123}$I at the indicated position(s). It is not required that the compounds comprise 100% $^{123}$I at the indicated positions, provided $^{123}$I is present in more than the natural abundance. Typically the $^{123}$I isotope is enriched to greater than 50%, greater than 60%, greater than 70%, greater than, 80% or greater than 90%, relative to $^{127}$I.

"$^{18}$F" refers to the radioactive isotope of fluorine having atomic mass 18. "F" or "$^{19}$F" refers to the abundant, non-radioactive fluorine isotope having atomic mass 19. The compounds of Formula I can comprise at least one $^{18}$F moiety. Throughout the present application, where structures depict a $^{18}$F moiety at a certain position it is meant that the F moiety at this position is enriched for $^{18}$F. In other words, the compounds contain more than the natural abundance of $^{18}$F at the indicated position(s). It is not required that the compounds comprise 100% $^{18}$F at the indicated positions, provided $^{18}$F is present in more than the natural abundance. Typically the $^{18}$F isotope is enriched to greater than 50%, greater than 60%, greater than 70%, greater than 80% or greater than 90%, relative to $^{19}$F.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol "  " (hereinafter can be referred to as "a point of attachment bond") denotes a bond that is a point of attachment between two chemical entities, one of which is depicted as being attached to the point of attachment bond and the other of which is not depicted as being attached to the point of attachment bond. For example, "XY  " indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or "XY  " infers that when R is "XY", the point of attachment bond is the same bond as the bond by which $R^3$ is depicted as being bonded to $CH_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

The invention disclosed herein is also meant to encompass the in vivo metabolic products of the disclosed compounds. Such products can result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

As used herein, a "subject" can be a human, non-human primate, mammal, rat, mouse, cow, horse, pig, sheep, goat, dog, cat and the like. The subject can be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, bladder cancer, pancreatic cancer, hepatocellular cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, bladder cancer, pancreatic cancer, hepatocellular cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances can or cannot occur, and that the description includes instances where said event or circumstance occurs and instances in which it does not. For example, "optionally substituted aryl" means that the aryl radical can or cannot be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent can be water, in which case the solvate can be a hydrate. Alternatively, the solvent can be an organic solvent. Thus, the compounds of the present invention can exist as a hydrate, including a monohydrate, dihydrate, hemihydrate, sesquihydrate, trihydrate, tetrahydrate and the like, as well as the corresponding solvated forms. The compound of the invention can be true solvates, while in other cases, the compound of the invention can merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"An "effective amount" refers to a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound can vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to a castration-resistant form. Typically, a prophylactic dose is used in subjects prior to or at an earlier stage of disease, so that a prophylactically effective amount can be less than a therapeutically effective amount.

"Treating" or "treatment" as used herein covers the treatment of the disease or condition of interest in a mammal, preferably a human, having the disease or condition of interest, and includes:
 (i) preventing the disease or condition from occurring in a mammal, in particular, when such mammal is predisposed to the condition but has not yet been diagnosed as having it;
 (ii) inhibiting the disease or condition, i.e., arresting its development;
 (iii) relieving the disease or condition, i.e., causing regression of the disease or condition; or
 (iv) relieving the symptoms resulting from the disease or condition, i.e., relieving pain without addressing the underlying disease or condition. As used herein, the terms "disease" and "condition" can be used interchangeably or can be different in that the particular malady or condition cannot have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)-for amino acids. The present invention is meant to include all such possible isomers, as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/ isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program, ChemDraw Ultra Version 11.0.1 and/or ChemDraw Ultra Version 14.0 and/or ChemDraw Professional 16.0.0.82 software naming program (CambridgeSoft), or the like. For complex chemical names employed herein, a substituent group is named before the group to which it attaches. For example, cyclopropyl ethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

Throughout the present specification, the terms "about" and/or "approximately" can be used in conjunction with numerical values and/or ranges. The term "about" is understood to mean those values near to a recited value. For example, "about 40 [units]" can mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" can be used interchangeably.

Throughout the present specification, numerical ranges are provided for certain quantities. It is to be understood that these ranges comprise all subranges therein. Thus, the range "from 50 to 80" includes all possible ranges therein (e.g, 51-79, 52-78, 53-77, 54-76, 55-75, 60-70, etc.). Furthermore, all values within a given range can be an endpoint for the range encompassed thereby (e.g, the range 50-80 includes the ranges with endpoints such as 55-80, 50-75, etc.).

II. Compounds and Pharmaceutical Compositions

As noted above, certain embodiments of the present invention are directed to compounds useful for treatment of various cancers, including various types of prostate cancers. While not wishing to be bound by theory, it is believed that binding of the compounds to the androgen receptor (for example at the N-terminal domain) can contribute to the activity of the disclosed compounds. The compounds of the present invention include halogenated phenyl groups (i.e., $R^{11a}$—$R^{11d}$ in Formula I) and/or sulfone bridging groups (i.e., X in Formula I is —$S(O)_2$— or compounds of Formula II) which impart improved properties to the compounds compared to compounds lacking the described $R^3$ moiety. For example, the improved properties include improved drug-like properties such as improved activity (e.g., androgen receptor (AR) modulation), longer half-life (e.g., in vivo); decreased toxicity; better solubility, improved formulation, better bioavailability, better pharmacokinetic profile; reduction in unwanted metabolites and the like.

In one embodiment the invention includes compounds which form covalent bonds with the androgen receptor (AR) (e.g., at the N-terminal domain), thus resulting in irreversible (or substantially irreversible) inhibition of the same. In this regard, the certain compounds of the present invention are designed to include functional groups capable of forming covalent bonds with a nucleophile under certain in vivo conditions. For example, in some embodiments the reactivity of compounds of the present invention is such that they will not substantially react with various nucleophiles (e.g., glutathione) when the compounds are free in solution. However, when the free mobility of the compounds is restricted, and an appropriate nucleophile is brought into close proximity to the compound, for example when the compounds associate with, or bind to, the androgen receptor, the compounds are capable of forming covalent bonds with certain nucleophiles (e.g., thiols).

The present invention includes all compounds which have the above described properties (i.e., binding and/or inhibiting to androgen receptor (AR)). In one embodiment, the present invention is directed to a compound having a structure of Formula I:

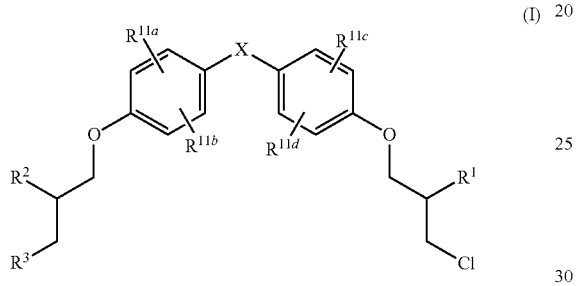
(I)

or a pharmaceutically acceptable salt, tautomer or stereoisomer thereof, wherein:

X is —S(O)$_n$— or —C(R$^8$R$^9$)—;
R$^1$ is H, —OH, or —OC(=O)R$^{13}$;
R$^2$ is —OH, or —OC(=O)R$^{13}$;
R$^3$ is halo, —OH, —OR$^4$, —OC(=O)R$^{13}$, —NH$_2$, —NHC(=O)R$^{13}$, —N(C(=O)R$^{13}$)$_2$, —NHS(O)$_n$R$^5$, —N(C(=O)R$^{13}$)(S(O)$_n$R$^5$), —N(C$_1$-C$_6$ alkyl)(S(O)$_n$ R$^5$), —S(O)$_n$R$^5$, —N$_3$, aryl, carbocyclyl, heteroaryl or heterocyclyl which are optionally substituted with one or more R$^6$;
R$^4$ is C$_1$-C$_6$ alkyl, C$_2$-C$_6$ alkenyl, C$_2$-C$_6$ alkynyl, aryl, carbocyclyl, heteroaryl or heterocyclyl which are optionally substituted with one or more R$^6$;
R$^5$ is each independently C$_1$-C$_6$ alkyl or aryl which are optionally substituted with one or more R$^6$;
R$^6$ is each independently selected from the group consisting of H, F, Cl, Br, I, $^{123}$I, —OH, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, —OH, —OS(O)$_2$-aryl, C$_1$-C$_6$ alkyl, C$_2$-C$_6$ alkenyl, or C$_2$-C$_6$ alkynyl;
R$^8$ and R$^9$ are each independently H or C$_1$-C$_6$ alkyl;
R$^{11a}$, R$^{11b}$, R$^{11c}$ and R$^{11d}$ are each independently H, methyl, F, Cl, Br, I, or $^{123}$I;
R$^{13}$ is C$_1$-C$_6$ alkyl; and
n is 0, 1, or 2;
wherein at least one of R$^{11a}$, R$^{11b}$, R$^{11c}$ and R$^{11d}$ is methyl, F, Cl, Br, I, or $^{123}$I.

In various embodiments, different stereoisomers of the compound of structure (I) are provided, for example in some embodiments the compound has one of the following structures (Ia), (Ib), (Ic) or (Id):

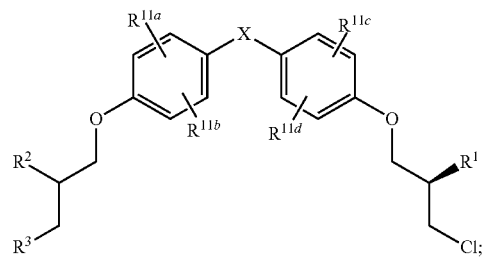
(Ia)

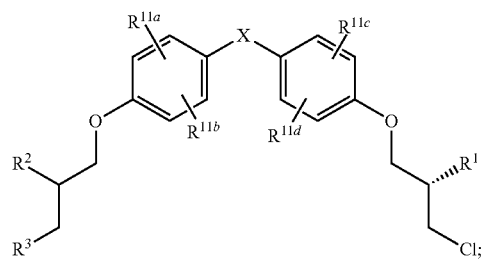
(Ib)

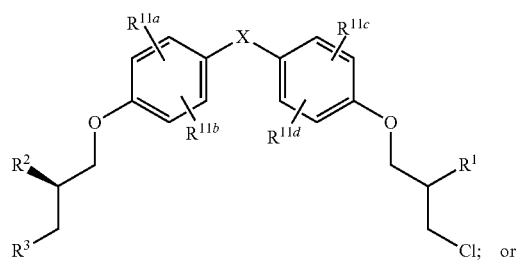
(Ic)

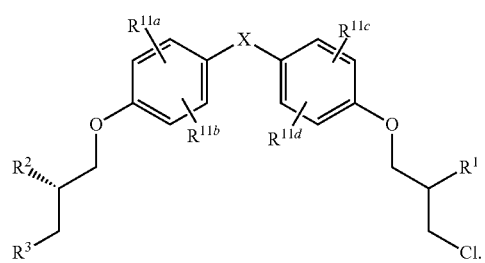
(Id)

In still other embodiments, the compound has one of the following structures (Ie), (If), (Ig) or (Ih):

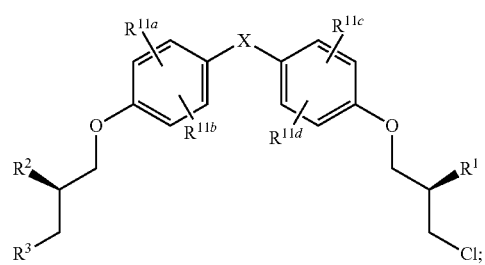
(Ie)

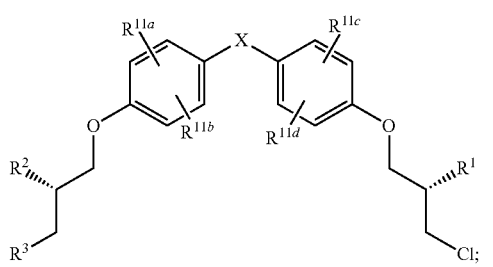
(If)

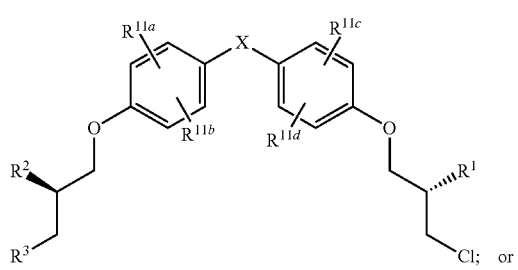
(Ig)

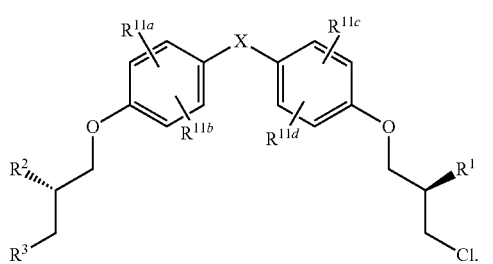
(Ih)

In one embodiment, X is —S(O)$_n$—. In some embodiments, X is —S(O)$_2$—. In another embodiment, X is —C(R$^8$R$^9$)—. In one embodiment X is —C(R$^8$R$^9$)—, wherein R$^8$ and R$^9$ are each independently H or C$_1$-C$_3$ alkyl. In another embodiment, X is —C(R$^8$R$^9$)—, wherein R$^8$ and R$^9$ are each C$_1$ alkyl. In some embodiments, X is —S(O)$_2$— or —C(CH$_3$)$_2$—.

In one embodiment, R$^1$ is —OH. In another embodiment, R$^1$ is —OC(=O)R$^{13}$. In some embodiments, R$^1$ is —OC(=O)R$^{13}$, wherein R$^{13}$ is C$_1$-C$_4$ alkyl. In other embodiments, R$^1$ is —OC(=O)R$^{13}$, wherein R$^{13}$ is methyl. In one embodiment, R$^1$ is H.

In one embodiment, R$^2$ is —OH. In another embodiment, R$^2$ is —OC(=O)R$^{13}$. In some embodiments, R$^2$ is —OC(=O)R$^{13}$, wherein R$^{13}$ is C$_1$-C$_4$ alkyl. In other embodiments, R$^2$ is —OC(=O)R$^{13}$, wherein R$^{13}$ is methyl.

In one embodiment, R$^3$ is —OH. In another embodiment, R$^3$ is —OC(=O)R$^{13}$. In some embodiments, R$^3$ is —OC(=O)R$^{13}$, wherein R$^{13}$ is C$_1$-C$_4$ alkyl. In other embodiments, R$^3$ is —OC(=O)R$^{13}$, wherein R$^{13}$ is methyl.

In some embodiments, at least one of R$^1$, R$^2$, or R$^3$ is —OH. In some embodiments, at least two of R$^1$, R$^2$, or R$^3$ are each —OH. In other embodiments, R$^1$ and R$^2$ are each —OH. In another embodiment, R$^1$, R$^2$, and R$^3$ are each —OH.

In some embodiments, at least one of R$^1$, R$^2$, or R$^3$ is —OC(=O)R$^{13}$, wherein R$^{13}$ is C$_1$-C$_4$ alkyl. In another embodiment, at least one of R$^1$, R$^2$, or R$^3$ is —OC(=O)R$^{13}$, wherein R$^{13}$ is methyl. In some embodiments, at least two of R$^1$, R$^2$, or R$^3$ are each —OC(=O)R$^{13}$, wherein R$^{13}$ is C$_1$-C$_4$ alkyl. In another embodiment, at least two of R$^1$, R$^2$, or R$^3$ are each —OC(=O)R$^{13}$, wherein R$^{13}$ is methyl. In other embodiments, R$^1$ and R$^2$ are each —OC(=O)R$^{13}$, wherein R$^{13}$ is methyl.

In some embodiments, one of R$^1$, R$^2$, or R$^3$ is —OC(=O)R$^{13}$, wherein R$^{13}$ is C$_1$-C$_4$ alkyl. In another embodiment, one of R$^1$, R$^2$, or R$^3$ is —OC(=O)R$^{13}$, wherein R$^{13}$ is methyl. In some embodiments, two of R$^1$, R$^2$, or R$^3$ are each —OC(=O)R$^{13}$, wherein R$^{13}$ is C$_1$-C$_4$ alkyl. In another embodiment, two of R$^1$, R$^2$, or R$^3$ are each —OC(=O)R$^{13}$, wherein R$^{13}$ is methyl. In some embodiments, R$^1$ and R$^2$ are each —OC(=O)R$^{13}$, wherein R$^{13}$ is C$_1$-C$_4$ alkyl. In another embodiment, R$^1$ and R$^2$ are each —OC(=O)R$^{13}$, wherein R$^{13}$ is methyl. In some embodiments, R$^1$, R$^2$, or R$^3$ are each —OC(=O)R$^{13}$, wherein R$^{13}$ is C$_1$-C$_4$ alkyl. In another embodiment, R$^1$, R$^2$, or R$^3$ are each —OC(=O)R$^{13}$, wherein R$^{13}$ is methyl.

In other embodiments, R$^3$ is —OR$^4$. In one embodiment, R$^3$ is —OR$^4$, wherein R$^4$ is C$_1$-C$_6$ alkyl. In another embodiment, R$^3$ is —OR$^4$, wherein R$^4$ is C$_1$-C$_3$ alkyl. In one embodiment, R$^3$ is —OR$^4$, wherein R$^4$ is methyl, ethyl, n-propyl, or t-propyl. In one embodiment, R$^3$ is —OR$^4$, wherein R$^4$ is methyl. In another embodiment, R$^3$ is —OR$^4$, wherein R$^4$ is t-propyl.

In other embodiments, R$^3$ is a halogen. In other embodiments, R$^3$ is F, Cl, Br, or I. In one embodiment, R$^3$ is F.

In other embodiments, R$^3$ is —NH$_2$, —NHC(=O)R$^{13}$, —N(C(=O)R$^{13}$)$_2$, —NHS(O)$_n$R$^5$, —N(C(=O)R$^{13}$)(S(O)$_n$R$^5$), or —N(C$_1$-C$_6$ alkyl)(S(O)$_n$R$^5$). In one embodiment, R$^3$ is a —NH$_2$. In one embodiment, R$^3$ is a —NHC(=O)R$^{13}$. In one embodiment, R$^3$ is a —N(C(=O)R$^{13}$)$_2$. In another embodiment, R$^3$ is a —NHS(O)$_n$R$^5$. In some embodiments, R$^3$ is a —NHS(O)$_2$R$^5$. In other embodiments, R$^3$ is a —NHS(O)$_2$R$^5$, wherein R$^5$ is C$_1$-C$_3$ alkyl. In one embodiment, R$^3$ is a —NHS(O)$_2$R$^5$, wherein R$^5$ is C$_1$ alkyl. In one embodiment, R$^3$ is a —N(C(=O)R$^{13}$)(S(O)$_n$R$^5$). In one embodiment, R$^3$ is a —N(C$_1$-C$_6$ alkyl)(S(O)$_n$R$^5$).

In other embodiments, R$^3$ is —NH$_2$, —NHC(=O)(C$_1$-C$_4$ alkyl), —N[(C(=O)(C$_1$-C$_4$ alkyl)]$_2$, —NHS(O)$_n$(C$_1$-C$_3$ alkyl), —N[C(=O)(C$_1$-C$_4$ alkyl)][(S(O)$_n$(C$_1$-C$_3$ alkyl)], or —N[C$_1$-C$_6$ alkyl][S(O)$_n$(C$_1$-C$_3$ alkyl)]. In some embodiments, R$^3$ is —NH(C(=O)CH$_3$) or —N(C(=O)CH$_3$)$_2$. In other embodiments, R$^3$ is —NHS(O)$_2$CH$_3$. In other embodiments, R$^3$ is —N(C(=O)CH$_3$)(S(O)$_2$CH$_3$).

In another embodiment, R$^3$ is a —S(O)$_n$R$^5$. In one embodiment, R$^3$ is a —S(O)$_2$R$^5$. In another embodiment, R$^3$ is a —S(O)$_2$(C$_1$-C$_3$ alkyl). In another embodiment, R$^3$ is a —S(O)$_2$CH$_3$. In other embodiments, R$^3$ is a —S(O)$_2$CH$_2$CH$_3$.

In some embodiments, R$^3$ is an optionally substituted 5 or 6 membered heteroaryl or an optionally substituted 3 to 7 membered heterocyclyl, wherein said heteroaryl or said heterocyclyl respectively comprise at least one N atom in the ring. In one embodiment, R$^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine. In a certain embodiment, R$^3$ is

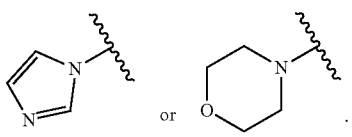 [SMILES: *n1ccnc1 ; *N1CCOCC1]

In one embodiment, at least one of $R^{11a}$, $R^{11b}$, $R^{11c}$ and $R^{11d}$ is Cl. In another embodiment, at least one of $R^{11a}$, $R^{11b}$, $R^{11c}$ and $R^{11d}$ is Br. In some embodiments, at least one of $R^{11a}$, $R^{11b}$, $R^{11c}$ and $R^{11d}$ is methyl.

In one embodiment, at least two of $R^{11a}$, $R^{11b}$, $R^{11c}$ and $R^{11d}$ are methyl, F, Cl, Br, I, or $^{123}$I. In another embodiment, exactly two of $R^{11a}$, $R^{11b}$, $R^{11c}$ and $R^{11d}$ are methyl, F, Cl, Br, I, or $^{123}$I.

In some embodiments, $R^{11a}$ and $R^{11b}$ are each H and $R^{11c}$ and $R^{11d}$ are each independently methyl, F, Cl, Br, I, or $^{123}$I. In one embodiment, $R^{11a}$ and $R^{11b}$ are each H, and $R^{11c}$ and $R^{11d}$ are each Cl. In one embodiment, $R^{11a}$ and $R^{11b}$ are each H, and $R^{11c}$ and $R^{11d}$ are each Br. In one embodiment, $R^{11a}$ and $R^{11b}$ are each H, and $R^{11c}$ and $R^{11d}$ are each methyl.

In some embodiments, $R^{11a}$ and $R^{11c}$ are each H, and $R^{11b}$ and $R^{11d}$ are each independently methyl, F, Cl, Br, I, or $^{123}$I. In one embodiment, $R^{11a}$ and $R^{11c}$ are each H, and $R^{11b}$ and $R^{11d}$ are each Cl. In one embodiment, $R^{11a}$ and $R^{11c}$ are each H, and $R^{11b}$ and $R^{11d}$ are each Br. In one embodiment, $R^{11a}$ and $R^{11c}$ are each H, and $R^{11b}$ and $R^{11d}$ are each methyl.

In some embodiments, $R^{13}$ is $C_1$-$C_3$ alkyl. In other embodiments, $R^{13}$ is methyl, ethyl, or propyl. In one embodiment, $R^{13}$ is a methyl.

In one embodiment, n is 0. In another embodiment n is 1. In some embodiments, n is 2.

The compounds for use in the imaging and treatment methods are described herein. In some embodiments, the compounds comprise one F, Cl, Br, I, or $^{123}$I substitution. For example in certain other embodiments, any three of $R^{11a}$, $R^{11b}$, $R^{11c}$ and $R^{11d}$ are each H, and the remaining one of $R^{11a}$, $R^{11b}$, $R^{11c}$ or $R^{11d}$ is F, Cl, Br, I or $^{123}$I. In some embodiments, the compounds comprise two F, Cl, Br, I or $^{123}$I substitutions on the phenyl rings (i.e., two of $R^{11a}$, $R^{11b}$, $R^{11c}$ and $R^{11d}$ are H, and the other two of $R^{11a}$, $R^{11b}$, $R^{11c}$ or $R^{11d}$ are F, Cl, Br, I or $^{123}$I). In other embodiments, the compounds comprise three F, Cl, Br, I or $^{123}$I substitutions (i.e., any one of $R^{11a}$, $R^{11b}$, $R^{11c}$ and $R^{11d}$ is H, and the remaining $R^{11a}$, $R^{11b}$, $R^{11c}$ or $R^{11d}$ is F, Cl, Br, I or $^{123}$I) and in other embodiments the compounds comprise four F, Cl, Br, I or $^{123}$I substitutions (i.e., each of $R^{11a}$, $R^{11b}$, $R^{11c}$ and $R^{11d}$ are F, Cl, Br, I or $^{123}$I).

In another embodiment, the compound comprises one or more of F, Cl, Br, I or $^{123}$I substitutions for $R^3$. In one embodiment, the compound comprises one or more of I or $^{123}$I substitutions for $R^3$.

In some embodiments, the compound comprises at least one $R^6$ substituent on $R^3$, wherein at least one $R^6$ is further substituted with at least one of F, Cl, Br, I or $^{123}$I. In another embodiment, $R^6$ substituent on $R^3$ is further substituted with at least one of I or $^{123}$I.

Favorable imaging and/or AR NTD modulating results can be obtained by substitution with F, Cl. Br, I or $^{123}$I at any of the "$R^{11}$" positions. In some of the foregoing embodiments, $R^{11a}$ is $^{123}$I. In other embodiments, $R^{11c}$ is $^{123}$I.

In some more specific embodiments of the compound of Formula I, the compound has one of the following structures from Table 1, or a pharmaceutically acceptable salt, tautomer, or stereoisomer thereof:

TABLE 1

| | Compounds | |
|---|---|---|
| No. | Structure | Name |
| 1 | | 3-(4-(2-(3,5-dichloro-4-(3-chloro-2-hydroxypropoxy)phenyl)propan-2-yl)phenoxy)propane-1,2-diol |
| 1a | | (R)-3-(4-(2-(3,5-dichloro-4-((S)-3-chloro-2-hydroxypropoxy)phenyl)propan-2-yl)phenoxy)propane-1,2-diol |

TABLE 1-continued

Compounds

| No. | Structure | Name |
|---|---|---|
| 1b | 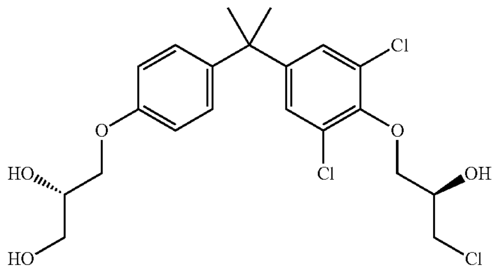 [SMILES: CC(C)(c1ccc(OC[C@@H](O)CO)cc1)c1cc(Cl)c(OC[C@@H](O)CCl)c(Cl)c1] | (S)-3-(4-(2-(3,5-dichloro-4-((R)-3-chloro-2-hydroxypropoxy)phenyl)propan-2-yl)phenoxy)propane-1,2-diol |
| 1c | 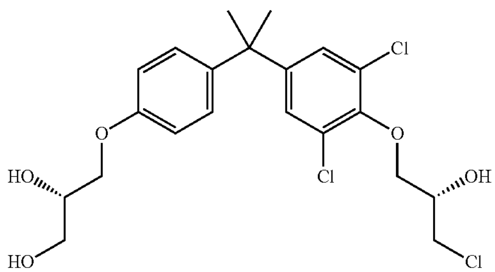 [SMILES: CC(C)(c1ccc(OC[C@@H](O)CO)cc1)c1cc(Cl)c(OC[C@H](O)CCl)c(Cl)c1] | (S)-3-(4-(2-(3,5-dichloro-4-((S)-3-chloro-2-hydroxypropoxy)phenyl)propan-2-yl)phenoxy)propane-1,2-diol |
| 1d | 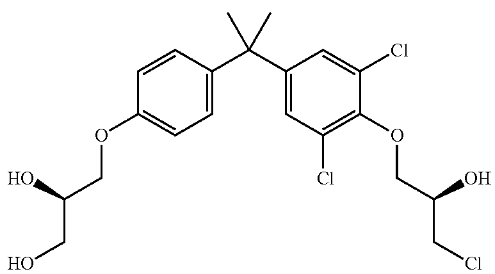 [SMILES: CC(C)(c1ccc(OC[C@H](O)CO)cc1)c1cc(Cl)c(OC[C@@H](O)CCl)c(Cl)c1] | (R)-3-(4-(2-(3,5-dichloro-4-((R)-3-chloro-2-hydroxypropoxy)phenyl)propan-2-yl)phenoxy)propane-1,2-diol |
| 2 | 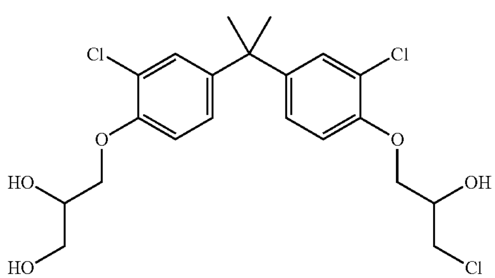 [SMILES: CC(C)(c1ccc(OCC(O)CO)c(Cl)c1)c1ccc(OCC(O)CCl)c(Cl)c1] | 3-(2-chloro-4-(2-(3-chloro-4-(3-chloro-2-hydroxypropoxy)phenyl)propan-2-yl)phenoxy)propane-1,2-diol |
| 2a | 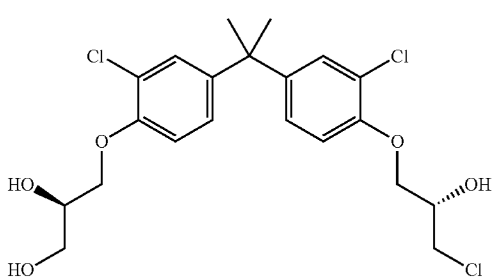 | (R)-3-(2-chloro-4-(2-(3-chloro-4-((S)-3-chloro-2-hydroxypropoxy)phenyl)propan-2-yl)phenoxy)propane-1,2-diol |

TABLE 1-continued

| No. | Structure | Name |
|---|---|---|
| 2b | 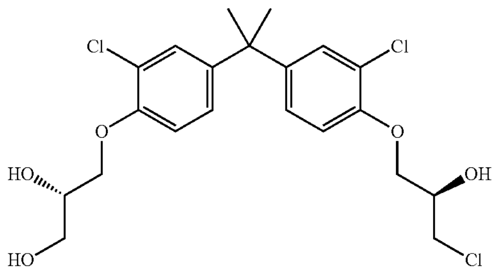 [SMILES: CC(C)(c1ccc(OC[C@@H](O)CO)c(Cl)c1)c1ccc(OC[C@@H](O)CCl)c(Cl)c1] | (S)-3-(2-chloro-4-(2-(3-chloro-4-((R)-3-chloro-2-hydroxypropoxy)phenyl)propan-2-yl)phenoxy)propane-1,2-diol |
| 2c | 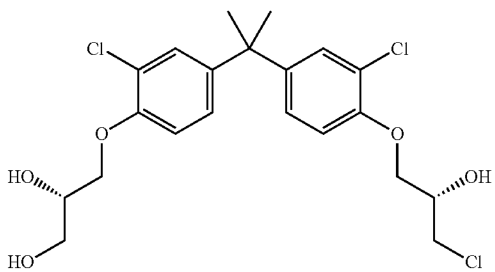 | (S)-3-(2-chloro-4-(2-(3-chloro-4-((S)-3-chloro-2-hydroxypropoxy)phenyl)propan-2-yl)phenoxy)propane-1,2-diol |
| 2d | 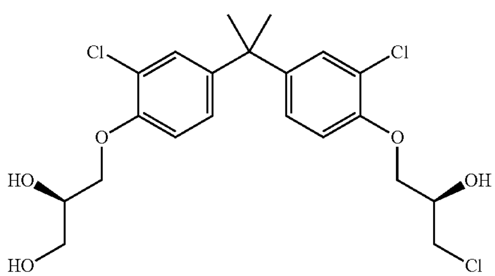 [SMILES: CC(C)(c1ccc(OC[C@H](O)CO)c(Cl)c1)c1ccc(OC[C@@H](O)CCl)c(Cl)c1] | (R)-3-(2-chloro-4-(2-(3-chloro-4-((R)-3-chloro-2-hydroxypropoxy)phenyl)propan-2-yl)phenoxy)propane-1,2-diol |
| 3 | 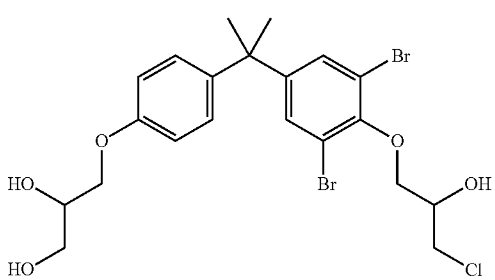 | 3-(4-(2-(3,5-dibromo-4-(3-chloro-2-hydroxypropoxy)phenyl)propan-2-yl)phenoxy)propane-1,2-diol |
| 3a | 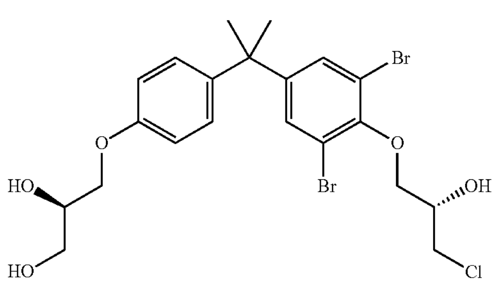 [SMILES: CC(C)(c1ccc(OC[C@H](O)CO)cc1)c1cc(Br)c(OC[C@H](O)CCl)c(Br)c1] | (R)-3-(4-(2-(3,5-dibromo-4-((S)-3-chloro-2-hydroxypropoxy)phenyl)propan-2-yl)phenoxy)propane-1,2-diol |

TABLE 1-continued

| No. | Structure | Name |
|---|---|---|
| 3b | 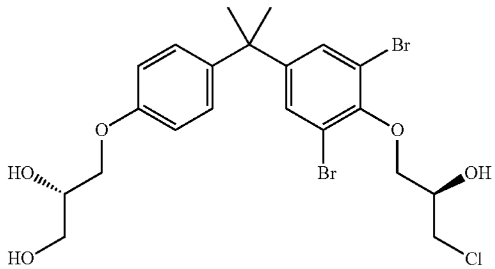 [SMILES: CC(C)(c1ccc(OC[C@@H](O)CO)cc1)c1cc(Br)c(OC[C@@H](O)CCl)c(Br)c1] | (S)-3-(4-(2-(3,5-dibromo-4-((R)-3-chloro-2-hydroxypropoxy)phenyl)propan-2-yl)phenoxy)propane-1,2-diol |
| 3c | 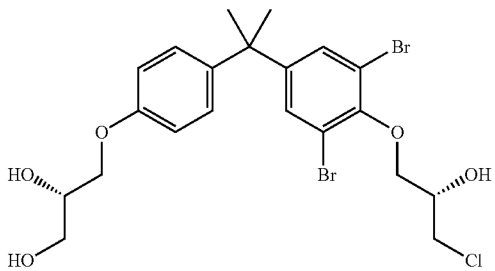 [SMILES: CC(C)(c1ccc(OC[C@@H](O)CO)cc1)c1cc(Br)c(OC[C@H](O)CCl)c(Br)c1] | (S)-3-(4-(2-(3,5-dibromo-4-((S)-3-chloro-2-hydroxypropoxy)phenyl)propan-2-yl)phenoxy)propane-1,2-diol |
| 3d | 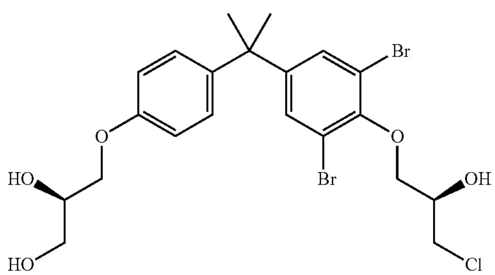 [SMILES: CC(C)(c1ccc(OC[C@H](O)CO)cc1)c1cc(Br)c(OC[C@@H](O)CCl)c(Br)c1] | (R)-3-(4-(2-(3,5-dibromo-4-((R)-3-chloro-2-hydroxypropoxy)phenyl)propan-2-yl)phenoxy)propane-1,2-diol |
| 4 | 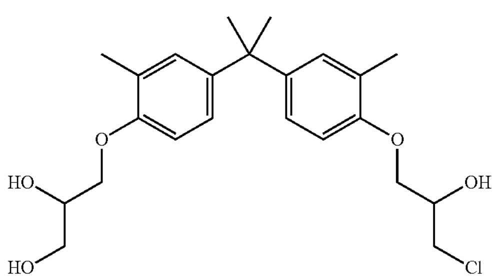 [SMILES: Cc1cc(C(C)(C)c2ccc(OCC(O)CCl)c(C)c2)ccc1OCC(O)CO] | 3-(4-(2-(4-(3-chloro-2-hydroxypropoxy)-3-methylphenyl)propan-2-yl)-2-methylphenoxy)propane-1,2-diol |
| 4a | 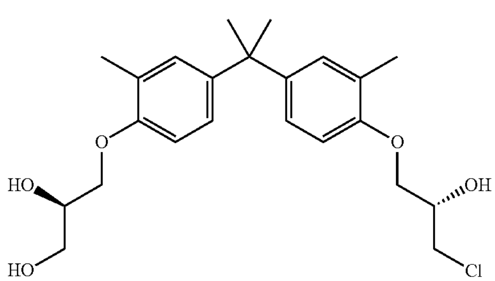 [SMILES: Cc1cc(C(C)(C)c2ccc(OC[C@H](O)CCl)c(C)c2)ccc1OC[C@H](O)CO] | (R)-3-(4-(2-(4-(S)-3-chloro-2-hydroxypropoxy)-3-methylphenyl)propan-2-yl)-2-methylphenoxy)propane-1,2-diol |

TABLE 1-continued

| No. | Structure | Name |
|---|---|---|
| 4b | 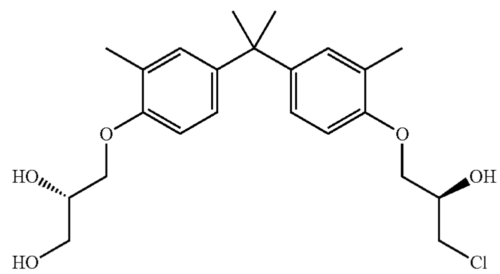 [SMILES: Cc1cc(C(C)(C)c2ccc(OC[C@@H](O)CCl)c(C)c2)ccc1OC[C@@H](O)CO] | (S)-3-(4-(2-(4-((R)-3-chloro-2-hydroxypropoxy)-3-methylphenyl)propan-2-yl)-2-methylphenoxy)propane-1,2-diol |
| 4c | 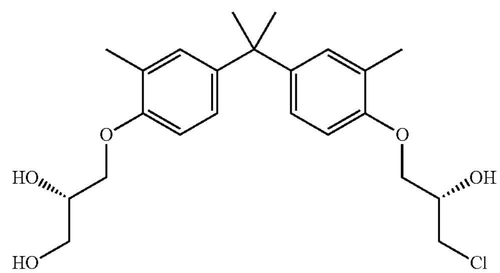 | (S)-3-(4-(2-(4-((S)-3-chloro-2-hydroxypropoxy)-3-methylphenyl)propan-2-yl)-2-methylphenoxy)propane-1,2-diol |
| 4d | 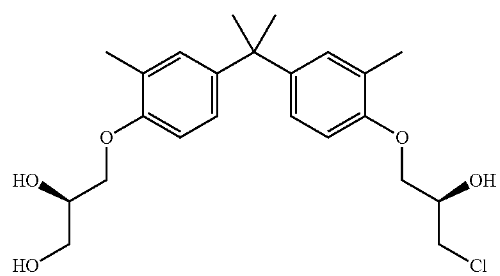 [SMILES: Cc1cc(C(C)(C)c2ccc(OC[C@@H](O)CCl)c(C)c2)ccc1OC[C@H](O)CO] | (R)-3-(4-(2-(4-((R)-3-chloro-2-hydroxypropoxy)-3-methylphenyl)propan-2-yl)-2-methylphenoxy)propane-1,2-diol |
| 5 | 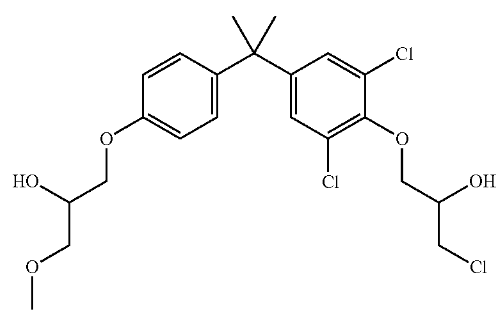 [SMILES: COCC(O)COc1ccc(C(C)(C)c2cc(Cl)c(OCC(O)CCl)c(Cl)c2)cc1] | 1-chloro-3-(2,6-dichloro-4-(2-(4-(2-hydroxy-3-methoxypropoxy)phenyl)propan-2-yl)phenoxy)propan-2-ol |
| 5a | 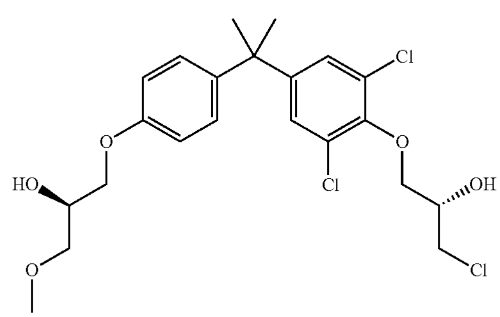 [SMILES: COC[C@@H](O)COc1ccc(C(C)(C)c2cc(Cl)c(OC[C@H](O)CCl)c(Cl)c2)cc1] | (S)-1-chloro-3-(2,6-dichloro-4-(2-(4-((R)-2-hydroxy-3-methoxypropoxy)phenyl)propan-2-yl)phenoxy)propan-2-ol |

TABLE 1-continued

| No. | Structure | Name |
|---|---|---|
| 5b | 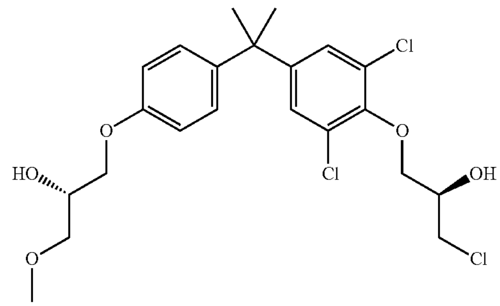 [SMILES: COC[C@H](O)COc1ccc(C(C)(C)c2cc(Cl)c(OC[C@@H](O)CCl)c(Cl)c2)cc1] | (R)-1-chloro-3-(2,6-dichloro-4-(2-(4-((S)-2-hydroxy-3-methoxypropoxy)phenyl)propan-2-yl)phenoxy)propan-2-ol |
| 5c | 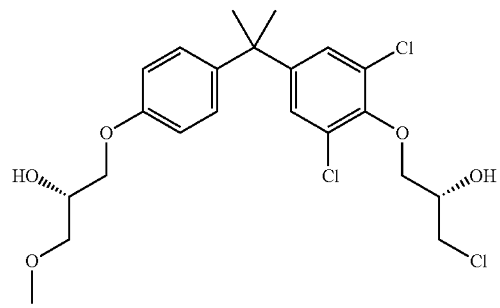 [SMILES: COC[C@H](O)COc1ccc(C(C)(C)c2cc(Cl)c(OC[C@H](O)CCl)c(Cl)c2)cc1] | (S)-1-chloro-3-(2,6-dichloro-4-(2-(4-((S)-2-hydroxy-3-methoxypropoxy)phenyl)propan-2-yl)phenoxy)propan-2-ol |
| 5d | 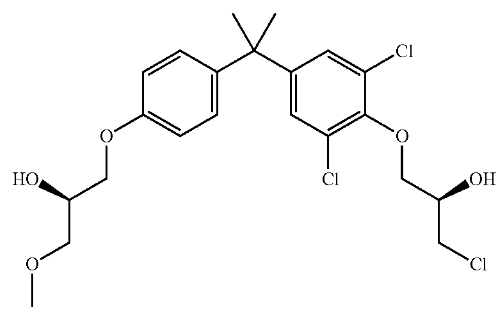 [SMILES: COC[C@@H](O)COc1ccc(C(C)(C)c2cc(Cl)c(OC[C@@H](O)CCl)c(Cl)c2)cc1] | (R)-1-chloro-3-(2,6-dichloro-4-(2-(4-((R)-2-hydroxy-3-methoxypropoxy)phenyl)propan-2-yl)phenoxy)propan-2-ol |
| 6 | 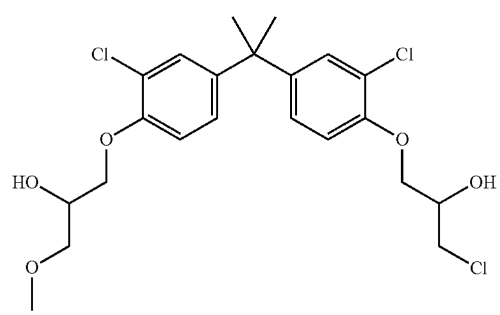 [SMILES: COCC(O)COc1ccc(C(C)(C)c2ccc(OCC(O)CCl)c(Cl)c2)cc1Cl] | 1-chloro-3-(2-chloro-4-(2-(3-chloro-4-(2-hydroxy-3-methoxypropoxy)phenyl)propan-2-yl)phenoxy)propan-2-ol |
| 6a | 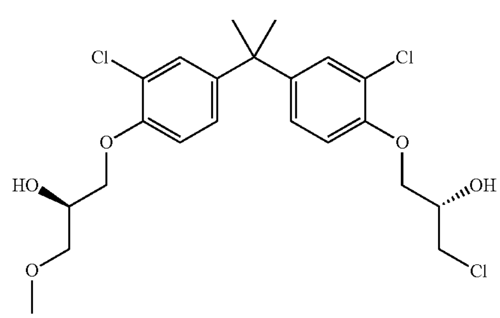 [SMILES: COC[C@@H](O)COc1ccc(C(C)(C)c2ccc(OC[C@H](O)CCl)c(Cl)c2)cc1Cl] | (S)-1-chloro-3-(2-chloro-4-(2-(3-chloro-4-((R)-2-hydroxy-3-methoxypropoxy)phenyl)propan-2-yl)phenoxy)propan-2-ol |

TABLE 1-continued

| No. | Structure | Name |
|---|---|---|
| 6b | 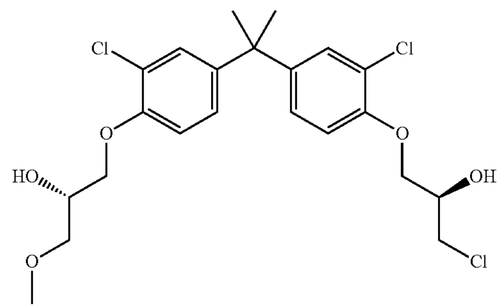 [SMILES: COC[C@H](O)COc1ccc(C(C)(C)c2ccc(OC[C@@H](O)CCl)c(Cl)c2)cc1Cl] | (R)-1-chloro-3-(2-chloro-4-(2-(3-chloro-4-((S)-2-hydroxy-3-methoxypropoxy)phenyl)propan-2-yl)phenoxy)propan-2-ol |
| 6c | 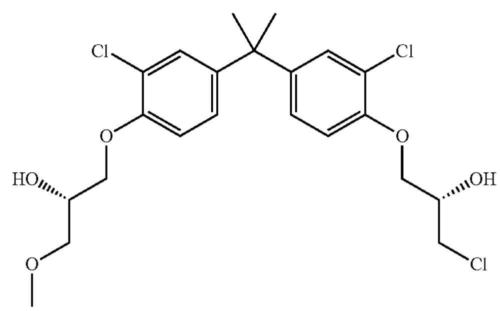 | (S)-1-chloro-3-(2-chloro-4-(2-(3-chloro-4-((S)-2-hydroxy-3-methoxypropoxy)phenyl)propan-2-yl)phenoxy)propan-2-ol |
| 6d | 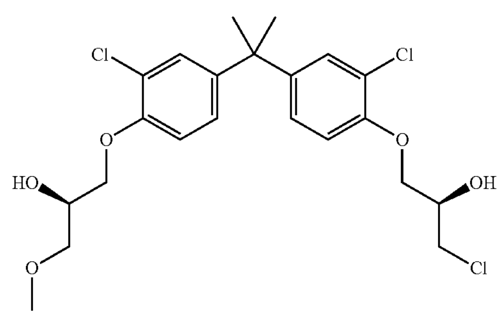 [SMILES: COC[C@@H](O)COc1ccc(C(C)(C)c2ccc(OC[C@@H](O)CCl)c(Cl)c2)cc1Cl] | (R)-1-chloro-3-(2-chloro-4-(2-(3-chloro-4-((R)-2-hydroxy-3-methoxypropoxy)phenyl)propan-2-yl)phenoxy)propan-2-ol |
| 7 | 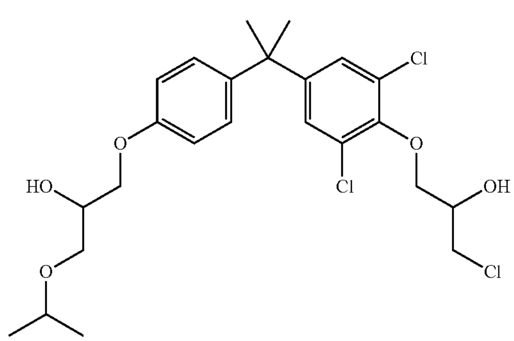 | 1-chloro-3-(2,6-dichloro-4-(2-(4-(2-hydroxy-3-isopropoxypropoxy)phenyl)propan-2-yl)phenoxy)propan-2-ol |

TABLE 1-continued

Compounds

| No. | Structure | Name |
|---|---|---|
| 7a | 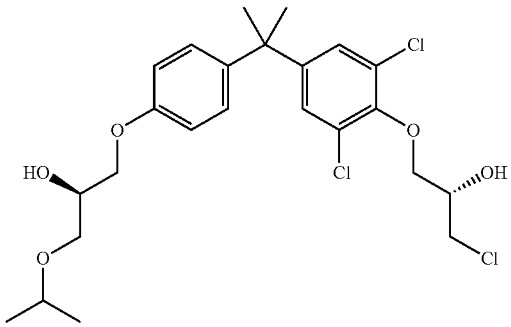 [SMILES: CC(C)OC[C@@H](O)COc1ccc(C(C)(C)c2cc(Cl)c(OC[C@H](O)CCl)c(Cl)c2)cc1] | (S)-1-chloro-3-(2,6-dichloro-4-(2-(4-((R)-2-hydroxy-3-isopropoxypropoxy)phenyl)propan-2-yl)phenoxy)propan-2-ol |
| 7b | 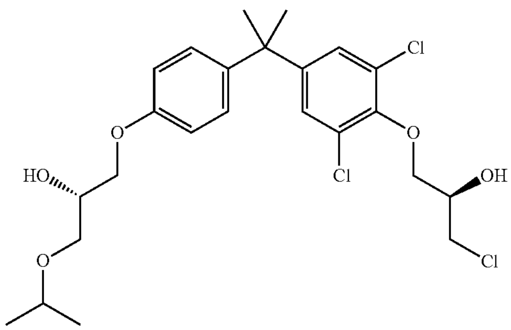 [SMILES: CC(C)OC[C@H](O)COc1ccc(C(C)(C)c2cc(Cl)c(OC[C@@H](O)CCl)c(Cl)c2)cc1] | (R)-1-chloro-3-(2,6-dichloro-4-(2-(4-((S)-2-hydroxy-3-isopropoxypropoxy)phenyl)propan-2-yl)phenoxy)propan-2-ol |
| 7c | 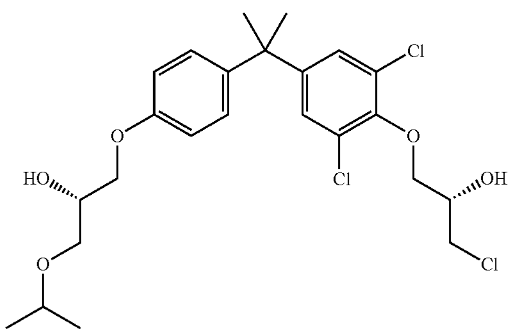 [SMILES: CC(C)OC[C@H](O)COc1ccc(C(C)(C)c2cc(Cl)c(OC[C@H](O)CCl)c(Cl)c2)cc1] | (S)-1-chloro-3-(2,6-dichloro-4-(2-(4-((S)-2-hydroxy-3-isopropoxypropoxy)phenyl)propan-2-yl)phenoxy)propan-2-ol |
| 7d | 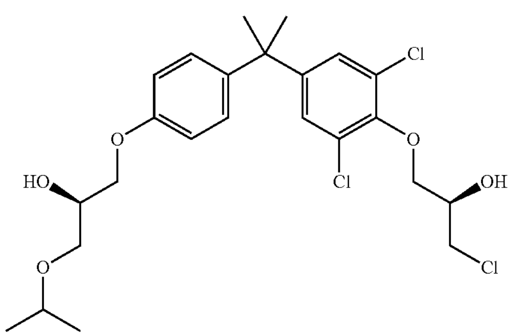 [SMILES: CC(C)OC[C@@H](O)COc1ccc(C(C)(C)c2cc(Cl)c(OC[C@@H](O)CCl)c(Cl)c2)cc1] | (R)-1-chloro-3-(2,6-dichloro-4-(2-(4-((R)-2-hydroxy-3-isopropoxypropoxy)phenyl)propan-2-yl)phenoxy)propan-2-ol |

TABLE 1-continued

| No. | Structure | Name |
|---|---|---|
| 8 | 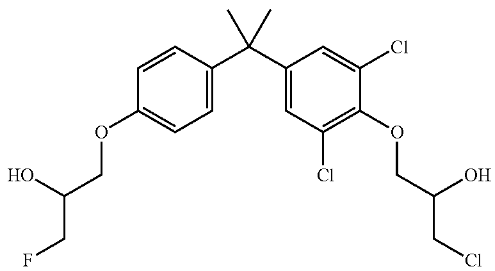 [SMILES: CC(C)(c1ccc(OCC(O)CF)cc1)c1cc(Cl)c(OCC(O)CCl)c(Cl)c1] | 1-chloro-3-(2,6-dichloro-4-(2-(4-(3-fluoro-2-hydroxypropoxy)phenyl)propan-2-yl)phenoxy)propan-2-ol |
| 8a | 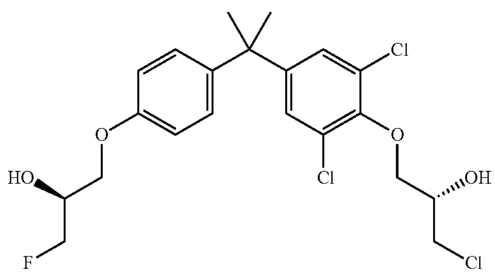 [SMILES: CC(C)(c1ccc(OC[C@H](O)CF)cc1)c1cc(Cl)c(OC[C@H](O)CCl)c(Cl)c1] | (S)-1-chloro-3-(2,6-dichloro-4-(2-(4-((S)-3-fluoro-2-hydroxypropoxy)phenyl)propan-2-yl)phenoxy)propan-2-ol |
| 8b | 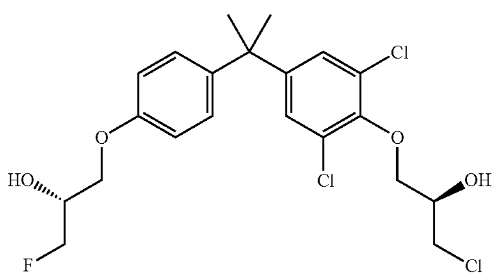 [SMILES: CC(C)(c1ccc(OC[C@@H](O)CF)cc1)c1cc(Cl)c(OC[C@@H](O)CCl)c(Cl)c1] | (R)-1-chloro-3-(2,6-dichloro-4-(2-(4-((R)-3-fluoro-2-hydroxypropoxy)phenyl)propan-2-yl)phenoxy)propan-2-ol |
| 8c | 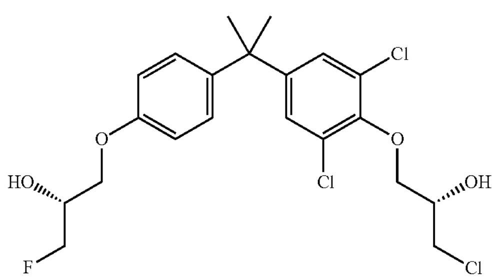 | (S)-1-chloro-3-(2,6-dichloro-4-(2-(4-((R)-3-fluoro-2-hydroxypropoxy)phenyl)propan-2-yl)phenoxy)propan-2-ol |
| 8d | 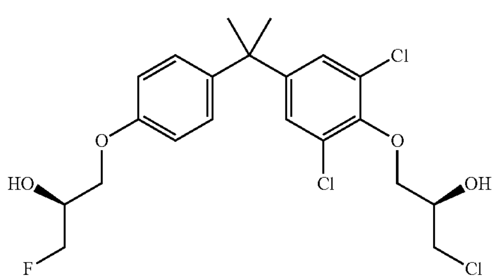 [SMILES: CC(C)(c1ccc(OC[C@H](O)CF)cc1)c1cc(Cl)c(OC[C@@H](O)CCl)c(Cl)c1] | (R)-1-chloro-3-(2,6-dichloro-4-(2-(4-((S)-3-fluoro-2-hydroxypropoxy)phenyl)propan-2-yl)phenoxy)propan-2-ol |

TABLE 1-continued

| No. | Structure | Name |
|---|---|---|
| 9 | 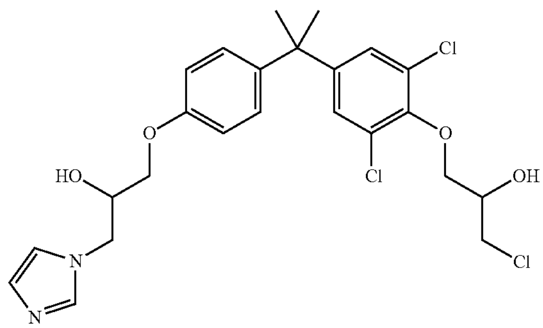 [SMILES: CC(C)(c1ccc(OCC(O)Cn2ccnc2)cc1)c1cc(Cl)c(OCC(O)CCl)c(Cl)c1] | 1-chloro-3-(2,6-dichloro-4-(2-(4-(2-hydroxy-3-(1H-imidazol-1-yl)propoxy)phenyl)propan-2-yl)phenoxy)propan-2-ol |
| 9a | 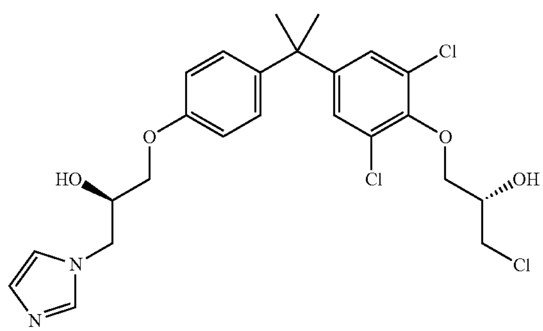 [SMILES: CC(C)(c1ccc(OC[C@H](O)Cn2ccnc2)cc1)c1cc(Cl)c(OC[C@H](O)CCl)c(Cl)c1] | (S)-1-chloro-3-(2,6-dichloro-4-(2-(4-((R)-2-hydroxy-3-(1H-imidazol-1-yl)propoxy)phenyl)propan-2-yl)phenoxy)propan-2-ol |
| 9b | 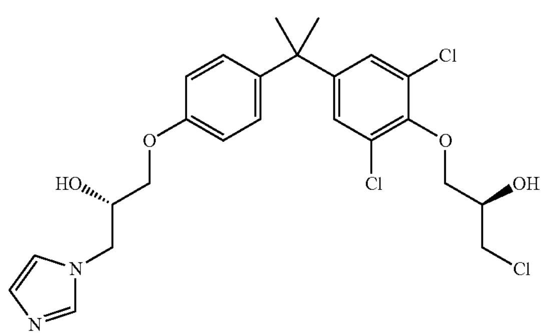 [SMILES: CC(C)(c1ccc(OC[C@@H](O)Cn2ccnc2)cc1)c1cc(Cl)c(OC[C@@H](O)CCl)c(Cl)c1] | (R)-1-chloro-3-(2,6-dichloro-4-(2-(4-((S)-2-hydroxy-3-(1H-imidazol-1-yl)propoxy)phenyl)propan-2-yl)phenoxy)propan-2-ol |
| 9c | 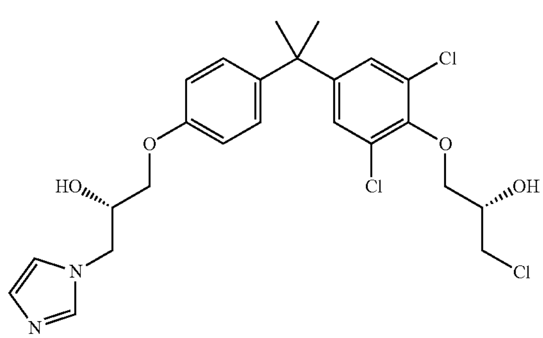 [SMILES: CC(C)(c1ccc(OC[C@@H](O)Cn2ccnc2)cc1)c1cc(Cl)c(OC[C@H](O)CCl)c(Cl)c1] | (S)-1-chloro-3-(2,6-dichloro-4-(2-(4-((S)-2-hydroxy-3-(1H-imidazol-1-yl)propoxy)phenyl)propan-2-yl)phenoxy)propan-2-ol |

TABLE 1-continued

| No. | Structure | Name |
|---|---|---|
| 9d | 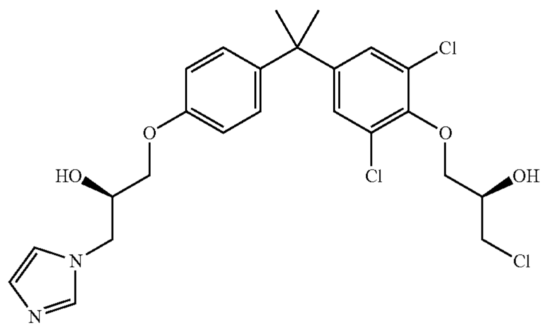 [SMILES: CC(C)(c1ccc(OC[C@H](O)Cn2ccnc2)cc1)c1cc(Cl)c(OC[C@@H](O)CCl)c(Cl)c1] | (R)-1-chloro-3-(2,6-dichloro-4-(2-(4-((R)-2-hydroxy-3-(1H-imidazol-1-yl)propoxy)phenyl)propan-2-yl)phenoxy)propan-2-ol |
| 10 | 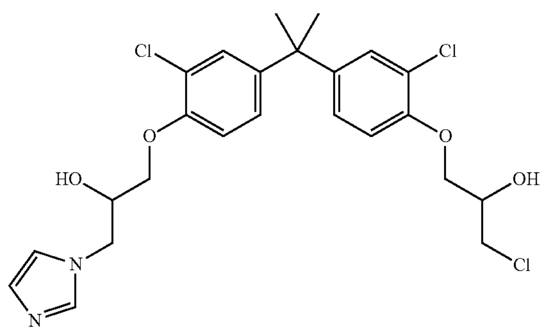 [SMILES: CC(C)(c1ccc(OCC(O)CCl)c(Cl)c1)c1ccc(OCC(O)Cn2ccnc2)c(Cl)c1] | 1-chloro-3-(2-chloro-4-(2-(3-chloro-4-(2-hydroxy-3-(1H-imidazol-1-yl)propoxy)phenyl)propan-2-yl)phenoxy)propan-2-ol |
| 10a | 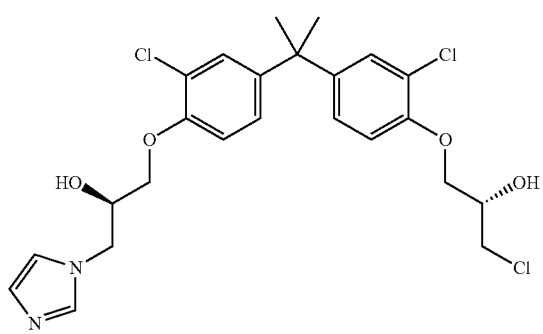 [SMILES: CC(C)(c1ccc(OC[C@H](O)CCl)c(Cl)c1)c1ccc(OC[C@H](O)Cn2ccnc2)c(Cl)c1] | (S)-1-chloro-3-(2-chloro-4-(2-(3-chloro-4-((R)-2-hydroxy-3-(1H-imidazol-1-yl)propoxy)phenyl)propan-2-yl)phenoxy)propan-2-ol |
| 10b | 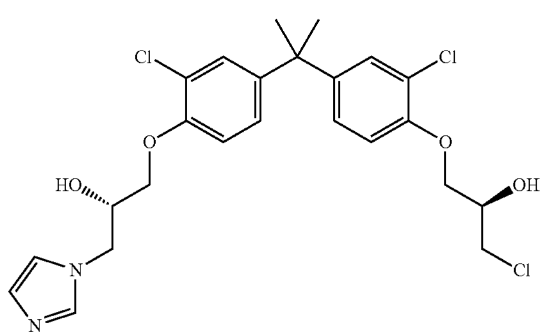 [SMILES: CC(C)(c1ccc(OC[C@@H](O)Cn2ccnc2)c(Cl)c1)c1ccc(OC[C@@H](O)CCl)c(Cl)c1] | (R)-1-chloro-3-(2-chloro-4-(2-(3-chloro-4-((S)-2-hydroxy-3-(1H-imidazol-1-yl)propoxy)phenyl)propan-2-yl)phenoxy)propan-2-ol |

TABLE 1-continued

| No. | Structure | Name |
|---|---|---|
| 10c | 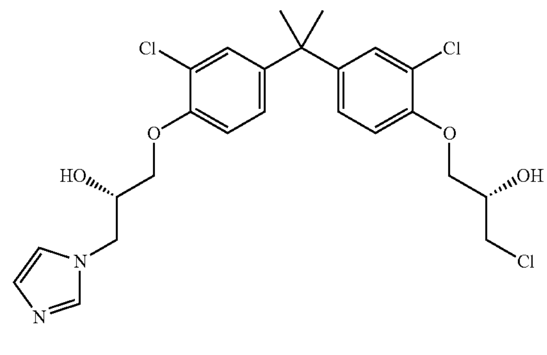 [SMILES: CC(C)(c1ccc(OC[C@H](O)CCl)c(Cl)c1)c1ccc(OC[C@@H](O)Cn2ccnc2)c(Cl)c1] | (S)-1-chloro-3-(2-chloro-4-(2-(3-chloro-4-((S)-2-hydroxy-3-(1H-imidazol-1-yl)propoxy)phenyl)propan-2-yl)phenoxy)propan-2-ol |
| 10d | 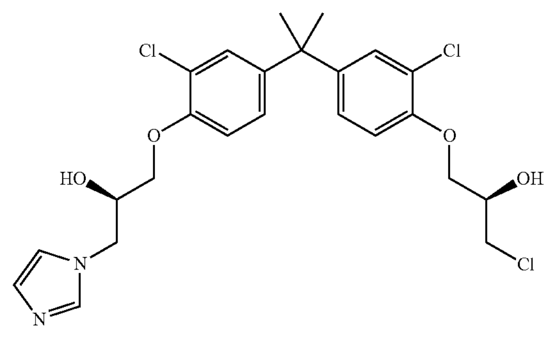 [SMILES: CC(C)(c1ccc(OC[C@@H](O)CCl)c(Cl)c1)c1ccc(OC[C@H](O)Cn2ccnc2)c(Cl)c1] | (R)-1-chloro-3-(2-chloro-4-(2-(3-chloro-4-((R)-2-hydroxy-3-(1H-imidazol-1-yl)propoxy)phenyl)propan-2-yl)phenoxy)propan-2-ol |
| 11 | 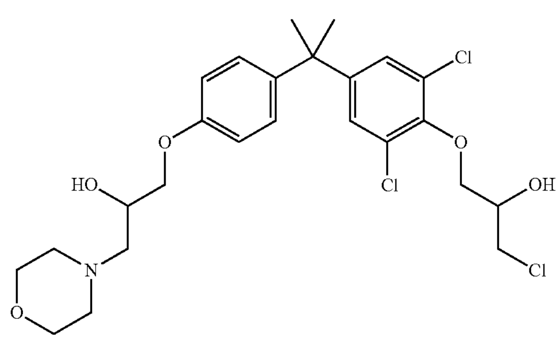 [SMILES: CC(C)(c1ccc(OCC(O)CN2CCOCC2)cc1)c1cc(Cl)c(OCC(O)CCl)c(Cl)c1] | 1-chloro-3-(2,6-dichloro-4-(2-(4-(2-hydroxy-3-morpholinopropoxy)phenyl)propan-2-yl)phenoxy)propan-2-ol |
| 11a | 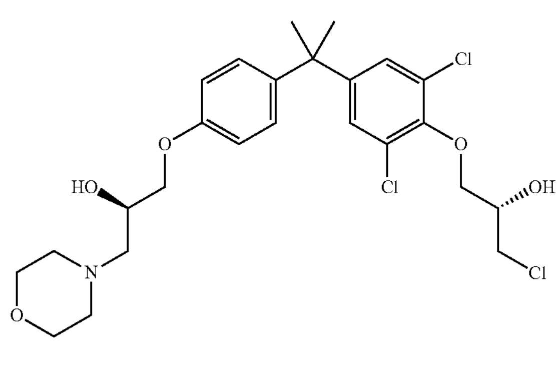 [SMILES: CC(C)(c1ccc(OC[C@H](O)CN2CCOCC2)cc1)c1cc(Cl)c(OC[C@H](O)CCl)c(Cl)c1] | (S)-1-chloro-3-(2,6-dichloro-4-(2-(4-((R)-2-hydroxy-3-morpholinopropoxy)phenyl)propan-2-yl)phenoxy)propan-2-ol |

TABLE 1-continued

Compounds

| No. | Structure | Name |
|---|---|---|
| 11b | 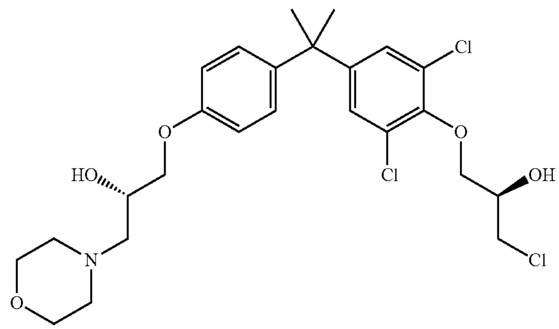 [SMILES: CC(C)(c1ccc(OC[C@@H](O)CN2CCOCC2)cc1)c1cc(Cl)c(OC[C@@H](O)CCl)c(Cl)c1] | (R)-1-chloro-3-(2,6-dichloro-4-(2-(4-((S)-2-hydroxy-3-morpholinopropoxy)phenyl)propan-2-yl)phenoxy)propan-2-ol |
| 11c | 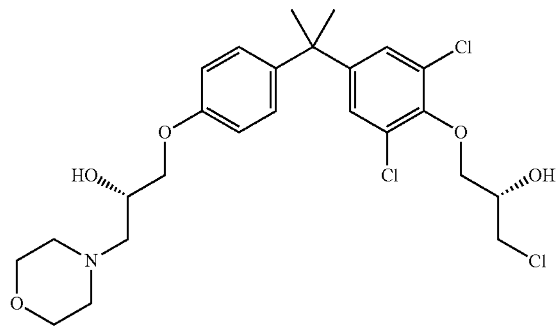 [SMILES: CC(C)(c1ccc(OC[C@@H](O)CN2CCOCC2)cc1)c1cc(Cl)c(OC[C@H](O)CCl)c(Cl)c1] | (S)-1-chloro-3-(2,6-dichloro-4-(2-(4-((S)-2-hydroxy-3-morpholinopropoxy)phenyl)propan-2-yl)phenoxy)propan-2-ol |
| 11d | 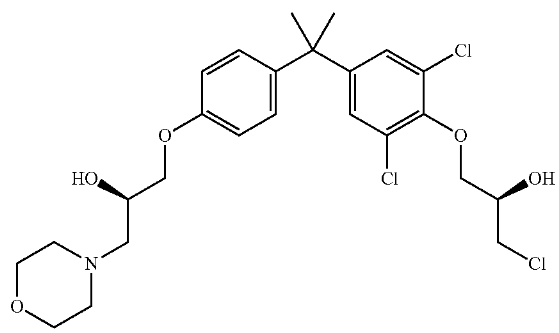 [SMILES: CC(C)(c1ccc(OC[C@H](O)CN2CCOCC2)cc1)c1cc(Cl)c(OC[C@@H](O)CCl)c(Cl)c1] | (R)-1-chloro-3-(2,6-dichloro-4-(2-(4-((R)-2-hydroxy-3-morpholinopropoxy)phenyl)propan-2-yl)phenoxy)propan-2-ol |
| 12 | 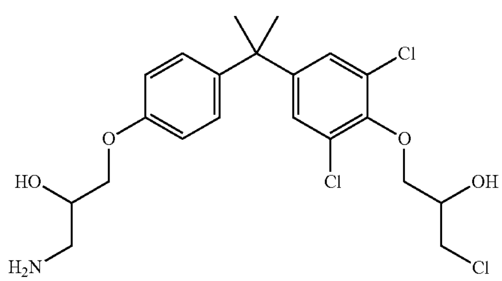 [SMILES: CC(C)(c1ccc(OCC(O)CN)cc1)c1cc(Cl)c(OCC(O)CCl)c(Cl)c1] | 1-amino-3-(4-(2-(3,5-dichloro-4-(3-chloro-2-hydroxypropoxy)phenyl)propan-2-yl)phenoxy)propan-2-ol |
| 12a | 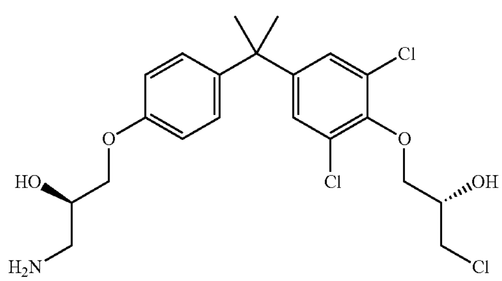 [SMILES: CC(C)(c1ccc(OC[C@H](O)CN)cc1)c1cc(Cl)c(OC[C@H](O)CCl)c(Cl)c1] | (R)-1-amino-3-(4-(2-(3,5-dichloro-4-((S)-3-chloro-2-hydroxypropoxy)phenyl)propan-2-yl)phenoxy)propan-2-ol |

TABLE 1-continued

| No. | Structure | Name |
|---|---|---|
| 12b | 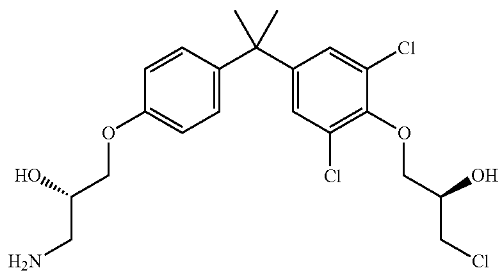 [SMILES: CC(C)(c1ccc(OC[C@@H](O)CN)cc1)c1cc(Cl)c(OC[C@@H](O)CCl)c(Cl)c1] | (S)-1-amino-3-(4-(2-(3,5-dichloro-4-((R)-3-chloro-2-hydroxypropoxy)phenyl)propan-2-yl)phenoxy)propan-2-ol |
| 12c | 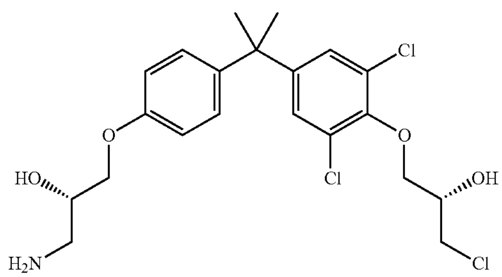 | (S)-1-amino-3-(4-(2-(3,5-dichloro-4-((S)-3-chloro-2-hydroxypropoxy)phenyl)propan-2-yl)phenoxy)propan-2-ol |
| 12d | 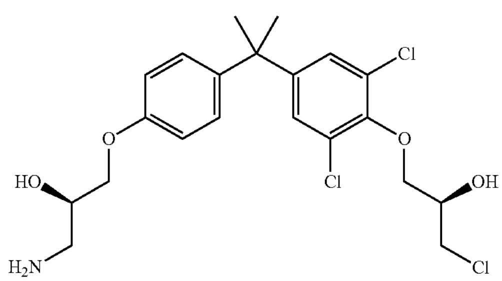 [SMILES: CC(C)(c1ccc(OC[C@H](O)CN)cc1)c1cc(Cl)c(OC[C@@H](O)CCl)c(Cl)c1] | (R)-1-amino-3-(4-(2-(3,5-dichloro-4-((R)-3-chloro-2-hydroxypropoxy)phenyl)propan-2-yl)phenoxy)propan-2-ol |
| 13 | 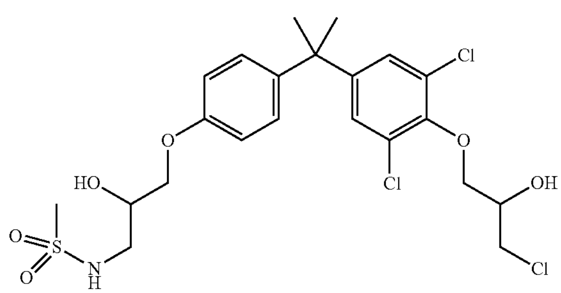 [SMILES: CC(C)(c1ccc(OCC(O)CNS(C)(=O)=O)cc1)c1cc(Cl)c(OCC(O)CCl)c(Cl)c1] | N-(3-(4-(2-(3,5-dichloro-4-(3-chloro-2-hydroxypropoxy)phenyl)propan-2-yl)phenoxy)-2-hydroxypropyl)methanesulfonamide |
| 13a | 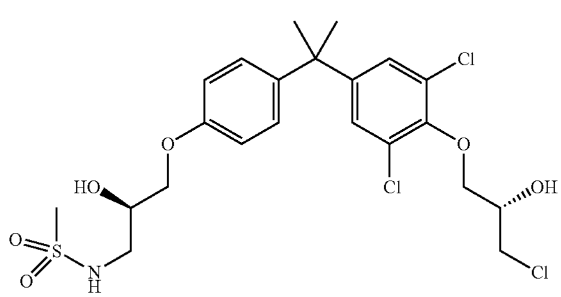 [SMILES: CC(C)(c1ccc(OC[C@H](O)CNS(C)(=O)=O)cc1)c1cc(Cl)c(OC[C@H](O)CCl)c(Cl)c1] | N-((R)-3-(4-(2-(3,5-dichloro-4-((S)-3-chloro-2-hydroxypropoxy)phenyl)propan-2-yl)phenoxy)-2-hydroxypropyl)methanesulfonamide |

TABLE 1-continued

| No. | Structure | Name |
|---|---|---|
| 13b | 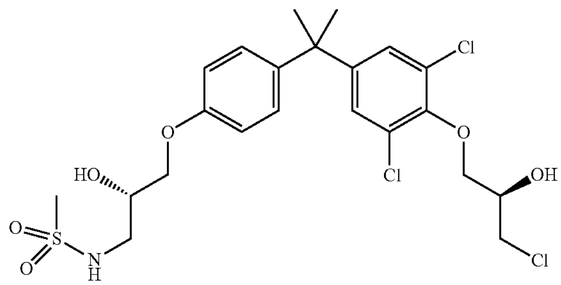 [SMILES: CC(C)(c1ccc(OC[C@@H](O)CNS(C)(=O)=O)cc1)c1cc(Cl)c(OC[C@@H](O)CCl)c(Cl)c1] | N-((S)-3-(4-(2-(3,5-dichloro-4-((R)-3-chloro-2-hydroxypropoxy)phenyl)propan-2-yl)phenoxy)-2-hydroxypropyl)methanesulfonamide |
| 13c | 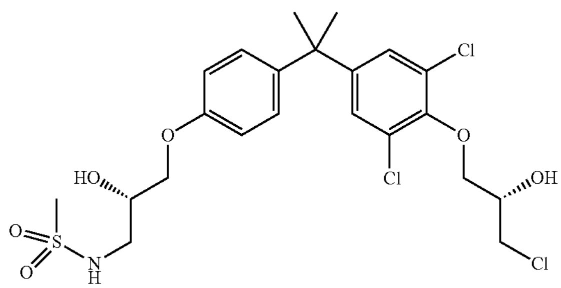 [SMILES: CC(C)(c1ccc(OC[C@@H](O)CNS(C)(=O)=O)cc1)c1cc(Cl)c(OC[C@H](O)CCl)c(Cl)c1] | N-((S)-3-(4-(2-(3,5-dichloro-4-((S)-3-chloro-2-hydroxypropoxy)phenyl)propan-2-yl)phenoxy)-2-hydroxypropyl)methanesulfonamide |
| 13d | 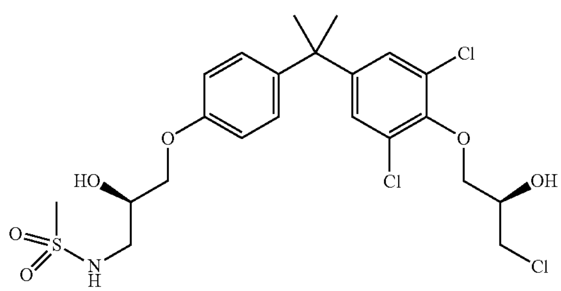 [SMILES: CC(C)(c1ccc(OC[C@H](O)CNS(C)(=O)=O)cc1)c1cc(Cl)c(OC[C@@H](O)CCl)c(Cl)c1] | N-((R)-3-(4-(2-(3,5-dichloro-4-((R)-3-chloro-2-hydroxypropoxy)phenyl)propan-2-yl)phenoxy)-2-hydroxypropyl)methanesulfonamide |
| 14 | 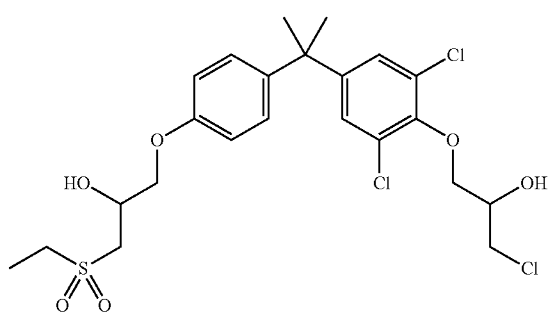 [SMILES: CCS(=O)(=O)CC(O)COc1ccc(C(C)(C)c2cc(Cl)c(OCC(O)CCl)c(Cl)c2)cc1] | 1-chloro-3-(2,6-dichloro-4-(2-(4-(2-hydroxy-3-(ethylsulfonyl)propoxy)phenyl)propan-2-yl)phenoxy)propan-2-ol |
| 14a | 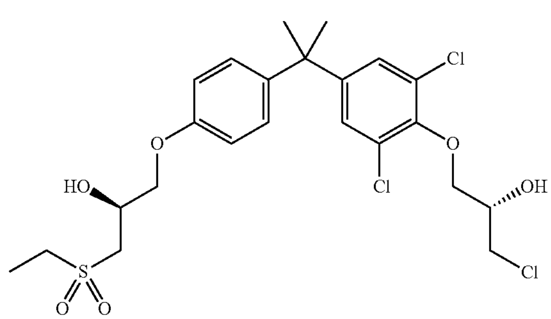 [SMILES: CCS(=O)(=O)C[C@@H](O)COc1ccc(C(C)(C)c2cc(Cl)c(OC[C@H](O)CCl)c(Cl)c2)cc1] | (S)-1-chloro-3-(2,6-dichloro-4-(2-(4-((S)-2-hydroxy-3-(ethylsulfonyl)propoxy)phenyl)propan-2-yl)phenoxy)propan-2-ol |

TABLE 1-continued

Compounds

| No. | Structure | Name |
|---|---|---|
| 14b | 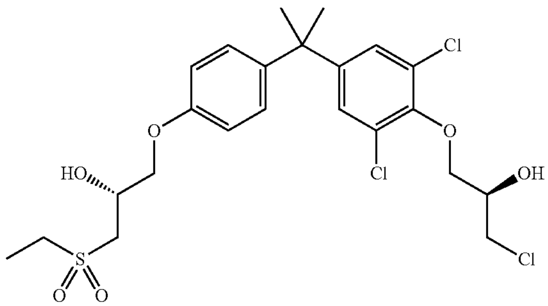 [SMILES: CCS(=O)(=O)C[C@H](O)COc1ccc(C(C)(C)c2cc(Cl)c(OC[C@@H](O)CCl)c(Cl)c2)cc1] | (R)-1-chloro-3-(2,6-dichloro-4-(2-(4-((R)-2-hydroxy-3-(ethylsulfonyl)propoxy)phenyl)propan-2-yl)phenoxy)propan-2-ol |
| 14c | 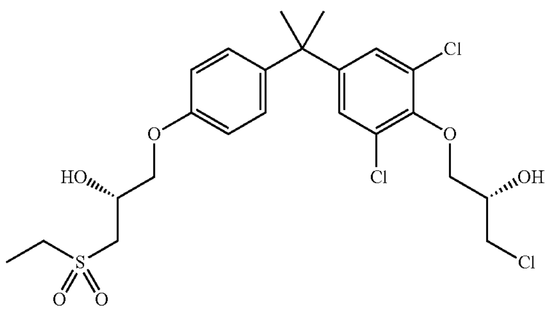 | (S)-1-chloro-3-(2,6-dichloro-4-(2-(4-((R)-2-hydroxy-3-(ethylsulfonyl)propoxy)phenyl)propan-2-yl)phenoxy)propan-2-ol |
| 14d | 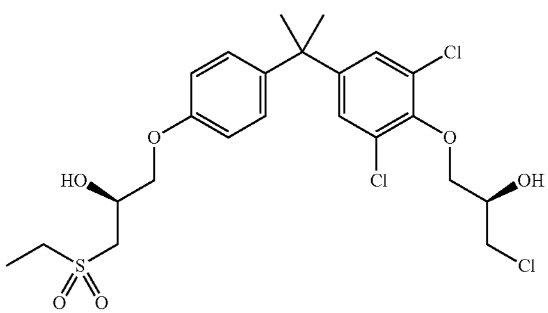 [SMILES: CCS(=O)(=O)C[C@@H](O)COc1ccc(C(C)(C)c2cc(Cl)c(OC[C@@H](O)CCl)c(Cl)c2)cc1] | (R)-1-chloro-3-(2,6-dichloro-4-(2-(4-((S)-2-hydroxy-3-(ethylsulfonyl)propoxy)phenyl)propan-2-yl)phenoxy)propan-2-ol |
| 15 | 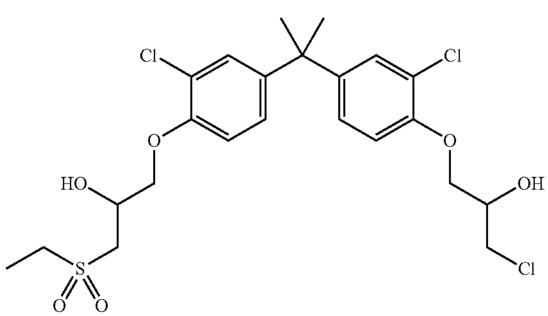 [SMILES: CCS(=O)(=O)CC(O)COc1ccc(C(C)(C)c2ccc(OCC(O)CCl)c(Cl)c2)cc1Cl] | 1-chloro-3-(2-chloro-4-(2-(3-chloro-4-(2-hydroxy-3-(ethylsulfonyl)propoxy)phenyl)propan-2-yl)phenoxy)propan-2-ol |
| 15a | 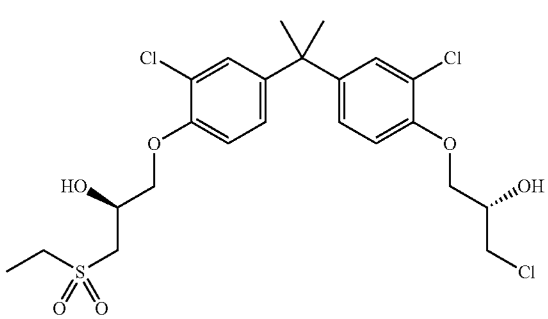 [SMILES: CCS(=O)(=O)C[C@@H](O)COc1ccc(C(C)(C)c2ccc(OC[C@H](O)CCl)c(Cl)c2)cc1Cl] | (S)-1-chloro-3-(2-chloro-4-(2-(3-chloro-4-((S)-2-hydroxy-3-(ethylsulfonyl)propoxy)phenyl)propan-2-yl)phenoxy)propan-2-ol |

TABLE 1-continued

| No. | Structure | Name |
|---|---|---|
| 15b | 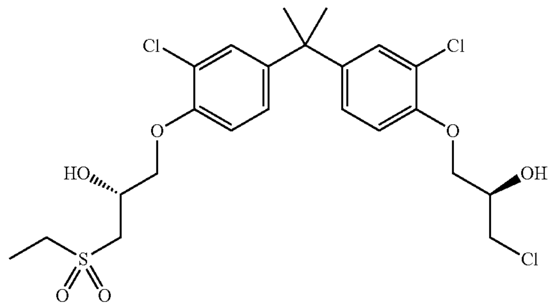 [SMILES: CCS(=O)(=O)C[C@H](O)COc1ccc(C(C)(C)c2ccc(OC[C@@H](O)CCl)c(Cl)c2)cc1Cl] | (R)-1-chloro-3-(2-chloro-4-(2-(3-chloro-4-((R)-2-hydroxy-3-(ethylsulfonyl)propoxy)phenyl)propan-2-yl)phenoxy)propan-2-ol |
| 15c | 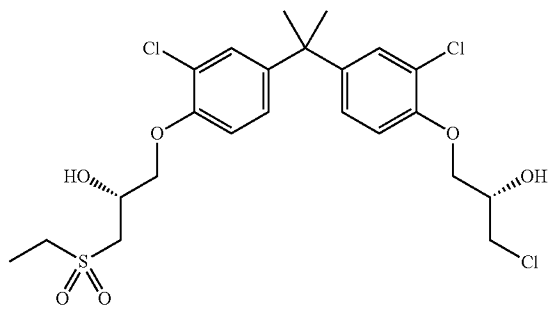 [SMILES: CCS(=O)(=O)C[C@H](O)COc1ccc(C(C)(C)c2ccc(OC[C@H](O)CCl)c(Cl)c2)cc1Cl] | (S)-1-chloro-3-(2-chloro-4-(2-(3-chloro-4-((R)-2-hydroxy-3-(ethylsulfonyl)propoxy)phenyl)propan-2-yl)phenoxy)propan-2-ol |
| 15d | 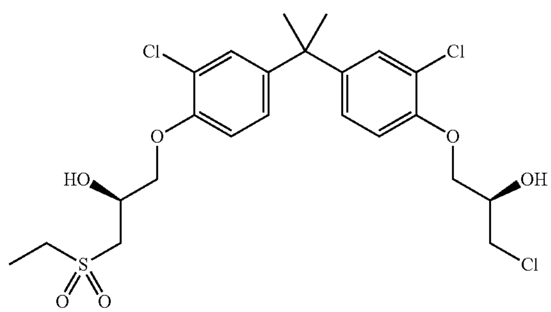 [SMILES: CCS(=O)(=O)C[C@@H](O)COc1ccc(C(C)(C)c2ccc(OC[C@@H](O)CCl)c(Cl)c2)cc1Cl] | (R)-1-chloro-3-(2-chloro-4-(2-(3-chloro-4-((S)-2-hydroxy-3-(ethylsulfonyl)propoxy)phenyl)propan-2-yl)phenoxy)propan-2-ol |
| 16 | 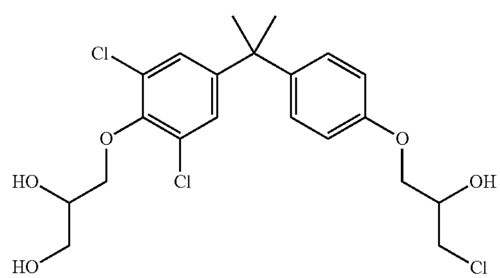 [SMILES: CC(C)(c1ccc(OCC(O)CCl)cc1)c1cc(Cl)c(OCC(O)CO)c(Cl)c1] | 3-(2,6-dichloro-4-(2-(4-(3-chloro-2-hydroxypropoxy)phenyl)propan-2-yl)phenoxy)propane-1,2-diol |
| 16a | 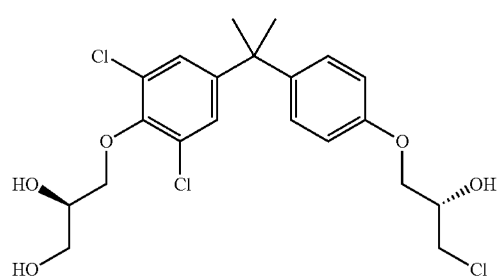 [SMILES: CC(C)(c1ccc(OC[C@H](O)CCl)cc1)c1cc(Cl)c(OC[C@H](O)CO)c(Cl)c1] | (R)-3-(2,6-dichloro-4-(2-(4-((S)-3-chloro-2-hydroxypropoxy)phenyl)propan-2-yl)phenoxy)propane-1,2-diol |

TABLE 1-continued

Compounds

| No. | Structure | Name |
|---|---|---|
| 16b | 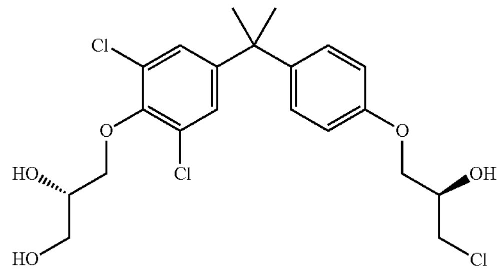 [SMILES: CC(C)(c1ccc(OC[C@@H](O)CCl)cc1)c1cc(Cl)c(OC[C@@H](O)CO)c(Cl)c1] | (S)-3-(2,6-dichloro-4-(2-(4-((R)-3-chloro-2-hydroxypropoxy)phenyl)propan-2-yl)phenoxy)propane-1,2-diol |
| 16c | 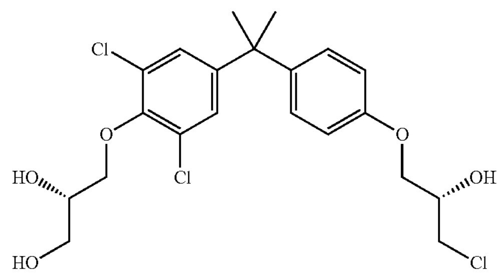 | (S)-3-(2,6-dichloro-4-(2-(4-((S)-3-chloro-2-hydroxypropoxy)phenyl)propan-2-yl)phenoxy)propane-1,2-diol |
| 16d | 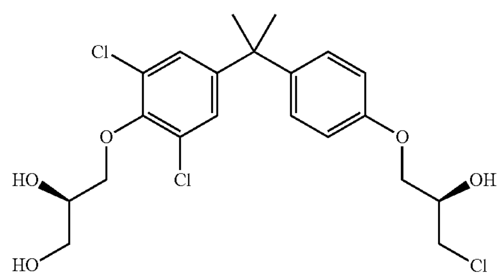 [SMILES: CC(C)(c1ccc(OC[C@@H](O)CCl)cc1)c1cc(Cl)c(OC[C@H](O)CO)c(Cl)c1] | (R)-3-(2,6-dichloro-4-(2-(4-((R)-3-chloro-2-hydroxypropoxy)phenyl)propan-2-yl)phenoxy)propane-1,2-diol |
| 17 | 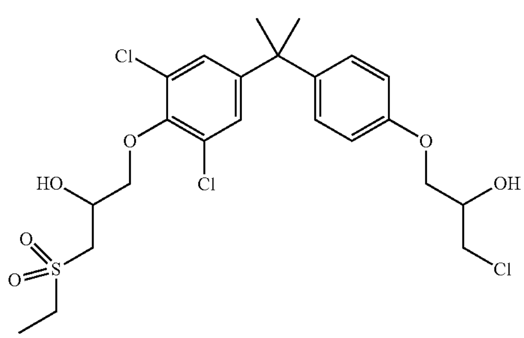 [SMILES: CCS(=O)(=O)CC(O)COc1c(Cl)cc(C(C)(C)c2ccc(OCC(O)CCl)cc2)cc1Cl] | 1-chloro-3-(4-(2-(3,5-dichloro-4-(3-(ethylsulfonyl)-2-hydroxypropoxy)phenyl)propan-2-yl)phenoxy)propan-2-ol |
| 17a | 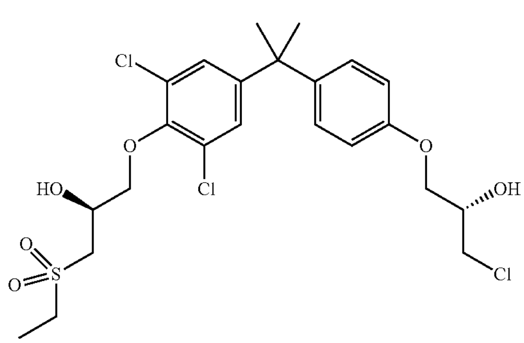 [SMILES: CCS(=O)(=O)C[C@@H](O)COc1c(Cl)cc(C(C)(C)c2ccc(OC[C@H](O)CCl)cc2)cc1Cl] | (S)-1-chloro-3-(4-(2-(3,5-dichloro-4-((S)-3-(ethylsulfonyl)-2-hydroxypropoxy)phenyl)propan-2-yl)phenoxy)propan-2-ol |

TABLE 1-continued

Compounds

| No. | Structure | Name |
|---|---|---|
| 17b | 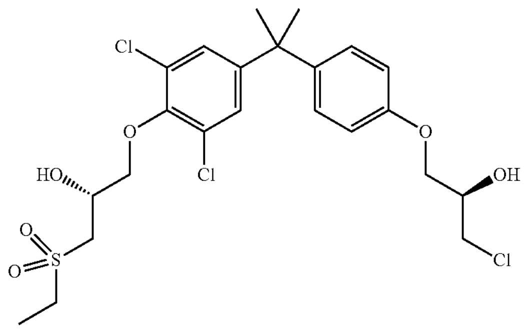 [SMILES: CCS(=O)(=O)C[C@H](O)COc1c(Cl)cc(C(C)(C)c2ccc(OC[C@@H](O)CCl)cc2)cc1Cl] | (R)-1-chloro-3-(4-(2-(3,5-dichloro-4-((R)-3-(ethylsulfonyl)-2-hydroxypropoxy)phenyl)propan-2-yl)phenoxy)propan-2-ol |
| 17c | 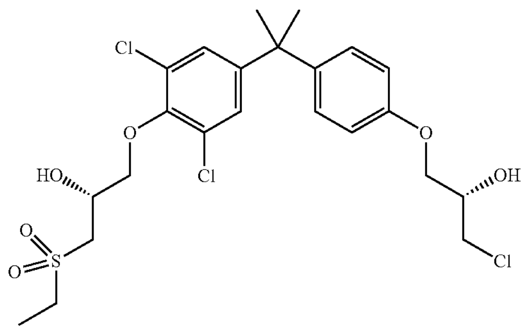 [SMILES: CCS(=O)(=O)C[C@H](O)COc1c(Cl)cc(C(C)(C)c2ccc(OC[C@H](O)CCl)cc2)cc1Cl] | (S)-1-chloro-3-(4-(2-(3,5-dichloro-4-((R)-3-(ethylsulfonyl)-2-hydroxypropoxy)phenyl)propan-2-yl)phenoxy)propan-2-ol |
| 17d | 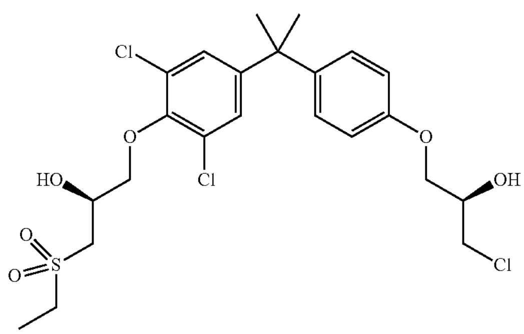 [SMILES: CCS(=O)(=O)C[C@@H](O)COc1c(Cl)cc(C(C)(C)c2ccc(OC[C@@H](O)CCl)cc2)cc1Cl] | (R)-1-chloro-3-(4-(2-(3,5-dichloro-4-((S)-3-(ethylsulfonyl)-2-hydroxypropoxy)phenyl)propan-2-yl)phenoxy)propan-2-ol |
| 18 | 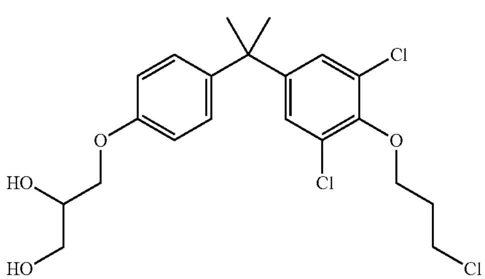 [SMILES: CC(C)(c1ccc(OCC(O)CO)cc1)c1cc(Cl)c(OCCCCl)c(Cl)c1] | 3-(4-(2-(3,5-dichloro-4-(3-chloropropoxy)phenyl)propan-2-yl)phenoxy)propane-1,2-diol |
| 18a | 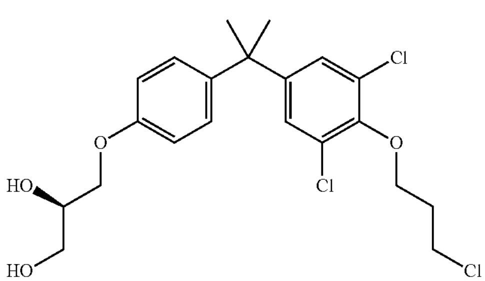 [SMILES: CC(C)(c1ccc(OC[C@H](O)CO)cc1)c1cc(Cl)c(OCCCCl)c(Cl)c1] | (R)-3-(4-(2-(3,5-dichloro-4-(3-chloropropoxy)phenyl)propan-2-yl)phenoxy)propane-1,2-diol |

TABLE 1-continued

| No. | Structure | Name |
|---|---|---|
| 18b | 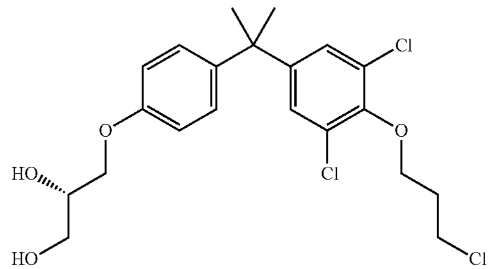 [SMILES: CC(C)(c1ccc(OC[C@@H](O)CO)cc1)c1cc(Cl)c(OCCCCl)c(Cl)c1] | (S)-3-(4-(2-(3,5-dichloro-4-(3-chloropropoxy)phenyl)propan-2-yl)phenoxy)propane-1,2-diol |
| 19 | 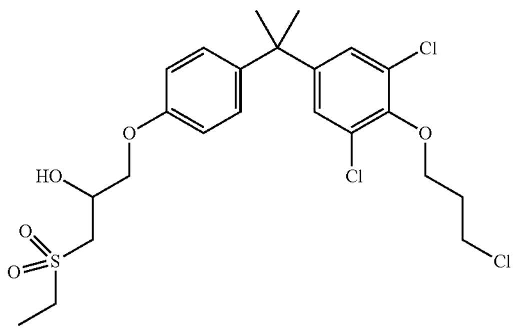 [SMILES: CCS(=O)(=O)CC(O)COc1ccc(C(C)(C)c2cc(Cl)c(OCCCCl)c(Cl)c2)cc1] | 1-(4-(2-(3,5-dichloro-4-(3-chloropropoxy)phenyl)propan-2-yl)phenoxy)-3-(ethylsulfonyl)propan-2-ol |
| 19a | 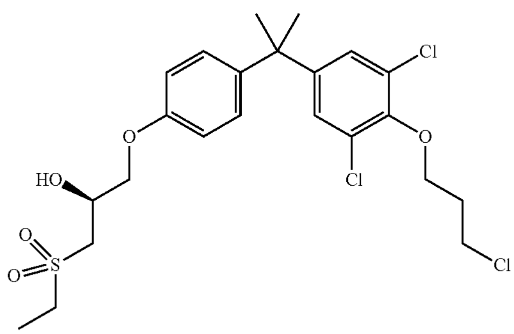 [SMILES: CCS(=O)(=O)C[C@@H](O)COc1ccc(C(C)(C)c2cc(Cl)c(OCCCCl)c(Cl)c2)cc1] | (S)-1-(4-(2-(3,5-dichloro-4-(3-chloropropoxy)phenyl)propan-2-yl)phenoxy)-3-(ethylsulfonyl)propan-2-ol |
| 19b | 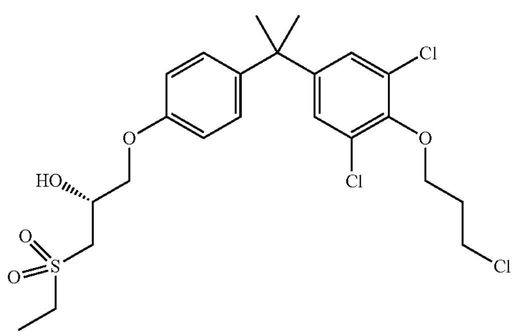 [SMILES: CCS(=O)(=O)C[C@H](O)COc1ccc(C(C)(C)c2cc(Cl)c(OCCCCl)c(Cl)c2)cc1] | (R)-1-(4-(2-(3,5-dichloro-4-(3-chloropropoxy)phenyl)propan-2-yl)phenoxy)-3-(ethylsulfonyl)propan-2-ol |
| 20 | 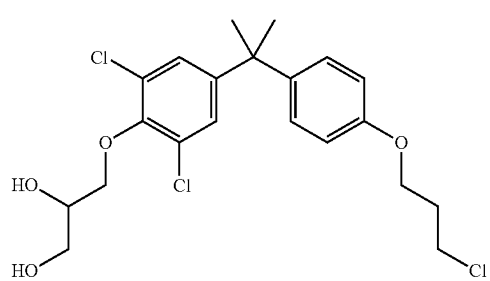 | 3-(2,6-dichloro-4-(2-(4-(3-chloropropoxy)phenyl)propan-2-yl)phenoxy)propane-1,2-diol |

TABLE 1-continued

| No. | Structure | Name |
|---|---|---|
| 20a | 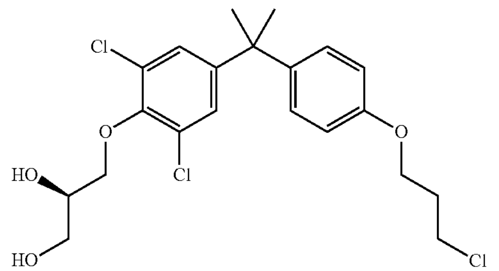 [SMILES: CC(C)(c1ccc(OCCCCl)cc1)c1cc(Cl)c(OC[C@H](O)CO)c(Cl)c1] | (R)-3-(2,6-dichloro-4-(2-(4-(3-chloropropoxy)phenyl)propan-2-yl)phenoxy)propane-1,2-diol |
| 20b | 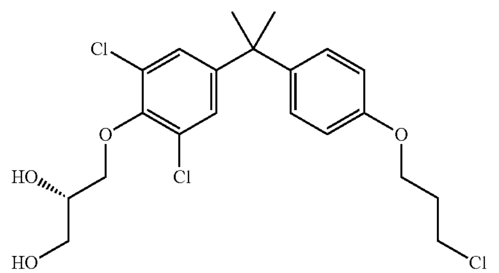 [SMILES: CC(C)(c1ccc(OCCCCl)cc1)c1cc(Cl)c(OC[C@@H](O)CO)c(Cl)c1] | (S)-3-(2,6-dichloro-4-(2-(4-(3-chloropropoxy)phenyl)propan-2-yl)phenoxy)propane-1,2-diol |
| 21 | 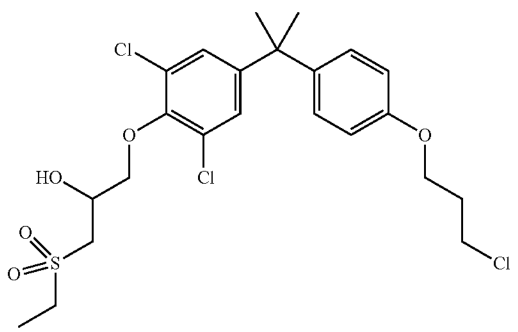 [SMILES: CCS(=O)(=O)CC(O)COc1c(Cl)cc(C(C)(C)c2ccc(OCCCCl)cc2)cc1Cl] | 1-(2,6-dichloro-4-(2-(4-(3-chloropropoxy)phenyl)propan-2-yl)phenoxy)-3-(ethylsulfonyl)propan-2-ol |
| 21a | 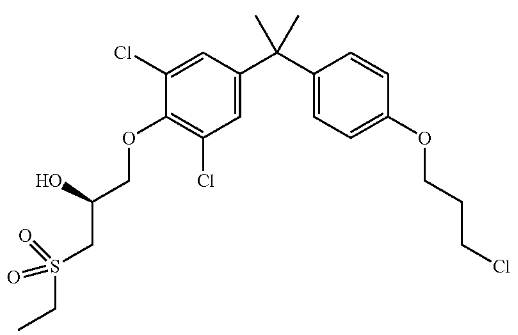 [SMILES: CCS(=O)(=O)C[C@@H](O)COc1c(Cl)cc(C(C)(C)c2ccc(OCCCCl)cc2)cc1Cl] | (S)-1-(2,6-dichloro-4-(2-(4-(3-chloropropoxy)phenyl)propan-2-yl)phenoxy)-3-(ethylsulfonyl)propan-2-ol |
| 21b | 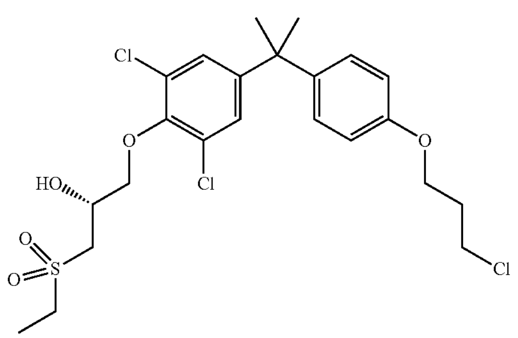 | (R)-1-(2,6-dichloro-4-(2-(4-(3-chloropropoxy)phenyl)propan-2-yl)phenoxy)-3-(ethylsulfonyl)propan-2-ol |

TABLE 1-continued

Compounds

| No. | Structure | Name |
|---|---|---|
| 22 | 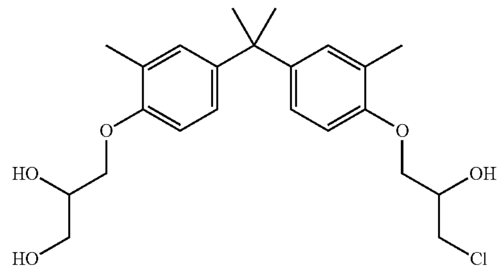 [SMILES: Cc1cc(C(C)(C)c2ccc(OCC(O)CCl)c(C)c2)ccc1OCC(O)CO] | 3-(4-(2-(4-(3-chloro-2-hydroxypropoxy)-3-methylphenyl)propan-2-yl)-2-methylphenoxy)propane-1,2-diol |
| 22a | 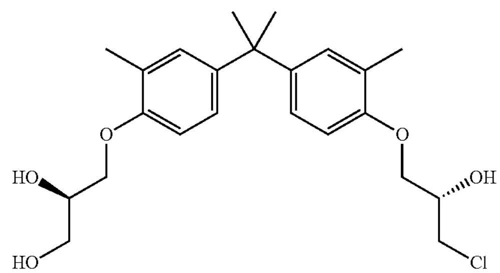 [SMILES: Cc1cc(C(C)(C)c2ccc(OC[C@H](O)CCl)c(C)c2)ccc1OC[C@H](O)CO] | (R)-3-(4-(2-(4-((S)-3-chloro-2-hydroxypropoxy)-3-methylphenyl)propan-2-yl)-2-methylphenoxy)propane-1,2-diol |
| 22b | 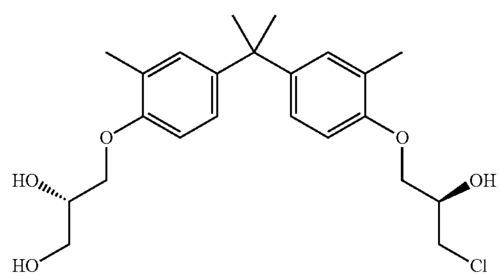 [SMILES: Cc1cc(C(C)(C)c2ccc(OC[C@@H](O)CCl)c(C)c2)ccc1OC[C@@H](O)CO] | (S)-3-(4-(2-(4-((R)-3-chloro-2-hydroxypropoxy)-3-methylphenyl)propan-2-yl)-2-methylphenoxy)propane-1,2-diol |
| 22c | 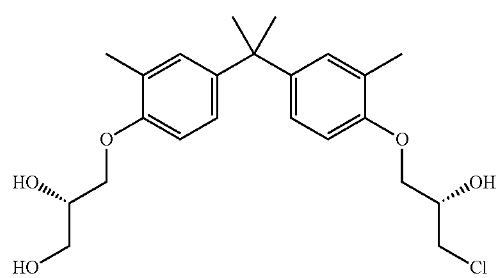 | (S)-3-(4-(2-(4-((S)-3-chloro-2-hydroxypropoxy)-3-methylphenyl)propan-2-yl)-2-methylphenoxy)propane-1,2-diol |
| 22d | 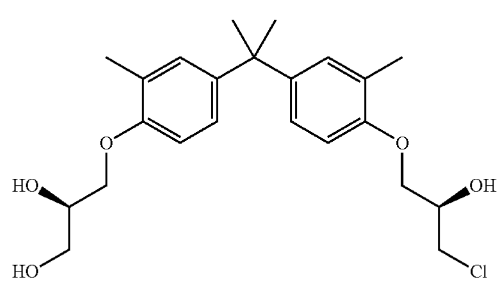 [SMILES: Cc1cc(C(C)(C)c2ccc(OC[C@@H](O)CCl)c(C)c2)ccc1OC[C@H](O)CO] | (R)-3-(4-(2-(4-((R)-3-chloro-2-hydroxypropoxy)-3-methylphenyl)propan-2-yl)-2-methylphenoxy)propane-1,2-diol |

In some embodiments of the compound of Formula I, the compound has one of the following structures from Table 2, or a pharmaceutically acceptable salt, tautomer, or stereoisomer thereof.

TABLE 2

| No. | Structure | Name |
|---|---|---|
| A1 | 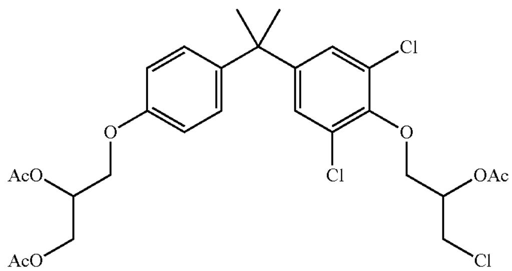 [SMILES: CC(=O)OCC(COc1ccc(C(C)(C)c2cc(Cl)c(OCC(CCl)OC(C)=O)c(Cl)c2)cc1)OC(C)=O] | 3-(4-(2-(4-(2-acetoxy-3-chloropropoxy)-3,5-dichlorophenyl)propan-2-yl)phenoxy)propane-1,2-diyl diacetate |
| A1a | 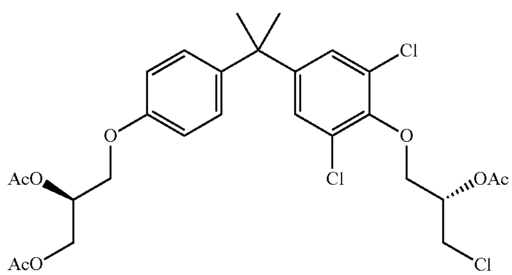 | (S)-3-(4-(2-(4-((S)-2-acetoxy-3-chloropropoxy)-3,5-dichlorophenyl)propan-2-yl)phenoxy)propane-1,2-diyl diacetate |
| A1b | 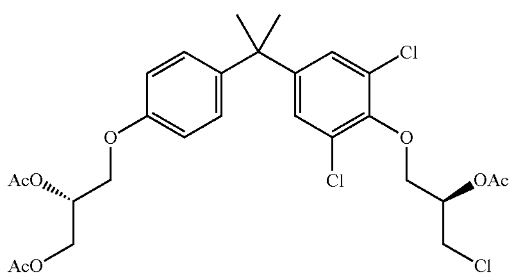 [SMILES: CC(=O)OC[C@@H](COc1ccc(C(C)(C)c2cc(Cl)c(OC[C@H](CCl)OC(C)=O)c(Cl)c2)cc1)OC(C)=O] | (R)-3-(4-(2-(4-((R)-2-acetoxy-3-chloropropoxy)-3,5-dichlorophenyl)propan-2-yl)phenoxy)propane-1,2-diyl diacetate |
| A1c | 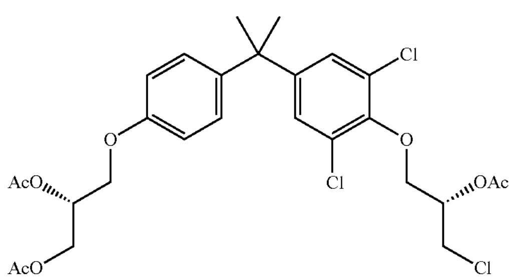 | (R)-3-(4-(2-(4-((S)-2-acetoxy-3-chloropropoxy)-3,5-dichlorophenyl)propan-2-yl)phenoxy)propane-1,2-diyl diacetate |
| A1d | 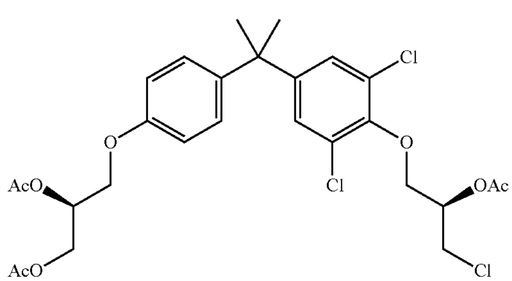 [SMILES: CC(=O)OC[C@H](COc1ccc(C(C)(C)c2cc(Cl)c(OC[C@H](CCl)OC(C)=O)c(Cl)c2)cc1)OC(C)=O] | (S)-3-(4-(2-(4-((R)-2-acetoxy-3-chloropropoxy)-3,5-dichlorophenyl)propan-2-yl)phenoxy)propane-1,2-diyl diacetate |

TABLE 2-continued

| No. | Structure | Name |
|---|---|---|
| B1 | 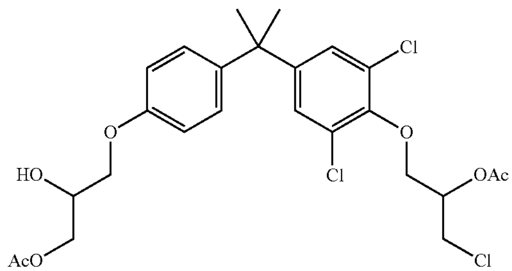 [SMILES: CC(=O)OCC(O)COc1ccc(C(C)(C)c2cc(Cl)c(OCC(CCl)OC(C)=O)c(Cl)c2)cc1] | 1-(4-(2-(4-(3-acetoxy-2-hydroxypropoxy)phenyl)propan-2-yl)-2,6-dichlorophenoxy)-3-chloropropan-2-yl acetate |
| B1a | 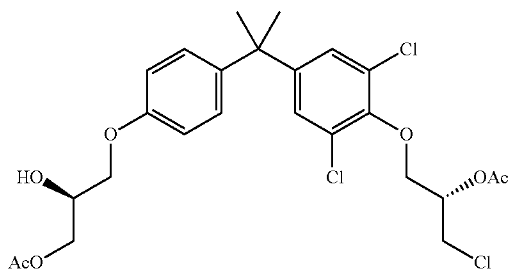 | (S)-1-(4-(2-(4-((S)-3-acetoxy-2-hydroxypropoxy)phenyl)propan-2-yl)-2,6-dichlorophenoxy)-3-chloropropan-2-yl acetate |
| B1b | 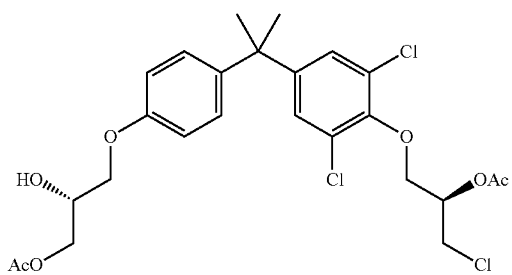 [SMILES: CC(=O)OC[C@H](O)COc1ccc(C(C)(C)c2cc(Cl)c(OC[C@H](CCl)OC(C)=O)c(Cl)c2)cc1] | (R)-1-(4-(2-(4-((R)-3-acetoxy-2-hydroxypropoxy)phenyl)propan-2-yl)-2,6-dichlorophenoxy)-3-chloropropan-2-yl acetate |
| B1c | 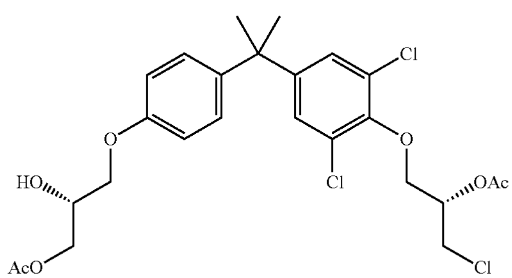 | (S)-1-(4-(2-(4-((R)-3-acetoxy-2-hydroxypropoxy)phenyl)propan-2-yl)-2,6-dichlorophenoxy)-3-chloropropan-2-yl acetate |
| B1d | 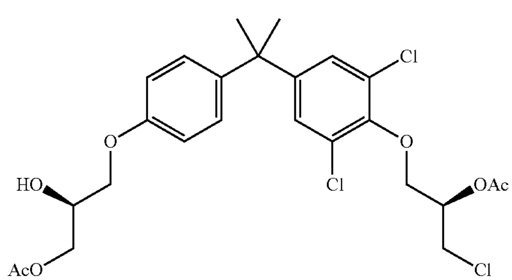 [SMILES: CC(=O)OC[C@@H](O)COc1ccc(C(C)(C)c2cc(Cl)c(OC[C@H](CCl)OC(C)=O)c(Cl)c2)cc1] | (R)-1-(4-(2-(4-((S)-3-acetoxy-2-hydroxypropoxy)phenyl)propan-2-yl)-2,6-dichlorophenoxy)-3-chloropropan-2-yl acetate |

TABLE 2-continued

| No. | Structure | Name |
| --- | --- | --- |
| C1 | 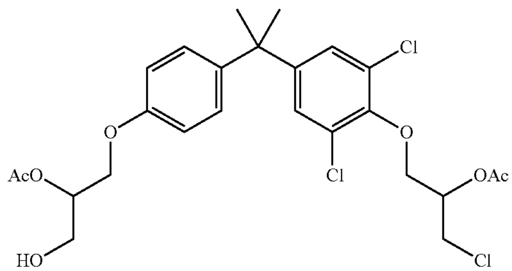 [SMILES: CC(=O)OC(CO)COc1ccc(C(C)(C)c2cc(Cl)c(OCC(CCl)OC(C)=O)c(Cl)c2)cc1] | 1-(4-(2-(4-(2-acetoxy-3-chloropropoxy)-3,5-dichlorophenyl)propan-2-yl)phenoxy)-3-hydroxypropan-2-yl acetate |
| C1a | 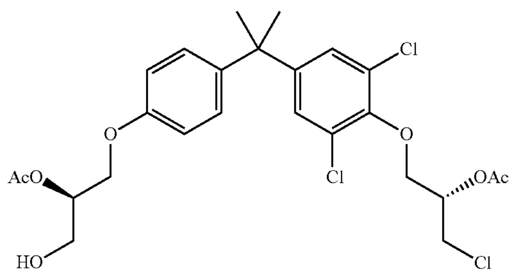 [SMILES: CC(=O)O[C@H](CO)COc1ccc(C(C)(C)c2cc(Cl)c(OC[C@@H](CCl)OC(C)=O)c(Cl)c2)cc1] | (R)-1-(4-(2-(4-((S)-2-acetoxy-3-chloropropoxy)-3,5-dichlorophenyl)propan-2-yl)phenoxy)-3-hydroxypropan-2-yl acetate |
| C1b | 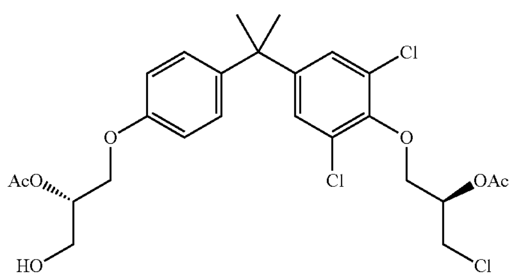 [SMILES: CC(=O)O[C@@H](CO)COc1ccc(C(C)(C)c2cc(Cl)c(OC[C@H](CCl)OC(C)=O)c(Cl)c2)cc1] | (S)-1-(4-(2-(4-((R)-2-acetoxy-3-chloropropoxy)-3,5-dichlorophenyl)propan-2-yl)phenoxy)-3-hydroxypropan-2-yl acetate |
| C1c | 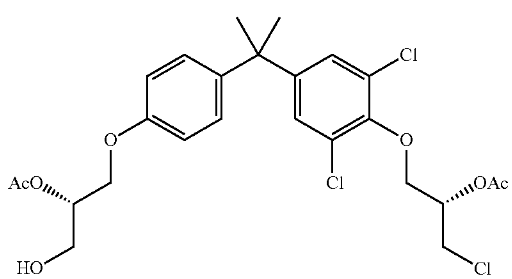 [SMILES: CC(=O)O[C@H](CCl)COc1c(Cl)cc(C(C)(C)c2ccc(OC[C@H](CO)OC(C)=O)cc2)cc1Cl] | (S)-1-(4-(2-(4-((S)-2-acetoxy-3-chloropropoxy)-3,5-dichlorophenyl)propan-2-yl)phenoxy)-3-hydroxypropan-2-yl acetate |
| C1d | 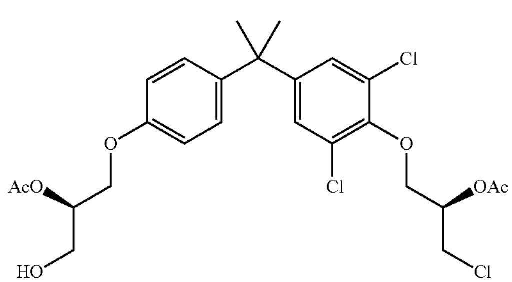 [SMILES: CC(=O)O[C@H](CO)COc1ccc(C(C)(C)c2cc(Cl)c(OC[C@H](CCl)OC(C)=O)c(Cl)c2)cc1] | (R)-1-(4-(2-(4-((R)-2-acetoxy-3-chloropropoxy)-3,5-dichlorophenyl)propan-2-yl)phenoxy)-3-hydroxypropan-2-yl acetate |

TABLE 2-continued

| No. | Structure | Name |
|---|---|---|
| D1 | 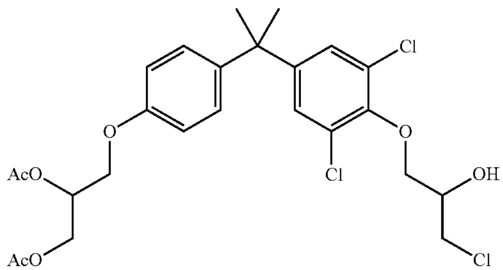 [SMILES: CC(=O)OCC(COc1ccc(C(C)(C)c2cc(Cl)c(OCC(O)CCl)c(Cl)c2)cc1)OC(C)=O] | 3-(4-(2-(3,5-dichloro-4-(3-chloro-2-hydroxypropoxy)phenyl)propan-2-yl)phenoxy)propane-1,2-diyl diacetate |
| D1a | 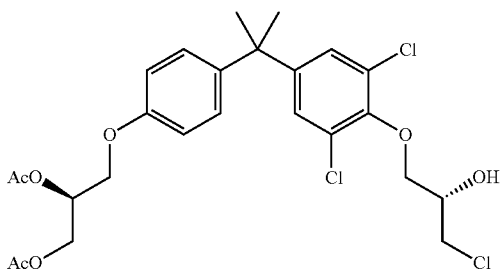 [SMILES: CC(=O)OC[C@H](COc1ccc(C(C)(C)c2cc(Cl)c(OC[C@H](O)CCl)c(Cl)c2)cc1)OC(C)=O] | (S)-3-(4-(2-(3,5-dichloro-4-((S)-3-chloro-2-hydroxypropoxy)phenyl)propan-2-yl)phenoxy)propane-1,2-diyl diacetate |
| D1b | 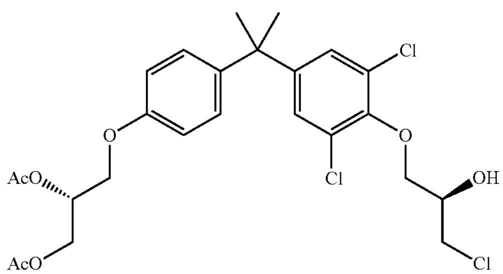 [SMILES: CC(=O)OC[C@@H](COc1ccc(C(C)(C)c2cc(Cl)c(OC[C@@H](O)CCl)c(Cl)c2)cc1)OC(C)=O] | (R)-3-(4-(2-(3,5-dichloro-4-((R)-3-chloro-2-hydroxypropoxy)phenyl)propan-2-yl)phenoxy)propane-1,2-diyl diacetate |
| D1c | 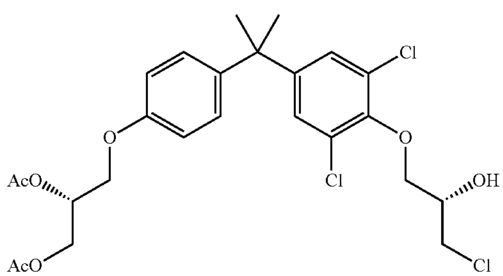 [SMILES: CC(=O)OC[C@@H](COc1ccc(C(C)(C)c2cc(Cl)c(OC[C@H](O)CCl)c(Cl)c2)cc1)OC(C)=O] | (R)-3-(4-(2-(3,5-dichloro-4-((S)-3-chloro-2-hydroxypropoxy)phenyl)propan-2-yl)phenoxy)propane-1,2-diyl diacetate |
| D1d | 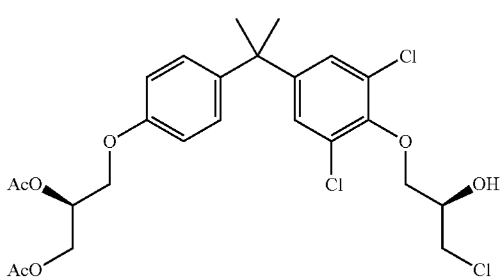 | (S)-3-(4-(2-(3,5-dichloro-4-((R)-3-chloro-2-hydroxypropoxy)phenyl)propan-2-yl)phenoxy)propane-1,2-diyl diacetate |

TABLE 2-continued

| No. | Structure | Name |
|---|---|---|
| E1 | 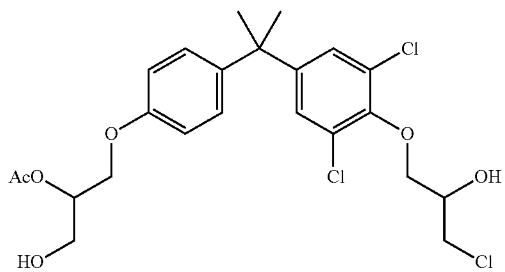 | 1-(4-(2-(3,5-dichloro-4-(3-chloro-2-hydroxypropoxy)phenyl)propan-2-yl)phenoxy)-3-hydroxypropan-2-yl acetate |
| E1a | 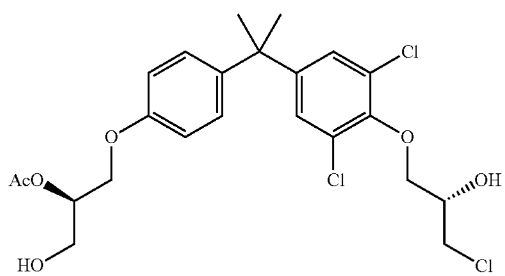 [SMILES: CC(=O)O[C@H](CO)COc1ccc(C(C)(C)c2cc(Cl)c(OC[C@H](O)CCl)c(Cl)c2)cc1] | (R)-1-(4-(2-(3,5-dichloro-4-((S)-3-chloro-2-hydroxypropoxy)phenyl)propan-2-yl)phenoxy)-3-hydroxypropan-2-yl acetate |
| E1b | 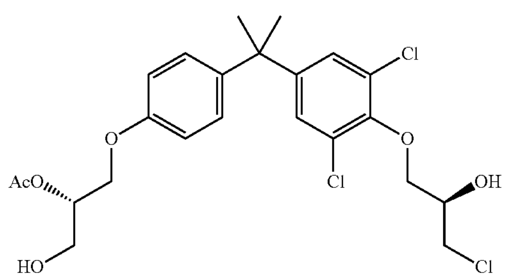 [SMILES: CC(=O)O[C@@H](CO)COc1ccc(C(C)(C)c2cc(Cl)c(OC[C@@H](O)CCl)c(Cl)c2)cc1] | (S)-1-(4-(2-(3,5-dichloro-4-((R)-3-chloro-2-hydroxypropoxy)phenyl)propan-2-yl)phenoxy)-3-hydroxypropan-2-yl acetate |
| E1c | 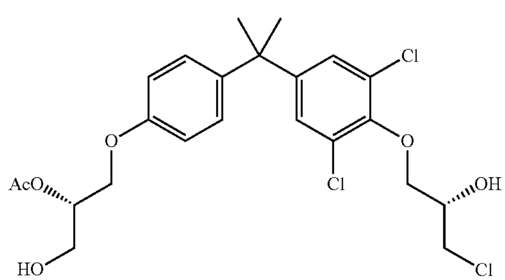 [SMILES: CC(=O)O[C@@H](CO)COc1ccc(C(C)(C)c2cc(Cl)c(OC[C@H](O)CCl)c(Cl)c2)cc1] | (S)-1-(4-(2-(3,5-dichloro-4-((S)-3-chloro-2-hydroxypropoxy)phenyl)propan-2-yl)phenoxy)-3-hydroxypropan-2-yl acetate |
| E1d | 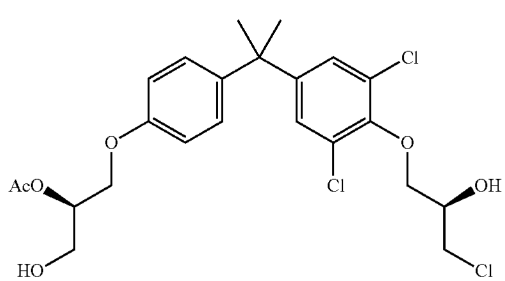 [SMILES: CC(=O)O[C@H](CO)COc1ccc(C(C)(C)c2cc(Cl)c(OC[C@@H](O)CCl)c(Cl)c2)cc1] | (R)-1-(4-(2-(3,5-dichloro-4-((R)-3-chloro-2-hydroxypropoxy)phenyl)propan-2-yl)phenoxy)-3-hydroxypropan-2-yl acetate |

TABLE 2-continued

| No. | Structure | Name |
|---|---|---|
| F1 | 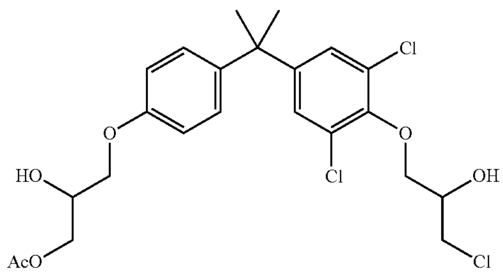 [SMILES: CC(=O)OCC(O)COc1ccc(C(C)(C)c2cc(Cl)c(OCC(O)CCl)c(Cl)c2)cc1] | 3-(4-(2-(3,5-dichloro-4-(3-chloro-2-hydroxypropoxy)phenyl)propan-2-yl)phenoxy)-2-hydroxypropyl acetate |
| F1a | 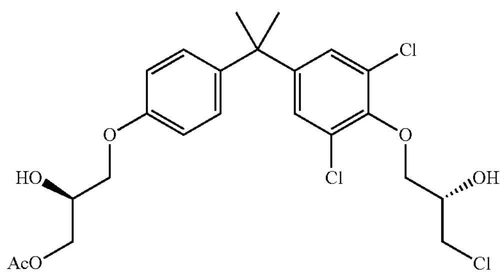 [SMILES: CC(=O)OC[C@@H](O)COc1ccc(C(C)(C)c2cc(Cl)c(OC[C@H](O)CCl)c(Cl)c2)cc1] | (S)-3-(4-(2-(3,5-dichloro-4-((S)-3-chloro-2-hydroxypropoxy)phenyl)propan-2-yl)phenoxy)-2-hydroxypropyl acetate |
| F1b | 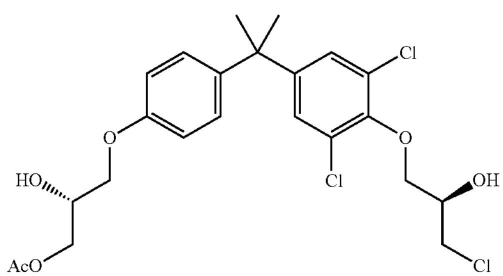 [SMILES: CC(=O)OC[C@H](O)COc1ccc(C(C)(C)c2cc(Cl)c(OC[C@@H](O)CCl)c(Cl)c2)cc1] | (R)-3-(4-(2-(3,5-dichloro-4-((R)-3-chloro-2-hydroxypropoxy)phenyl)propan-2-yl)phenoxy)-2-hydroxypropyl acetate |
| F1c | 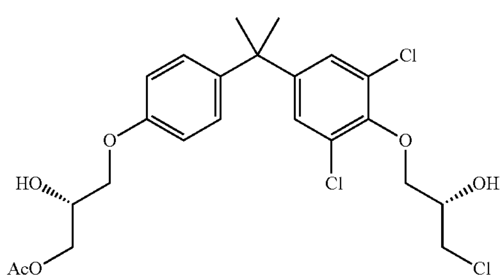 [SMILES: CC(=O)OC[C@H](O)COc1ccc(C(C)(C)c2cc(Cl)c(OC[C@H](O)CCl)c(Cl)c2)cc1] | (R)-3-(4-(2-(3,5-dichloro-4-((S)-3-chloro-2-hydroxypropoxy)phenyl)propan-2-yl)phenoxy)-2-hydroxypropyl acetate |
| F1d | 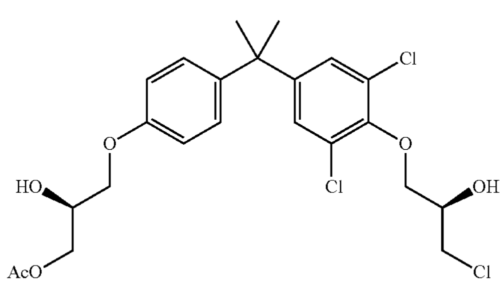 | (S)-3-(4-(2-(3,5-dichloro-4-((R)-3-chloro-2-hydroxypropoxy)phenyl)propan-2-yl)phenoxy)-2-hydroxypropyl acetate |

TABLE 2-continued

| Compounds | | |
|---|---|---|
| No. | Structure | Name |
| G1 | | 1-chloro-3-(2,6-dichloro-4-(2-(4-(2,3-dihydroxypropoxy)phenyl)propan-2-yl)phenoxy)propan-2-yl acetate |
| G1a | | (S)-1-chloro-3-(2,6-dichloro-4-(2-(4-((R)-2,3-dihydroxypropoxy)phenyl)propan-2-yl)phenoxy)propan-2-yl acetate |
| G1b | | (R)-1-chloro-3-(2,6-dichloro-4-(2-(4-((S)-2,3-dihydroxypropoxy)phenyl)propan-2-yl)phenoxy)propan-2-yl acetate |
| G1c | | (S)-1-chloro-3-(2,6-dichloro-4-(2-(4-((S)-2,3-dihydroxypropoxy)phenyl)propan-2-yl)phenoxy)propan-2-yl acetate |
| G1d | | (R)-1-chloro-3-(2,6-dichloro-4-(2-(4-((R)-2,3-dihydroxypropoxy)phenyl)propan-2-yl)phenoxy)propan-2-yl acetate |

TABLE 2-continued

| No. | Structure | Name |
|---|---|---|
| A2 | 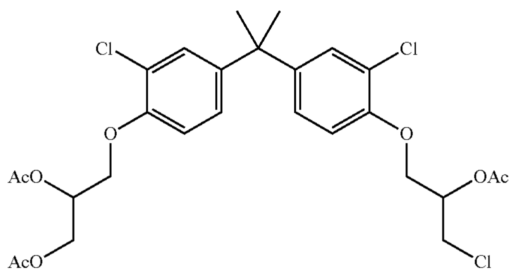 [SMILES: CC(=O)OCC(COc1ccc(C(C)(C)c2ccc(OCC(CCl)OC(C)=O)c(Cl)c2)cc1Cl)OC(C)=O] | 3-(4-(2-(4-(2-acetoxy-3-chloropropoxy)-3-chlorophenyl)propan-2-yl)-2-chlorophenoxy)propane-1,2-diyl diacetate |
| A2a | 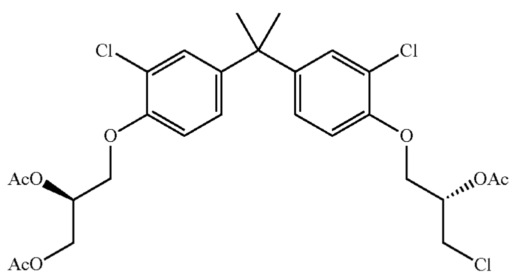 [SMILES: CC(=O)OC[C@H](COc1ccc(C(C)(C)c2ccc(OC[C@@H](CCl)OC(C)=O)c(Cl)c2)cc1Cl)OC(C)=O] | (S)-3-(4-(2-(4-((S)-2-acetoxy-3-chloropropoxy)-3-chlorophenyl)propan-2-yl)-2-chlorophenoxy)propane-1,2-diyl diacetate |
| A2b | 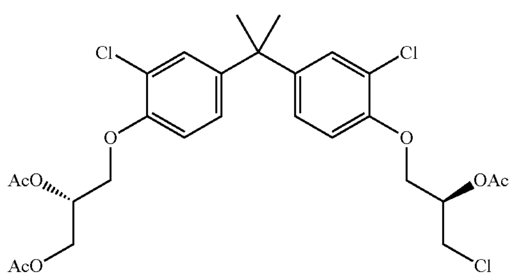 [SMILES: CC(=O)OC[C@@H](COc1ccc(C(C)(C)c2ccc(OC[C@H](CCl)OC(C)=O)c(Cl)c2)cc1Cl)OC(C)=O] | (R)-3-(4-(2-(4-((R)-2-acetoxy-3-chloropropoxy)-3-chlorophenyl)propan-2-yl)-2-chlorophenoxy)propane-1,2-diyl diacetate |
| A2c | 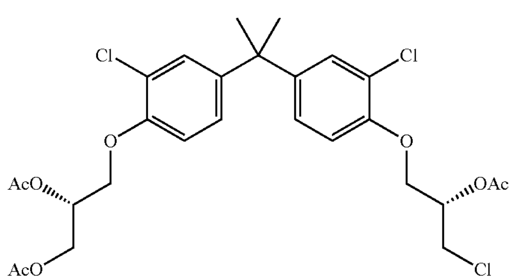 [SMILES: CC(=O)OC[C@@H](COc1ccc(C(C)(C)c2ccc(OC[C@@H](CCl)OC(C)=O)c(Cl)c2)cc1Cl)OC(C)=O] | (R)-3-(4-(2-(4-((S)-2-acetoxy-3-chloropropoxy)-3-chlorophenyl)propan-2-yl)-2-chlorophenoxy)propane-1,2-diyl diacetate |
| A2d | 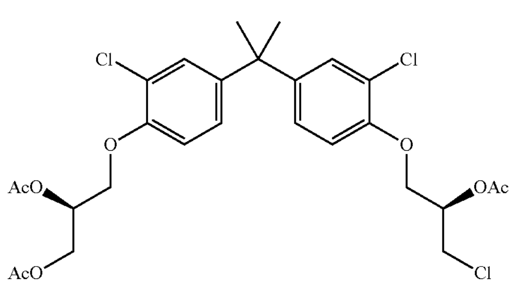 [SMILES: CC(=O)OC[C@H](COc1ccc(C(C)(C)c2ccc(OC[C@H](CCl)OC(C)=O)c(Cl)c2)cc1Cl)OC(C)=O] | (S)-3-(4-(2-(4-((R)-2-acetoxy-3-chloropropoxy)-3-chlorophenyl)propan-2-yl)-2-chlorophenoxy)propane-1,2-diyl diacetate |

TABLE 2-continued

| No. | Structure | Name |
|---|---|---|
| A3 | 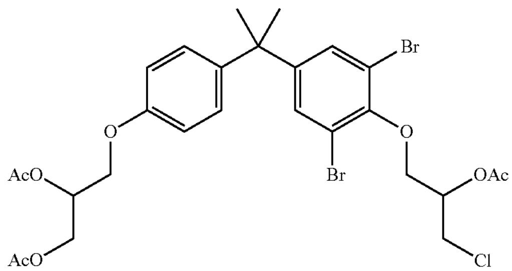 [SMILES: CC(=O)OCC(COc1ccc(C(C)(C)c2cc(Br)c(OCC(CCl)OC(C)=O)c(Br)c2)cc1)OC(C)=O] | 3-(4-(2-(4-(2-acetoxy-3-chloropropoxy)-3,5-dibromophenyl)propan-2-yl)phenoxy)propane-1,2-diyl diacetate |
| A3a | 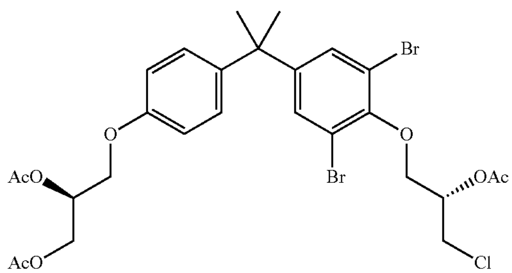 [SMILES: CC(=O)OC[C@H](COc1ccc(C(C)(C)c2cc(Br)c(OC[C@@H](CCl)OC(C)=O)c(Br)c2)cc1)OC(C)=O] | (S)-3-(4-(2-(4-((S)-2-acetoxy-3-chloropropoxy)-3,5-dibromophenyl)propan-2-yl)phenoxy)propane-1,2-diyl diacetate |
| A3b | 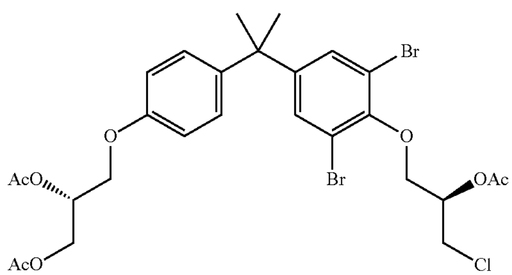 [SMILES: CC(=O)OC[C@@H](COc1ccc(C(C)(C)c2cc(Br)c(OC[C@H](CCl)OC(C)=O)c(Br)c2)cc1)OC(C)=O] | (R)-3-(4-(2-(4-((R)-2-acetoxy-3-chloropropoxy)-3,5-dibromophenyl)propan-2-yl)phenoxy)propane-1,2-diyl diacetate |
| A3c | 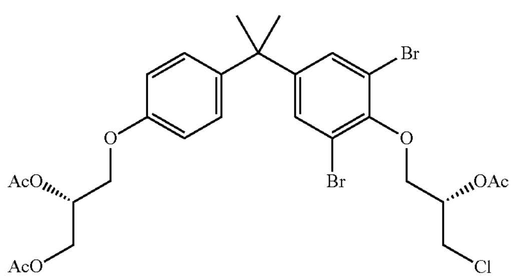 | (R)-3-(4-(2-(4-((S)-2-acetoxy-3-chloropropoxy)-3,5-dibromophenyl)propan-2-yl)phenoxy)propane-1,2-diyl diacetate |
| A3d | 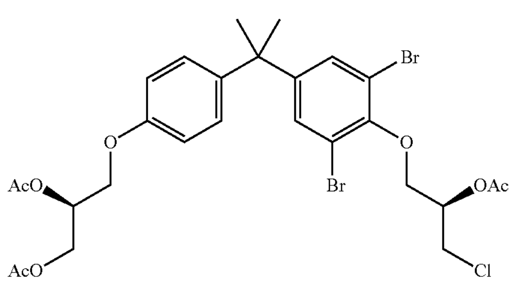 [SMILES: CC(=O)OC[C@H](COc1ccc(C(C)(C)c2cc(Br)c(OC[C@H](CCl)OC(C)=O)c(Br)c2)cc1)OC(C)=O] | (S)-3-(4-(2-(4-((R)-2-acetoxy-3-chloropropoxy)-3,5-dibromophenyl)propan-2-yl)phenoxy)propane-1,2-diyl diacetate |

TABLE 2-continued

| No. | Structure | Name |
|-----|-----------|------|
| A4 | 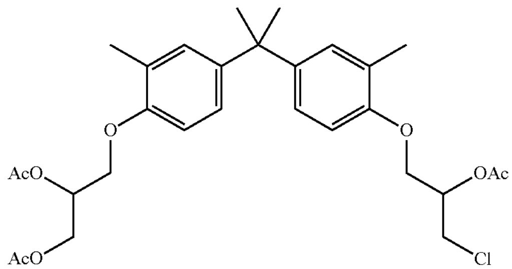 [SMILES: CC(=O)OCC(COc1ccc(C(C)(C)c2ccc(OCC(CCl)OC(C)=O)c(C)c2)cc1C)OC(C)=O] | 3-(4-(2-(4-(2-acetoxy-3-chloropropoxy)-3-methylphenyl)propan-2-yl)-2-methylphenoxy)propane-1,2-diyl diacetate |
| A4a | 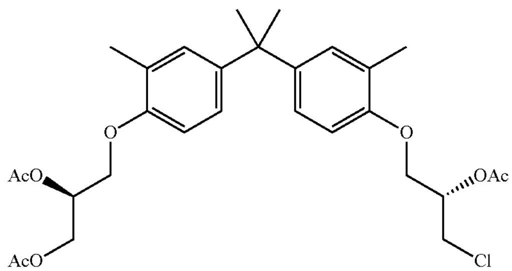 [SMILES: CC(=O)OC[C@H](COc1ccc(C(C)(C)c2ccc(OC[C@@H](CCl)OC(C)=O)c(C)c2)cc1C)OC(C)=O] | (S)-3-(4-(2-(4-((S)-2-acetoxy-3-chloropropoxy)-3-methylphenyl)propan-2-yl)-2-methylphenoxy)propane-1,2-diyl diacetate |
| A4b | 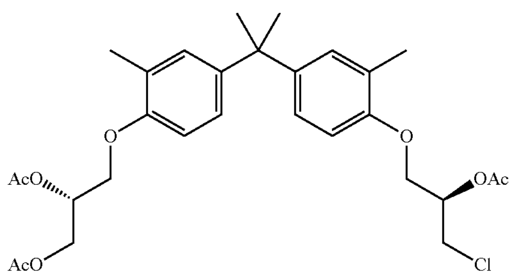 [SMILES: CC(=O)OC[C@@H](COc1ccc(C(C)(C)c2ccc(OC[C@H](CCl)OC(C)=O)c(C)c2)cc1C)OC(C)=O] | (R)-3-(4-(2-(4-((R)-2-acetoxy-3-chloropropoxy)-3-methylphenyl)propan-2-yl)-2-methylphenoxy)propane-1,2-diyl diacetate |
| A4c | 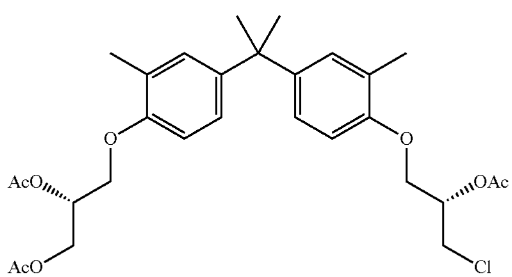 | (R)-3-(4-(2-(4-((S)-2-acetoxy-3-chloropropoxy)-3-methylphenyl)propan-2-yl)-2-methylphenoxy)propane-1,2-diyl diacetate |
| A4d | 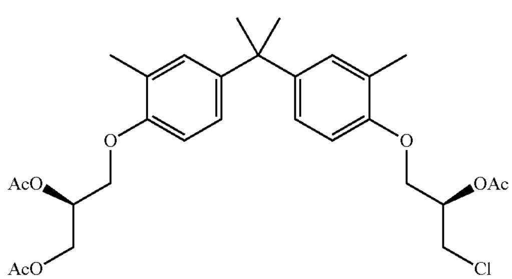 [SMILES: CC(=O)OC[C@H](COc1ccc(C(C)(C)c2ccc(OC[C@H](CCl)OC(C)=O)c(C)c2)cc1C)OC(C)=O] | (S)-3-(4-(2-(4-((R)-2-acetoxy-3-chloropropoxy)-3-methylphenyl)propan-2-yl)-2-methylphenoxy)propane-1,2-diyl diacetate |

TABLE 2-continued

Compounds

| No. | Structure | Name |
|---|---|---|
| A5 | 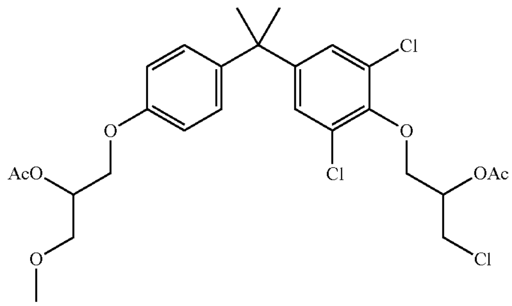 [SMILES: COCC(COc1ccc(C(C)(C)c2cc(Cl)c(OCC(CCl)OC(C)=O)c(Cl)c2)cc1)OC(C)=O] | 1-(4-(2-(4-(2-acetoxy-3-chloropropoxy)-3,5-dichlorophenyl)propan-2-yl)phenoxy)-3-methoxypropan-2-yl acetate |
| A5a | 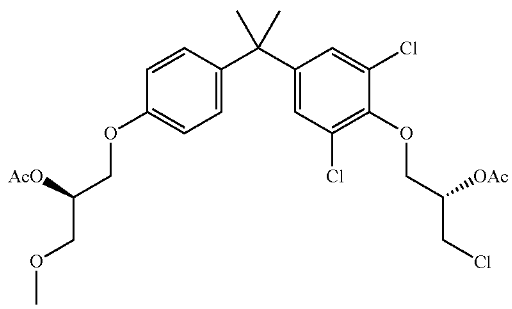 [SMILES: COC[C@H](COc1ccc(C(C)(C)c2cc(Cl)c(OC[C@@H](CCl)OC(C)=O)c(Cl)c2)cc1)OC(C)=O] | (R)-1-(4-(2-(4-((S)-2-acetoxy-3-chloropropoxy)-3,5-dichlorophenyl)propan-2-yl)phenoxy)-3-methoxypropan-2-yl acetate |
| A5b | 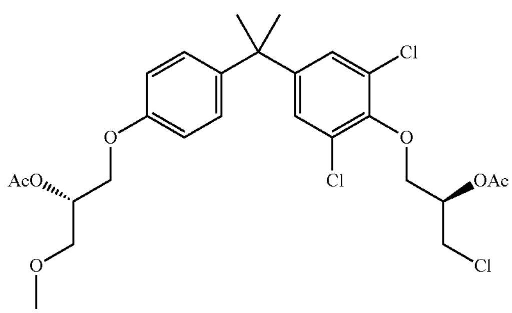 [SMILES: COC[C@@H](COc1ccc(C(C)(C)c2cc(Cl)c(OC[C@H](CCl)OC(C)=O)c(Cl)c2)cc1)OC(C)=O] | (S)-1-(4-(2-(4-((R)-2-acetoxy-3-chloropropoxy)-3,5-dichlorophenyl)propan-2-yl)phenoxy)-3-methoxypropan-2-yl acetate |
| A5c | 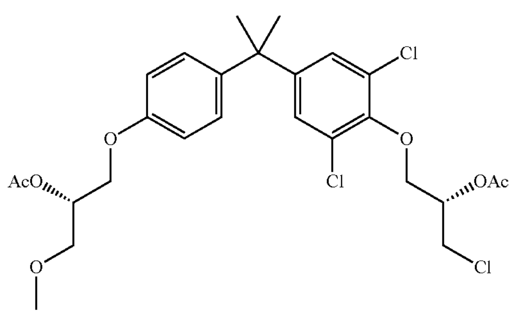 [SMILES: COC[C@@H](COc1ccc(C(C)(C)c2cc(Cl)c(OC[C@@H](CCl)OC(C)=O)c(Cl)c2)cc1)OC(C)=O] | (S)-1-(4-(2-(4-((S)-2-acetoxy-3-chloropropoxy)-3,5-dichlorophenyl)propan-2-yl)phenoxy)-3-methoxypropan-2-yl acetate |
| A5d | 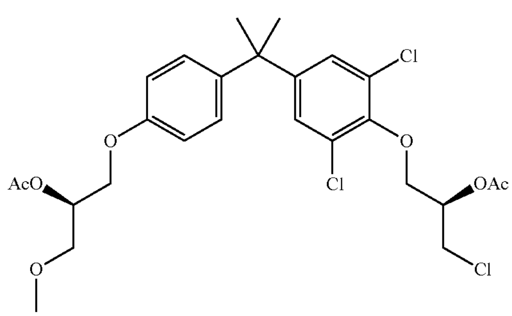 [SMILES: COC[C@H](COc1ccc(C(C)(C)c2cc(Cl)c(OC[C@H](CCl)OC(C)=O)c(Cl)c2)cc1)OC(C)=O] | (R)-1-(4-(2-(4-((R)-2-acetoxy-3-chloropropoxy)-3,5-dichlorophenyl)propan-2-yl)phenoxy)-3-methoxypropan-2-yl acetate |

TABLE 2-continued

Compounds

| No. | Structure | Name |
|---|---|---|
| B5 | 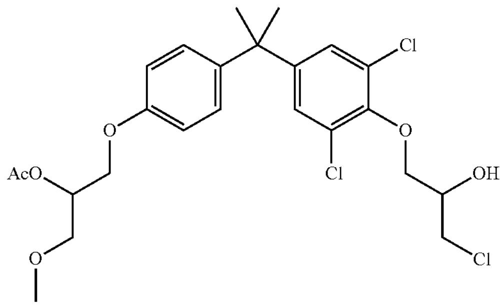 [SMILES: COCC(COc1ccc(C(C)(C)c2cc(Cl)c(OCC(O)CCl)c(Cl)c2)cc1)OC(C)=O] | 1-(4-(2-(3,5-dichloro-4-(3-chloro-2-hydroxypropoxy)phenyl)propan-2-yl)phenoxy)-3-methoxypropan-2-yl acetate |
| B5a | 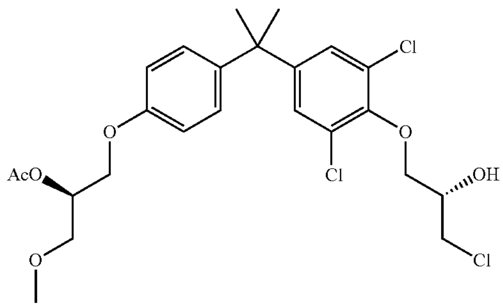 [SMILES: COC[C@H](COc1ccc(C(C)(C)c2cc(Cl)c(OC[C@H](O)CCl)c(Cl)c2)cc1)OC(C)=O] | (R)-1-(4-(2-(3,5-dichloro-4-((S)-3-chloro-2-hydroxypropoxy)phenyl)propan-2-yl)phenoxy)-3-methoxypropan-2-yl acetate |
| B5b | 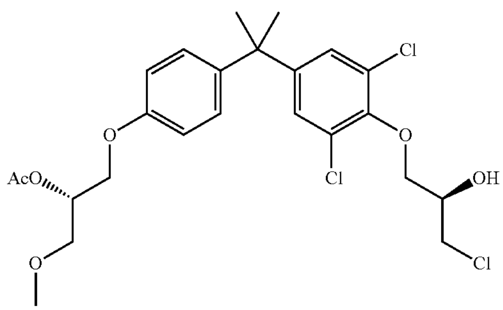 [SMILES: COC[C@@H](COc1ccc(C(C)(C)c2cc(Cl)c(OC[C@@H](O)CCl)c(Cl)c2)cc1)OC(C)=O] | (S)-1-(4-(2-(3,5-dichloro-4-((R)-3-chloro-2-hydroxypropoxy)phenyl)propan-2-yl)phenoxy)-3-methoxypropan-2-yl acetate |
| B5c | 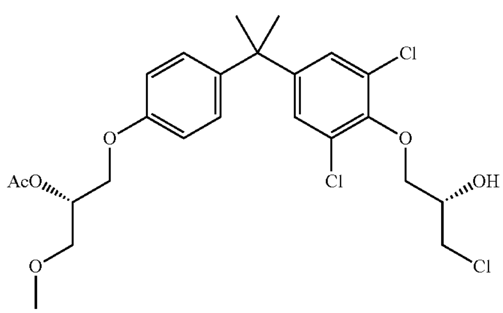 | (S)-1-(4-(2-(3,5-dichloro-4-((S)-3-chloro-2-hydroxypropoxy)phenyl)propan-2-yl)phenoxy)-3-methoxypropan-2-yl acetate |
| B5d | 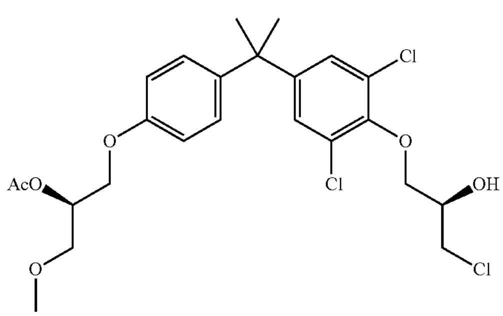 [SMILES: COC[C@H](COc1ccc(C(C)(C)c2cc(Cl)c(OC[C@@H](O)CCl)c(Cl)c2)cc1)OC(C)=O] | (R)-1-(4-(2-(3,5-dichloro-4-((R)-3-chloro-2-hydroxypropoxy)phenyl)propan-2-yl)phenoxy)-3-methoxypropan-2-yl acetate |

TABLE 2-continued

Compounds

| No. | Structure | Name |
|---|---|---|
| C5 | 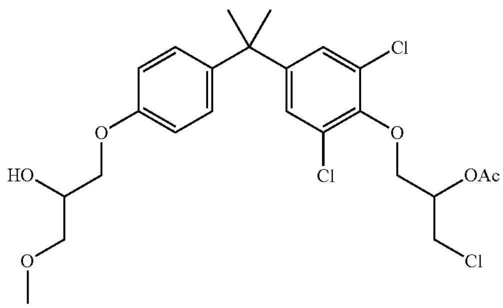 [SMILES: COCC(O)COc1ccc(C(C)(C)c2cc(Cl)c(OCC(CCl)OC(C)=O)c(Cl)c2)cc1] | 1-chloro-3-(2,6-dichloro-4-(2-(4-(2-hydroxy-3-methoxypropoxy)phenyl)propan-2-yl)phenoxy)propan-2-yl acetate |
| C5a | 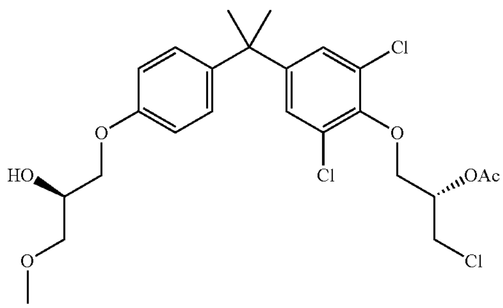 [SMILES: COC[C@@H](O)COc1ccc(C(C)(C)c2cc(Cl)c(OC[C@@H](CCl)OC(C)=O)c(Cl)c2)cc1] | (S)-1-chloro-3-(2,6-dichloro-4-(2-(4-((R)-2-hydroxy-3-methoxypropoxy)phenyl)propan-2-yl)phenoxy)propan-2-yl acetate |
| C5b | 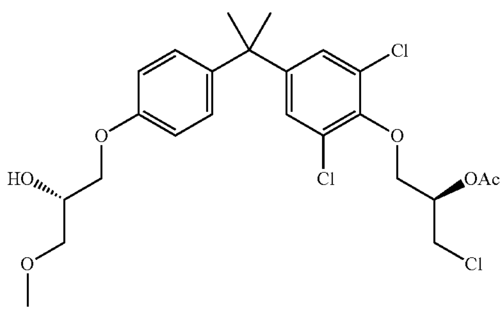 [SMILES: COC[C@H](O)COc1ccc(C(C)(C)c2cc(Cl)c(OC[C@H](CCl)OC(C)=O)c(Cl)c2)cc1] | (R)-1-chloro-3-(2,6-dichloro-4-(2-(4-((S)-2-hydroxy-3-methoxypropoxy)phenyl)propan-2-yl)phenoxy)propan-2-yl acetate |
| C5c | 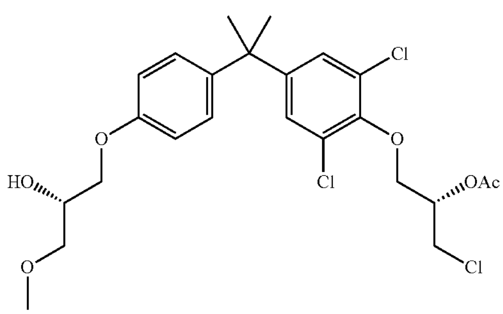 [SMILES: COC[C@H](O)COc1ccc(C(C)(C)c2cc(Cl)c(OC[C@@H](CCl)OC(C)=O)c(Cl)c2)cc1] | (S)-1-chloro-3-(2,6-dichloro-4-(2-(4-((S)-2-hydroxy-3-methoxypropoxy)phenyl)propan-2-yl)phenoxy)propan-2-yl acetate |
| C5d | 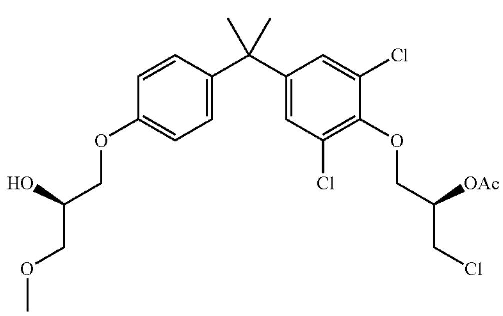 [SMILES: COC[C@@H](O)COc1ccc(C(C)(C)c2cc(Cl)c(OC[C@H](CCl)OC(C)=O)c(Cl)c2)cc1] | (R)-1-chloro-3-(2,6-dichloro-4-(2-(4-((R)-2-hydroxy-3-methoxypropoxy)phenyl)propan-2-yl)phenoxy)propan-2-yl acetate |

TABLE 2-continued

Compounds

| No. | Structure | Name |
|---|---|---|
| A6 | 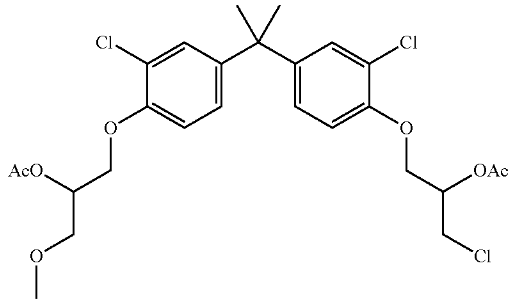 [SMILES: COCC(COc1ccc(C(C)(C)c2ccc(OCC(CCl)OC(C)=O)c(Cl)c2)cc1Cl)OC(C)=O] | 1-(4-(2-(4-(2-acetoxy-3-chloropropoxy)-3-chlorophenyl)propan-2-yl)-2-chlorophenoxy)-3-methoxypropan-2-yl acetate |
| A6a | 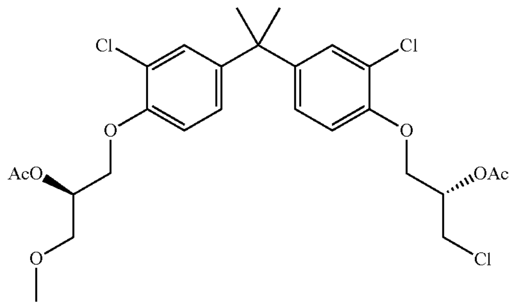 [SMILES: COC[C@H](COc1ccc(C(C)(C)c2ccc(OC[C@@H](CCl)OC(C)=O)c(Cl)c2)cc1Cl)OC(C)=O] | (R)-1-(4-(2-(4-((S)-2-acetoxy-3-chloropropoxy)-3-chlorophenyl)propan-2-yl)-2-chlorophenoxy)-3-methoxypropan-2-yl acetate |
| A6b | 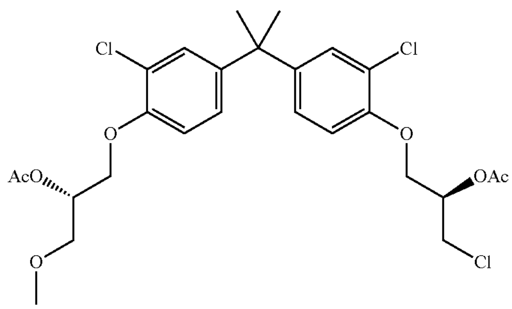 [SMILES: COC[C@@H](COc1ccc(C(C)(C)c2ccc(OC[C@H](CCl)OC(C)=O)c(Cl)c2)cc1Cl)OC(C)=O] | (S)-1-(4-(2-(4-((R)-2-acetoxy-3-chloropropoxy)-3-chlorophenyl)propan-2-yl)-2-chlorophenoxy)-3-methoxypropan-2-yl acetate |
| A6c | 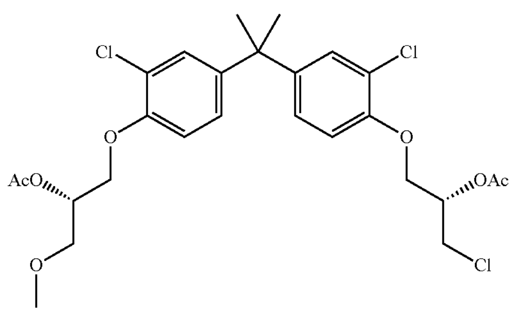 [SMILES: COC[C@@H](COc1ccc(C(C)(C)c2ccc(OC[C@@H](CCl)OC(C)=O)c(Cl)c2)cc1Cl)OC(C)=O] | (S)-1-(4-(2-(4-((S)-2-acetoxy-3-chloropropoxy)-3-chlorophenyl)propan-2-yl)-2-chlorophenoxy)-3-methoxypropan-2-yl acetate |
| A6d | 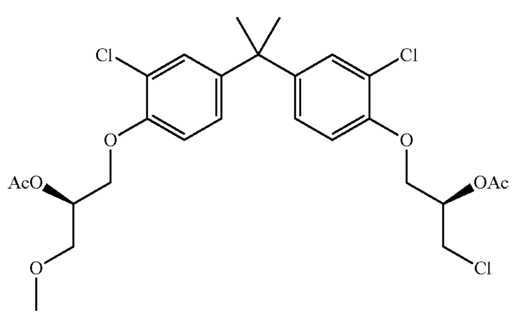 [SMILES: COC[C@H](COc1ccc(C(C)(C)c2ccc(OC[C@H](CCl)OC(C)=O)c(Cl)c2)cc1Cl)OC(C)=O] | (R)-1-(4-(2-(4-((R)-2-acetoxy-3-chloropropoxy)-3-chlorophenyl)propan-2-yl)-2-chlorophenoxy)-3-methoxypropan-2-yl acetate |

TABLE 2-continued

Compounds

| No. | Structure | Name |
|---|---|---|
| A7 | 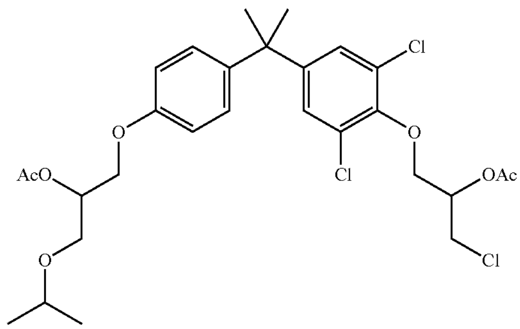 | 1-(4-(2-(4-(2-acetoxy-3-chloropropoxy)-3,5-dichlorophenyl)propan-2-yl)phenoxy)-3-isopropoxypropan-2-yl acetate |
| A7a | 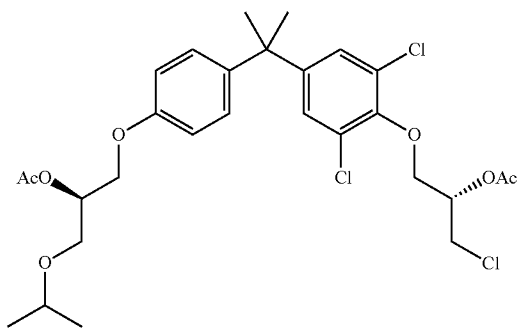 [SMILES: CC(=O)O[C@H](CCl)COc1c(Cl)cc(C(C)(C)c2ccc(OC[C@@H](COC(C)C)OC(C)=O)cc2)cc1Cl] | (R)-1-(4-(2-(4-((S)-2-acetoxy-3-chloropropoxy)-3,5-dichlorophenyl)propan-2-yl)phenoxy)-3-isopropoxypropan-2-yl acetate |
| A7b | 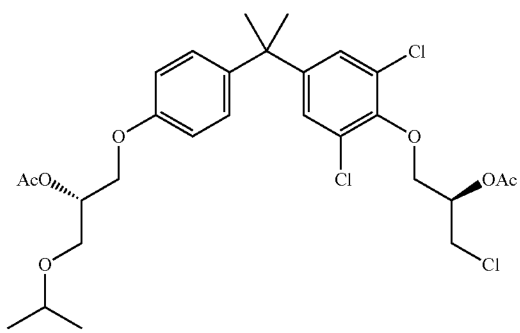 | (S)-1-(4-(2-(4-((R)-2-acetoxy-3-chloropropoxy)-3,5-dichlorophenyl)propan-2-yl)phenoxy)-3-isopropoxypropan-2-yl acetate |
| A7c | 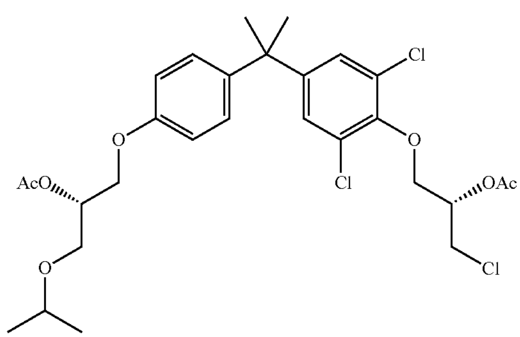 [SMILES: CC(=O)O[C@H](CCl)COc1c(Cl)cc(C(C)(C)c2ccc(OC[C@H](COC(C)C)OC(C)=O)cc2)cc1Cl] | (S)-1-(4-(2-(4-((S)-2-acetoxy-3-chloropropoxy)-3,5-dichlorophenyl)propan-2-yl)phenoxy)-3-isopropoxypropan-2-yl acetate |

TABLE 2-continued

| No. | Structure | Name |
|---|---|---|
| A7d | 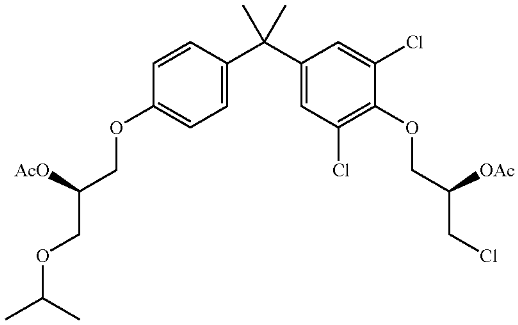 [SMILES: CC(=O)O[C@@H](CCl)COc1c(Cl)cc(C(C)(C)c2ccc(OC[C@@H](COC(C)C)OC(C)=O)cc2)cc1Cl] | (R)-1-(4-(2-(4-((R)-2-acetoxy-3-chloropropoxy)-3,5-dichlorophenyl)propan-2-yl)phenoxy)-3-isopropoxypropan-2-yl acetate |
| B7 | 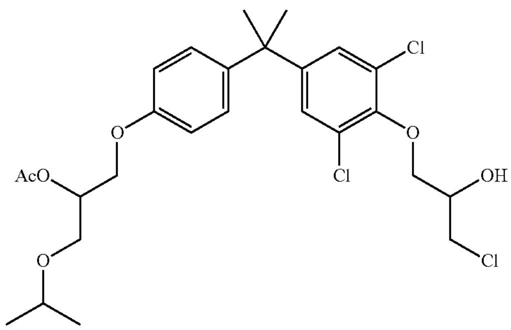 [SMILES: CC(=O)OC(COc1ccc(C(C)(C)c2cc(Cl)c(OCC(O)CCl)c(Cl)c2)cc1)COC(C)C] | 1-(4-(2-(3,5-dichloro-4-(3-chloro-2-hydroxypropoxy)phenyl)propan-2-yl)phenoxy)-3-isopropoxypropan-2-yl acetate |
| B7a | 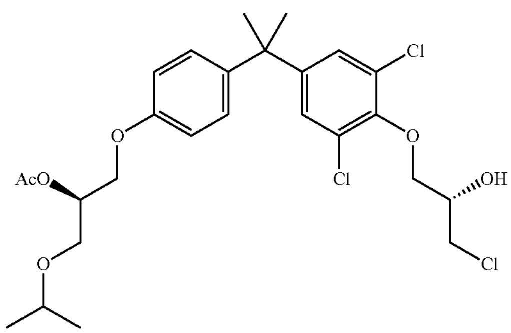 [SMILES: CC(=O)O[C@@H](COc1ccc(C(C)(C)c2cc(Cl)c(OC[C@H](O)CCl)c(Cl)c2)cc1)COC(C)C] | (R)-1-(4-(2-(3,5-dichloro-4-((S)-3-chloro-2-hydroxypropoxy)phenyl)propan-2-yl)phenoxy)-3-isopropoxypropan-2-yl acetate |
| B7b | 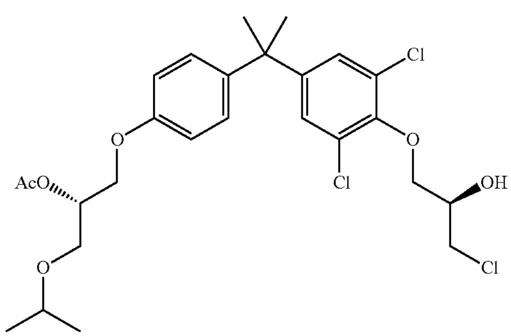 | (S)-1-(4-(2-(3,5-dichloro-4-((R)-3-chloro-2-hydroxypropoxy)phenyl)propan-2-yl)phenoxy)-3-isopropoxypropan-2-yl acetate |

TABLE 2-continued

| No. | Structure | Name |
|---|---|---|
| B7c | 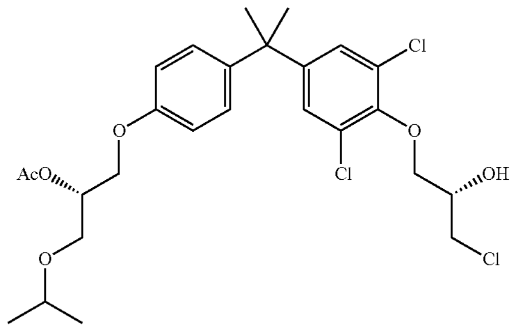 [SMILES: CC(=O)O[C@H](COc1ccc(C(C)(C)c2cc(Cl)c(OC[C@H](O)CCl)c(Cl)c2)cc1)COC(C)C] | (S)-1-(4-(2-(3,5-dichloro-4-((S)-3-chloro-2-hydroxypropoxy)phenyl)propan-2-yl)phenoxy)-3-isopropoxypropan-2-yl acetate |
| B7d | 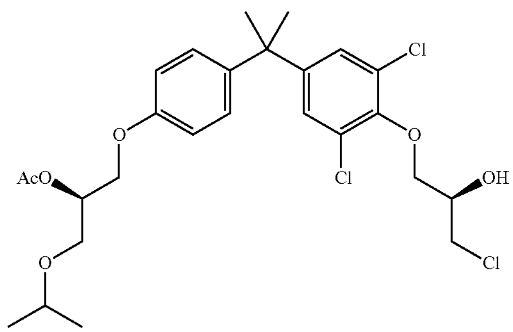 [SMILES: CC(=O)O[C@@H](COc1ccc(C(C)(C)c2cc(Cl)c(OC[C@@H](O)CCl)c(Cl)c2)cc1)COC(C)C] | (R)-1-(4-(2-(3,5-dichloro-4-((R)-3-chloro-2-hydroxypropoxy)phenyl)propan-2-yl)phenoxy)-3-isopropoxypropan-2-yl acetate |
| C7 | 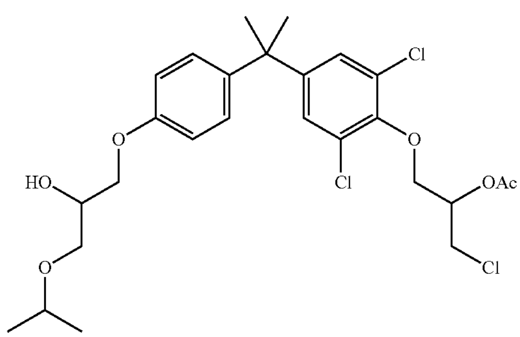 [SMILES: CC(=O)OC(CCl)COc1c(Cl)cc(C(C)(C)c2ccc(OCC(O)COC(C)C)cc2)cc1Cl] | 1-chloro-3-(2,6-dichloro-4-(2-(4-(2-hydroxy-3-isopropoxypropoxy)phenyl)propan-2-yl)phenoxy)propan-2-yl acetate |
| C7a | 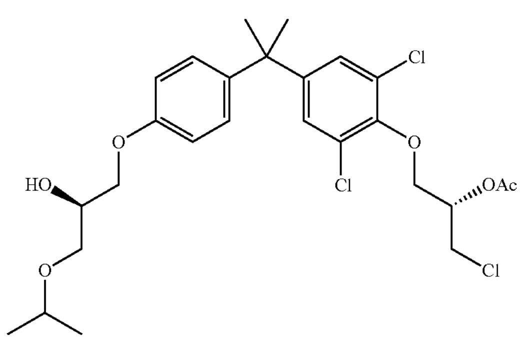 [SMILES: CC(=O)O[C@H](CCl)COc1c(Cl)cc(C(C)(C)c2ccc(OC[C@H](O)COC(C)C)cc2)cc1Cl] | (S)-1-chloro-3-(2,6-dichloro-4-(2-(4-((R)-2-hydroxy-3-isopropoxypropoxy)phenyl)propan-2-yl)phenoxy)propan-2-yl acetate |

TABLE 2-continued

Compounds

| No. | Structure | Name |
|---|---|---|
| C7b | 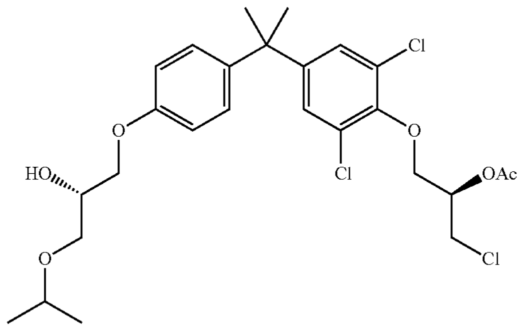 [SMILES: CC(=O)O[C@@H](CCl)COc1c(Cl)cc(C(C)(C)c2ccc(OC[C@@H](O)COC(C)C)cc2)cc1Cl] | (R)-1-chloro-3-(2,6-dichloro-4-(2-(4-((S)-2-hydroxy-3-isopropoxypropoxy)phenyl)propan-2-yl)phenoxy)propan-2-yl acetate |
| C7c | 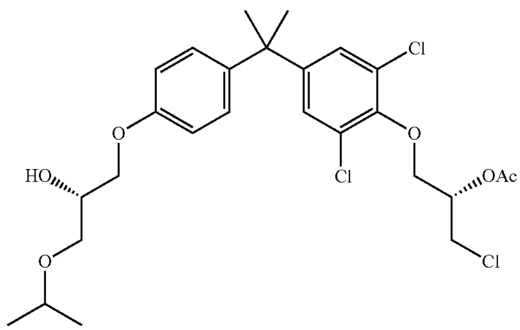 [SMILES: CC(=O)O[C@H](CCl)COc1c(Cl)cc(C(C)(C)c2ccc(OC[C@@H](O)COC(C)C)cc2)cc1Cl] | (S)-1-chloro-3-(2,6-dichloro-4-(2-(4-((S)-2-hydroxy-3-isopropoxypropoxy)phenyl)propan-2-yl)phenoxy)propan-2-yl acetate |
| C7d | 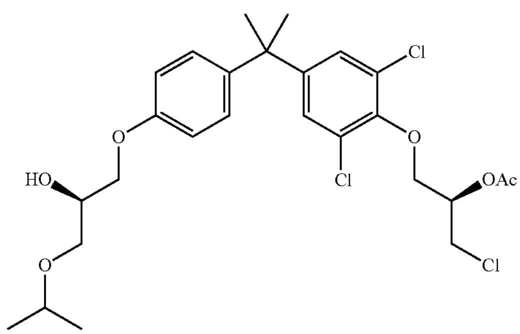 [SMILES: CC(=O)O[C@@H](CCl)COc1c(Cl)cc(C(C)(C)c2ccc(OC[C@H](O)COC(C)C)cc2)cc1Cl] | (R)-1-chloro-3-(2,6-dichloro-4-(2-(4-((R)-2-hydroxy-3-isopropoxypropoxy)phenyl)propan-2-yl)phenoxy)propan-2-yl acetate |
| A8 | 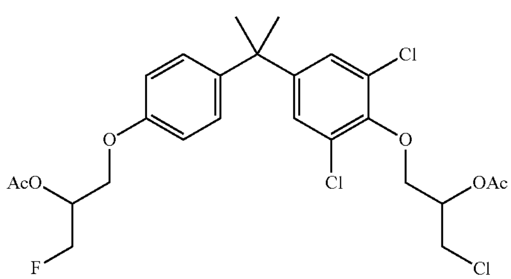 [SMILES: CC(=O)OC(CF)COc1ccc(C(C)(C)c2cc(Cl)c(OCC(CCl)OC(C)=O)c(Cl)c2)cc1] | 1-(4-(2-(4-(2-acetoxy-3-chloropropoxy)-3,5-dichlorophenyl)propan-2-yl)phenoxy)-3-fluoropropan-2-yl acetate |
| A8a | 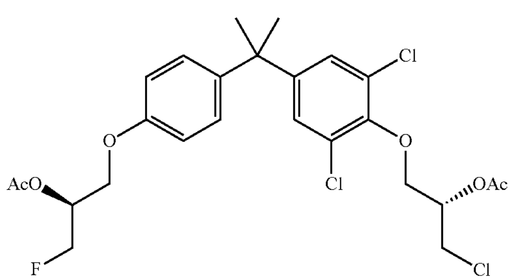 [SMILES: CC(=O)O[C@H](CF)COc1ccc(C(C)(C)c2cc(Cl)c(OC[C@@H](CCl)OC(C)=O)c(Cl)c2)cc1] | (S)-1-(4-(2-(4-((S)-2-acetoxy-3-chloropropoxy)-3,5-dichlorophenyl)propan-2-yl)phenoxy)-3-fluoropropan-2-yl acetate |

TABLE 2-continued

| No. | Structure | Name |
|---|---|---|
| A8b | 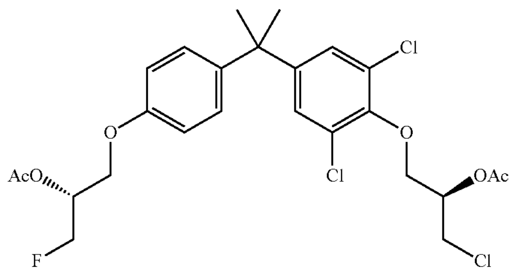 [SMILES: CC(=O)O[C@@H](CF)COc1ccc(C(C)(C)c2cc(Cl)c(OC[C@H](CCl)OC(C)=O)c(Cl)c2)cc1] | (R)-1-(4-(2-(4-((R)-2-acetoxy-3-chloropropoxy)-3,5-dichlorophenyl)propan-2-yl)phenoxy)-3-fluoropropan-2-yl acetate |
| A8c | 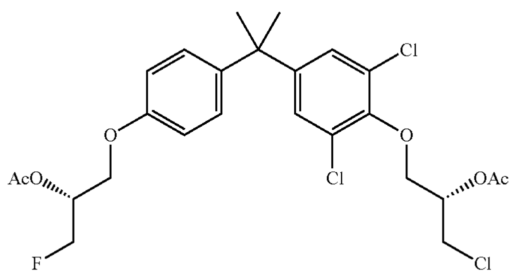 [SMILES: CC(=O)O[C@H](CCl)COc1c(Cl)cc(C(C)(C)c2ccc(OC[C@H](CF)OC(C)=O)cc2)cc1Cl] | (R)-1-(4-(2-(4-((S)-2-acetoxy-3-chloropropoxy)-3,5-dichlorophenyl)propan-2-yl)phenoxy)-3-fluoropropan-2-yl acetate |
| A8d | 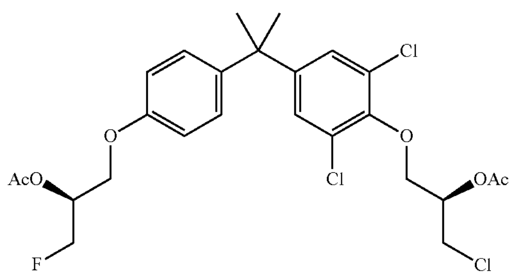 [SMILES: CC(=O)O[C@H](CF)COc1ccc(C(C)(C)c2cc(Cl)c(OC[C@H](CCl)OC(C)=O)c(Cl)c2)cc1] | (S)-1-(4-(2-(4-((R)-2-acetoxy-3-chloropropoxy)-3,5-dichlorophenyl)propan-2-yl)phenoxy)-3-fluoropropan-2-yl acetate |
| A9 | 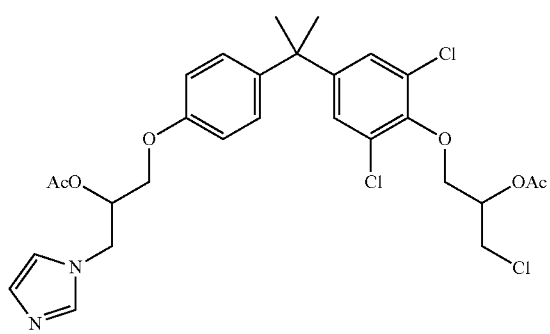 | 1-(4-(2-(4-(2-acetoxy-3-(1H-imidazol-1-yl)propoxy)phenyl)propan-2-yl)-2,6-dichlorophenoxy)-3-chloropropan-2-yl acetate |
| A9a | 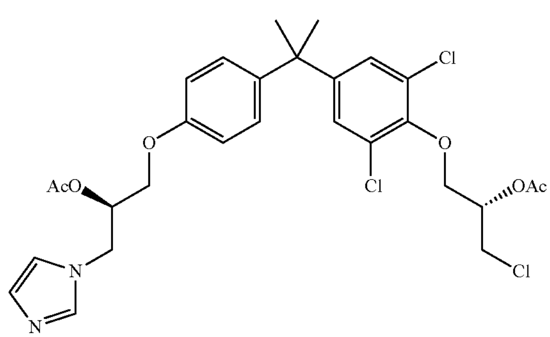 [SMILES: CC(=O)O[C@H](CCl)COc1c(Cl)cc(C(C)(C)c2ccc(OC[C@@H](Cn3ccnc3)OC(C)=O)cc2)cc1Cl] | (S)-1-(4-(2-(4-((R)-2-acetoxy-3-(1H-imidazol-1-yl)propoxy)phenyl)propan-2-yl)-2,6-dichlorophenoxy)-3-chloropropan-2-yl acetate |

TABLE 2-continued

| No. | Structure | Name |
|---|---|---|
| A9b | 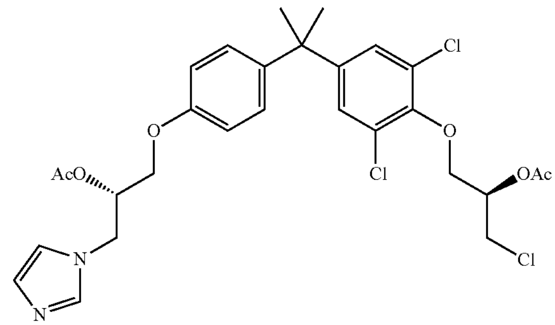 | (R)-1-(4-(2-(4-((S)-2-acetoxy-3-(1H-imidazol-1-yl)propoxy)phenyl)propan-2-yl)-2,6-dichlorophenoxy)-3-chloropropan-2-yl acetate |
| A9c | 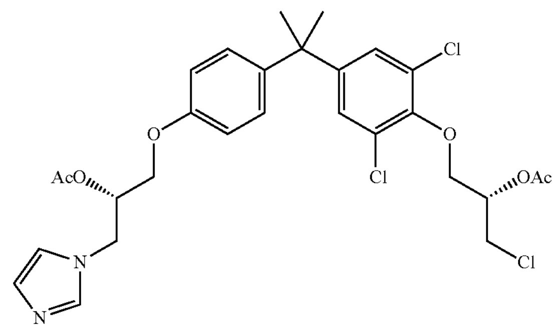 [SMILES: CC(=O)O[C@H](CCl)COc1c(Cl)cc(C(C)(C)c2ccc(OC[C@H](Cn3ccnc3)OC(C)=O)cc2)cc1Cl] | ((S)-1-(4-(2-(4-((S)-2-acetoxy-3-(1H-imidazol-1-yl)propoxy)phenyl)propan-2-yl)-2,6-dichlorophenoxy)-3-chloropropan-2-yl acetate |
| A9d | 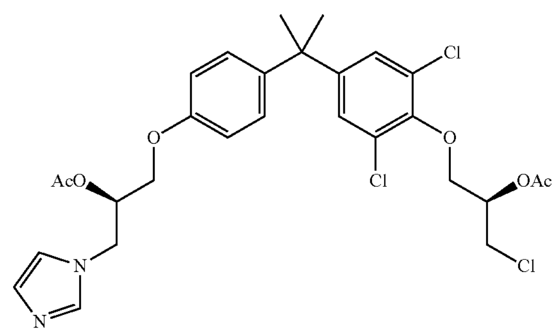 [SMILES: CC(=O)O[C@@H](CCl)COc1c(Cl)cc(C(C)(C)c2ccc(OC[C@@H](Cn3ccnc3)OC(C)=O)cc2)cc1Cl] | (R)-1-(4-(2-(4-((R)-2-acetoxy-3-(1H-imidazol-1-yl)propoxy)phenyl)propan-2-yl)-2,6-dichlorophenoxy)-3-chloropropan-2-yl acetate |
| B9 | 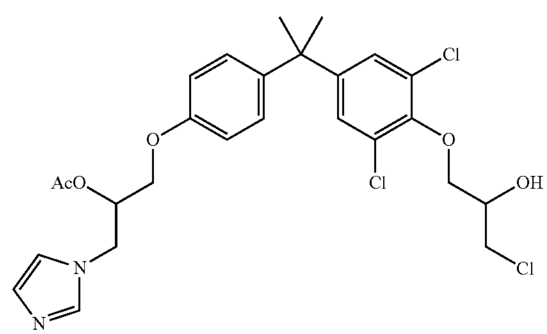 | 1-(4-(2-(3,5-dichloro-4-(3-chloro-2-hydroxypropoxy)phenyl)propan-2-yl)phenoxy)-3-(1H-imidazol-1-yl)propan-2-yl acetate |

TABLE 2-continued

| No. | Structure | Name |
|---|---|---|
| B9a | 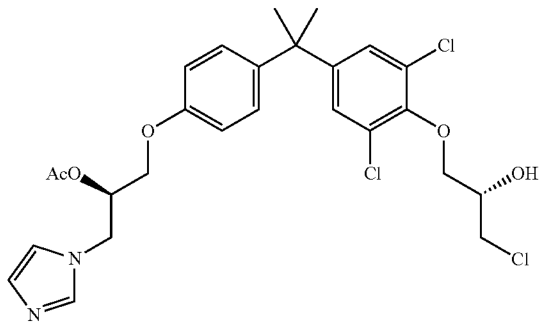 [SMILES: CC(=O)O[C@@H](COc1ccc(C(C)(C)c2cc(Cl)c(OC[C@H](O)CCl)c(Cl)c2)cc1)Cn1ccnc1] | (R)-1-(4-(2-(3,5-dichloro-4-((S)-3-chloro-2-hydroxypropoxy)phenyl)propan-2-yl)phenoxy)-3-(1H-imidazol-1-yl)propan-2-yl acetate |
| B9b | 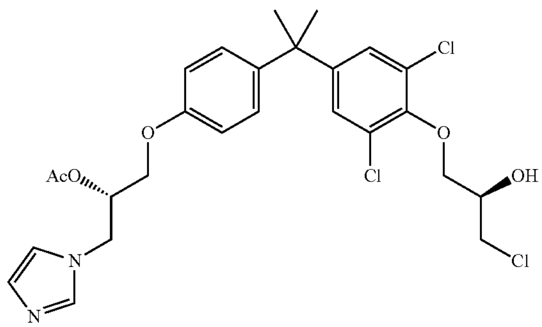 [SMILES: CC(=O)O[C@H](COc1ccc(C(C)(C)c2cc(Cl)c(OC[C@@H](O)CCl)c(Cl)c2)cc1)Cn1ccnc1] | (S)-1-(4-(2-(3,5-dichloro-4-((R)-3-chloro-2-hydroxypropoxy)phenyl)propan-2-yl)phenoxy)-3-(1H-imidazol-1-yl)propan-2-yl acetate |
| B9c | 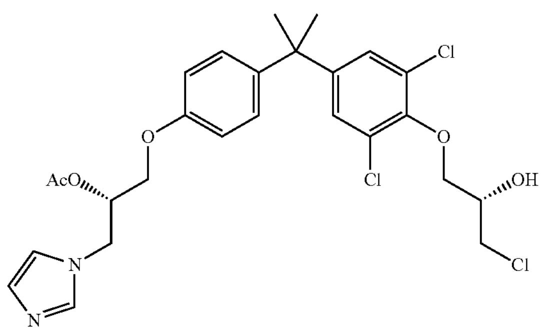 [SMILES: CC(=O)O[C@H](COc1ccc(C(C)(C)c2cc(Cl)c(OC[C@H](O)CCl)c(Cl)c2)cc1)Cn1ccnc1] | (S)-1-(4-(2-(3,5-dichloro-4-((S)-3-chloro-2-hydroxypropoxy)phenyl)propan-2-yl)phenoxy)-3-(1H-imidazol-1-yl)propan-2-yl acetate |
| B9d | 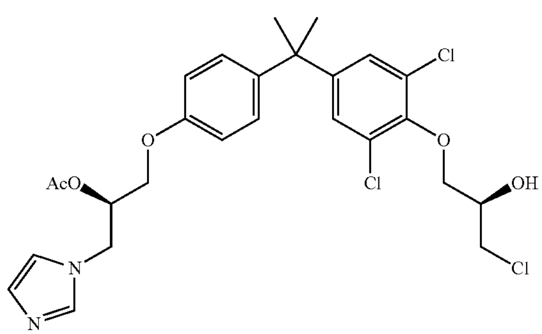 [SMILES: CC(=O)O[C@@H](COc1ccc(C(C)(C)c2cc(Cl)c(OC[C@@H](O)CCl)c(Cl)c2)cc1)Cn1ccnc1] | (R)-1-(4-(2-(3,5-dichloro-4-((R)-3-chloro-2-hydroxypropoxy)phenyl)propan-2-yl)phenoxy)-3-(1H-imidazol-1-yl)propan-2-yl acetate |

TABLE 2-continued

| No. | Structure | Name |
|---|---|---|
| C9 | 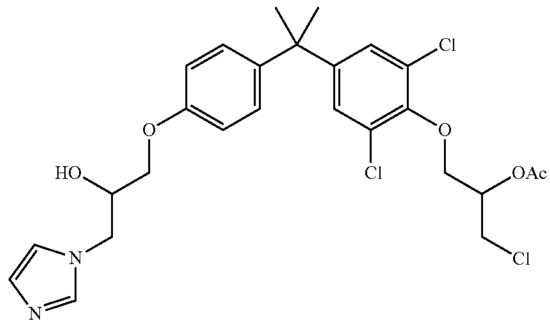 [SMILES: CC(=O)OC(CCl)COc1c(Cl)cc(C(C)(C)c2ccc(OCC(O)Cn3ccnc3)cc2)cc1Cl] | 1-chloro-3-(2,6-dichloro-4-(2-(4-(2-hydroxy-3-(1H-imidazol-1-yl)propoxy)phenyl)propan-2-yl)phenoxy)propan-2-yl acetate |
| C9a | 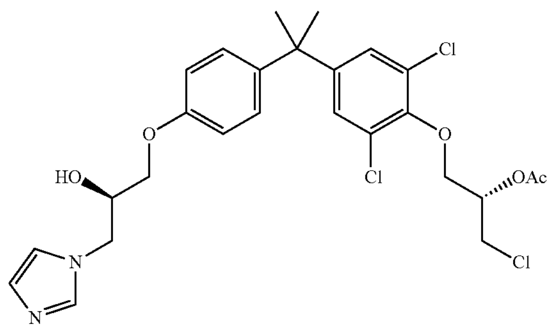 [SMILES: CC(=O)O[C@H](CCl)COc1c(Cl)cc(C(C)(C)c2ccc(OC[C@H](O)Cn3ccnc3)cc2)cc1Cl] | (S)-1-chloro-3-(2,6-dichloro-4-(2-(4-((R)-2-hydroxy-3-(1H-imidazol-1-yl)propoxy)phenyl)propan-2-yl)phenoxy)propan-2-yl acetate |
| C9b | 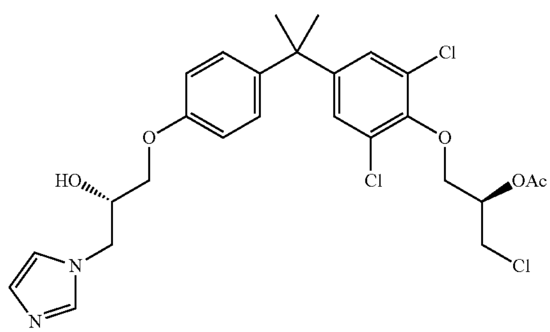 [SMILES: CC(=O)O[C@@H](CCl)COc1c(Cl)cc(C(C)(C)c2ccc(OC[C@@H](O)Cn3ccnc3)cc2)cc1Cl] | (R)-1-chloro-3-(2,6-dichloro-4-(2-(4-((S)-2-hydroxy-3-(1H-imidazol-1-yl)propoxy)phenyl)propan-2-yl)phenoxy)propan-2-yl acetate |
| C9c | 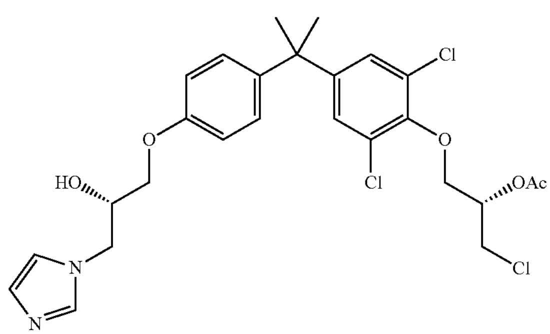 [SMILES: CC(=O)O[C@H](CCl)COc1c(Cl)cc(C(C)(C)c2ccc(OC[C@@H](O)Cn3ccnc3)cc2)cc1Cl] | (S)-1-chloro-3-(2,6-dichloro-4-(2-(4-((S)-2-hydroxy-3-(1H-imidazol-1-yl)propoxy)phenyl)propan-2-yl)phenoxy)propan-2-yl acetate |

TABLE 2-continued

| No. | Structure | Name |
|---|---|---|
| C9d | 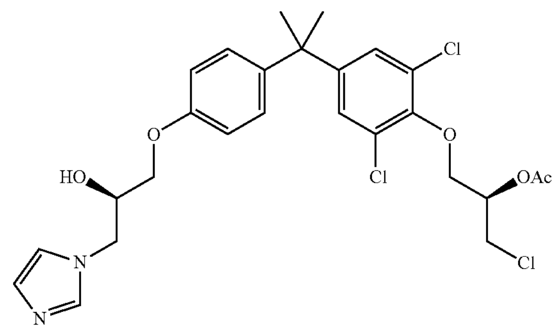 [SMILES: CC(=O)O[C@@H](CCl)COc1c(Cl)cc(C(C)(C)c2ccc(OC[C@H](O)Cn3ccnc3)cc2)cc1Cl] | (R)-1-chloro-3-(2,6-dichloro-4-(2-(4-((R)-2-hydroxy-3-(1H-imidazol-1-yl)propoxy)phenyl)propan-2-yl)phenoxy)propan-2-yl acetate |
| A10 | 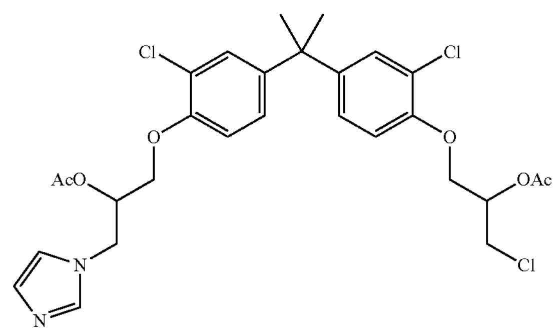 [SMILES: CC(=O)OC(CCl)COc1ccc(C(C)(C)c2ccc(OCC(Cn3ccnc3)OC(C)=O)c(Cl)c2)cc1Cl] | 1-(4-(2-(4-(2-acetoxy-3-(1H-imidazol-1-yl)propoxy)-3-chlorophenyl)propan-2-yl)-2-chlorophenoxy)-3-chloropropan-2-yl acetate |
| A10a | 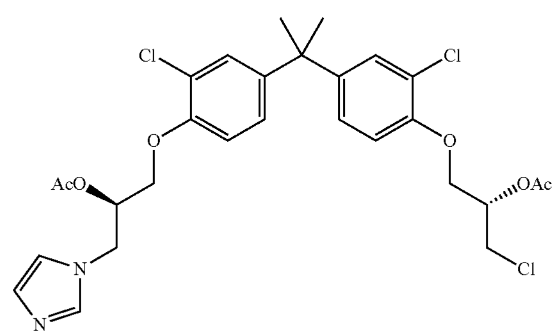 [SMILES: CC(=O)O[C@H](CCl)COc1ccc(C(C)(C)c2ccc(OC[C@@H](Cn3ccnc3)OC(C)=O)c(Cl)c2)cc1Cl] | (S)-1-(4-(2-(4-((R)-2-acetoxy-3-(1H-imidazol-1-yl)propoxy)-3-chlorophenyl)propan-2-yl)-2-chlorophenoxy)-3-chloropropan-2-yl acetate |
| A10b | 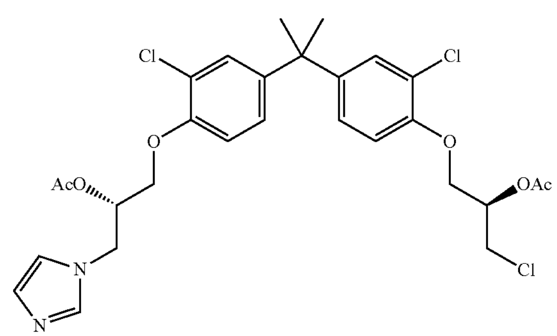 [SMILES: CC(=O)O[C@H](COc1ccc(C(C)(C)c2ccc(OC[C@H](CCl)OC(C)=O)c(Cl)c2)cc1Cl)Cn1ccnc1] | (R)-1-(4-(2-(4-((S)-2-acetoxy-3-(1H-imidazol-1-yl)propoxy)-3-chlorophenyl)propan-2-yl)-2-chlorophenoxy)-3-chloropropan-2-yl acetate |

TABLE 2-continued

| No. | Structure | Name |
|---|---|---|
| A10c | 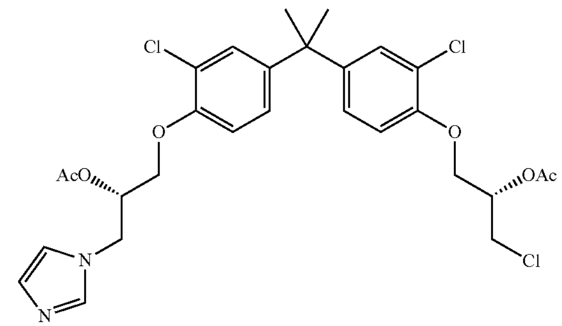 [SMILES: CC(=O)O[C@H](CCl)COc1ccc(C(C)(C)c2ccc(OC[C@H](Cn3ccnc3)OC(C)=O)c(Cl)c2)cc1Cl] | (S)-1-(4-(2-(4-(((S)-2-acetoxy-3-(1H-imidazol-1-yl)propoxy)-3-chlorophenyl)propan-2-yl)-2-chlorophenoxy)-3-chloropropan-2-yl acetate |
| A10d | 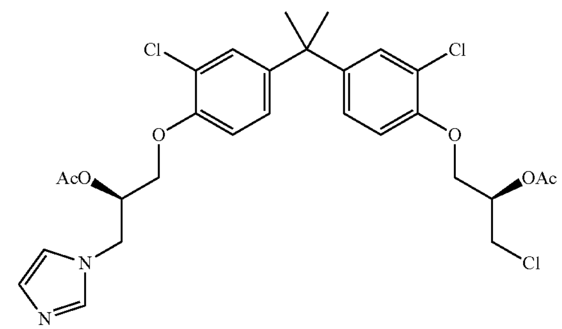 [SMILES: CC(=O)O[C@@H](CCl)COc1ccc(C(C)(C)c2ccc(OC[C@@H](Cn3ccnc3)OC(C)=O)c(Cl)c2)cc1Cl] | (R)-1-(4-(2-(4-(((R)-2-acetoxy-3-(1H-imidazol-1-yl)propoxy)-3-chlorophenyl)propan-2-yl)-2-chlorophenoxy)-3-chloropropan-2-yl acetate |
| A11 | 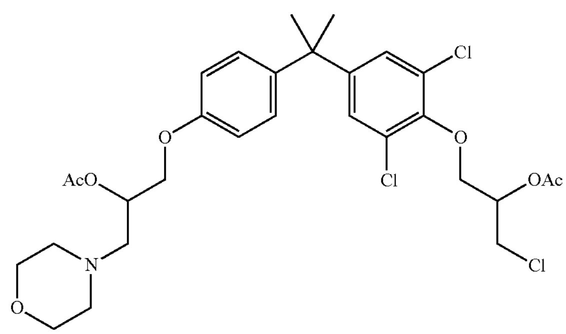 [SMILES: CC(=O)OC(CCl)COc1c(Cl)cc(C(C)(C)c2ccc(OCC(CN3CCOCC3)OC(C)=O)cc2)cc1Cl] | 1-(4-(2-(4-(2-acetoxy-3-chloropropoxy)-3,5-dichlorophenyl)propan-2-yl)phenoxy)-3-morpholinopropan-2-yl acetate |
| A11a | 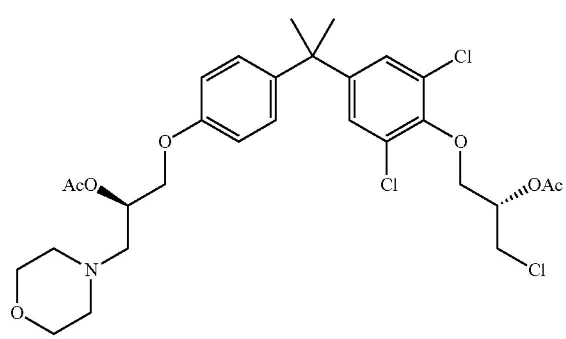 [SMILES: CC(=O)O[C@H](CCl)COc1c(Cl)cc(C(C)(C)c2ccc(OC[C@@H](CN3CCOCC3)OC(C)=O)cc2)cc1Cl] | (R)-1-(4-(2-(4-(((S)-2-acetoxy-3-chloropropoxy)-3,5-dichlorophenyl)propan-2-yl)phenoxy)-3-morpholinopropan-2-yl acetate |

TABLE 2-continued

Compounds

| No. | Structure | Name |
|---|---|---|
| A11b | 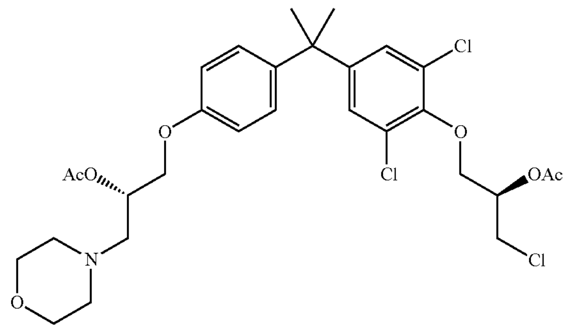 [SMILES: CC(=O)O[C@H](COc1ccc(C(C)(C)c2cc(Cl)c(OC[C@H](CCl)OC(C)=O)c(Cl)c2)cc1)CN1CCOCC1] | (S)-1-(4-(2-(4-((R)-2-acetoxy-3-chloropropoxy)-3,5-dichlorophenyl)propan-2-yl)phenoxy)-3-morpholinopropan-2-yl acetate |
| A11c | 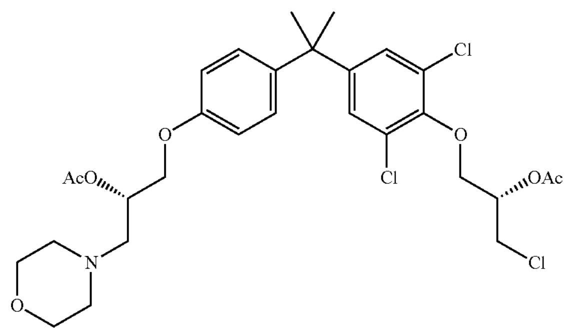 [SMILES: CC(=O)O[C@H](CCl)COc1c(Cl)cc(C(C)(C)c2ccc(OC[C@H](CN3CCOCC3)OC(C)=O)cc2)cc1Cl] | (S)-1-(4-(2-(4-((S)-2-acetoxy-3-chloropropoxy)-3,5-dichlorophenyl)propan-2-yl)phenoxy)-3-morpholinopropan-2-yl acetate |
| A11d | 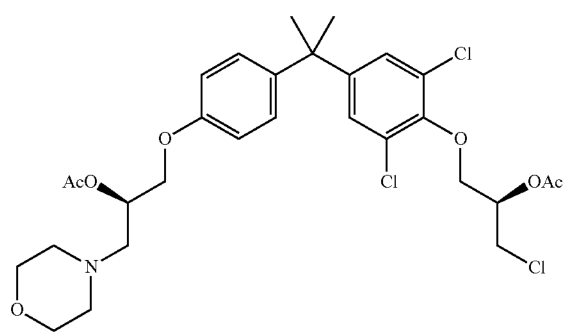 [SMILES: CC(=O)O[C@@H](CCl)COc1c(Cl)cc(C(C)(C)c2ccc(OC[C@@H](CN3CCOCC3)OC(C)=O)cc2)cc1Cl] | (R)-1-(4-(2-(4-((R)-2-acetoxy-3-chloropropoxy)-3,5-dichlorophenyl)propan-2-yl)phenoxy)-3-morpholinopropan-2-yl acetate |
| B11 | 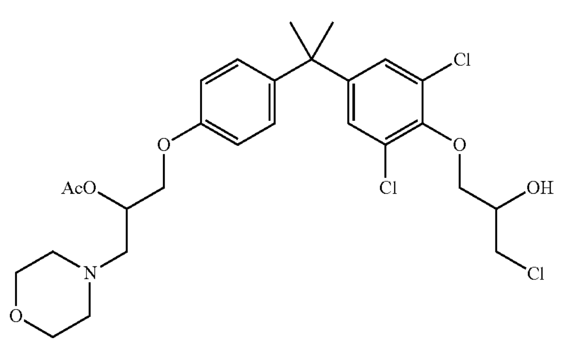 [SMILES: CC(=O)OC(COc1ccc(C(C)(C)c2cc(Cl)c(OCC(O)CCl)c(Cl)c2)cc1)CN1CCOCC1] | 1-(4-(2-(3,5-dichloro-4-(3-chloro-2-hydroxypropoxy)phenyl)propan-2-yl)phenoxy)-3-morpholinopropan-2-yl acetate |

TABLE 2-continued

| No. | Structure | Name |
|---|---|---|
| B11a | 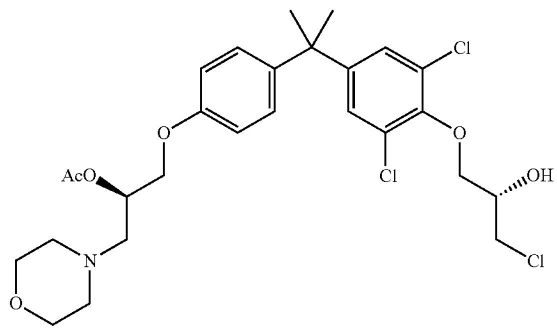 [SMILES: CC(=O)O[C@@H](COc1ccc(C(C)(C)c2cc(Cl)c(OC[C@H](O)CCl)c(Cl)c2)cc1)CN1CCOCC1] | (R)-1-(4-(2-(3,5-dichloro-4-((S)-3-chloro-2-hydroxypropoxy)phenyl)propan-2-yl)phenoxy)-3-morpholinopropan-2-yl acetate |
| B11b | 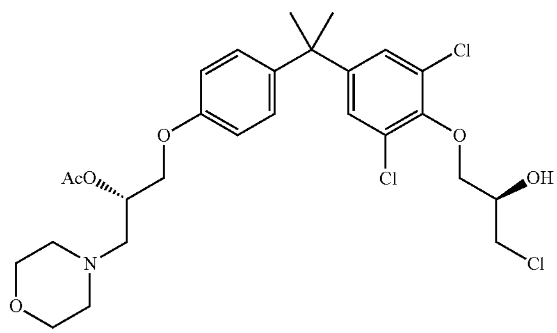 | (S)-1-(4-(2-(3,5-dichloro-4-((R)-3-chloro-2-hydroxypropoxy)phenyl)propan-2-yl)phenoxy)-3-morpholinopropan-2-yl acetate |
| B11c | 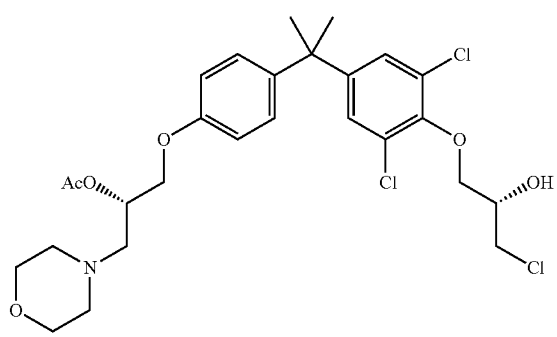 [SMILES: CC(=O)O[C@H](COc1ccc(C(C)(C)c2cc(Cl)c(OC[C@H](O)CCl)c(Cl)c2)cc1)CN1CCOCC1] | (S)-1-(4-(2-(3,5-dichloro-4-((S)-3-chloro-2-hydroxypropoxy)phenyl)propan-2-yl)phenoxy)-3-morpholinopropan-2-yl acetate |
| B11d | 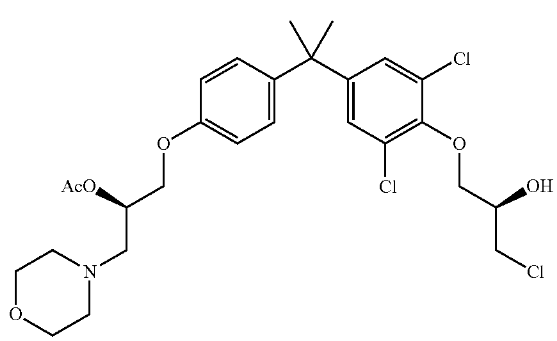 [SMILES: CC(=O)O[C@@H](COc1ccc(C(C)(C)c2cc(Cl)c(OC[C@@H](O)CCl)c(Cl)c2)cc1)CN1CCOCC1] | (R)-1-(4-(2-(3,5-dichloro-4-((R)-3-chloro-2-hydroxypropoxy)phenyl)propan-2-yl)phenoxy)-3-morpholinopropan-2-yl acetate |

TABLE 2-continued

| No. | Structure | Name |
|---|---|---|
| C11 | 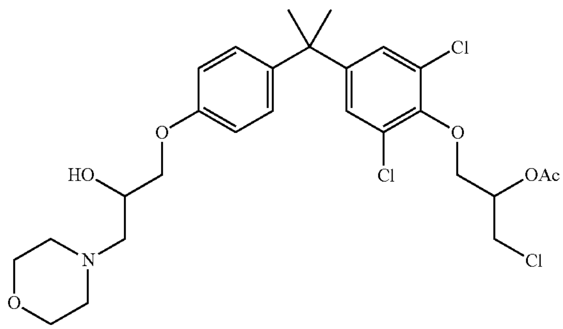 [SMILES: CC(=O)OC(CCl)COc1c(Cl)cc(C(C)(C)c2ccc(OCC(O)CN3CCOCC3)cc2)cc1Cl] | 1-chloro-3-(2,6-dichloro-4-(2-(4-(2-hydroxy-3-morpholinopropoxy)phenyl)propan-2-yl)phenoxy)propan-2-yl acetate |
| C11a | 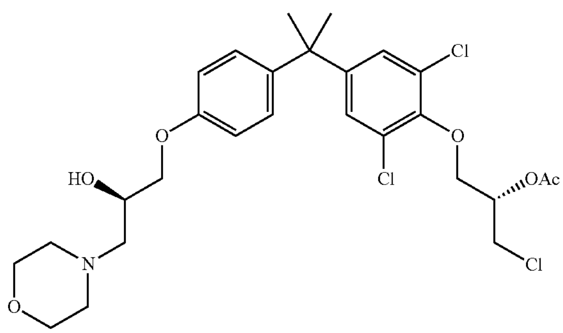 | (S)-1-chloro-3-(2,6-dichloro-4-(2-(4-((R)-2-hydroxy-3-morpholinopropoxy)phenyl)propan-2-yl)phenoxy)propan-2-yl acetate |
| C11b | 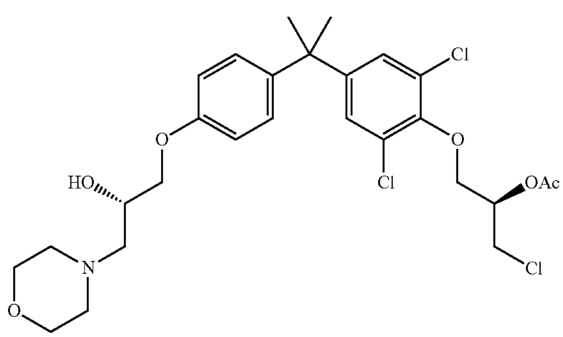 [SMILES: CC(=O)O[C@@H](CCl)COc1c(Cl)cc(C(C)(C)c2ccc(OC[C@@H](O)CN3CCOCC3)cc2)cc1Cl] | (R)-1-chloro-3-(2,6-dichloro-4-(2-(4-((S)-2-hydroxy-3-morpholinopropoxy)phenyl)propan-2-yl)phenoxy)propan-2-yl acetate |
| C11c | 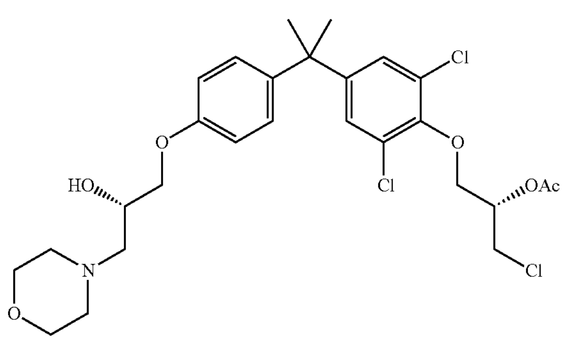 [SMILES: CC(=O)O[C@H](CCl)COc1c(Cl)cc(C(C)(C)c2ccc(OC[C@@H](O)CN3CCOCC3)cc2)cc1Cl] | (S)-1-chloro-3-(2,6-dichloro-4-(2-(4-((S)-2-hydroxy-3-morpholinopropoxy)phenyl)propan-2-yl)phenoxy)propan-2-yl acetate |

TABLE 2-continued

| No. | Structure | Name |
|---|---|---|
| C11d | 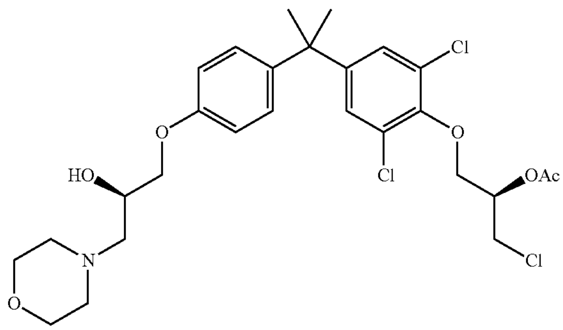 [SMILES: CC(=O)O[C@@H](CCl)COc1c(Cl)cc(C(C)(C)c2ccc(OC[C@H](O)CN3CCOCC3)cc2)cc1Cl] | (R)-1-chloro-3-(2,6-dichloro-4-(2-(4-((R)-2-hydroxy-3-morpholinopropoxy)phenyl)propan-2-yl)phenoxy)propan-2-yl acetate |
| A12 | 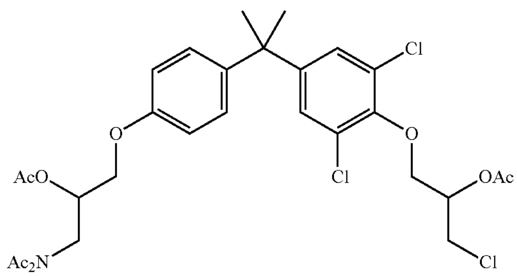 | 1-(4-(2-(4-(2-acetoxy-3-(N-acetylacetamido)propoxy)phenyl)propan-2-yl)-2,6-dichlorophenoxy)-3-chloropropan-2-yl acetate |
| A12a | 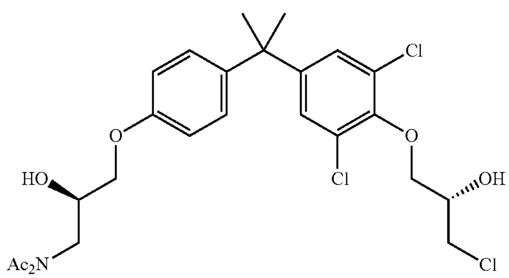 | N-acetyl-N-((R)-3-(4-(2-(3,5-dichloro-4-((S)-3-chloro-2-hydroxypropoxy)phenyl)propan-2-yl)phenoxy)-2-hydroxypropyl)acetamide |
| A12b | 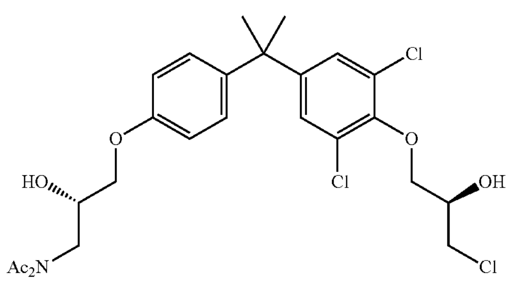 | N-acetyl-N-((R)-3-(4-(2-(3,5-dichloro-4-((S)-3-chloro-2-hydroxypropoxy)phenyl)propan-2-yl)phenoxy)-2-hydroxypropyl)acetamide |
| A12c | 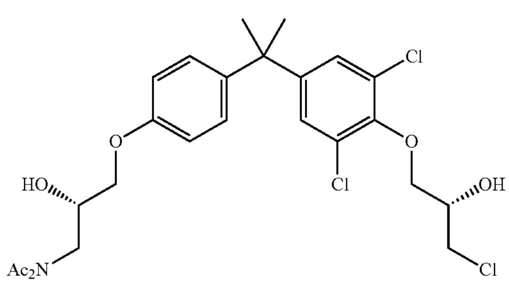 | N-acetyl-N-((S)-3-(4-(2-(3,5-dichloro-4-((S)-3-chloro-2-hydroxypropoxy)phenyl)propan-2-yl)phenoxy)-2-hydroxypropyl)acetamide |

TABLE 2-continued

| No. | Structure | Name |
|---|---|---|
| A12d | 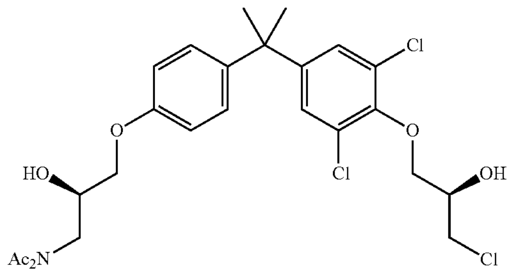 | N-acetyl-N-((R)-3-(4-(2-(3,5-dichloro-4-((R)-3-chloro-2-hydroxypropoxy)phenyl)propan-2-yl)phenoxy)-2-hydroxypropyl)acetamide |
| B12 | 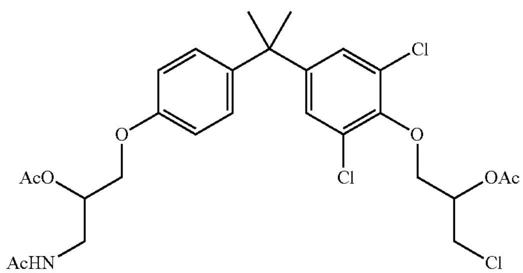 [SMILES: CC(=O)NCC(COc1ccc(C(C)(C)c2cc(Cl)c(OCC(CCl)OC(C)=O)c(Cl)c2)cc1)OC(C)=O] | 1-(4-(2-(4-(3-acetamido-2-acetoxypropoxy)phenyl)propan-2-yl)-2,6-dichlorophenoxy)-3-chloropropan-2-yl acetate |
| B12a | 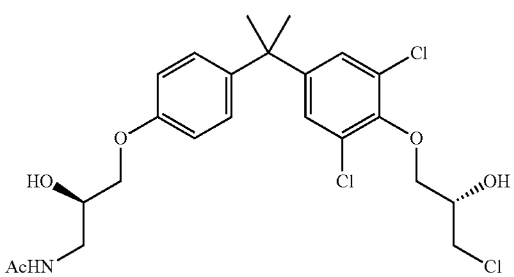 [SMILES: CC(=O)NC[C@@H](O)COc1ccc(C(C)(C)c2cc(Cl)c(OC[C@H](O)CCl)c(Cl)c2)cc1] | N-((R)-3-(4-(2-(3,5-dichloro-4-((S)-3-chloro-2-hydroxypropoxy)phenyl)propan-2-yl)phenoxy)-2-hydroxypropyl)acetamide |
| B12b | 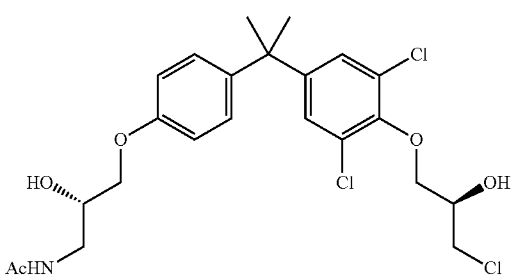 [SMILES: CC(=O)NC[C@H](O)COc1ccc(C(C)(C)c2cc(Cl)c(OC[C@@H](O)CCl)c(Cl)c2)cc1] | N-((S)-3-(4-(2-(3,5-dichloro-4-((R)-3-chloro-2-hydroxypropoxy)phenyl)propan-2-yl)phenoxy)-2-hydroxypropyl)acetamide |
| B12c | 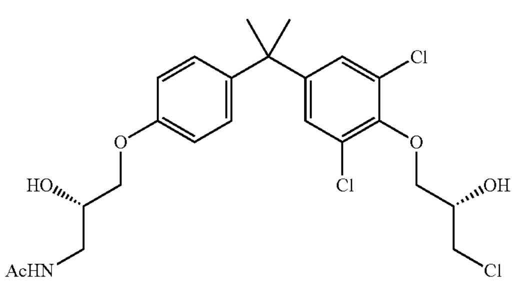 [SMILES: CC(=O)NC[C@H](O)COc1ccc(C(C)(C)c2cc(Cl)c(OC[C@H](O)CCl)c(Cl)c2)cc1] | N-((S)-3-(4-(2-(3,5-dichloro-4-((S)-3-chloro-2-hydroxypropoxy)phenyl)propan-2-yl)phenoxy)-2-hydroxypropyl)acetamide |

TABLE 2-continued

| No. | Structure | Name |
|---|---|---|
| B12d | 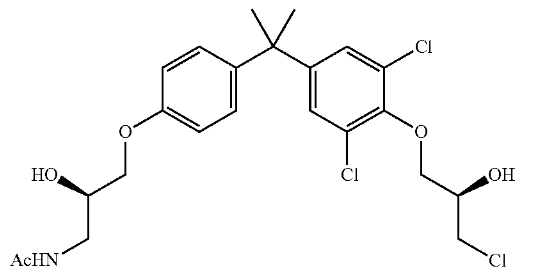 [SMILES: CC(=O)NC[C@@H](O)COc1ccc(C(C)(C)c2cc(Cl)c(OC[C@@H](O)CCl)c(Cl)c2)cc1] | N-((R)-3-(4-(2-(3,5-dichloro-4-((R)-3-chloro-2-hydroxypropoxy)phenyl)propan-2-yl)phenoxy)-2-hydroxypropyl)acetamide |
| A13 | 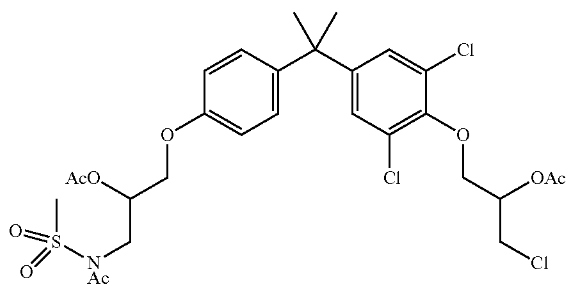 | 1-(4-(2-(4-(2-acetoxy-3-(N-(methylsulfonyl)acetamido)propoxy)phenyl)propan-2-yl)-2,6-dichlorophenoxy)-3-chloropropan-2-yl acetate |
| A13a | 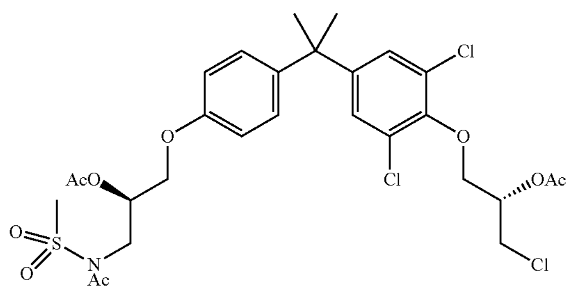 | (S)-1-(4-(2-(4-((R)-2-acetoxy-3-(N-(methylsulfonyl)acetamido)propoxy)phenyl)propan-2-yl)-2,6-dichlorophenoxy)-3-chloropropan-2-yl acetate |
| A13b | 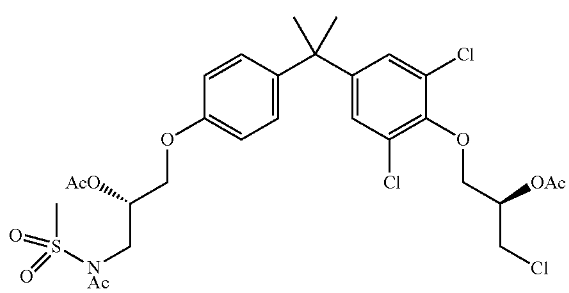 | (R)-1-(4-(2-(4-((S)-2-acetoxy-3-(N-(methylsulfonyl)acetamido)propoxy)phenyl)propan-2-yl)-2,6-dichlorophenoxy)-3-chloropropan-2-yl acetate |
| A13c | 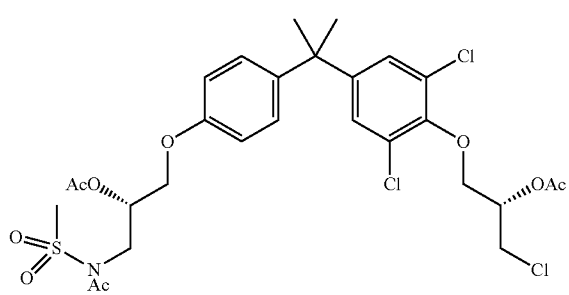 | (S)-1-(4-(2-(4-((S)-2-acetoxy-3-(N-(methylsulfonyl)acetamido)propoxy)phenyl)propan-2-yl)-2,6-dichlorophenoxy)-3-chloropropan-2-yl acetate |

TABLE 2-continued

| No. | Structure | Name |
|---|---|---|
| A13d | 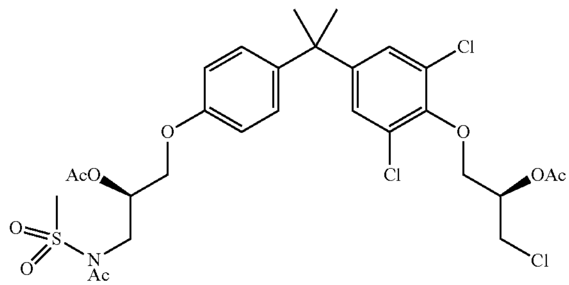 | (R)-1-(4-(2-(4-((R)-2-acetoxy-3-(N-(methylsulfonyl)acetamido)propoxy) phenyl)propan-2-yl)-2,6-dichlorophenoxy)-3-chloropropan-2-yl acetate |
| B13 | 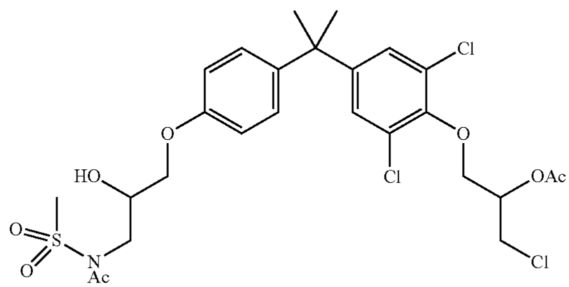 | 1-chloro-3-(2,6-dichloro-4-(2-(4-(2-hydroxy-3-(N-(methylsulfonyl)acetamido)propoxy) phenyl)propan-2-yl)phenoxy)propan-2-yl acetate |
| B13a | 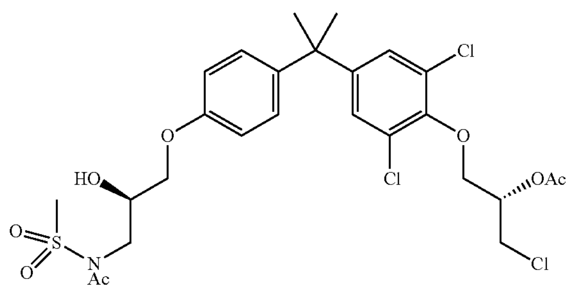 | (S)-1-chloro-3-(2,6-dichloro-4-(2-(4-((R)-2-hydroxy-3-(N-(methylsulfonyl)acetamido)propoxy) phenyl)propan-2-yl)phenoxy)propan-2-yl acetate |
| B13b | 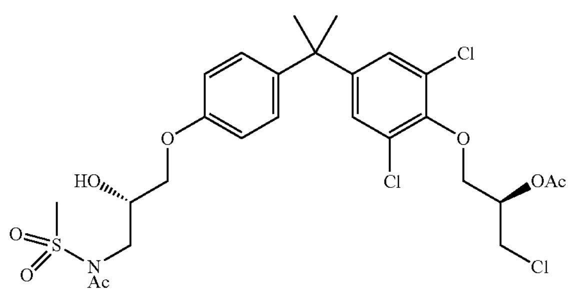 | (R)-1-chloro-3-(2,6-dichloro-4-(2-(4-((S)-2-hydroxy-3-(N-(methylsulfonyl)acetamido)propoxy) phenyl)propan-2-yl)phenoxy)propan-2-yl acetate |
| B13c | 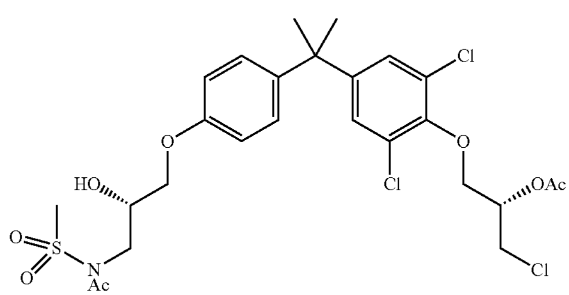 | (S)-1-chloro-3-(2,6-dichloro-4-(2-(4-((S)-2-hydroxy-3-(N-(methylsulfonyl)acetamido)propoxy) phenyl)propan-2-yl)phenoxy)propan-2-yl acetate |

TABLE 2-continued

| No. | Structure | Name |
|---|---|---|
| B13d | 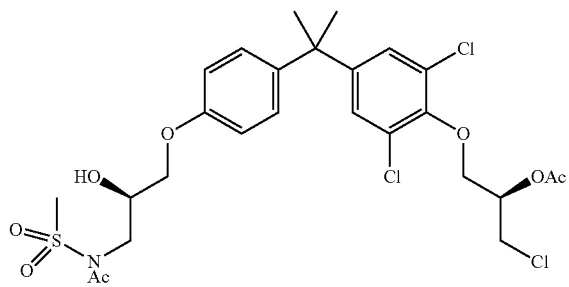 | (R)-1-chloro-3-(2,6-dichloro-4-(2-(4-((R)-2-hydroxy-3-(N-(methylsulfonyl)acetamido)propoxy)phenyl)propan-2-yl)phenoxy)propan-2-yl acetate |
| C13 | 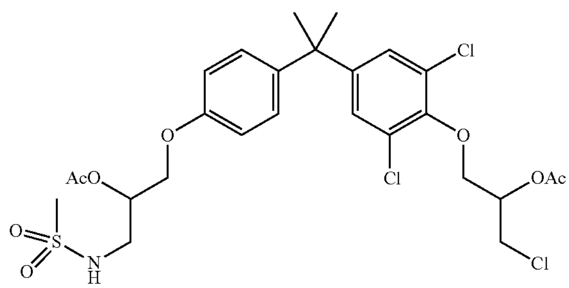 [SMILES: CC(=O)OC(CNS(C)(=O)=O)COc1ccc(C(C)(C)c2cc(Cl)c(OCC(CCl)OC(C)=O)c(Cl)c2)cc1] | 1-(4-(2-(4-(2-acetoxy-3-(methylsulfonamido)propoxy)phenyl)propan-2-yl)-2,6-dichlorophenoxy)-3-chloropropan-2-yl acetate |
| C13a | 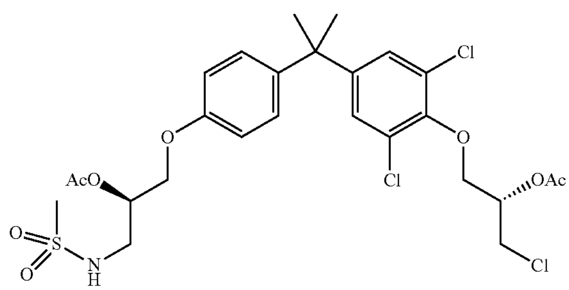 | (S)-1-(4-(2-(4-((R)-2-acetoxy-3-(methylsulfonamido)propoxy)phenyl)propan-2-yl)-2,6-dichlorophenoxy)-3-chloropropan-2-yl acetate |
| C13b | 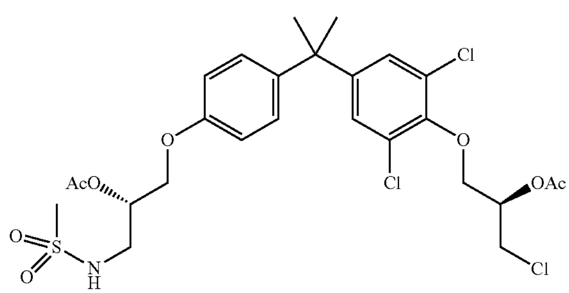 | (R)-1-(4-(2-(4-((S)-2-acetoxy-3-(methylsulfonamido)propoxy)phenyl)propan-2-yl)-2,6-dichlorophenoxy)-3-chloropropan-2-yl acetate |
| C13c | 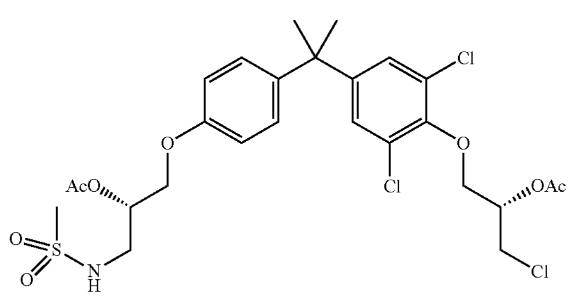 [SMILES: CC(=O)O[C@H](CCl)COc1c(Cl)cc(C(C)(C)c2ccc(OC[C@H](CNS(C)(=O)=O)OC(C)=O)cc2)cc1Cl] | (S)-1-(4-(2-(4-((S)-2-acetoxy-3-(methylsulfonamido)propoxy)phenyl)propan-2-yl)-2,6-dichlorophenoxy)-3-chloropropan-2-yl acetate |

TABLE 2-continued

| No. | Structure | Name |
|---|---|---|
| C13d | 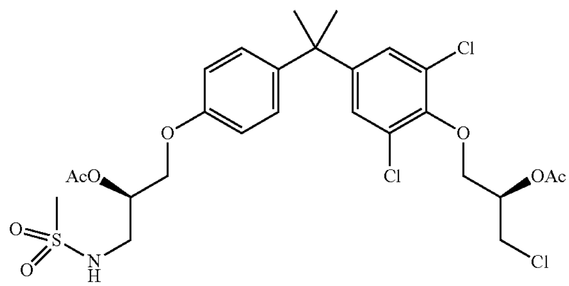 [SMILES: CC(=O)O[C@H](CNS(C)(=O)=O)COc1ccc(C(C)(C)c2cc(Cl)c(OC[C@H](CCl)OC(C)=O)c(Cl)c2)cc1] | (R)-1-(4-(2-(4-((R)-2-acetoxy-3-(methylsulfonamido)propoxy)phenyl)propan-2-yl)-2,6-dichlorophenoxy)-3-chloropropan-2-yl acetate |
| D13 | 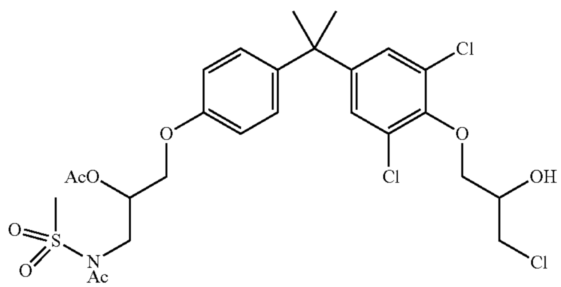 | 1-(4-(2-(3,5-dichloro-4-(3-chloro-2-hydroxypropoxy)phenyl)propan-2-yl)phenoxy)-3-(N-(methylsulfonyl)acetamido)propan-2-yl acetate |
| D13a | 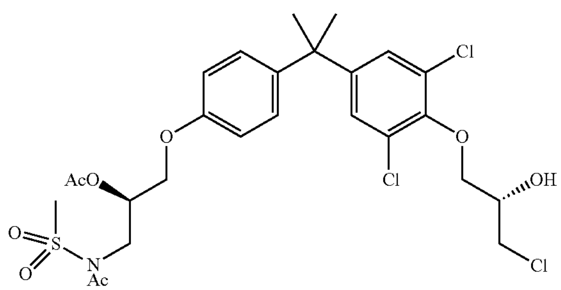 | (R)-1-(4-(2-(3,5-dichloro-4-((S)-3-chloro-2-hydroxypropoxy)phenyl)propan-2-yl)phenoxy)-3-(N-(methylsulfonyl)acetamido)propan-2-yl acetate |
| D13b | 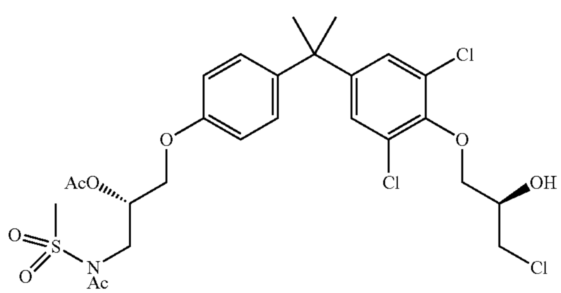 | (S)-1-(4-(2-(3,5-dichloro-4-((R)-3-chloro-2-hydroxypropoxy)phenyl)propan-2-yl)phenoxy)-3-(N-(methylsulfonyl)acetamido)propan-2-yl acetate |
| D13c | 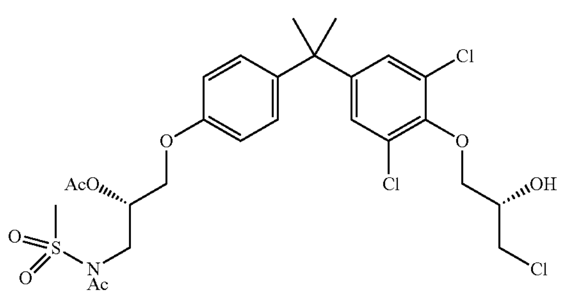 | (S)-1-(4-(2-(3,5-dichloro-4-((S)-3-chloro-2-hydroxypropoxy)phenyl)propan-2-yl)phenoxy)-3-(N-(methylsulfonyl)acetamido)propan-2-yl acetate |

TABLE 2-continued

| No. | Structure | Name |
|---|---|---|
| D13d | 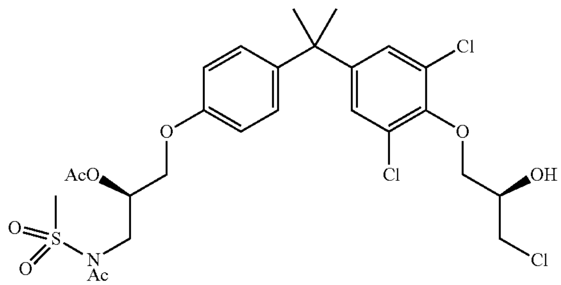 | (R)-1-(4-(2-(3,5-dichloro-4-((R)-3-chloro-2-hydroxypropoxy)phenyl)propan-2-yl)phenoxy)-3-(N-(methylsulfonyl)acetamido)propan-2-yl acetate |
| E13 | 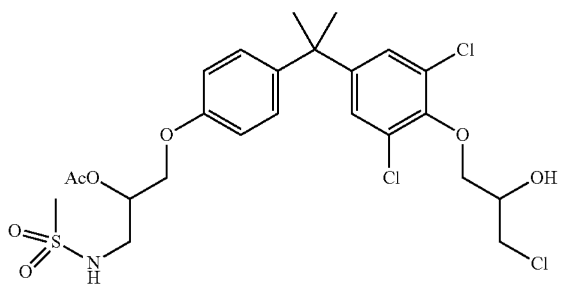 [SMILES: CC(=O)OC(CNS(C)(=O)=O)COc1ccc(C(C)(C)c2cc(Cl)c(OCC(O)CCl)c(Cl)c2)cc1] | 1-(4-(2-(3,5-dichloro-4-(3-chloro-2-hydroxypropoxy)phenyl)propan-2-yl)phenoxy)-3-(methylsulfonamido)propan-2-yl acetate |
| E13a | 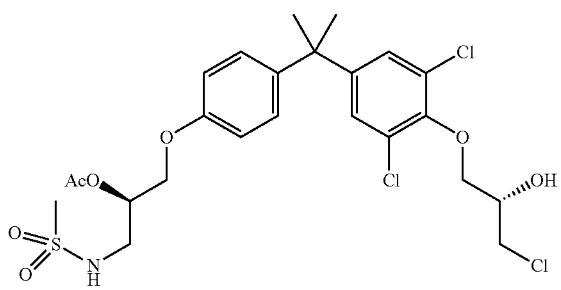 [SMILES: CC(=O)O[C@H](CNS(C)(=O)=O)COc1ccc(C(C)(C)c2cc(Cl)c(OC[C@H](O)CCl)c(Cl)c2)cc1] | (R)-1-(4-(2-(3,5-dichloro-4-((S)-3-chloro-2-hydroxypropoxy)phenyl)propan-2-yl)phenoxy)-3-(methylsulfonamido)propan-2-yl acetate |
| E13b | 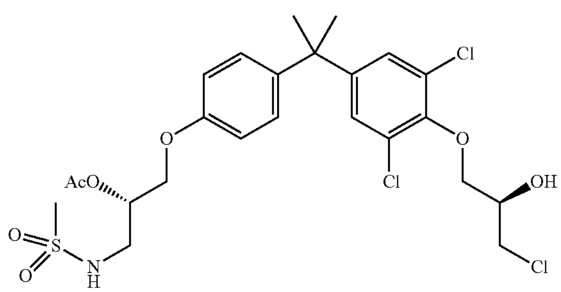 | (S)-1-(4-(2-(3,5-dichloro-4-((R)-3-chloro-2-hydroxypropoxy)phenyl)propan-2-yl)phenoxy)-3-(methylsulfonamido)propan-2-yl acetate |
| E13c | 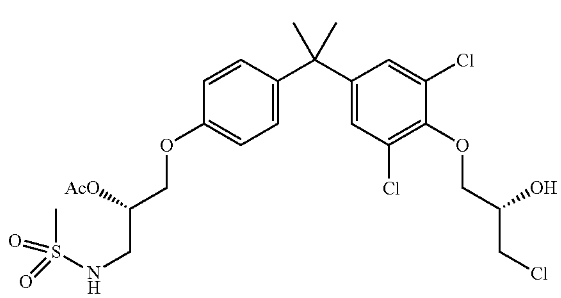 [SMILES: CC(=O)O[C@@H](CNS(C)(=O)=O)COc1ccc(C(C)(C)c2cc(Cl)c(OC[C@H](O)CCl)c(Cl)c2)cc1] | (S)-1-(4-(2-(3,5-dichloro-4-((S)-3-chloro-2-hydroxypropoxy)phenyl)propan-2-yl)phenoxy)-3-(methylsulfonamido)propan-2-yl acetate |

TABLE 2-continued

| No. | Structure | Name |
|---|---|---|
| E13d | 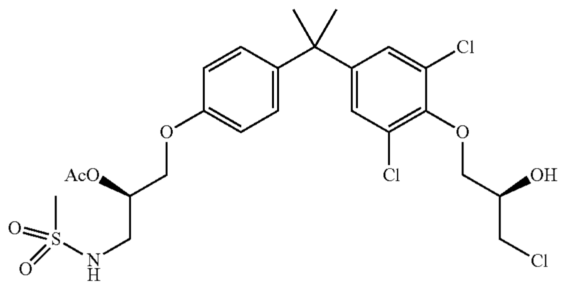 [SMILES: CC(=O)O[C@H](CNS(C)(=O)=O)COc1ccc(C(C)(C)c2cc(Cl)c(OC[C@@H](O)CCl)c(Cl)c2)cc1] | (R)-1-(4-(2-(3,5-dichloro-4-((R)-3-chloro-2-hydroxypropoxy)phenyl)propan-2-yl)phenoxy)-3-(methylsulfonamido)propan-2-yl acetate |
| F13 | 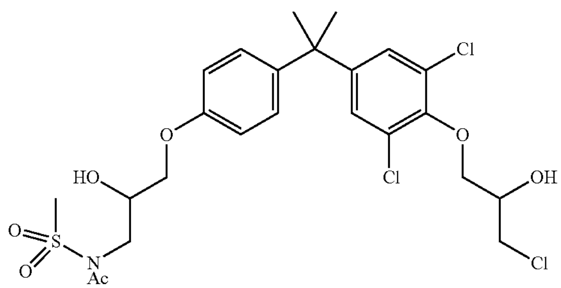 | N-(3-(4-(2-(3,5-dichloro-4-(3-chloro-2-hydroxypropoxy)phenyl)propan-2-yl)phenoxy)-2-hydroxypropyl)-N-(methylsulfonyl)acetamide |
| F13a | 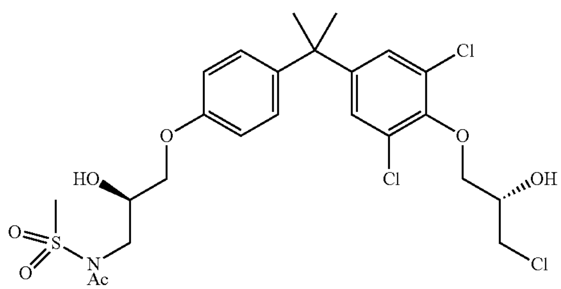 | N-((R)-3-(4-(2-(3,5-dichloro-4-((S)-3-chloro-2-hydroxypropoxy)phenyl)propan-2-yl)phenoxy)-2-hydroxypropyl)-N-(methylsulfonyl)acetamide |
| F13b | 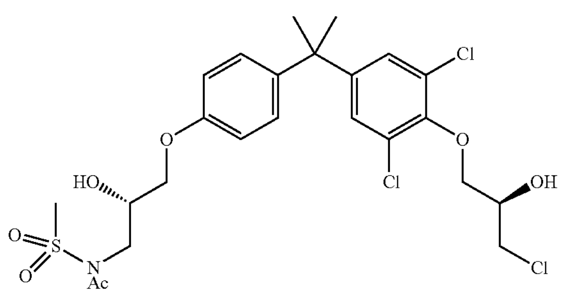 | N-((S)-3-(4-(2-(3,5-dichloro-4-((R)-3-chloro-2-hydroxypropoxy)phenyl)propan-2-yl)phenoxy)-2-hydroxypropyl)-N-(methylsulfonyl)acetamide |
| F13c | 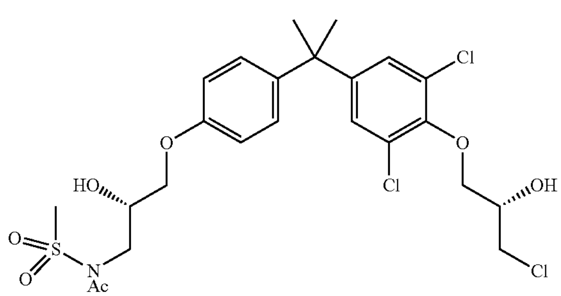 | N-((S)-3-(4-(2-(3,5-dichloro-4-((S)-3-chloro-2-hydroxypropoxy)phenyl)propan-2-yl)phenoxy)-2-hydroxypropyl)-N-(methylsulfonyl)acetamide |

TABLE 2-continued

| No. | Structure | Name |
|---|---|---|
| F13d | 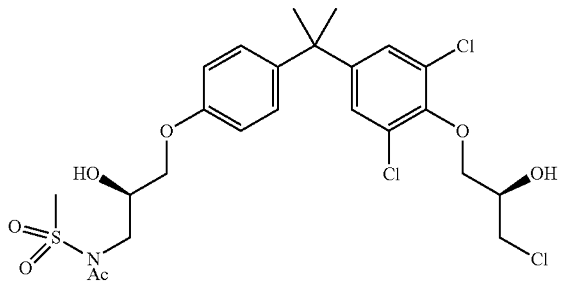 | N-((R)-3-(4-(2-(3,5-dichloro-4-((R)-3-chloro-2-hydroxypropoxy)phenyl)propan-2-yl)phenoxy)-2-hydroxypropyl)-N-(methylsulfonyl)acetamide |
| G13 | 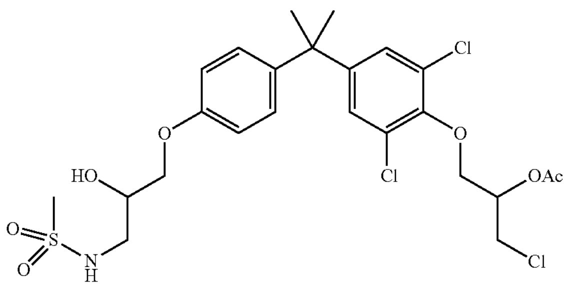 | 1-chloro-3-(2,6-dichloro-4-(2-(4-(2-hydroxy-3-(methylsulfonamido)propoxy)phenyl)propan-2-yl)phenoxy)propan-2-yl acetate |
| G13a | 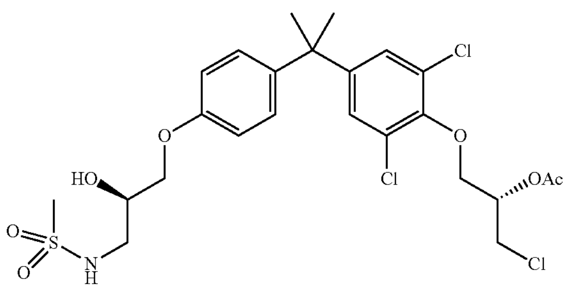 | (S)-1-chloro-3-(2,6-dichloro-4-(2-(4-((R)-2-hydroxy-3-(methylsulfonamido)propoxy)phenyl)propan-2-yl)phenoxy)propan-2-yl acetate |
| G13b | 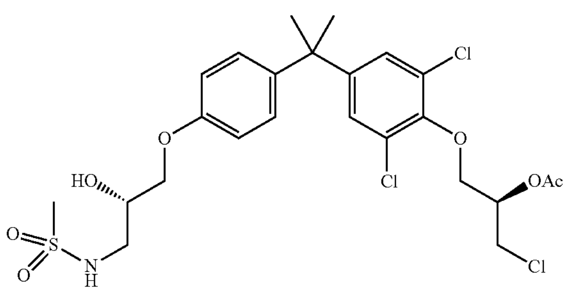 [SMILES: CC(=O)O[C@@H](CCl)COc1c(Cl)cc(C(C)(C)c2ccc(OC[C@@H](O)CNS(C)(=O)=O)cc2)cc1Cl] | (R)-1-chloro-3-(2,6-dichloro-4-(2-(4-((S)-2-hydroxy-3-(methylsulfonamido)propoxy)phenyl)propan-2-yl)phenoxy)propan-2-yl acetate |
| G13c | 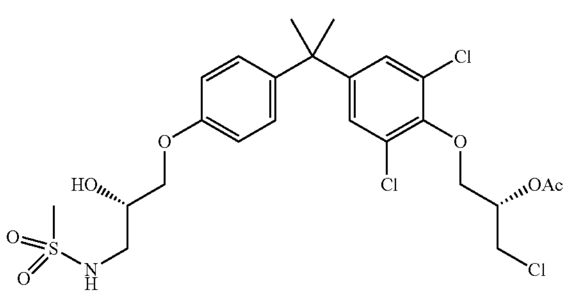 | (S)-1-chloro-3-(2,6-dichloro-4-(2-(4-((S)-2-hydroxy-3-(methylsulfonamido)propoxy)phenyl)propan-2-yl)phenoxy)propan-2-yl acetate |

TABLE 2-continued

| No. | Structure | Name |
|---|---|---|
| G13d | 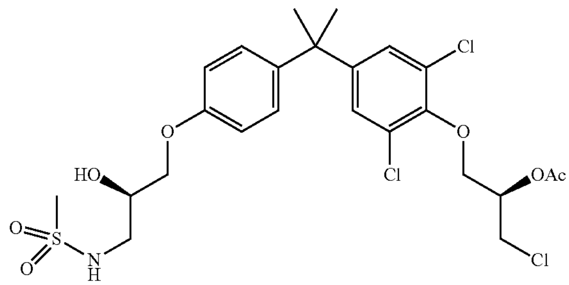 [SMILES: CC(=O)O[C@@H](CCl)COc1c(Cl)cc(C(C)(C)c2ccc(OC[C@H](O)CNS(C)(=O)=O)cc2)cc1Cl] | (R)-1-chloro-3-(2,6-dichloro-4-(2-(4-((R)-2-hydroxy-3-(methylsulfonamido)propoxy)phenyl)propan-2-yl)phenoxy)propan-2-yl acetate |
| A14 | 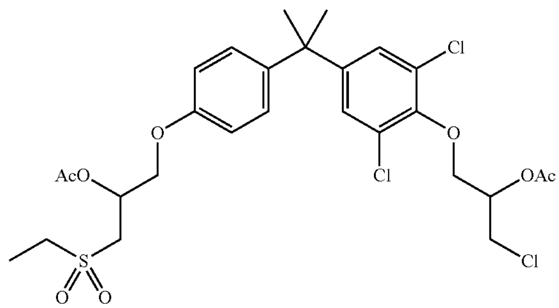 | 1-(4-(2-(4-(2-acetoxy-3-(ethylsulfonyl)propoxy)phenyl)propan-2-yl)-2,6-dichlorophenoxy)-3-chloropropan-2-yl acetate |
| A14a | 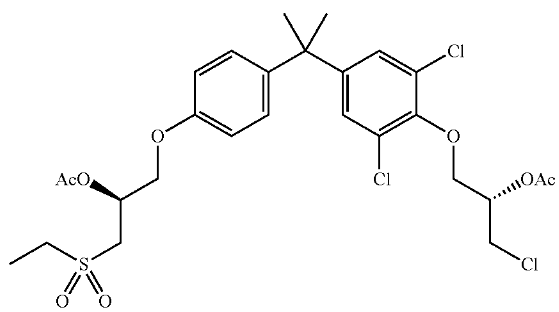 | (S)-1-(4-(2-(4-((S)-2-acetoxy-3-(ethylsulfonyl)propoxy)phenyl)propan-2-yl)-2,6-dichlorophenoxy)-3-chloropropan-2-yl acetate |
| A14b | 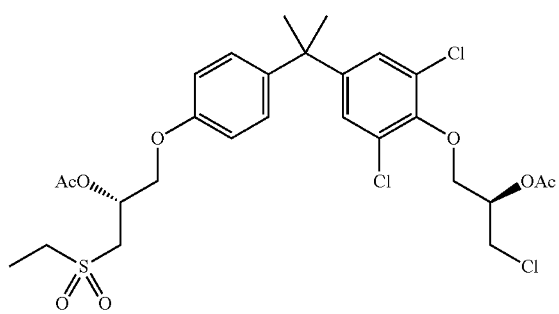 [SMILES: CCS(=O)(=O)C[C@@H](COc1ccc(C(C)(C)c2cc(Cl)c(OC[C@H](CCl)OC(C)=O)c(Cl)c2)cc1)OC(C)=O] | (R)-1-(4-(2-(4-((R)-2-acetoxy-3-(ethylsulfonyl)propoxy)phenyl)propan-2-yl)-2,6-dichlorophenoxy)-3-chloropropan-2-yl acetate |
| A14c | 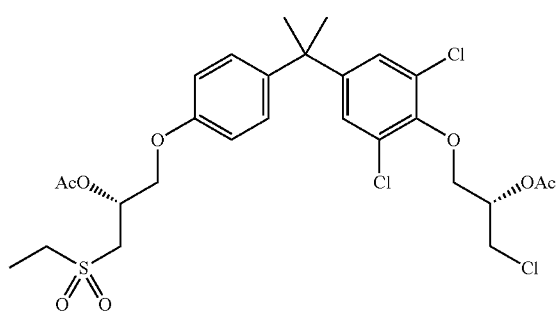 [SMILES: CCS(=O)(=O)C[C@@H](COc1ccc(C(C)(C)c2cc(Cl)c(OC[C@@H](CCl)OC(C)=O)c(Cl)c2)cc1)OC(C)=O] | (S)-1-(4-(2-(4-((R)-2-acetoxy-3-(ethylsulfonyl)propoxy)phenyl)propan-2-yl)-2,6-dichlorophenoxy)-3-chloropropan-2-yl acetate |

TABLE 2-continued

Compounds

| No. | Structure | Name |
|---|---|---|
| A14d | 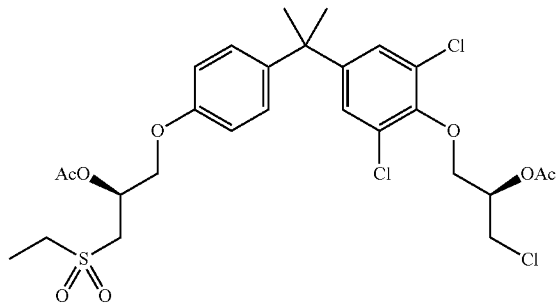 [SMILES: CCS(=O)(=O)C[C@H](COc1ccc(C(C)(C)c2cc(Cl)c(OC[C@H](CCl)OC(C)=O)c(Cl)c2)cc1)OC(C)=O] | (R)-1-(4-(2-(4-((S)-2-acetoxy-3-(ethylsulfonyl)propoxy)phenyl)propan-2-yl)-2,6-dichlorophenoxy)-3-chloropropan-2-yl acetate |
| B14 | 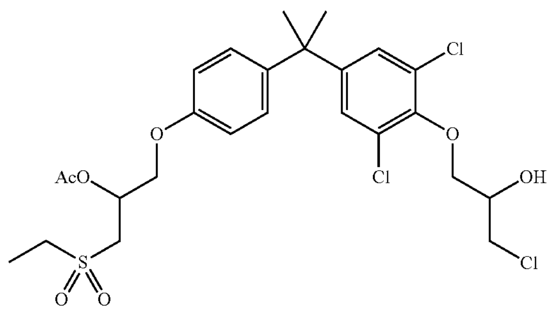 | 1-(4-(2-(3,5-dichloro-4-(3-chloro-2-hydroxypropoxy)phenyl)propan-2-yl)phenoxy)-3-(ethylsulfonyl)propan-2-yl acetate |
| B14a | 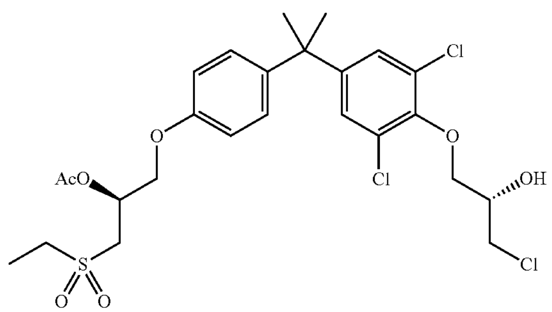 [SMILES: CCS(=O)(=O)C[C@H](COc1ccc(C(C)(C)c2cc(Cl)c(OC[C@H](O)CCl)c(Cl)c2)cc1)OC(C)=O] | (S)-1-(4-(2-(3,5-dichloro-4-((S)-3-chloro-2-hydroxypropoxy)phenyl)propan-2-yl)phenoxy)-3-(ethylsulfonyl)propan-2-yl acetate |
| B14b | 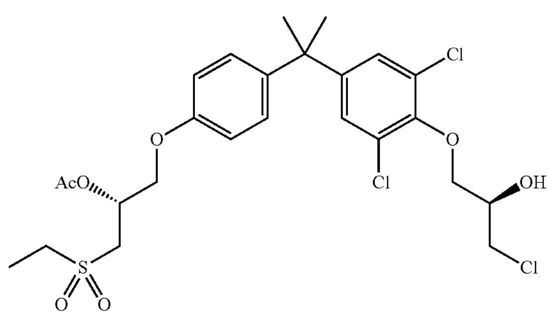 [SMILES: CCS(=O)(=O)C[C@@H](COc1ccc(C(C)(C)c2cc(Cl)c(OC[C@@H](O)CCl)c(Cl)c2)cc1)OC(C)=O] | (R)-1-(4-(2-(3,5-dichloro-4-((R)-3-chloro-2-hydroxypropoxy)phenyl)propan-2-yl)phenoxy)-3-(ethylsulfonyl)propan-2-yl acetate |
| B14c | 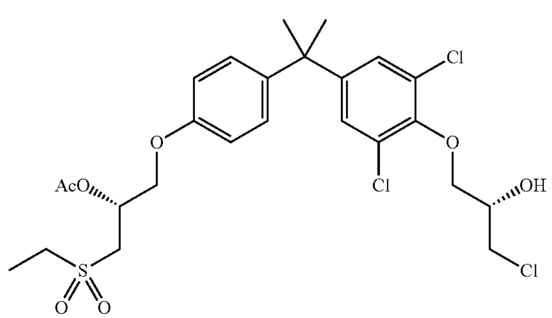 [SMILES: CCS(=O)(=O)C[C@@H](COc1ccc(C(C)(C)c2cc(Cl)c(OC[C@H](O)CCl)c(Cl)c2)cc1)OC(C)=O] | (R)-1-(4-(2-(3,5-dichloro-4-((S)-3-chloro-2-hydroxypropoxy)phenyl)propan-2-yl)phenoxy)-3-(ethylsulfonyl)propan-2-yl acetate |

TABLE 2-continued

Compounds

| No. | Structure | Name |
| --- | --- | --- |
| B14d | 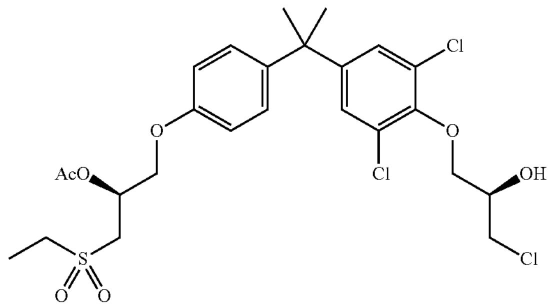 [SMILES: CCS(=O)(=O)C[C@H](COc1ccc(C(C)(C)c2cc(Cl)c(OC[C@@H](O)CCl)c(Cl)c2)cc1)OC(C)=O] | (S)-1-(4-(2-(3,5-dichloro-4-((R)-3-chloro-2-hydroxypropoxy)phenyl)propan-2-yl)phenoxy)-3-(ethylsulfonyl)propan-2-yl acetate |
| C14 | 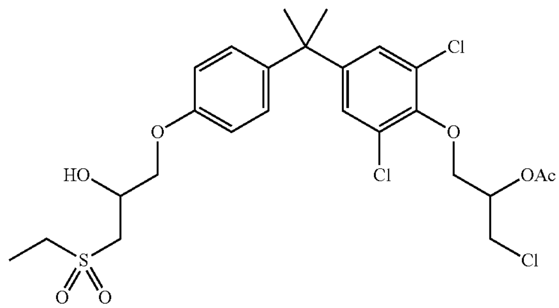 [SMILES: CCS(=O)(=O)CC(O)COc1ccc(C(C)(C)c2cc(Cl)c(OCC(CCl)OC(C)=O)c(Cl)c2)cc1] | 1-chloro-3-(2,6-dichloro-4-(2-(4-(3-(ethylsulfonyl)-2-hydroxypropoxy)phenyl)propan-2-yl)phenoxy)propan-2-yl acetate |
| C14a | 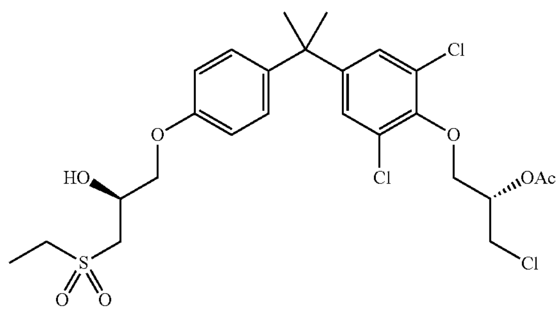 | (S)-1-chloro-3-(2,6-dichloro-4-(2-(4-((S)-3-(ethylsulfonyl)-2-hydroxypropoxy)phenyl)propan-2-yl)phenoxy)propan-2-yl acetate |
| C14b | 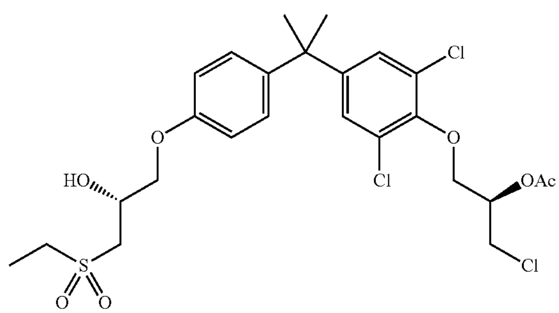 [SMILES: CCS(=O)(=O)C[C@H](O)COc1ccc(C(C)(C)c2cc(Cl)c(OC[C@H](CCl)OC(C)=O)c(Cl)c2)cc1] | (R)-1-chloro-3-(2,6-dichloro-4-(2-(4-((R)-3-(ethylsulfonyl)-2-hydroxypropoxy)phenyl)propan-2-yl)phenoxy)propan-2-yl acetate |
| C14c | 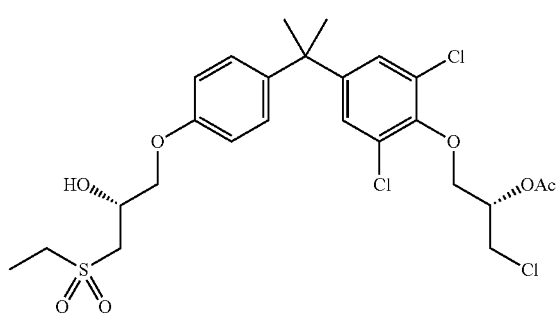 [SMILES: CCS(=O)(=O)C[C@H](O)COc1ccc(C(C)(C)c2cc(Cl)c(OC[C@@H](CCl)OC(C)=O)c(Cl)c2)cc1] | (S)-1-chloro-3-(2,6-dichloro-4-(2-(4-((R)-3-(ethylsulfonyl)-2-hydroxypropoxy)phenyl)propan-2-yl)phenoxy)propan-2-yl acetate |

TABLE 2-continued

Compounds

| No. | Structure | Name |
|---|---|---|
| C14d | 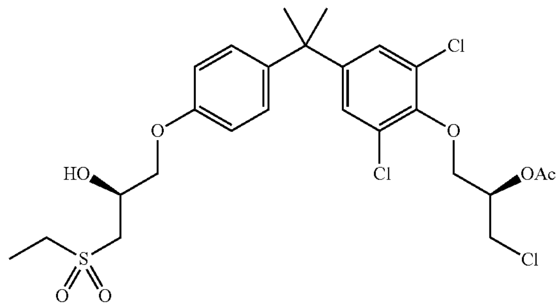 [SMILES: CCS(=O)(=O)C[C@@H](O)COc1ccc(C(C)(C)c2cc(Cl)c(OC[C@H](CCl)OC(C)=O)c(Cl)c2)cc1] | (R)-1-chloro-3-(2,6-dichloro-4-(2-(4-((S)-3-(ethylsulfonyl)-2-hydroxypropoxy)phenyl)propan-2-yl)phenoxy)propan-2-yl acetate |
| A15 | 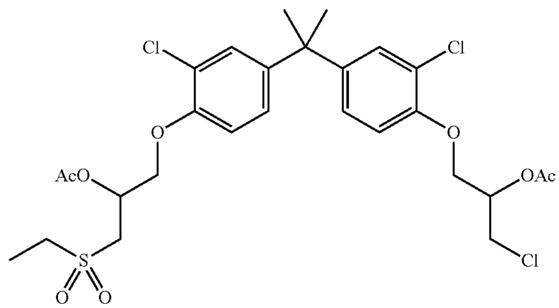 [SMILES: CCS(=O)(=O)CC(COc1ccc(C(C)(C)c2ccc(OCC(CCl)OC(C)=O)c(Cl)c2)cc1Cl)OC(C)=O] | 1-(4-(2-(4-(2-acetoxy-3-(ethylsulfonyl)propoxy)-3-chlorophenyl)propan-2-yl)-2-chlorophenoxy)-3-chloropropan-2-yl acetate |
| A15a | 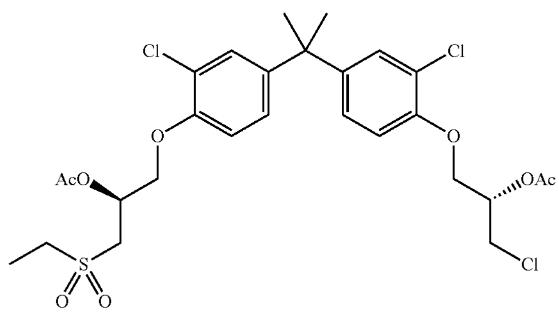 [SMILES: CCS(=O)(=O)C[C@H](COc1ccc(C(C)(C)c2ccc(OC[C@@H](CCl)OC(C)=O)c(Cl)c2)cc1Cl)OC(C)=O] | (S)-1-(4-(2-(4-((S)-2-acetoxy-3-(ethylsulfonyl)propoxy)-3-chlorophenyl)propan-2-yl)-2-chlorophenoxy)-3-chloropropan-2-yl acetate |
| A15b | 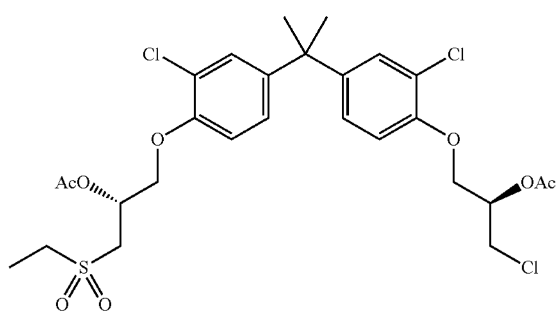 [SMILES: CCS(=O)(=O)C[C@@H](COc1ccc(C(C)(C)c2ccc(OC[C@H](CCl)OC(C)=O)c(Cl)c2)cc1Cl)OC(C)=O] | (R)-1-(4-(2-(4-((R)-2-acetoxy-3-(ethylsulfonyl)propoxy)-3-chlorophenyl)propan-2-yl)-2-chlorophenoxy)-3-chloropropan-2-yl acetate |
| A15c | 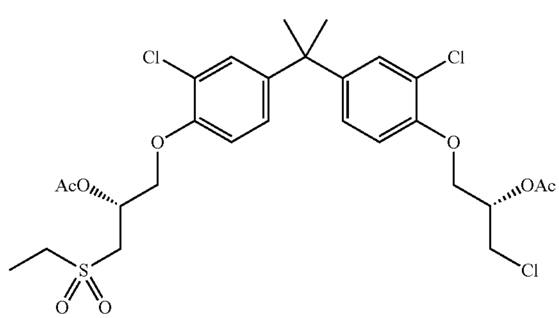 [SMILES: CCS(=O)(=O)C[C@@H](COc1ccc(C(C)(C)c2ccc(OC[C@@H](CCl)OC(C)=O)c(Cl)c2)cc1Cl)OC(C)=O] | (S)-1-(4-(2-(4-((R)-2-acetoxy-3-(ethylsulfonyl)propoxy)-3-chlorophenyl)propan-2-yl)-2-chlorophenoxy)-3-chloropropan-2-yl acetate |

TABLE 2-continued

| No. | Structure | Name |
|---|---|---|
| A15d | 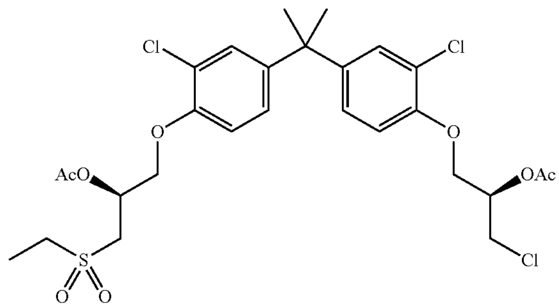 [SMILES: CCS(=O)(=O)C[C@H](COc1ccc(C(C)(C)c2ccc(OC[C@H](CCl)OC(C)=O)c(Cl)c2)cc1Cl)OC(C)=O] | (R)-1-(4-(2-(4-((S)-2-acetoxy-3-(ethylsulfonyl)propoxy)-3-chlorophenyl)propan-2-yl)-2-chlorophenoxy)-3-chloropropan-2-yl acetate |
| A16 | 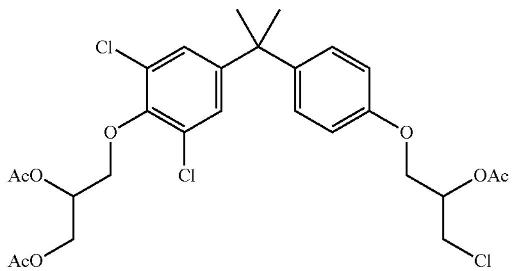 [SMILES: CC(=O)OCC(COc1c(Cl)cc(C(C)(C)c2ccc(OCC(CCl)OC(C)=O)cc2)cc1Cl)OC(C)=O] | 3-(4-(2-(4-(2-acetoxy-3-chloropropoxy)phenyl)propan-2-yl)-2,6-dichlorophenoxy)propane-1,2-diyl diacetate |
| A16a | 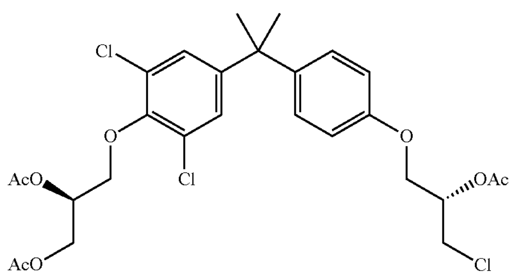 [SMILES: CC(=O)OC[C@H](COc1c(Cl)cc(C(C)(C)c2ccc(OC[C@@H](CCl)OC(C)=O)cc2)cc1Cl)OC(C)=O] | (S)-3-(4-(2-(4-((S)-2-acetoxy-3-chloropropoxy)phenyl)propan-2-yl)-2,6-dichlorophenoxy)propane-1,2-diyl diacetate |
| A16b | 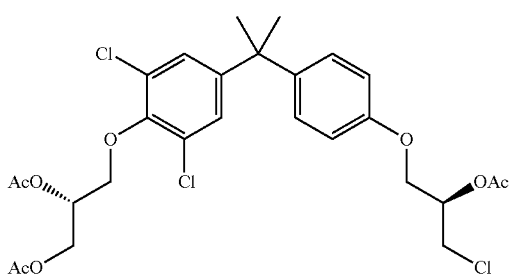 [SMILES: CC(=O)OC[C@@H](COc1c(Cl)cc(C(C)(C)c2ccc(OC[C@H](CCl)OC(C)=O)cc2)cc1Cl)OC(C)=O] | (R)-3-(4-(2-(4-((R)-2-acetoxy-3-chloropropoxy)phenyl)propan-2-yl)-2,6-dichlorophenoxy)propane-1,2-diyl diacetate |
| A16c | 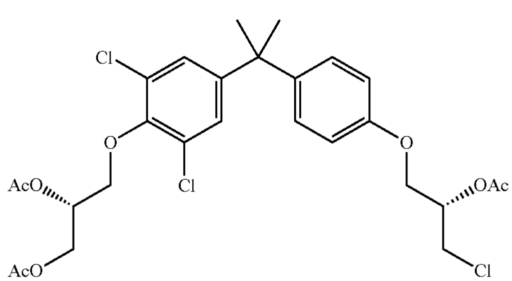 [SMILES: CC(=O)OC[C@@H](COc1c(Cl)cc(C(C)(C)c2ccc(OC[C@@H](CCl)OC(C)=O)cc2)cc1Cl)OC(C)=O] | (R)-3-(4-(2-(4-((S)-2-acetoxy-3-chloropropoxy)phenyl)propan-2-yl)-2,6-dichlorophenoxy)propane-1,2-diyl diacetate |

TABLE 2-continued

Compounds

| No. | Structure | Name |
|---|---|---|
| A16d | 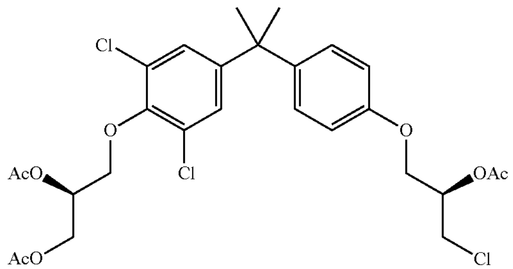 [SMILES: CC(=O)OC[C@H](COc1c(Cl)cc(C(C)(C)c2ccc(OC[C@H](CCl)OC(C)=O)cc2)cc1Cl)OC(C)=O] | (S)-3-(4-(2-(4-((R)-2-acetoxy-3-chloropropoxy)phenyl)propan-2-yl)-2,6-dichlorophenoxy)propane-1,2-diyl diacetate |
| A17 | 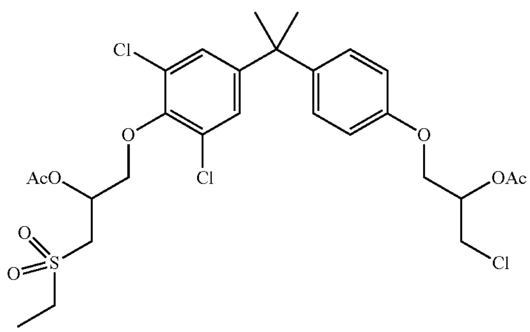 [SMILES: CCS(=O)(=O)CC(COc1c(Cl)cc(C(C)(C)c2ccc(OCC(CCl)OC(C)=O)cc2)cc1Cl)OC(C)=O] | 1-(4-(2-(4-(2-acetoxy-3-(ethylsulfonyl)propoxy)-3,5-dichlorophenyl)propan-2-yl)phenoxy)-3-chloropropan-2-yl acetate |
| A17a | 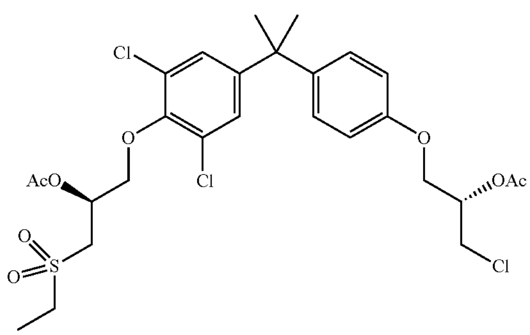 [SMILES: CCS(=O)(=O)C[C@H](COc1c(Cl)cc(C(C)(C)c2ccc(OC[C@@H](CCl)OC(C)=O)cc2)cc1Cl)OC(C)=O] | (S)-1-(4-(2-(4-((S)-2-acetoxy-3-(ethylsulfonyl)propoxy)-3,5-dichlorophenyl)propan-2-yl)phenoxy)-3-chloropropan-2-yl acetate |
| A17b | 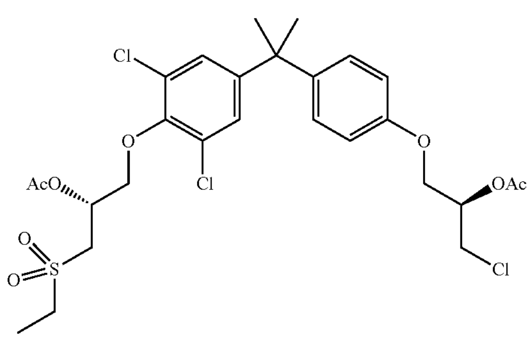 [SMILES: CCS(=O)(=O)C[C@@H](COc1c(Cl)cc(C(C)(C)c2ccc(OC[C@H](CCl)OC(C)=O)cc2)cc1Cl)OC(C)=O] | (R)-1-(4-(2-(4-((R)-2-acetoxy-3-(ethylsulfonyl)propoxy)-3,5-dichlorophenyl)propan-2-yl)phenoxy)-3-chloropropan-2-yl acetate |

TABLE 2-continued

| No. | Structure | Name |
|---|---|---|
| A17c | 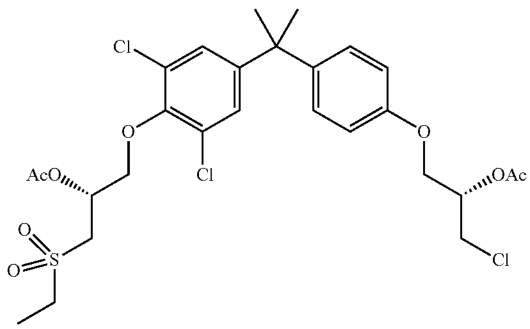 [SMILES: CCS(=O)(=O)C[C@@H](COc1c(Cl)cc(C(C)(C)c2ccc(OC[C@@H](CCl)OC(C)=O)cc2)cc1Cl)OC(C)=O] | (S)-1-(4-(2-(4-((R)-2-acetoxy-3-(ethylsulfonyl)propoxy)-3,5-dichlorophenyl)propan-2-yl)phenoxy)-3-chloropropan-2-yl acetate |
| A17d | 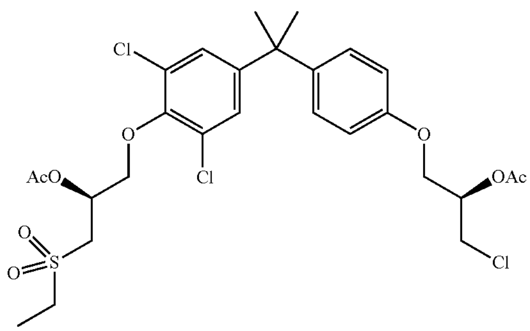 [SMILES: CCS(=O)(=O)C[C@H](COc1c(Cl)cc(C(C)(C)c2ccc(OC[C@H](CCl)OC(C)=O)cc2)cc1Cl)OC(C)=O] | (R)-1-(4-(2-(4-((S)-2-acetoxy-3-(ethylsulfonyl)propoxy)-3,5-dichlorophenyl)propan-2-yl)phenoxy)-3-chloropropan-2-yl acetate |
| A18 | 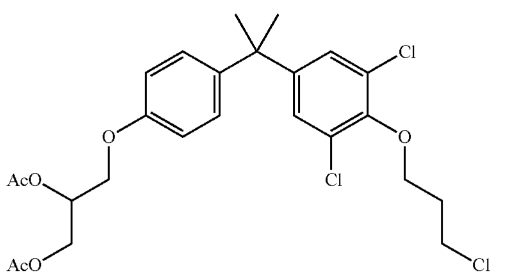 | 3-(4-(2-(3,5-dichloro-4-(3-chloropropoxy)phenyl)propan-2-yl)phenoxy)propane-1,2-diyl diacetate |
| A18a | 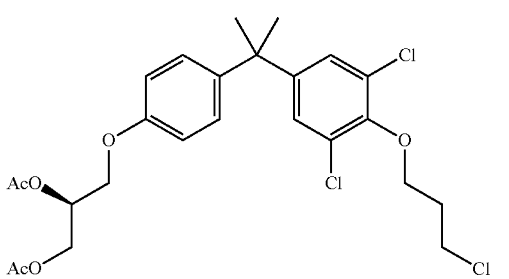 [SMILES: CC(=O)OC[C@H](COc1ccc(C(C)(C)c2cc(Cl)c(OCCCCl)c(Cl)c2)cc1)OC(C)=O] | (S)-3-(4-(2-(3,5-dichloro-4-(3-chloropropoxy)phenyl)propan-2-yl)phenoxy)propane-1,2-diyl diacetate |
| A18b | 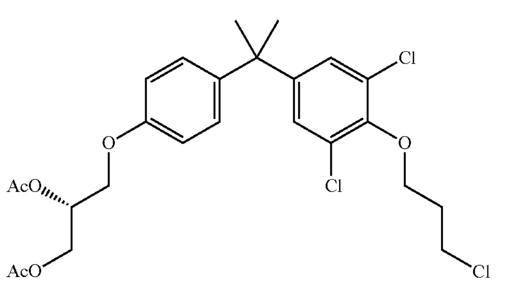 [SMILES: CC(=O)OC[C@@H](COc1ccc(C(C)(C)c2cc(Cl)c(OCCCCl)c(Cl)c2)cc1)OC(C)=O] | (R)-3-(4-(2-(3,5-dichloro-4-(3-chloropropoxy)phenyl)propan-2-yl)phenoxy)propane-1,2-diyl diacetate |

TABLE 2-continued

| No. | Structure | Name |
|---|---|---|
| A19 | 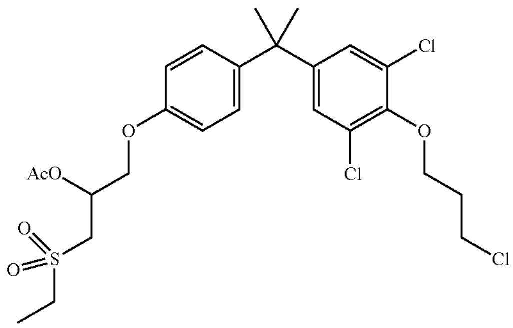 | 1-(4-(2-(3,5-dichloro-4-(3-chloropropoxy)phenyl)propan-2-yl)phenoxy)-3-(ethylsulfonyl)propan-2-yl acetate |
| A19a | 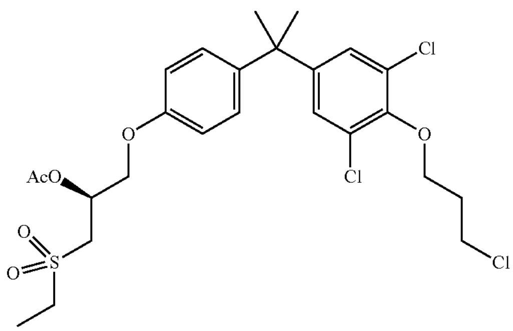 [SMILES: CCS(=O)(=O)C[C@H](COc1ccc(C(C)(C)c2cc(Cl)c(OCCCCl)c(Cl)c2)cc1)OC(C)=O] | (S)-1-(4-(2-(3,5-dichloro-4-(3-chloropropoxy)phenyl)propan-2-yl)phenoxy)-3-(ethylsulfonyl)propan-2-yl acetate |
| A19b | 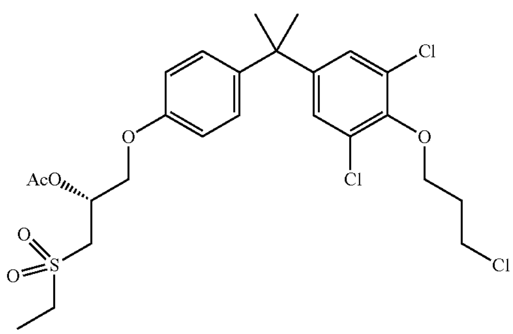 | (R)-1-(4-(2-(3,5-dichloro-4-(3-chloropropoxy)phenyl)propan-2-yl)phenoxy)-3-(ethylsulfonyl)propan-2-yl acetate |
| A20 | 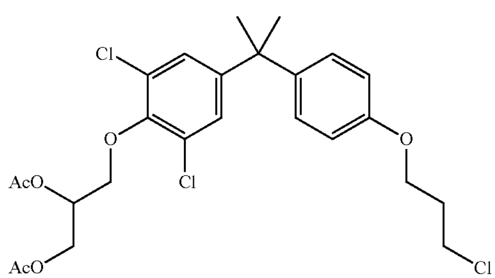 [SMILES: CC(=O)OCC(COc1c(Cl)cc(C(C)(C)c2ccc(OCCCCl)cc2)cc1Cl)OC(C)=O] | 3-(2,6-dichloro-4-(2-(4-(3-chloropropoxy)phenyl)propan-2-yl)phenoxy)propane-1,2-diyl diacetate |
| A20a | 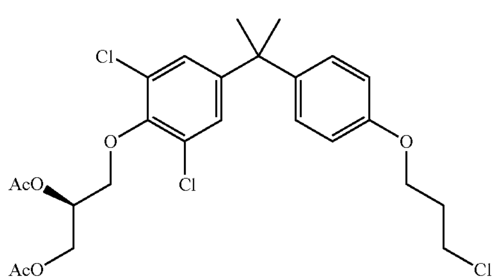 [SMILES: CC(=O)OC[C@H](COc1c(Cl)cc(C(C)(C)c2ccc(OCCCCl)cc2)cc1Cl)OC(C)=O] | (S)-3-(2,6-dichloro-4-(2-(4-(3-chloropropoxy)phenyl)propan-2-yl)phenoxy)propane-1,2-diyl diacetate |

TABLE 2-continued

| No. | Structure | Name |
|---|---|---|
| A20b | 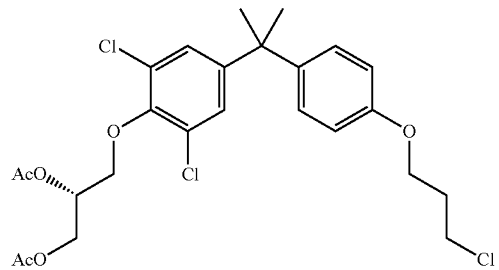 [SMILES: CC(=O)OC[C@@H](COc1c(Cl)cc(C(C)(C)c2ccc(OCCCCl)cc2)cc1Cl)OC(C)=O] | (R)-3-(2,6-dichloro-4-(2-(4-(3-chloropropoxy)phenyl)propan-2-yl)phenoxy)propane-1,2-diyl diacetate |
| A21 | 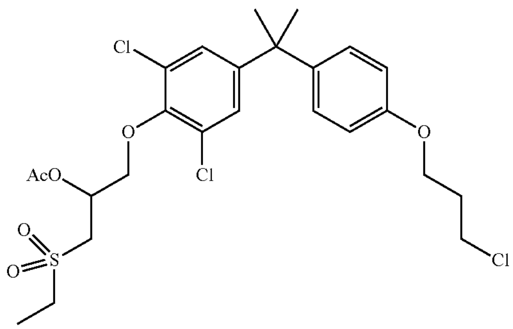 [SMILES: CCS(=O)(=O)CC(COc1c(Cl)cc(C(C)(C)c2ccc(OCCCCl)cc2)cc1Cl)OC(C)=O] | 1-(2,6-dichloro-4-(2-(4-(3-chloropropoxy)phenyl)propan-2-yl)phenoxy)-3-(ethylsulfonyl)propan-2-yl acetate |
| A21a | 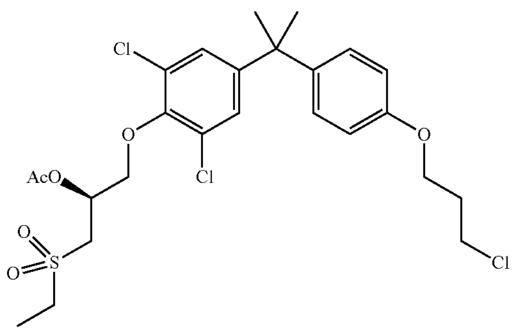 [SMILES: CCS(=O)(=O)C[C@H](COc1c(Cl)cc(C(C)(C)c2ccc(OCCCCl)cc2)cc1Cl)OC(C)=O] | (S)-1-(2,6-dichloro-4-(2-(4-(3-chloropropoxy)phenyl)propan-2-yl)phenoxy)-3-(ethylsulfonyl)propan-2-yl acetate |
| A21b | 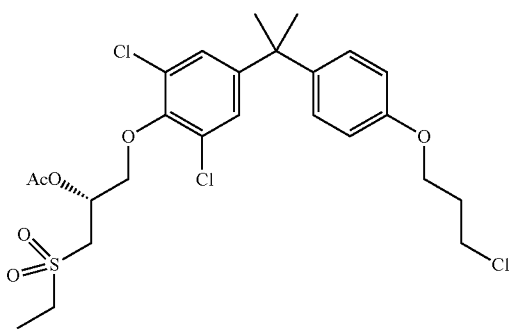 [SMILES: CCS(=O)(=O)C[C@@H](COc1c(Cl)cc(C(C)(C)c2ccc(OCCCCl)cc2)cc1Cl)OC(C)=O] | (R)-1-(2,6-dichloro-4-(2-(4-(3-chloropropoxy)phenyl)propan-2-yl)phenoxy)-3-(ethylsulfonyl)propan-2-yl acetate |
| A22 | 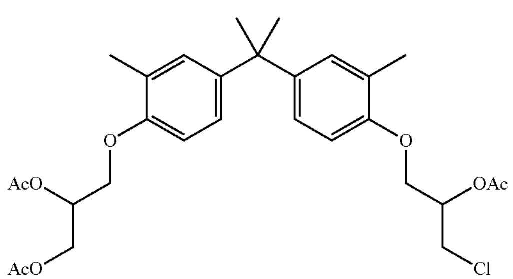 [SMILES: CC(=O)OCC(COc1ccc(C(C)(C)c2ccc(OCC(CCl)OC(C)=O)c(C)c2)cc1C)OC(C)=O] | 3-(4-(2-(4-(2-acetoxy-3-chloropropoxy)-3-methylphenyl)propan-2-yl)-2-methylphenoxy)propane-1,2-diyl diacetate |

TABLE 2-continued

Compounds

| No. | Structure | Name |
|---|---|---|
| A22a | 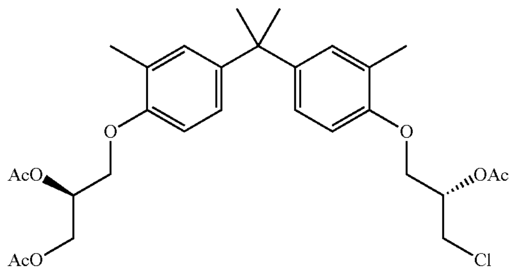 [SMILES: CC(=O)OC[C@H](COc1ccc(C(C)(C)c2ccc(OC[C@@H](CCl)OC(C)=O)c(C)c2)cc1C)OC(C)=O] | (S)-3-(4-(2-(4-((S)-2-acetoxy-3-chloropropoxy)-3-methylphenyl)propan-2-yl)-2-methylphenoxy)propane-1,2-diyl diacetate |
| A22b | 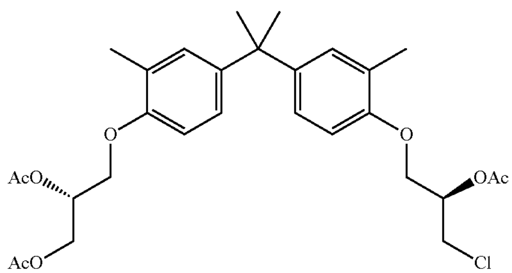 [SMILES: CC(=O)OC[C@@H](COc1ccc(C(C)(C)c2ccc(OC[C@H](CCl)OC(C)=O)c(C)c2)cc1C)OC(C)=O] | (R)-3-(4-(2-(4-((R)-2-acetoxy-3-chloropropoxy)-3-methylphenyl)propan-2-yl)-2-methylphenoxy)propane-1,2-diyl diacetate |
| A22c | 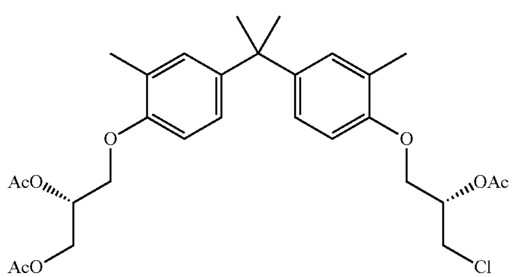 [SMILES: CC(=O)OC[C@@H](COc1ccc(C(C)(C)c2ccc(OC[C@@H](CCl)OC(C)=O)c(C)c2)cc1C)OC(C)=O] | (R)-3-(4-(2-(4-((S)-2-acetoxy-3-chloropropoxy)-3-methylphenyl)propan-2-yl)-2-methylphenoxy)propane-1,2-diyl diacetate |
| A22d | 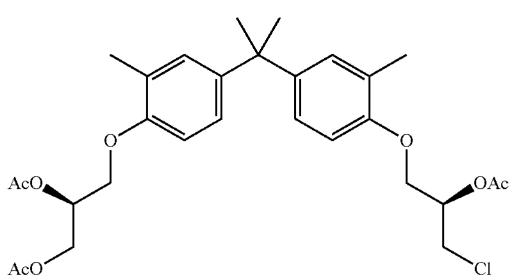 [SMILES: CC(=O)OC[C@H](COc1ccc(C(C)(C)c2ccc(OC[C@H](CCl)OC(C)=O)c(C)c2)cc1C)OC(C)=O] | (S)-3-(4-(2-(4-((R)-2-acetoxy-3-chloropropoxy)-3-methylphenyl)propan-2-yl)-2-methylphenoxy)propane-1,2-diyl diacetate |

In some more specific embodiments of the compound of Formula I, the compound has one of the following structures from Table 3, or a pharmaceutically acceptable salt, tautomer, or stereoisomer thereof:

TABLE 3

| No. | Structure | Name |
|---|---|---|
| 40 | 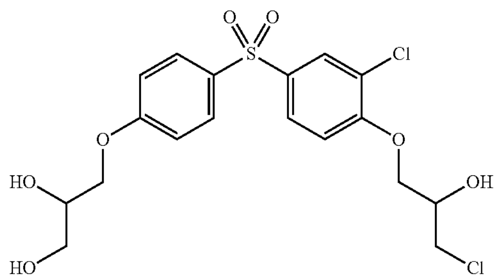 [SMILES: O=S(=O)(c1ccc(OCC(O)CO)cc1)c1ccc(OCC(O)CCl)c(Cl)c1] | 3-(4-((3-chloro-4-(3-chloro-2-hydroxypropoxy)phenyl)sulfonyl)phenoxy)propane-1,2-diol |
| 40a | 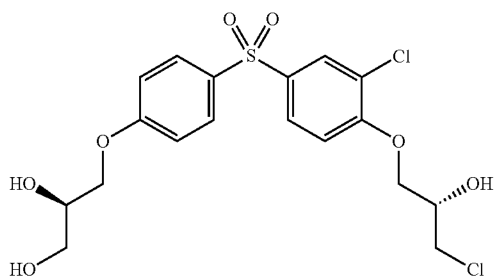 [SMILES: O=S(=O)(c1ccc(OC[C@H](O)CO)cc1)c1ccc(OC[C@H](O)CCl)c(Cl)c1] | (R)-3-(4-((3-chloro-4-((S)-3-chloro-2-hydroxypropoxy)phenyl)sulfonyl)phenoxy)propane-1,2-diol |
| 40b | 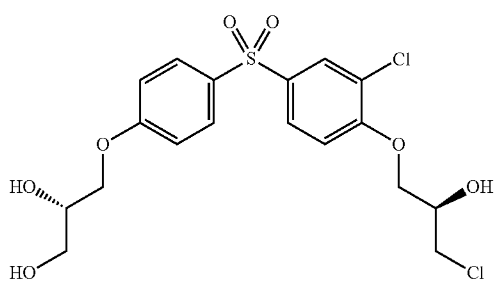 [SMILES: O=S(=O)(c1ccc(OC[C@@H](O)CO)cc1)c1ccc(OC[C@@H](O)CCl)c(Cl)c1] | (S)-3-(4-((3-chloro-4-((R)-3-chloro-2-hydroxypropoxy)phenyl)sulfonyl)phenoxy)propane-1,2-diol |
| 40c | 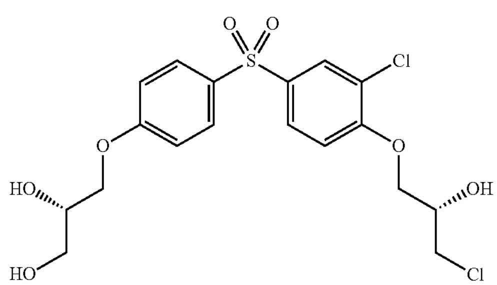 [SMILES: O=S(=O)(c1ccc(OC[C@@H](O)CO)cc1)c1ccc(OC[C@H](O)CCl)c(Cl)c1] | (S)-3-(4-((3-chloro-4-((S)-3-chloro-2-hydroxypropoxy)phenyl)sulfonyl)phenoxy)propane-1,2-diol |
| 40d | 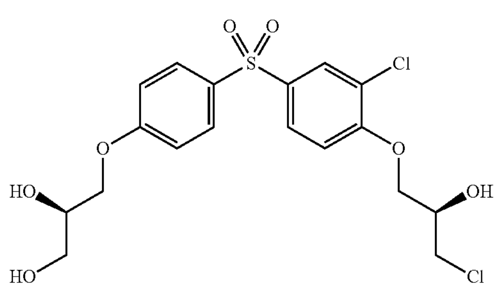 [SMILES: O=S(=O)(c1ccc(OC[C@H](O)CO)cc1)c1ccc(OC[C@@H](O)CCl)c(Cl)c1] | (R)-3-(4-((3-chloro-4-((R)-3-chloro-2-hydroxypropoxy)phenyl)sulfonyl)phenoxy)propane-1,2-diol |

TABLE 3-continued

| No. | Structure | Name |
|---|---|---|
| 41 | 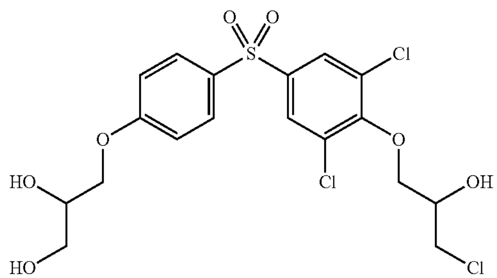 [SMILES: O=S(=O)(c1ccc(OCC(O)CO)cc1)c1cc(Cl)c(OCC(O)CCl)c(Cl)c1] | 3-(4-((3,5-dichloro-4-(3-chloro-2-hydroxypropoxy)phenyl)sulfonyl)phenoxy)propane-1,2-diol |
| 41a | 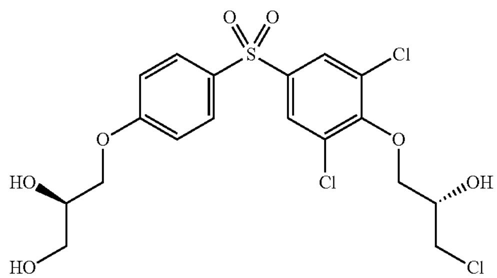 [SMILES: O=S(=O)(c1ccc(OC[C@H](O)CO)cc1)c1cc(Cl)c(OC[C@H](O)CCl)c(Cl)c1] | (R)-3-(4-((3,5-dichloro-4-((S)-3-chloro-2-hydroxypropoxy)phenyl)sulfonyl)phenoxy)propane-1,2-diol |
| 41b | 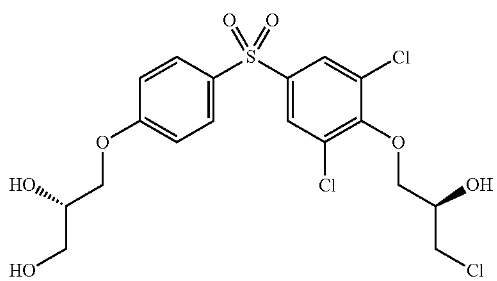 [SMILES: O=S(=O)(c1ccc(OC[C@@H](O)CO)cc1)c1cc(Cl)c(OC[C@@H](O)CCl)c(Cl)c1] | (S)-3-(4-((3,5-dichloro-4-((R)-3-chloro-2-hydroxypropoxy)phenyl)sulfonyl)phenoxy)propane-1,2-diol |
| 41c | 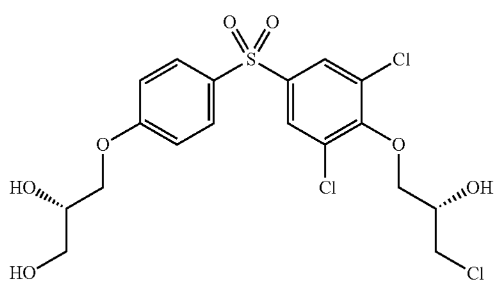 [SMILES: O=S(=O)(c1ccc(OC[C@@H](O)CO)cc1)c1cc(Cl)c(OC[C@H](O)CCl)c(Cl)c1] | (S)-3-(4-((3,5-dichloro-4-((S)-3-chloro-2-hydroxypropoxy)phenyl)sulfonyl)phenoxy)propane-1,2-diol |
| 41d | 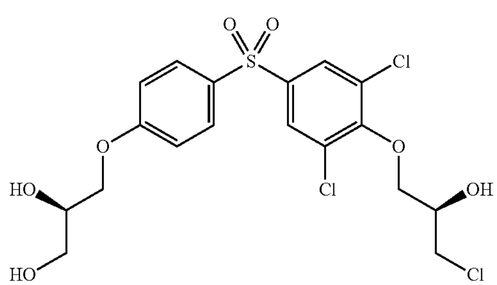 [SMILES: O=S(=O)(c1ccc(OC[C@H](O)CO)cc1)c1cc(Cl)c(OC[C@@H](O)CCl)c(Cl)c1] | (R)-3-(4-((3,5-dichloro-4-((R)-3-chloro-2-hydroxypropoxy)phenyl)sulfonyl)phenoxy)propane-1,2-diol |

TABLE 3-continued

| No. | Structure | Name |
|---|---|---|
| 42 | 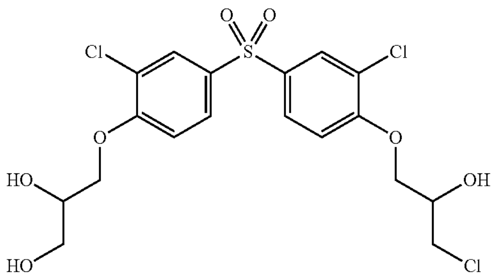 [SMILES: O=S(=O)(c1ccc(OCC(O)CO)c(Cl)c1)c1ccc(OCC(O)CCl)c(Cl)c1] | 3-(2-chloro-4-((3-chloro-4-(3-chloro-2-hydroxypropoxy)phenyl)sulfonyl)phenoxy)propane-1,2-diol |
| 42a | 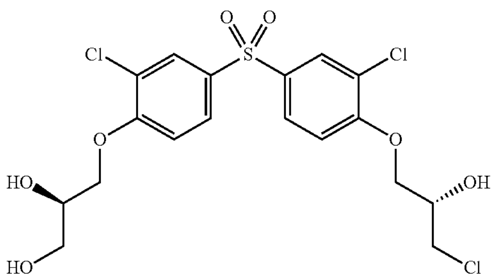 [SMILES: O=S(=O)(c1ccc(OC[C@H](O)CO)c(Cl)c1)c1ccc(OC[C@H](O)CCl)c(Cl)c1] | (R)-3-(2-chloro-4-((3-chloro-4-((S)-3-chloro-2-hydroxypropoxy)phenyl)sulfonyl)phenoxy)propane-1,2-diol |
| 42b | 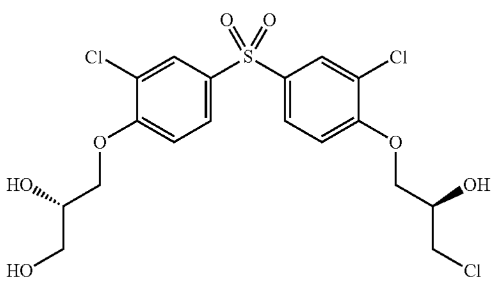 [SMILES: O=S(=O)(c1ccc(OC[C@@H](O)CO)c(Cl)c1)c1ccc(OC[C@@H](O)CCl)c(Cl)c1] | (S)-3-(2-chloro-4-((3-chloro-4-((R)-3-chloro-2-hydroxypropoxy)phenyl)sulfonyl)phenoxy)propane-1,2-diol |
| 42c | 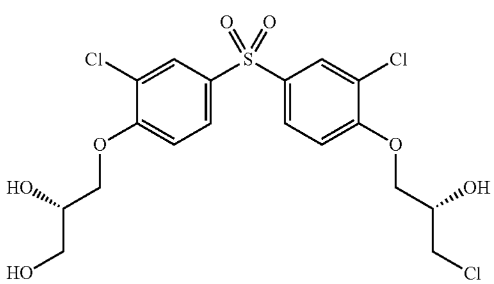 [SMILES: O=S(=O)(c1ccc(OC[C@H](O)CCl)c(Cl)c1)c1ccc(OC[C@@H](O)CO)c(Cl)c1] | (S)-3-(2-chloro-4-((3-chloro-4-((S)-3-chloro-2-hydroxypropoxy)phenyl)sulfonyl)phenoxy)propane-1,2-diol |
| 42d | 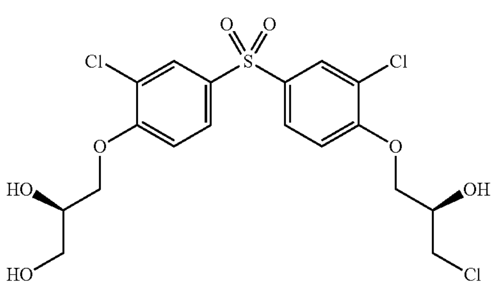 [SMILES: O=S(=O)(c1ccc(OC[C@H](O)CO)c(Cl)c1)c1ccc(OC[C@@H](O)CCl)c(Cl)c1] | (R)-3-(2-chloro-4-((3-chloro-4-((R)-3-chloro-2-hydroxypropoxy)phenyl)sulfonyl)phenoxy)propane-1,2-diol |

TABLE 3-continued

| No. | Structure | Name |
|---|---|---|
| 43 | 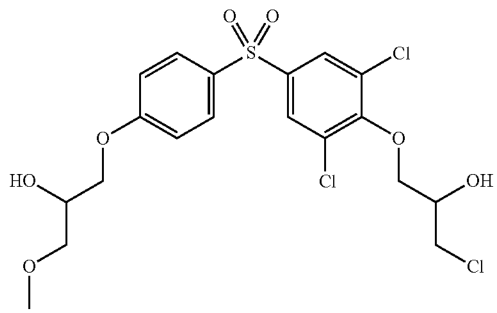 [SMILES: COCC(O)COc1ccc(S(=O)(=O)c2cc(Cl)c(OCC(O)CCl)c(Cl)c2)cc1] | 1-chloro-3-(2,6-dichloro-4-((4-(2-hydroxy-3-methoxypropoxy)phenyl)sulfonyl)phenoxy)propan-2-ol |
| 43a | 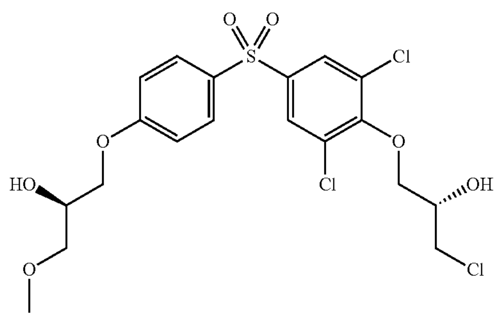 [SMILES: COC[C@@H](O)COc1ccc(S(=O)(=O)c2cc(Cl)c(OC[C@H](O)CCl)c(Cl)c2)cc1] | (S)-1-chloro-3-(2,6-dichloro-4-((4-((R)-2-hydroxy-3-methoxypropoxy)phenyl)sulfonyl)phenoxy)propan-2-ol |
| 43b | 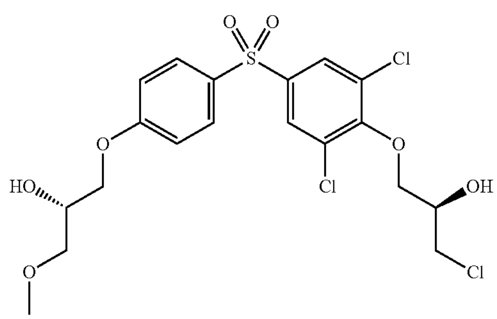 [SMILES: COC[C@H](O)COc1ccc(S(=O)(=O)c2cc(Cl)c(OC[C@@H](O)CCl)c(Cl)c2)cc1] | (R)-1-chloro-3-(2,6-dichloro-4-((4-((S)-2-hydroxy-3-methoxypropoxy)phenyl)sulfonyl)phenoxy)propan-2-ol |
| 43c | 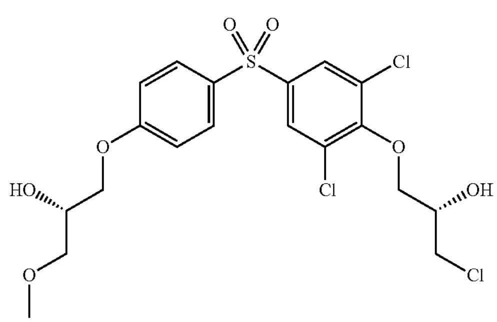 [SMILES: COC[C@H](O)COc1ccc(S(=O)(=O)c2cc(Cl)c(OC[C@H](O)CCl)c(Cl)c2)cc1] | (S)-1-chloro-3-(2,6-dichloro-4-((4-((S)-2-hydroxy-3-methoxypropoxy)phenyl)sulfonyl)phenoxy)propan-2-ol |
| 43d | 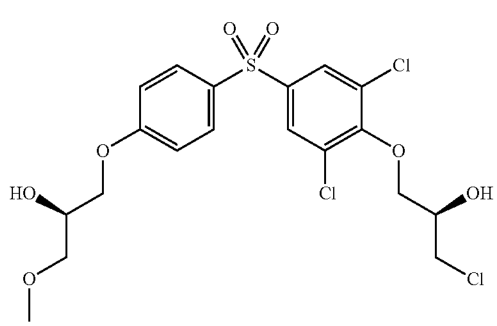 [SMILES: COC[C@@H](O)COc1ccc(S(=O)(=O)c2cc(Cl)c(OC[C@@H](O)CCl)c(Cl)c2)cc1] | (R)-1-chloro-3-(2,6-dichloro-4-((4-((R)-2-hydroxy-3-methoxypropoxy)phenyl)sulfonyl)phenoxy)propan-2-ol |

TABLE 3-continued

| Compounds | | |
|---|---|---|
| No. | Structure | Name |
| 44 | | 1-chloro-3-(2-chloro-4-((3-chloro-4-(2-hydroxy-3-methoxypropoxy)phenyl)sulfonyl)phenoxy)propan-2-ol |
| 44a | | (S)-1-chloro-3-(2-chloro-4-((3-chloro-4-((R)-2-hydroxy-3-methoxypropoxy)phenyl)sulfonyl)phenoxy)propan-2-ol |
| 44b | | (R)-1-chloro-3-(2-chloro-4-((3-chloro-4-((S)-2-hydroxy-3-methoxypropoxy)phenyl)sulfonyl)phenoxy)propan-2-ol |
| 44c | | (S)-1-chloro-3-(2-chloro-4-((3-chloro-4-((S)-2-hydroxy-3-methoxypropoxy)phenyl)sulfonyl)phenoxy)propan-2-ol |

TABLE 3-continued

| No. | Structure | Name |
|---|---|---|
| 44d | 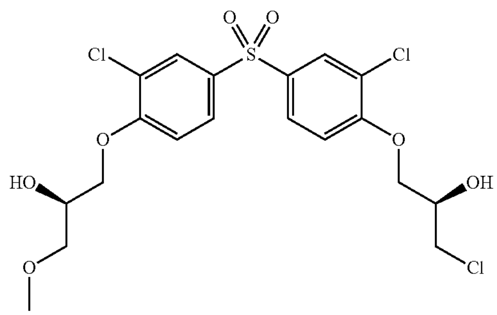 [SMILES: COC[C@@H](O)COc1ccc(S(=O)(=O)c2ccc(OC[C@@H](O)CCl)c(Cl)c2)cc1Cl] | (R)-1-chloro-3-(2-chloro-4-((3-chloro-4-((R)-2-hydroxy-3-methoxypropoxy)phenyl)sulfonyl)phenoxy)propan-2-ol |
| 45 | 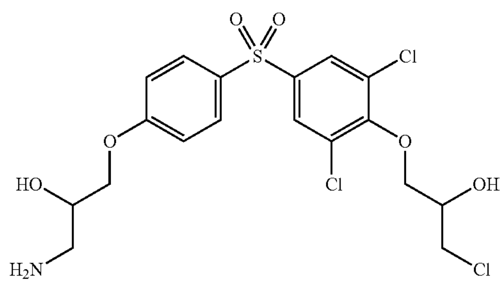 [SMILES: NCC(O)COc1ccc(S(=O)(=O)c2cc(Cl)c(OCC(O)CCl)c(Cl)c2)cc1] | 1-amino-3-(4-((3,5-dichloro-4-(3-chloro-2-hydroxypropoxy)phenyl)sulfonyl)phenoxy)propan-2-ol |
| 45a | 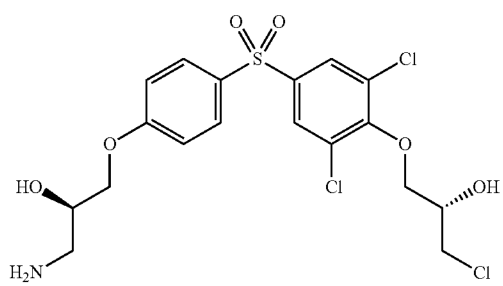 [SMILES: NC[C@@H](O)COc1ccc(S(=O)(=O)c2cc(Cl)c(OC[C@H](O)CCl)c(Cl)c2)cc1] | (R)-1-amino-3-(4-((3,5-dichloro-4-((S)-3-chloro-2-hydroxypropoxy)phenyl)sulfonyl)phenoxy)propan-2-ol |
| 45b | 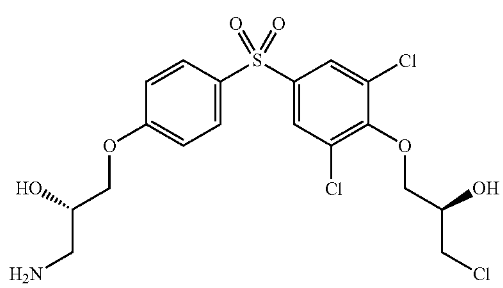 [SMILES: NC[C@H](O)COc1ccc(S(=O)(=O)c2cc(Cl)c(OC[C@@H](O)CCl)c(Cl)c2)cc1] | (S)-1-amino-3-(4-((3,5-dichloro-4-((R)-3-chloro-2-hydroxypropoxy)phenyl)sulfonyl)phenoxy)propan-2-ol |
| 45c | 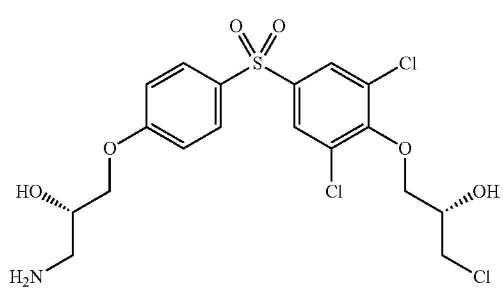 [SMILES: NC[C@H](O)COc1ccc(S(=O)(=O)c2cc(Cl)c(OC[C@H](O)CCl)c(Cl)c2)cc1] | (S)-1-amino-3-(4-((3,5-dichloro-4-((S)-3-chloro-2-hydroxypropoxy)phenyl)sulfonyl)phenoxy)propan-2-ol |

TABLE 3-continued

| No. | Structure | Name |
|---|---|---|
| 45d | 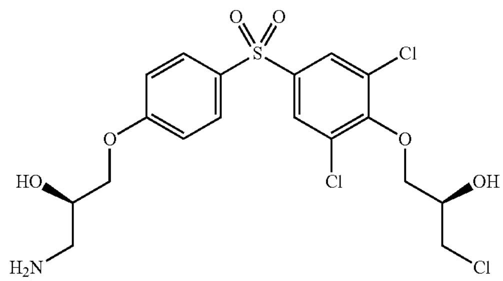 [SMILES: NC[C@@H](O)COc1ccc(S(=O)(=O)c2cc(Cl)c(OC[C@@H](O)CCl)c(Cl)c2)cc1] | (R)-1-amino-3-(4-((3,5-dichloro-4-((R)-3-chloro-2-hydroxypropoxy)phenyl)sulfonyl)phenoxy)propan-2-ol |
| 46 | 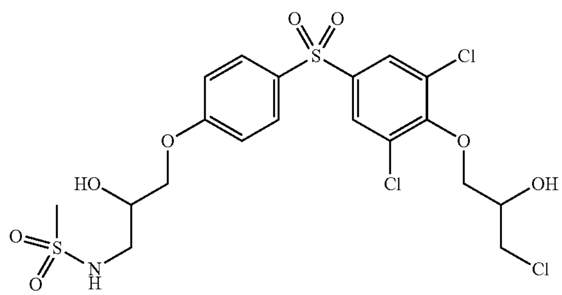 [SMILES: CS(=O)(=O)NCC(O)COc1ccc(S(=O)(=O)c2cc(Cl)c(OCC(O)CCl)c(Cl)c2)cc1] | N-(3-(4-((3,5-dichloro-4-(3-chloro-2-hydroxypropoxy)phenyl)sulfonyl)phenoxy)-2-hydroxypropyl)methanesulfonamide |
| 46a | 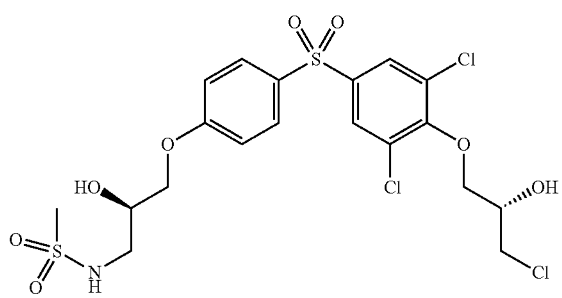 [SMILES: CS(=O)(=O)NC[C@@H](O)COc1ccc(S(=O)(=O)c2cc(Cl)c(OC[C@H](O)CCl)c(Cl)c2)cc1] | N-((R)-3-(4-((3,5-dichloro-4-((S)-3-chloro-2-hydroxypropoxy)phenyl)sulfonyl)phenoxy)-2-hydroxypropyl)methanesulfonamide |
| 46b | 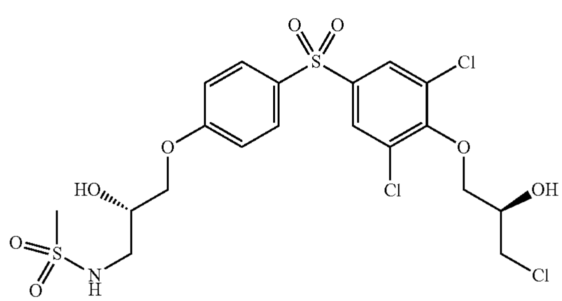 [SMILES: CS(=O)(=O)NC[C@H](O)COc1ccc(S(=O)(=O)c2cc(Cl)c(OC[C@@H](O)CCl)c(Cl)c2)cc1] | N-((S)-3-(4-((3,5-dichloro-4-((R)-3-chloro-2-hydroxypropoxy)phenyl)sulfonyl)phenoxy)-2-hydroxypropyl)methanesulfonamide |
| 46c | 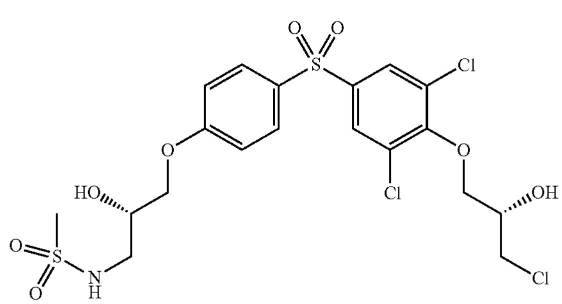 [SMILES: CS(=O)(=O)NC[C@H](O)COc1ccc(S(=O)(=O)c2cc(Cl)c(OC[C@H](O)CCl)c(Cl)c2)cc1] | N-((S)-3-(4-((3,5-dichloro-4-((S)-3-chloro-2-hydroxypropoxy)phenyl)sulfonyl)phenoxy)-2-hydroxypropyl)methanesulfonamide |

TABLE 3-continued

| No. | Structure | Name |
|---|---|---|
| 46d | 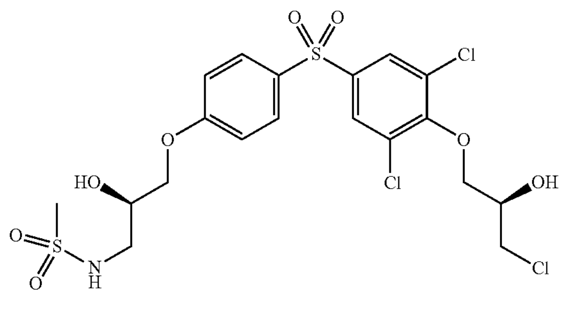 [SMILES: CS(=O)(=O)NC[C@@H](O)COc1ccc(S(=O)(=O)c2cc(Cl)c(OC[C@@H](O)CCl)c(Cl)c2)cc1] | N-((R)-3-(4-((3,5-dichloro-4-((R)-3-chloro-2-hydroxypropoxy)phenyl)sulfonyl)phenoxy)-2-hydroxypropyl)methanesulfonamide |
| 47 | 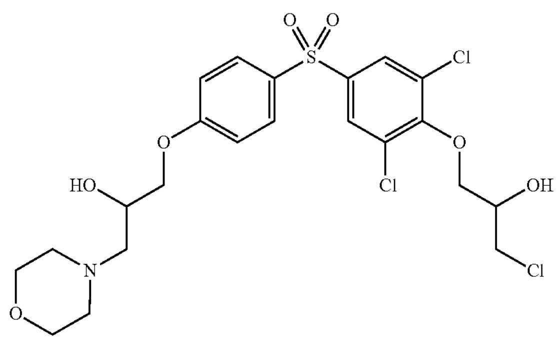 [SMILES: O=S(=O)(c1ccc(OCC(O)CN2CCOCC2)cc1)c1cc(Cl)c(OCC(O)CCl)c(Cl)c1] | 1-chloro-3-(2,6-dichloro-4-((4-(2-hydroxy-3-morpholinopropoxy)phenyl)sulfonyl)phenoxy)propan-2-ol |
| 47a | 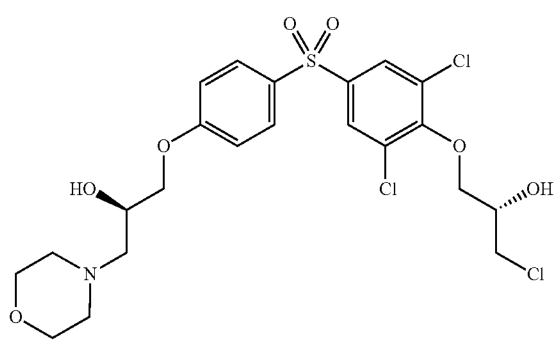 [SMILES: O=S(=O)(c1ccc(OC[C@H](O)CN2CCOCC2)cc1)c1cc(Cl)c(OC[C@H](O)CCl)c(Cl)c1] | (S)-1-chloro-3-(2,6-dichloro-4-((4-((R)-2-hydroxy-3-morpholinopropoxy)phenyl)sulfonyl)phenoxy)propan-2-ol |
| 47b | 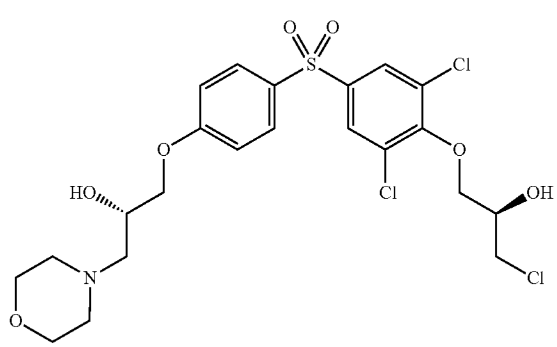 [SMILES: O=S(=O)(c1ccc(OC[C@@H](O)CN2CCOCC2)cc1)c1cc(Cl)c(OC[C@@H](O)CCl)c(Cl)c1] | (R)-1-chloro-3-(2,6-dichloro-4-((4-((S)-2-hydroxy-3-morpholinopropoxy)phenyl)sulfonyl)phenoxy)propan-2-ol |

TABLE 3-continued

| No. | Structure | Name |
|---|---|---|
| 47c | 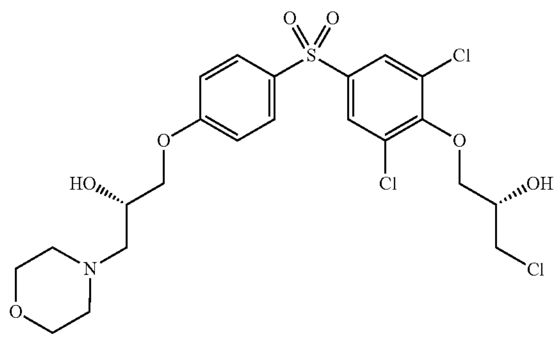 [SMILES: O=S(=O)(c1ccc(OC[C@@H](O)CN2CCOCC2)cc1)c1cc(Cl)c(OC[C@H](O)CCl)c(Cl)c1] | (S)-1-chloro-3-(2,6-dichloro-4-((4-((S)-2-hydroxy-3-morpholinopropoxy)phenyl)sulfonyl)phenoxy)propan-2-ol |
| 47d | 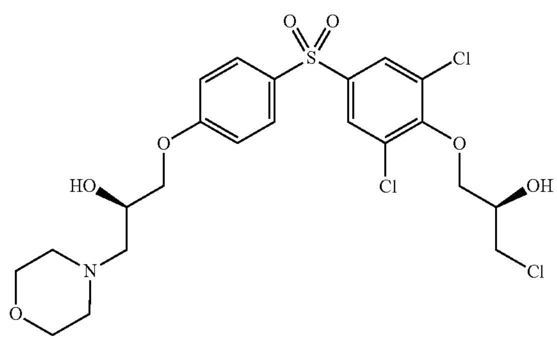 [SMILES: O=S(=O)(c1ccc(OC[C@H](O)CN2CCOCC2)cc1)c1cc(Cl)c(OC[C@@H](O)CCl)c(Cl)c1] | (R)-1-chloro-3-(2,6-dichloro-4-((4-((R)-2-hydroxy-3-morpholinopropoxy)phenyl)sulfonyl)phenoxy)propan-2-ol |
| 48 | 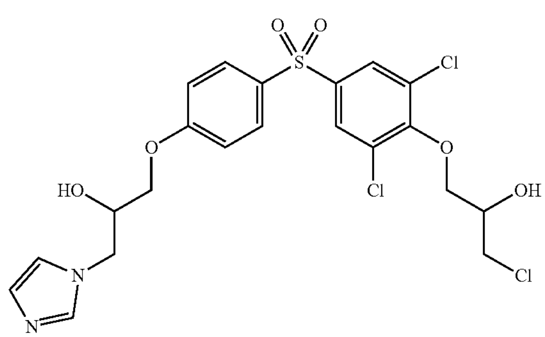 [SMILES: O=S(=O)(c1ccc(OCC(O)Cn2ccnc2)cc1)c1cc(Cl)c(OCC(O)CCl)c(Cl)c1] | 1-chloro-3-(2,6-dichloro-4-((4-(2-hydroxy-3-(1H-imidazol-1-yl)propoxy)phenyl)sulfonyl)phenoxy)propan-2-ol |
| 48a | 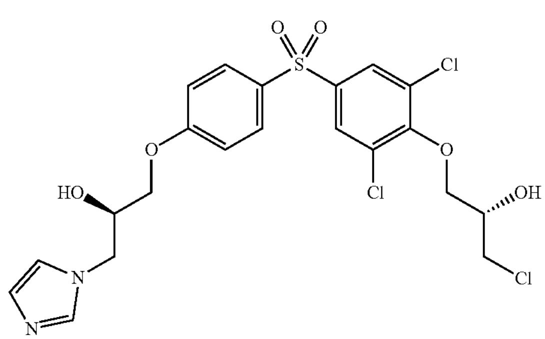 [SMILES: O=S(=O)(c1ccc(OC[C@H](O)Cn2ccnc2)cc1)c1cc(Cl)c(OC[C@H](O)CCl)c(Cl)c1] | (S)-1-chloro-3-(2,6-dichloro-4-((4-((R)-2-hydroxy-3-(1H-imidazol-1-yl)propoxy)phenyl)sulfonyl)phenoxy)propan-2-ol |

TABLE 3-continued

| No. | Structure | Name |
|---|---|---|
| 48b | 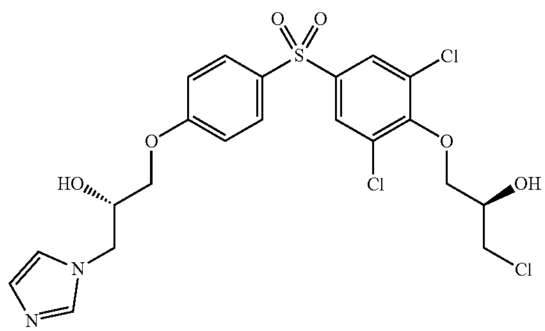 [SMILES: O=S(=O)(c1ccc(OC[C@@H](O)Cn2ccnc2)cc1)c1cc(Cl)c(OC[C@@H](O)CCl)c(Cl)c1] | (R)-1-chloro-3-(2,6-dichloro-4-((4-((S)-2-hydroxy-3-(1H-imidazol-1-yl)propoxy)phenyl)sulfonyl)phenoxy)propan-2-ol |
| 48c | 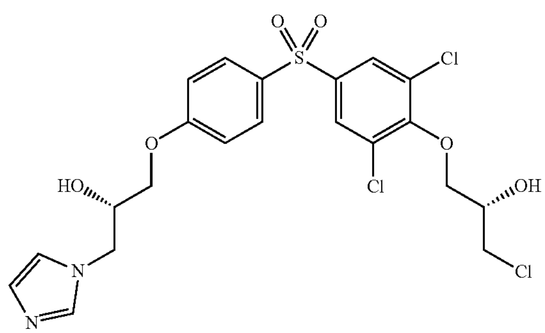 [SMILES: O=S(=O)(c1ccc(OC[C@@H](O)Cn2ccnc2)cc1)c1cc(Cl)c(OC[C@H](O)CCl)c(Cl)c1] | (S)-1-chloro-3-(2,6-dichloro-4-((4-((S)-2-hydroxy-3-(1H-imidazol-1-yl)propoxy)phenyl)sulfonyl)phenoxy)propan-2-ol |
| 48d | 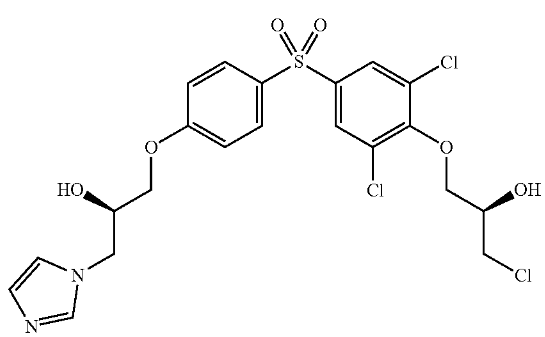 [SMILES: O=S(=O)(c1ccc(OC[C@H](O)Cn2ccnc2)cc1)c1cc(Cl)c(OC[C@@H](O)CCl)c(Cl)c1] | (R)-1-chloro-3-(2,6-dichloro-4-((4-((R)-2-hydroxy-3-(1H-imidazol-1-yl)propoxy)phenyl)sulfonyl)phenoxy)propan-2-ol |
| 49 | 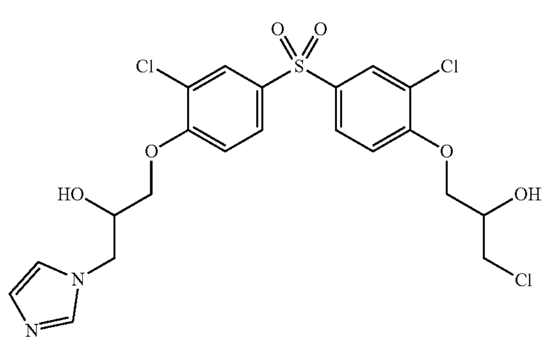 [SMILES: O=S(=O)(c1ccc(OCC(O)CCl)c(Cl)c1)c1ccc(OCC(O)Cn2ccnc2)c(Cl)c1] | 1-chloro-3-(2-chloro-4-((3-chloro-4-(2-hydroxy-3-(1H-imidazol-1-yl)propoxy)phenyl)sulfonyl)phenoxy)propan-2-ol |

TABLE 3-continued

| No. | Structure | Name |
|---|---|---|
| 49a | 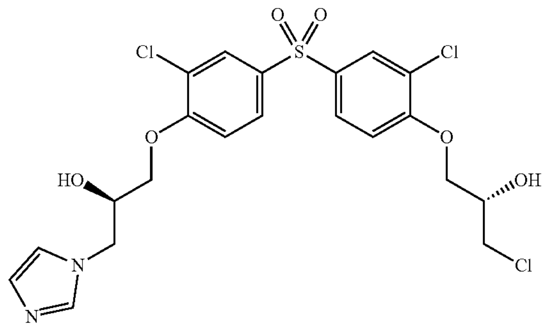 [SMILES: O=S(=O)(c1ccc(OC[C@H](O)CCl)c(Cl)c1)c1ccc(OC[C@H](O)Cn2ccnc2)c(Cl)c1] | (S)-1-chloro-3-(2-chloro-4-((3-chloro-4-((R)-2-hydroxy-3-(1H-imidazol-1-yl)propoxy)phenyl)sulfonyl)phenoxy)propan-2-ol |
| 49b | 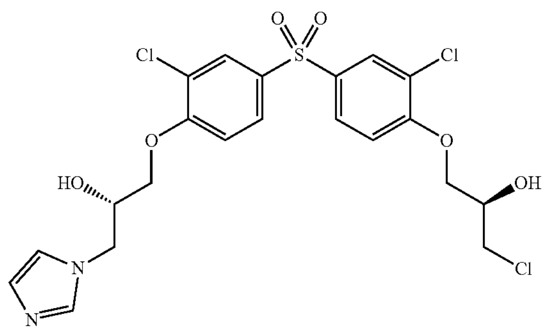 [SMILES: O=S(=O)(c1ccc(OC[C@@H](O)Cn2ccnc2)c(Cl)c1)c1ccc(OC[C@@H](O)CCl)c(Cl)c1] | (R)-1-chloro-3-(2-chloro-4-((3-chloro-4-((S)-2-hydroxy-3-(1H-imidazol-1-yl)propoxy)phenyl)sulfonyl)phenoxy)propan-2-ol |
| 49c | 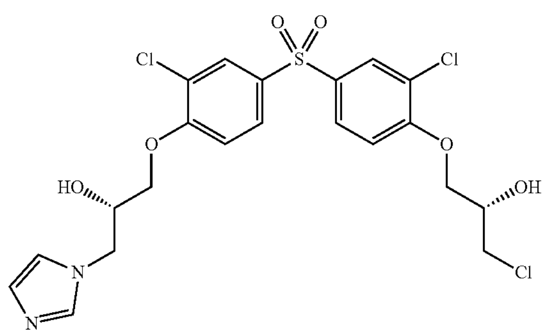 [SMILES: O=S(=O)(c1ccc(OC[C@H](O)CCl)c(Cl)c1)c1ccc(OC[C@@H](O)Cn2ccnc2)c(Cl)c1] | (S)-1-chloro-3-(2-chloro-4-((3-chloro-4-((S)-2-hydroxy-3-(1H-imidazol-1-yl)propoxy)phenyl)sulfonyl)phenoxy)propan-2-ol |
| 49d | 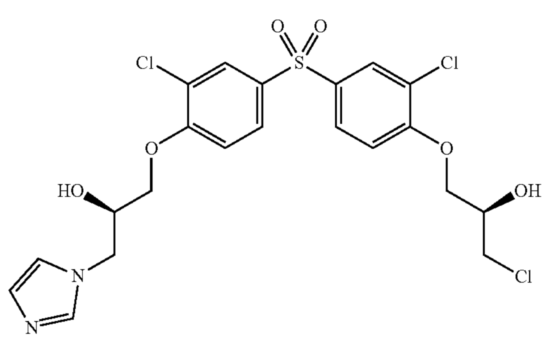 [SMILES: O=S(=O)(c1ccc(OC[C@@H](O)CCl)c(Cl)c1)c1ccc(OC[C@H](O)Cn2ccnc2)c(Cl)c1] | (R)-1-chloro-3-(2-chloro-4-((3-chloro-4-((R)-2-hydroxy-3-(1H-imidazol-1-yl)propoxy)phenyl)sulfonyl)phenoxy)propan-2-ol |

TABLE 3-continued

| No. | Structure | Name |
|---|---|---|
| 50 | 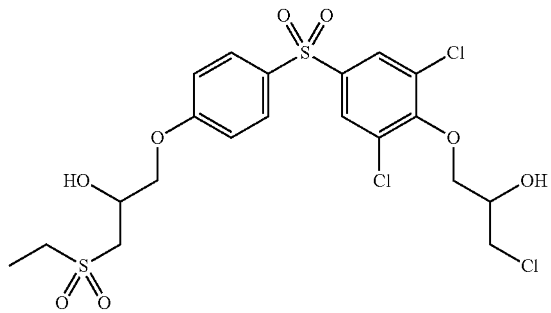 [SMILES: CCS(=O)(=O)CC(O)COc1ccc(S(=O)(=O)c2cc(Cl)c(OCC(O)CCl)c(Cl)c2)cc1] | 1-chloro-3-(2,6-dichloro-4-((4-(2-hydroxy-3-(ethylsulfonyl)propoxy)phenyl)sulfonyl)phenoxy)propan-2-ol |
| 50a | 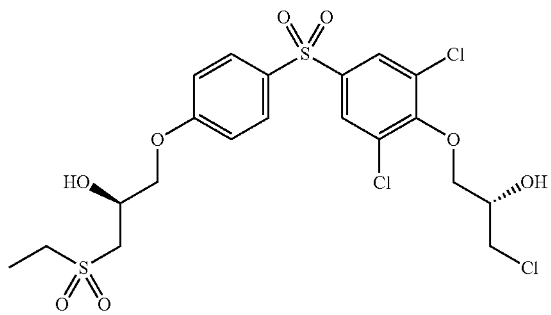 [SMILES: CCS(=O)(=O)C[C@@H](O)COc1ccc(S(=O)(=O)c2cc(Cl)c(OC[C@H](O)CCl)c(Cl)c2)cc1] | (S)-1-chloro-3-(2,6-dichloro-4-((4-((S)-2-hydroxy-3-(ethylsulfonyl)propoxy)phenyl)sulfonyl)phenoxy)propan-2-ol |
| 50b | 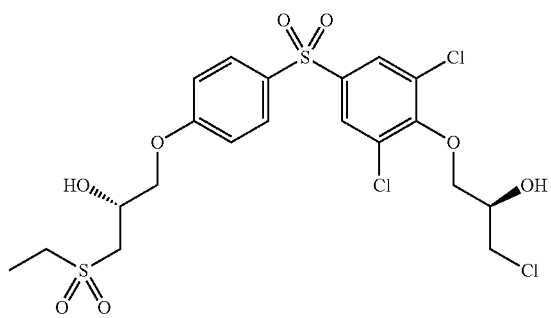 [SMILES: CCS(=O)(=O)C[C@H](O)COc1ccc(S(=O)(=O)c2cc(Cl)c(OC[C@@H](O)CCl)c(Cl)c2)cc1] | (R)-1-chloro-3-(2,6-dichloro-4-((4-((R)-2-hydroxy-3-(ethylsulfonyl)propoxy)phenyl)sulfonyl)phenoxy)propan-2-ol |
| 50c | 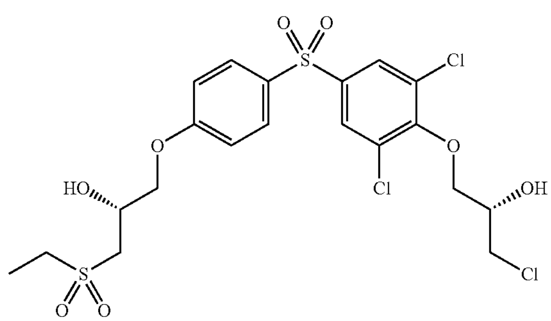 [SMILES: CCS(=O)(=O)C[C@H](O)COc1ccc(S(=O)(=O)c2cc(Cl)c(OC[C@H](O)CCl)c(Cl)c2)cc1] | (S)-1-chloro-3-(2,6-dichloro-4-((4-((R)-2-hydroxy-3-(ethylsulfonyl)propoxy)phenyl)sulfonyl)phenoxy)propan-2-ol |
| 50d | 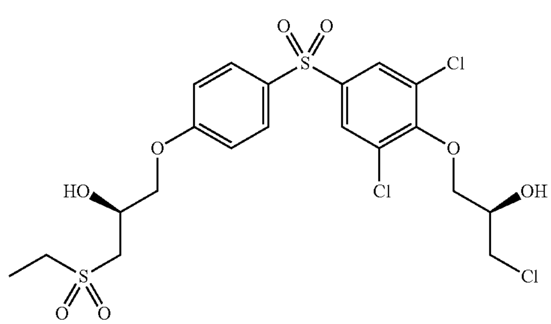 [SMILES: CCS(=O)(=O)C[C@@H](O)COc1ccc(S(=O)(=O)c2cc(Cl)c(OC[C@@H](O)CCl)c(Cl)c2)cc1] | (R)-1-chloro-3-(2,6-dichloro-4-((4-((S)-2-hydroxy-3-(ethylsulfonyl)propoxy)phenyl)sulfonyl)phenoxy)propan-2-ol |

TABLE 3-continued

| No. | Structure | Name |
|---|---|---|
| 51 | 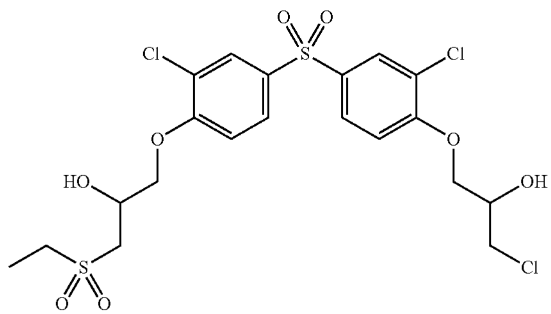 [SMILES: CCS(=O)(=O)CC(O)COc1ccc(S(=O)(=O)c2ccc(OCC(O)CCl)c(Cl)c2)cc1Cl] | 1-chloro-3-(2-chloro-4-((3-chloro-4-(2-hydroxy-3-(ethylsulfonyl)propoxy)phenyl)sulfonyl)phenoxy)propan-2-ol |
| 51a | 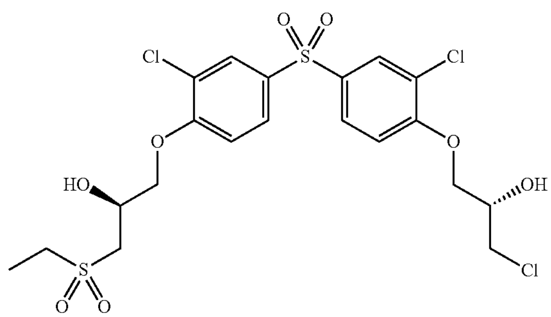 [SMILES: CCS(=O)(=O)C[C@@H](O)COc1ccc(S(=O)(=O)c2ccc(OC[C@H](O)CCl)c(Cl)c2)cc1Cl] | (S)-1-chloro-3-(2-chloro-4-((3-chloro-4-((S)-2-hydroxy-3-(ethylsulfonyl)propoxy)phenyl)sulfonyl)phenoxy)propan-2-ol |
| 51b | 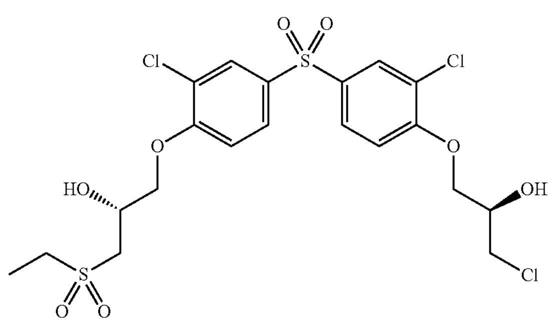 [SMILES: CCS(=O)(=O)C[C@H](O)COc1ccc(S(=O)(=O)c2ccc(OC[C@@H](O)CCl)c(Cl)c2)cc1Cl] | (R)-1-chloro-3-(2-chloro-4-((3-chloro-4-((R)-2-hydroxy-3-(ethylsulfonyl)propoxy)phenyl)sulfonyl)phenoxy)propan-2-ol |
| 51c | 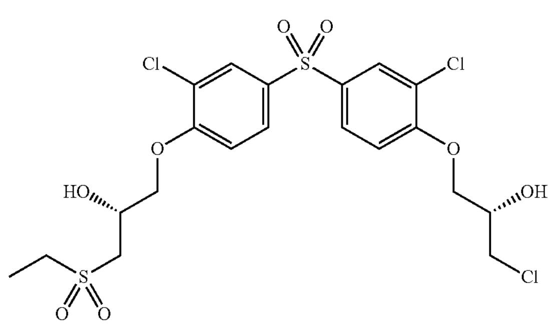 [SMILES: CCS(=O)(=O)C[C@H](O)COc1ccc(S(=O)(=O)c2ccc(OC[C@H](O)CCl)c(Cl)c2)cc1Cl] | (S)-1-chloro-3-(2-chloro-4-((3-chloro-4-((R)-2-hydroxy-3-(ethylsulfonyl)propoxy)phenyl)sulfonyl)phenoxy)propan-2-ol |

TABLE 3-continued

| No. | Structure | Name |
|---|---|---|
| 51d | 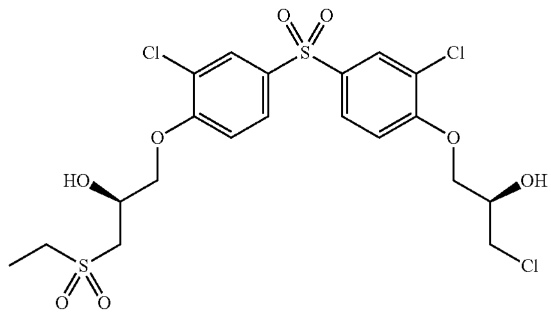 [SMILES: CCS(=O)(=O)C[C@@H](O)COc1ccc(S(=O)(=O)c2ccc(OC[C@@H](O)CCl)c(Cl)c2)cc1Cl] | (R)-1-chloro-3-(2-chloro-4-((3-chloro-4-((S)-2-hydroxy-3-(ethylsulfonyl)propoxy)phenyl)sulfonyl)phenoxy)propan-2-ol |
| 52 | 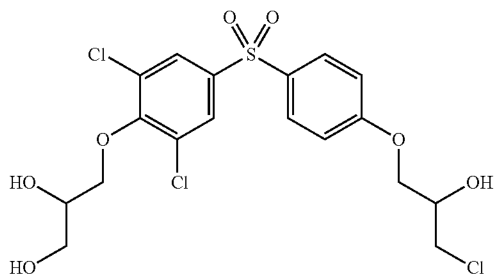 [SMILES: O=S(=O)(c1ccc(OCC(O)CCl)cc1)c1cc(Cl)c(OCC(O)CO)c(Cl)c1] | 3-(2,6-dichloro-4-((4-(3-chloro-2-hydroxypropoxy)phenyl)sulfonyl)phenoxy)propane-1,2-diol |
| 52a | 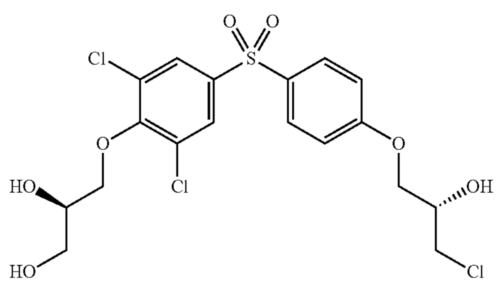 [SMILES: O=S(=O)(c1ccc(OC[C@H](O)CCl)cc1)c1cc(Cl)c(OC[C@H](O)CO)c(Cl)c1] | (R)-3-(2,6-dichloro-4-((4-((S)-3-chloro-2-hydroxypropoxy)phenyl)sulfonyl)phenoxy)propane-1,2-diol |
| 52b | 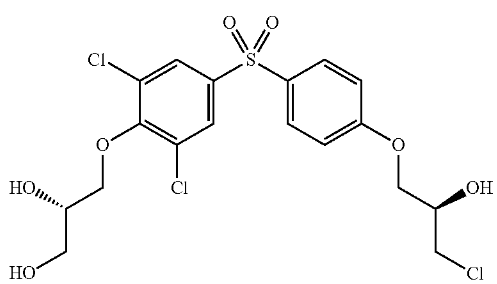 [SMILES: O=S(=O)(c1ccc(OC[C@@H](O)CCl)cc1)c1cc(Cl)c(OC[C@@H](O)CO)c(Cl)c1] | (S)-3-(2,6-dichloro-4-((4-((R)-3-chloro-2-hydroxypropoxy)phenyl)sulfonyl)phenoxy)propane-1,2-diol |
| 52c | 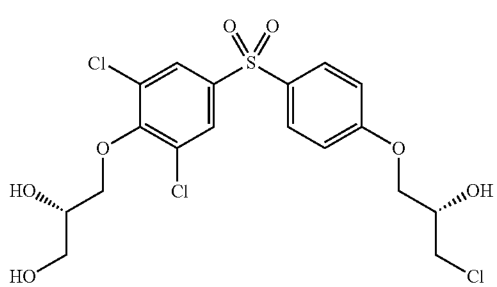 [SMILES: O=S(=O)(c1ccc(OC[C@H](O)CCl)cc1)c1cc(Cl)c(OC[C@@H](O)CO)c(Cl)c1] | (S)-3-(2,6-dichloro-4-((4-((S)-3-chloro-2-hydroxypropoxy)phenyl)sulfonyl)phenoxy)propane-1,2-diol |

TABLE 3-continued

| No. | Structure | Name |
|---|---|---|
| 52d | 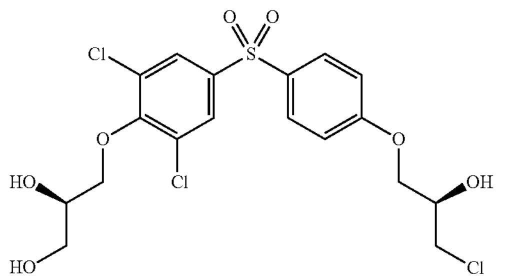 [SMILES: O=S(=O)(c1ccc(OC[C@@H](O)CCl)cc1)c1cc(Cl)c(OC[C@H](O)CO)c(Cl)c1] | (R)-3-(2,6-dichloro-4-((4-((R)-3-chloro-2-hydroxypropoxy)phenyl)sulfonyl)phenoxy)propane-1,2-diol |
| 53 | 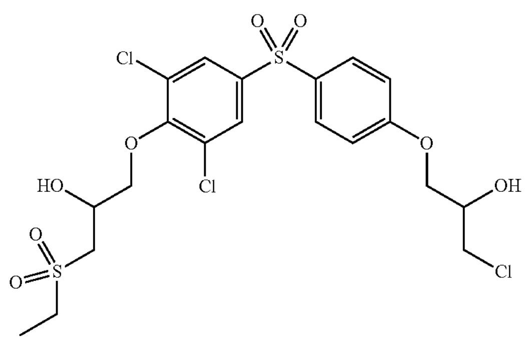 [SMILES: CCS(=O)(=O)CC(O)COc1c(Cl)cc(S(=O)(=O)c2ccc(OCC(O)CCl)cc2)cc1Cl] | 1-chloro-3-(4-((3,5-dichloro-4-(3-(ethylsulfonyl)-2-hydroxypropoxy)phenyl)sulfonyl)phenoxy)propan-2-ol |
| 53a | 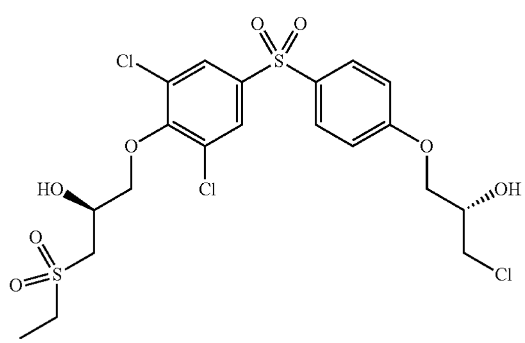 [SMILES: CCS(=O)(=O)C[C@@H](O)COc1c(Cl)cc(S(=O)(=O)c2ccc(OC[C@H](O)CCl)cc2)cc1Cl] | (S)-1-chloro-3-(4-((3,5-dichloro-4-((S)-3-(ethylsulfonyl)-2-hydroxypropoxy)phenyl)sulfonyl)phenoxy)propan-2-ol |
| 53b | 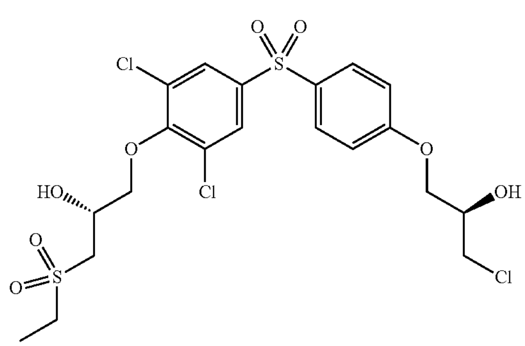 [SMILES: CCS(=O)(=O)C[C@H](O)COc1c(Cl)cc(S(=O)(=O)c2ccc(OC[C@@H](O)CCl)cc2)cc1Cl] | (R)-1-chloro-3-(4-((3,5-dichloro-4-((R)-3-(ethylsulfonyl)-2-hydroxypropoxy)phenyl)sulfonyl)phenoxy)propan-2-ol |

TABLE 3-continued

| No. | Structure | Name |
|---|---|---|
| 53c | 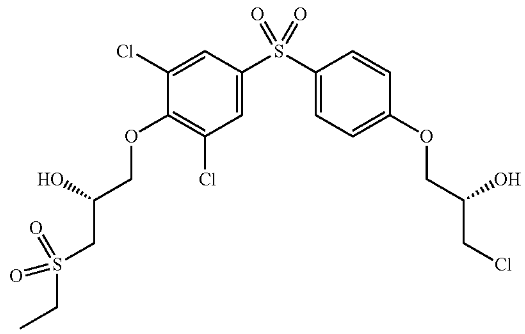 [SMILES: CCS(=O)(=O)C[C@H](O)COc1c(Cl)cc(S(=O)(=O)c2ccc(OC[C@H](O)CCl)cc2)cc1Cl] | (S)-1-chloro-3-(4-((3,5-dichloro-4-((R)-3-(ethylsulfonyl)-2-hydroxypropoxy)phenyl)sulfonyl)phenoxy)propan-2-ol |
| 53d | 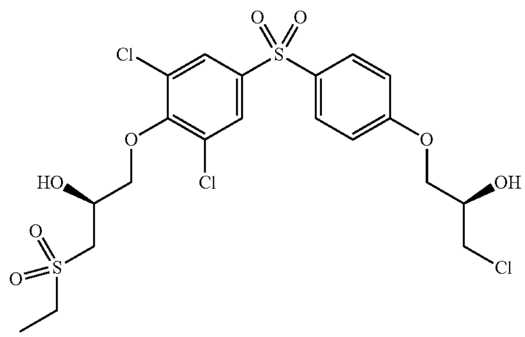 [SMILES: CCS(=O)(=O)C[C@@H](O)COc1c(Cl)cc(S(=O)(=O)c2ccc(OC[C@@H](O)CCl)cc2)cc1Cl] | (R)-1-chloro-3-(4-((3,5-dichloro-4-((S)-3-(ethylsulfonyl)-2-hydroxypropoxy)phenyl)sulfonyl)phenoxy)propan-2-ol |
| 54 | 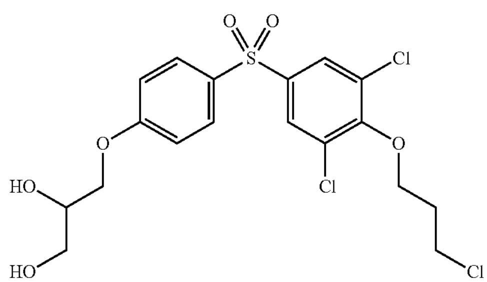 [SMILES: O=S(=O)(c1ccc(OCC(O)CO)cc1)c1cc(Cl)c(OCCCCl)c(Cl)c1] | 3-(4-((3,5-dichloro-4-(3-chloropropoxy)phenyl)sulfonyl)phenoxy)propane-1,2-diol |
| 54a | 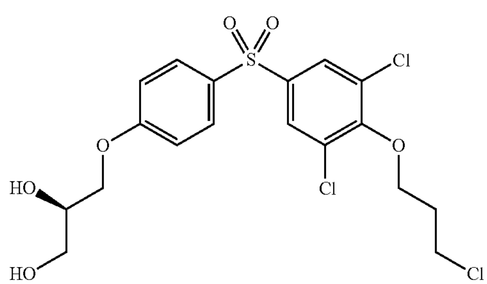 [SMILES: O=S(=O)(c1ccc(OC[C@H](O)CO)cc1)c1cc(Cl)c(OCCCCl)c(Cl)c1] | (R)-3-(4-((3,5-dichloro-4-(3-chloropropoxy)phenyl)sulfonyl)phenoxy)propane-1,2-diol |
| 54b | 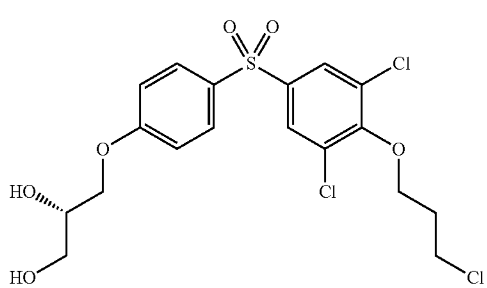 [SMILES: O=S(=O)(c1ccc(OC[C@@H](O)CO)cc1)c1cc(Cl)c(OCCCCl)c(Cl)c1] | (S)-3-(4-((3,5-dichloro-4-(3-chloropropoxy)phenyl)sulfonyl)phenoxy)propane-1,2-diol |

TABLE 3-continued

| No. | Structure | Name |
|---|---|---|
| 55 | 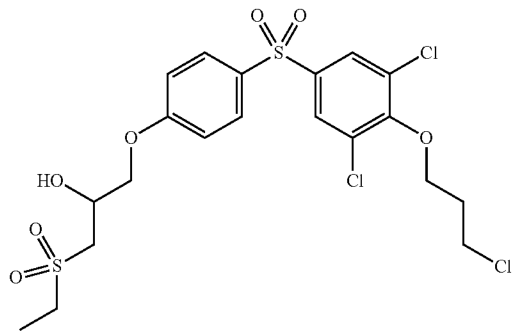 [SMILES: CCS(=O)(=O)CC(O)COc1ccc(S(=O)(=O)c2cc(Cl)c(OCCCCl)c(Cl)c2)cc1] | 1-(4-((3,5-dichloro-4-(3-chloropropoxy)phenyl)sulfonyl)phenoxy)-3-(ethylsulfonyl)propan-2-ol |
| 55a | 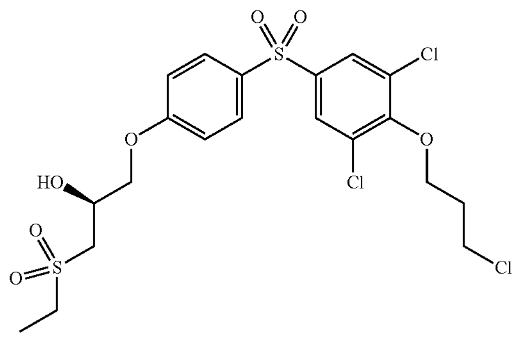 [SMILES: CCS(=O)(=O)C[C@@H](O)COc1ccc(S(=O)(=O)c2cc(Cl)c(OCCCCl)c(Cl)c2)cc1] | (S)-1-(4-((3,5-dichloro-4-(3-chloropropoxy)phenyl)sulfonyl)phenoxy)-3-(ethylsulfonyl)propan-2-ol |
| 55b | 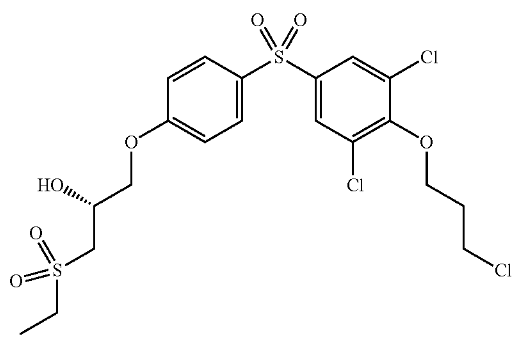 [SMILES: CCS(=O)(=O)C[C@H](O)COc1ccc(S(=O)(=O)c2cc(Cl)c(OCCCCl)c(Cl)c2)cc1] | (R)-1-(4-((3,5-dichloro-4-(3-chloropropoxy)phenyl)sulfonyl)phenoxy)-3-(ethylsulfonyl)propan-2-ol |
| 56 | 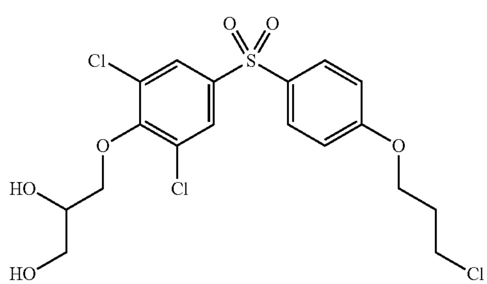 [SMILES: O=S(=O)(c1ccc(OCCCCl)cc1)c1cc(Cl)c(OCC(O)CO)c(Cl)c1] | 3-(2,6-dichloro-4-((4-(3-chloropropoxy)phenyl)sulfonyl)phenoxy)propane-1,2-diol |
| 56a | 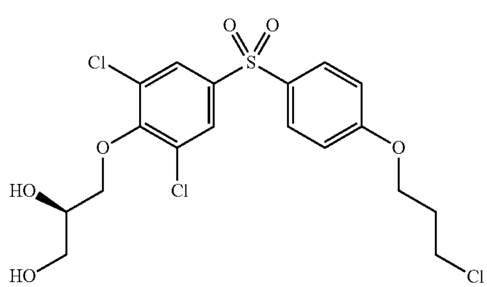 [SMILES: O=S(=O)(c1ccc(OCCCCl)cc1)c1cc(Cl)c(OC[C@H](O)CO)c(Cl)c1] | (R)-3-(2,6-dichloro-4-((4-(3-chloropropoxy)phenyl)sulfonyl)phenoxy)propane-1,2-diol |

TABLE 3-continued

Compounds

| No. | Structure | Name |
|---|---|---|
| 56b | 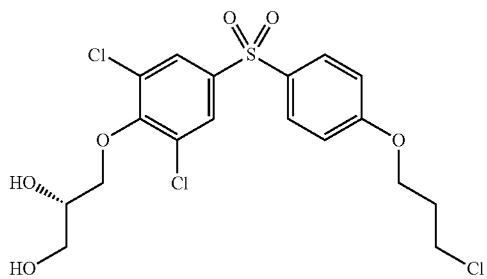 [SMILES: O=S(=O)(c1ccc(OCCCCl)cc1)c1cc(Cl)c(OC[C@@H](O)CO)c(Cl)c1] | (S)-3-(2,6-dichloro-4-((4-(3-chloropropoxy)phenyl)sulfonyl)phenoxy)propane-1,2-diol |
| 57 | 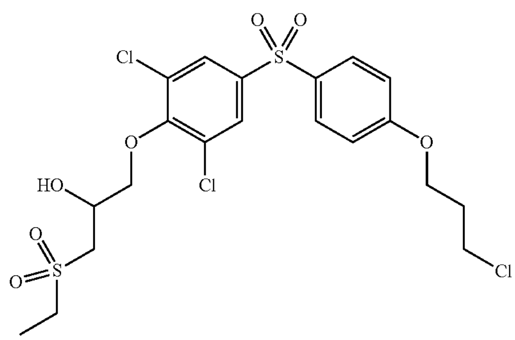 [SMILES: CCS(=O)(=O)CC(O)COc1c(Cl)cc(S(=O)(=O)c2ccc(OCCCCl)cc2)cc1Cl] | 1-(2,6-dichloro-4-((4-(3-chloropropoxy)phenyl)sulfonyl)phenoxy)-3-(ethylsulfonyl)propan-2-ol |
| 57a | 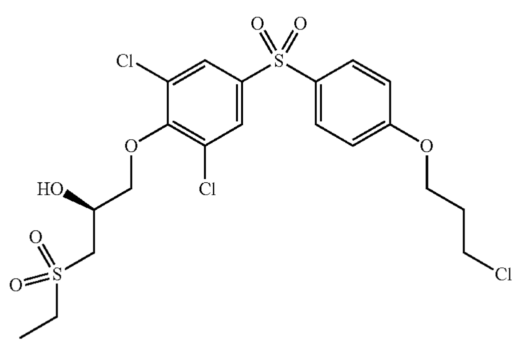 [SMILES: CCS(=O)(=O)C[C@@H](O)COc1c(Cl)cc(S(=O)(=O)c2ccc(OCCCCl)cc2)cc1Cl] | (S)-1-(2,6-dichloro-4-((4-(3-chloropropoxy)phenyl)sulfonyl)phenoxy)-3-(ethylsulfonyl)propan-2-ol |
| 57b | 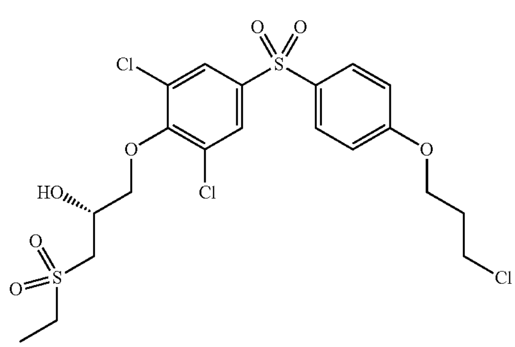 [SMILES: CCS(=O)(=O)C[C@H](O)COc1c(Cl)cc(S(=O)(=O)c2ccc(OCCCCl)cc2)cc1Cl] | (R)-1-(2,6-dichloro-4-((4-(3-chloropropoxy)phenyl)sulfonyl)phenoxy)-3-(ethylsulfonyl)propan-2-ol |

In some more specific embodiments of the compound of Formula I, the compound has one of the following structures from Table 4, or a pharmaceutically acceptable salt, tautomer, or stereoisomer thereof:

TABLE 4

| No. | Structure | Name |
|---|---|---|
| A40 | 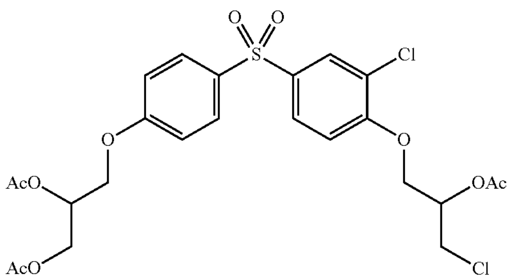 [SMILES: CC(=O)OCC(COc1ccc(S(=O)(=O)c2ccc(OCC(CCl)OC(C)=O)c(Cl)c2)cc1)OC(C)=O] | 3-(4-((4-(2-acetoxy-3-chloropropoxy)-3-chlorophenyl)sulfonyl)phenoxy)propane-1,2-diyl diacetate |
| A40a | 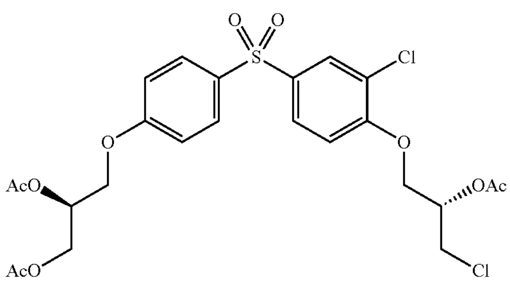 [SMILES: CC(=O)OC[C@H](COc1ccc(S(=O)(=O)c2ccc(OC[C@@H](CCl)OC(C)=O)c(Cl)c2)cc1)OC(C)=O] | (S)-3-(4-((4-((S)-2-acetoxy-3-chloropropoxy)-3-chlorophenyl)sulfonyl)phenoxy)propane-1,2-diyl diacetate |
| A40b | 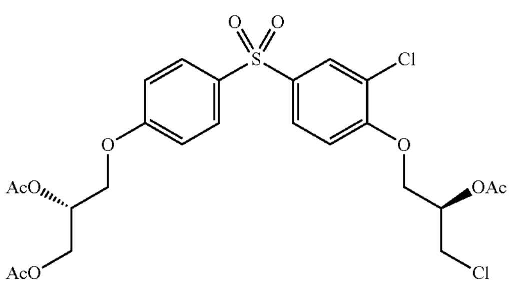 [SMILES: CC(=O)OC[C@@H](COc1ccc(S(=O)(=O)c2ccc(OC[C@H](CCl)OC(C)=O)c(Cl)c2)cc1)OC(C)=O] | (R)-3-(4-((4-((R)-2-acetoxy-3-chloropropoxy)-3-chlorophenyl)sulfonyl)phenoxy)propane-1,2-diyl diacetate |
| A40c | 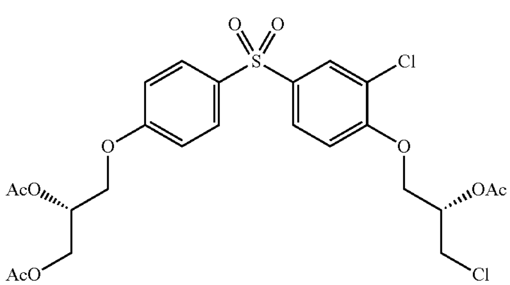 [SMILES: CC(=O)OC[C@@H](COc1ccc(S(=O)(=O)c2ccc(OC[C@@H](CCl)OC(C)=O)c(Cl)c2)cc1)OC(C)=O] | (R)-3-(4-((4-((S)-2-acetoxy-3-chloropropoxy)-3-chlorophenyl)sulfonyl)phenoxy)propane-1,2-diyl diacetate |
| A40d | 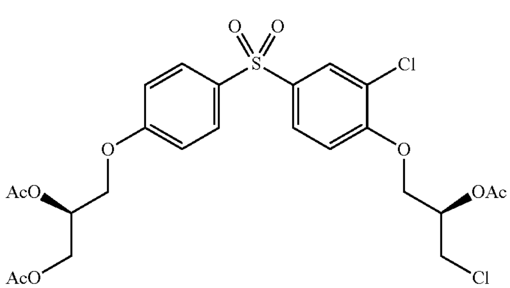 [SMILES: CC(=O)OC[C@H](COc1ccc(S(=O)(=O)c2ccc(OC[C@H](CCl)OC(C)=O)c(Cl)c2)cc1)OC(C)=O] | (S)-3-(4-((4-((R)-2-acetoxy-3-chloropropoxy)-3-chlorophenyl)sulfonyl)phenoxy)propane-1,2-diyl diacetate |

TABLE 4-continued

| No. | Structure | Name |
|---|---|---|
| A41 | 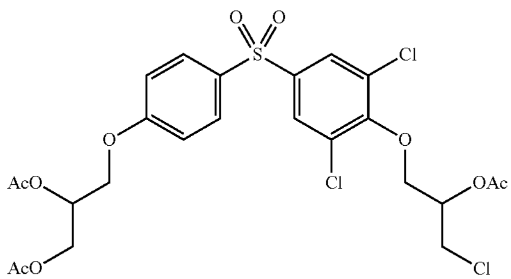 [SMILES: CC(=O)OCC(COc1ccc(S(=O)(=O)c2cc(Cl)c(OCC(CCl)OC(C)=O)c(Cl)c2)cc1)OC(C)=O] | 3-(4-((4-(2-acetoxy-3-chloropropoxy)-3,5-dichlorophenyl)sulfonyl)phenoxy)propane-1,2-diyl diacetate |
| A41a | 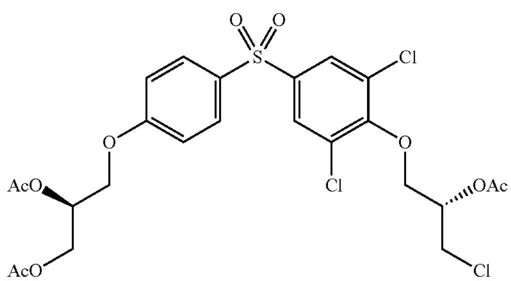 [SMILES: CC(=O)OC[C@H](COc1ccc(S(=O)(=O)c2cc(Cl)c(OC[C@@H](CCl)OC(C)=O)c(Cl)c2)cc1)OC(C)=O] | (S)-3-(4-((4-((S)-2-acetoxy-3-chloropropoxy)-3,5-dichlorophenyl)sulfonyl)phenoxy)propane-1,2-diyl diacetate |
| A41b | 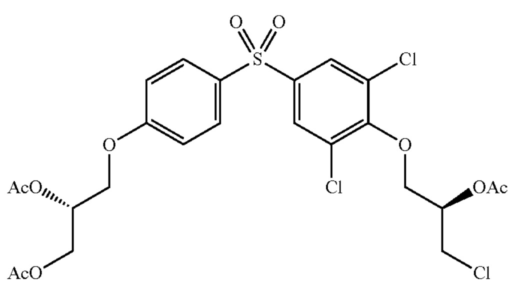 [SMILES: CC(=O)OC[C@@H](COc1ccc(S(=O)(=O)c2cc(Cl)c(OC[C@H](CCl)OC(C)=O)c(Cl)c2)cc1)OC(C)=O] | (R)-3-(4-((4-((R)-2-acetoxy-3-chloropropoxy)-3,5-dichlorophenyl)sulfonyl)phenoxy)propane-1,2-diyl diacetate |
| A41c | 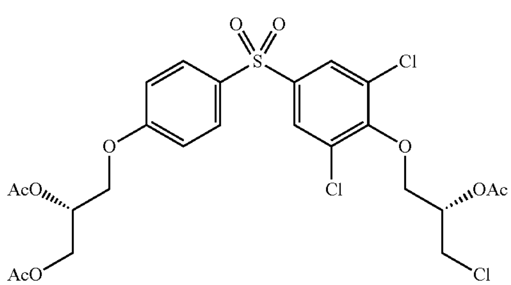 [SMILES: CC(=O)OC[C@@H](COc1ccc(S(=O)(=O)c2cc(Cl)c(OC[C@@H](CCl)OC(C)=O)c(Cl)c2)cc1)OC(C)=O] | (R)-3-(4-((4-((S)-2-acetoxy-3-chloropropoxy)-3,5-dichlorophenyl)sulfonyl)phenoxy)propane-1,2-diyl diacetate |
| A41d | 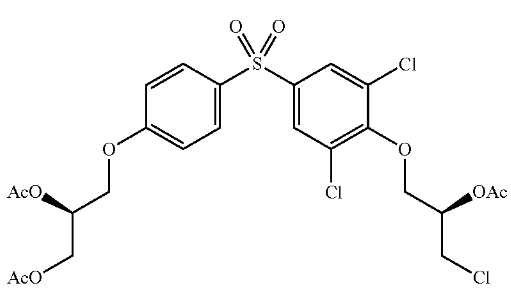 [SMILES: CC(=O)OC[C@H](COc1ccc(S(=O)(=O)c2cc(Cl)c(OC[C@H](CCl)OC(C)=O)c(Cl)c2)cc1)OC(C)=O] | (S)-3-(4-((4-((R)-2-acetoxy-3-chloropropoxy)-3,5-dichlorophenyl)sulfonyl)phenoxy)propane-1,2-diyl diacetate |

TABLE 4-continued

| No. | Structure | Name |
|---|---|---|
| A42 | 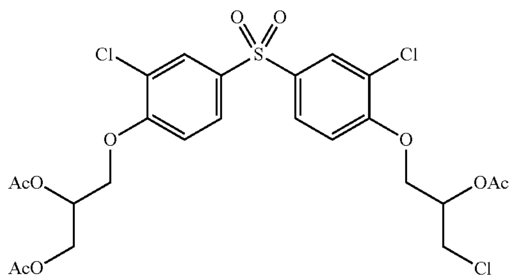 [SMILES: CC(=O)OCC(COc1ccc(S(=O)(=O)c2ccc(OCC(CCl)OC(C)=O)c(Cl)c2)cc1Cl)OC(C)=O] | 3-(4-((4-(2-acetoxy-3-chloropropoxy)-3-chlorophenyl)sulfonyl)-2-chlorophenoxy)propane-1,2-diyl diacetate |
| A42a | 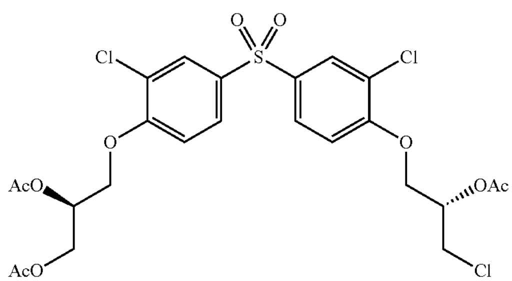 [SMILES: CC(=O)OC[C@H](COc1ccc(S(=O)(=O)c2ccc(OC[C@@H](CCl)OC(C)=O)c(Cl)c2)cc1Cl)OC(C)=O] | (S)-3-(4-((4-((S)-2-acetoxy-3-chloropropoxy)-3-chlorophenyl)sulfonyl)-2-chlorophenoxy)propane-1,2-diyl diacetate |
| A42b | 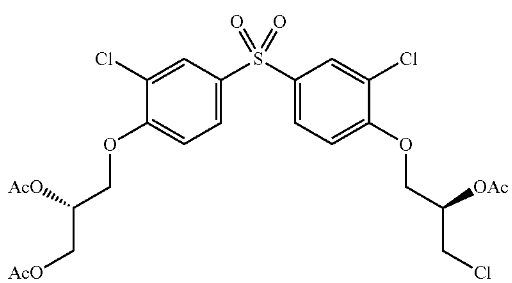 [SMILES: CC(=O)OC[C@@H](COc1ccc(S(=O)(=O)c2ccc(OC[C@H](CCl)OC(C)=O)c(Cl)c2)cc1Cl)OC(C)=O] | (R)-3-(4-((4-((R)-2-acetoxy-3-chloropropoxy)-3-chlorophenyl)sulfonyl)-2-chlorophenoxy)propane-1,2-diyl diacetate |
| A42c | 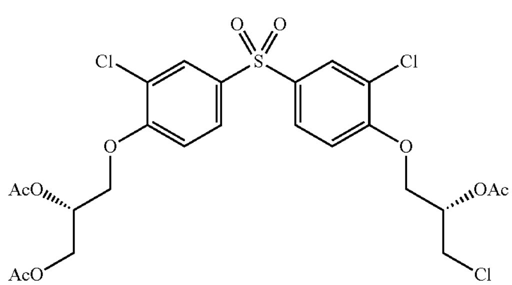 [SMILES: CC(=O)OC[C@@H](COc1ccc(S(=O)(=O)c2ccc(OC[C@@H](CCl)OC(C)=O)c(Cl)c2)cc1Cl)OC(C)=O] | (R)-3-(4-((4-((S)-2-acetoxy-3-chloropropoxy)-3-chlorophenyl)sulfonyl)-2-chlorophenoxy)propane-1,2-diyl diacetate |
| A42d | 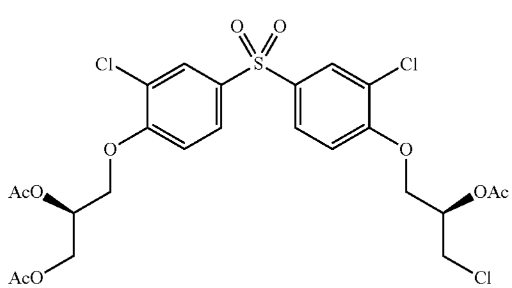 [SMILES: CC(=O)OC[C@H](COc1ccc(S(=O)(=O)c2ccc(OC[C@H](CCl)OC(C)=O)c(Cl)c2)cc1Cl)OC(C)=O] | (S)-3-(4-((4-((R)-2-acetoxy-3-chloropropoxy)-3-chlorophenyl)sulfonyl)-2-chlorophenoxy)propane-1,2-diyl diacetate |

TABLE 4-continued

Compounds

| No. | Structure | Name |
|---|---|---|
| A43 | 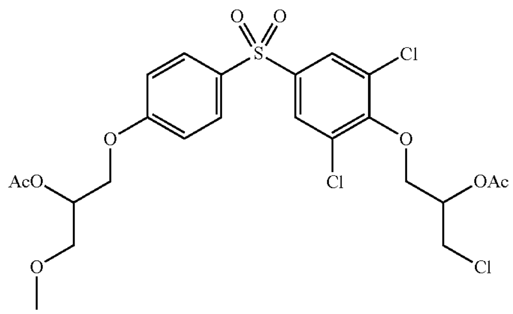 [SMILES: COCC(COc1ccc(S(=O)(=O)c2cc(Cl)c(OCC(CCl)OC(C)=O)c(Cl)c2)cc1)OC(C)=O] | 1-(4-((4-(2-acetoxy-3-chloropropoxy)-3,5-dichlorophenyl)sulfonyl)phenoxy)-3-methoxypropan-2-yl acetate |
| A43a | 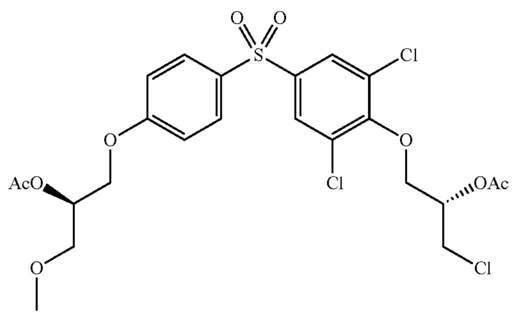 [SMILES: COC[C@H](COc1ccc(S(=O)(=O)c2cc(Cl)c(OC[C@@H](CCl)OC(C)=O)c(Cl)c2)cc1)OC(C)=O] | (R)-1-(4-((4-((S)-2-acetoxy-3-chloropropoxy)-3,5-dichlorophenyl)sulfonyl)phenoxy)-3-methoxypropan-2-yl acetate |
| A43b | 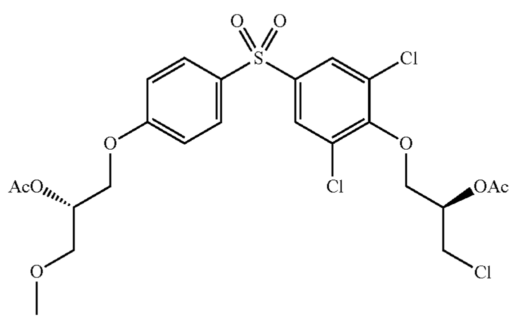 [SMILES: COC[C@@H](COc1ccc(S(=O)(=O)c2cc(Cl)c(OC[C@H](CCl)OC(C)=O)c(Cl)c2)cc1)OC(C)=O] | (S)-1-(4-((4-((R)-2-acetoxy-3-chloropropoxy)-3,5-dichlorophenyl)sulfonyl)phenoxy)-3-methoxypropan-2-yl acetate |
| A43c | 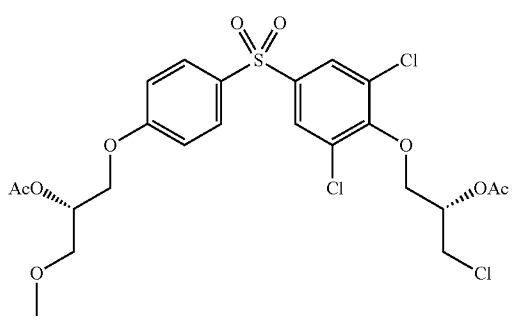 [SMILES: COC[C@@H](COc1ccc(S(=O)(=O)c2cc(Cl)c(OC[C@@H](CCl)OC(C)=O)c(Cl)c2)cc1)OC(C)=O] | (S)-1-(4-((4-((S)-2-acetoxy-3-chloropropoxy)-3,5-dichlorophenyl)sulfonyl)phenoxy)-3-methoxypropan-2-yl acetate |
| A43d | 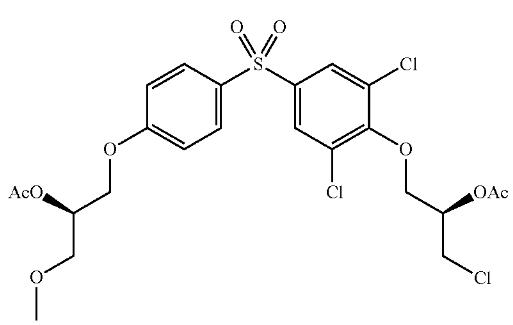 [SMILES: COC[C@H](COc1ccc(S(=O)(=O)c2cc(Cl)c(OC[C@H](CCl)OC(C)=O)c(Cl)c2)cc1)OC(C)=O] | (R)-1-(4-((4-((R)-2-acetoxy-3-chloropropoxy)-3,5-dichlorophenyl)sulfonyl)phenoxy)-3-methoxypropan-2-yl acetate |

TABLE 4-continued

| No. | Structure | Name |
|---|---|---|
| A44 | 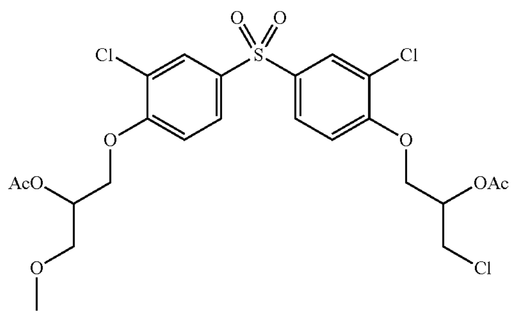 [SMILES: COCC(COc1ccc(S(=O)(=O)c2ccc(OCC(CCl)OC(C)=O)c(Cl)c2)cc1Cl)OC(C)=O] | 1-(4-((4-(2-acetoxy-3-chloropropoxy)-3-chlorophenyl)sulfonyl)-2-chlorophenoxy)-3-methoxypropan-2-yl acetate |
| A44a | 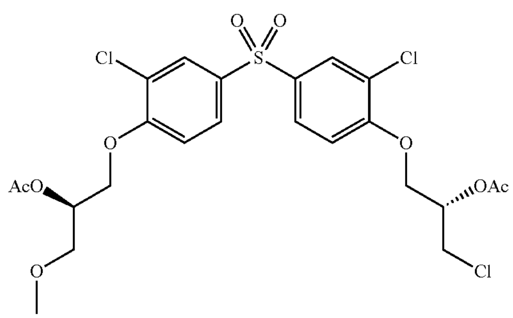 [SMILES: COC[C@H](COc1ccc(S(=O)(=O)c2ccc(OC[C@@H](CCl)OC(C)=O)c(Cl)c2)cc1Cl)OC(C)=O] | (R)-1-(4-((4-((S)-2-acetoxy-3-chloropropoxy)-3-chlorophenyl)sulfonyl)-2-chlorophenoxy)-3-methoxypropan-2-yl acetate |
| A44b | 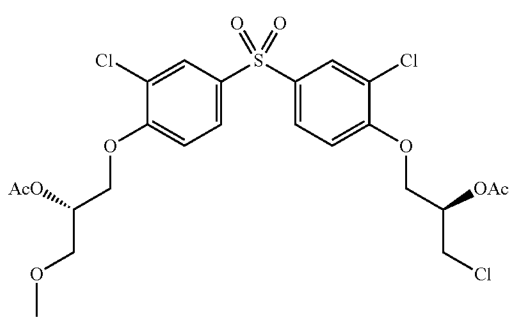 [SMILES: COC[C@@H](COc1ccc(S(=O)(=O)c2ccc(OC[C@H](CCl)OC(C)=O)c(Cl)c2)cc1Cl)OC(C)=O] | (S)-1-(4-((4-((R)-2-acetoxy-3-chloropropoxy)-3-chlorophenyl)sulfonyl)-2-chlorophenoxy)-3-methoxypropan-2-yl acetate |
| A44c | 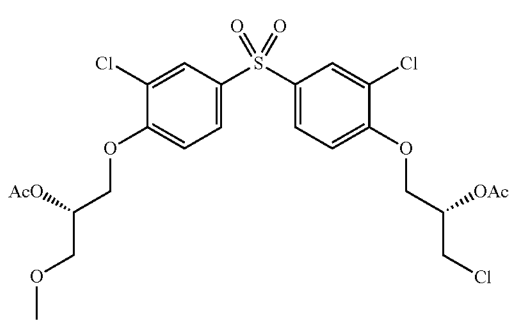 [SMILES: COC[C@@H](COc1ccc(S(=O)(=O)c2ccc(OC[C@@H](CCl)OC(C)=O)c(Cl)c2)cc1Cl)OC(C)=O] | (S)-1-(4-((4-((S)-2-acetoxy-3-chloropropoxy)-3-chlorophenyl)sulfonyl)-2-chlorophenoxy)-3-methoxypropan-2-yl acetate |

TABLE 4-continued

| No. | Structure | Name |
|---|---|---|
| A44d | 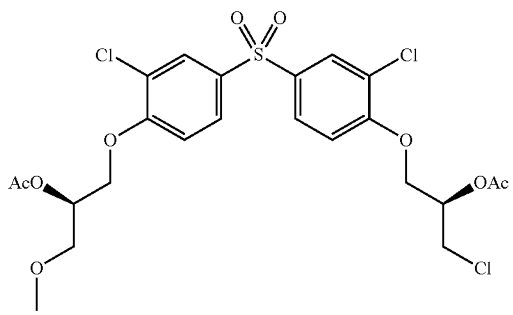 [SMILES: COC[C@H](COc1ccc(S(=O)(=O)c2ccc(OC[C@H](CCl)OC(C)=O)c(Cl)c2)cc1Cl)OC(C)=O] | (R)-1-(4-((4-((R)-2-acetoxy-3-chloropropoxy)-3-chlorophenyl)sulfonyl)-2-chlorophenoxy)-3-methoxypropan-2-yl acetate |
| A45 | 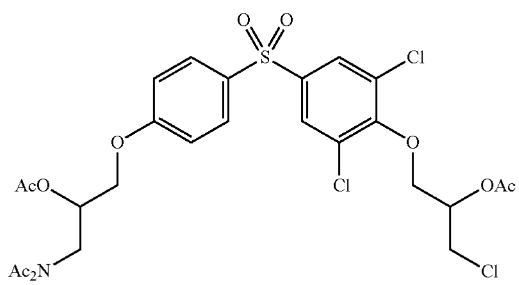 | 1-(4-((4-(2-acetoxy-3-(N-acetylacetamido)propoxy)phenyl)sulfonyl)-2,6-dichlorophenoxy)-3-chloropropan-2-yl acetate |
| A45a | 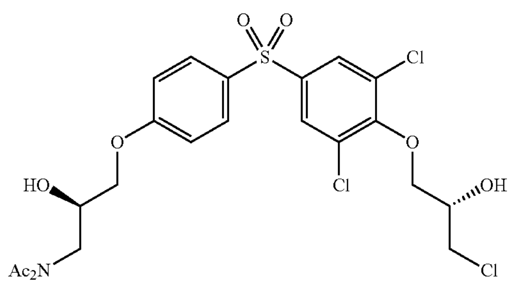 | N-acetyl-N-((R)-3-(4-((3,5-dichloro-4-((S)-3-chloro-2-hydroxypropoxy)phenyl)sulfonyl)phenoxy)-2-hydroxypropyl)acetamide |
| A45b | 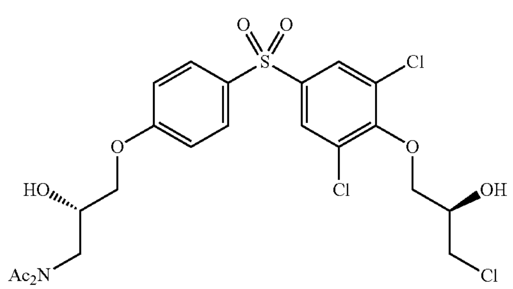 | N-acetyl-N-((S)-3-(4-((3,5-dichloro-4-((R)-3-chloro-2-hydroxypropoxy)phenyl)sulfonyl)phenoxy)-2-hydroxypropyl)acetamide |
| A45c | 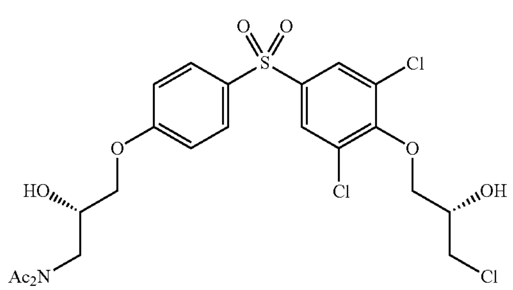 | N-acetyl-N-((S)-3-(4-((3,5-dichloro-4-((S)-3-chloro-2-hydroxypropoxy)phenyl)sulfonyl)phenoxy)-2-hydroxypropyl)acetamide |

TABLE 4-continued

| No. | Structure | Name |
|---|---|---|
| A45d | 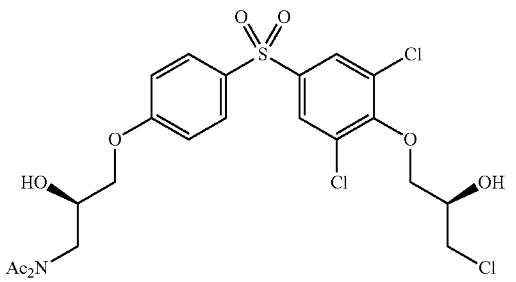 | N-acetyl-N-((R)-3-(4-((3,5-dichloro-4-((R)-3-chloro-2-hydroxypropoxy)phenyl)sulfonyl)phenoxy)-2-hydroxypropyl)acetamide |
| B45 | 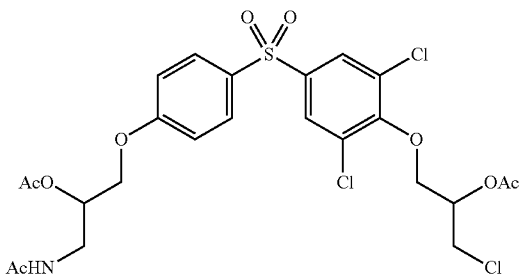 [SMILES: CC(=O)NCC(COc1ccc(S(=O)(=O)c2cc(Cl)c(OCC(CCl)OC(C)=O)c(Cl)c2)cc1)OC(C)=O] | 1-(4-((4-(3-acetamido-2-acetoxypropoxy)phenyl)sulfonyl)-2,6-dichlorophenoxy)-3-chloropropan-2-yl acetate |
| B45a | 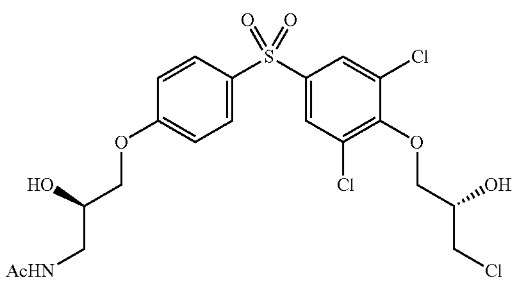 [SMILES: CC(=O)NC[C@@H](O)COc1ccc(S(=O)(=O)c2cc(Cl)c(OC[C@H](O)CCl)c(Cl)c2)cc1] | N-((R)-3-(4-((3,5-dichloro-4-((S)-3-chloro-2-hydroxypropoxy)phenyl)sulfonyl)phenoxy)-2-hydroxypropyl)acetamide |
| B45b | 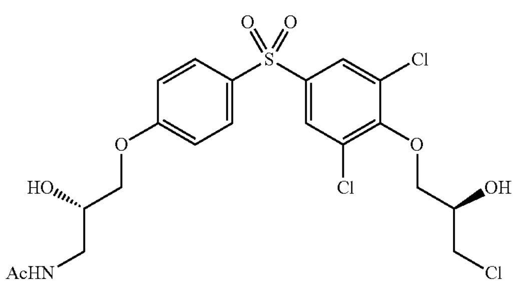 [SMILES: CC(=O)NC[C@H](O)COc1ccc(S(=O)(=O)c2cc(Cl)c(OC[C@@H](O)CCl)c(Cl)c2)cc1] | N-((S)-3-(4-((3,5-dichloro-4-((R)-3-chloro-2-hydroxypropoxy)phenyl)sulfonyl)phenoxy)-2-hydroxypropyl)acetamide |
| B45c | 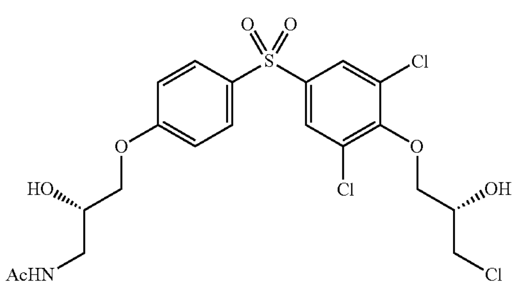 [SMILES: CC(=O)NC[C@H](O)COc1ccc(S(=O)(=O)c2cc(Cl)c(OC[C@H](O)CCl)c(Cl)c2)cc1] | N-((S)-3-(4-((3,5-dichloro-4-((S)-3-chloro-2-hydroxypropoxy)phenyl)sulfonyl)phenoxy)-2-hydroxypropyl)acetamide |

TABLE 4-continued

| No. | Structure | Name |
|---|---|---|
| B45d | 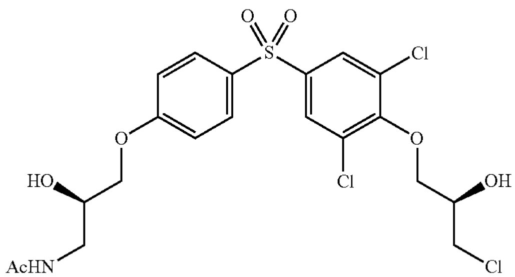 [SMILES: CC(=O)NC[C@@H](O)COc1ccc(S(=O)(=O)c2cc(Cl)c(OC[C@@H](O)CCl)c(Cl)c2)cc1] | N-((R)-3-(4-((3,5-dichloro-4-((R)-3-chloro-2-hydroxypropoxy)phenyl)sulfonyl)phenoxy)-2-hydroxypropyl)acetamide |
| A46 | 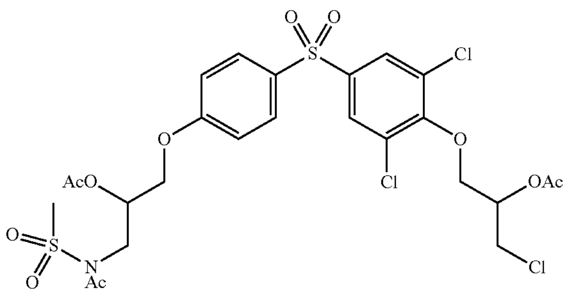 | 1-(4-((4-(2-acetoxy-3-(N-(methylsulfonyl)acetamido)propoxy)phenyl)sulfonyl)-2,6-dichlorophenoxy)-3-chloropropan-2-yl acetate |
| A46a | 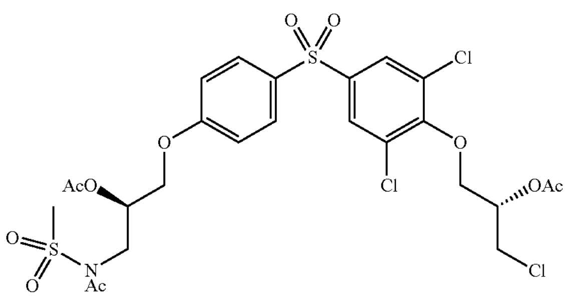 | (S)-1-(4-((4-((R)-2-acetoxy-3-(N-(methylsulfonyl)acetamido)propoxy)phenyl)sulfonyl)-2,6-dichlorophenoxy)-3-chloropropan-2-yl acetate |
| A46b | 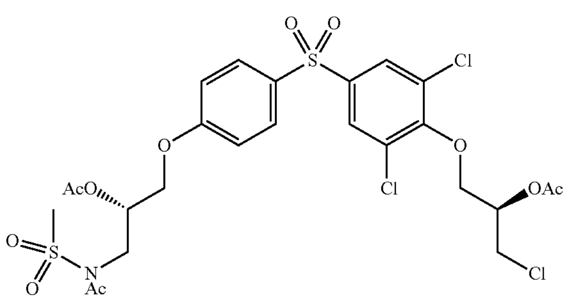 | (R)-1-(4-((4-((S)-2-acetoxy-3-(N-(methylsulfonyl)acetamido)propoxy)phenyl)sulfonyl)-2,6-dichlorophenoxy)-3-chloropropan-2-yl acetate |
| A46c | 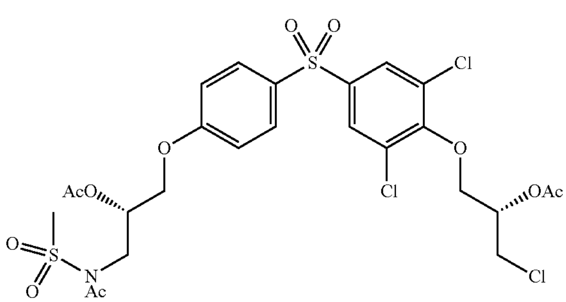 | (S)-1-(4-((4-((S)-2-acetoxy-3-(N-(methylsulfonyl)acetamido)propoxy)phenyl)sulfonyl)-2,6-dichlorophenoxy)-3-chloropropan-2-yl acetate |

TABLE 4-continued

| No. | Structure | Name |
|---|---|---|
| A46d | 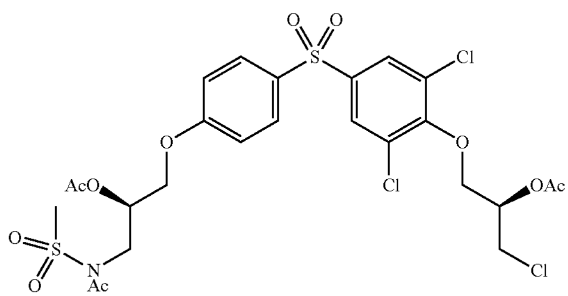 | (R)-1-(4-((4-((R)-2-acetoxy-3-(N-(methylsulfonyl)acetamido)propoxy)phenyl)sulfonyl)-2,6-dichlorophenoxy)-3-chloropropan-2-yl acetate |
| A47 | 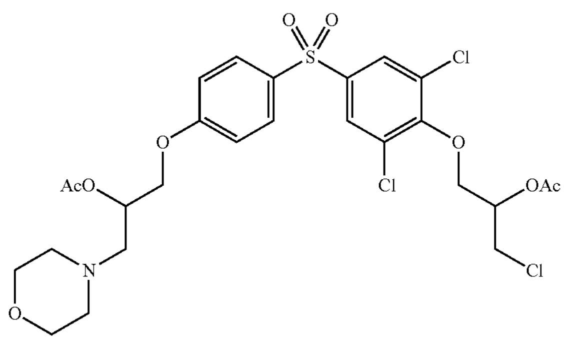 [SMILES: CC(=O)OC(CCl)COc1c(Cl)cc(S(=O)(=O)c2ccc(OCC(CN3CCOCC3)OC(C)=O)cc2)cc1Cl] | 1-(4-((4-(2-acetoxy-3-chloropropoxy)-3,5-dichlorophenyl)sulfonyl)phenoxy)-3-morpholinopropan-2-yl acetate |
| A47a | 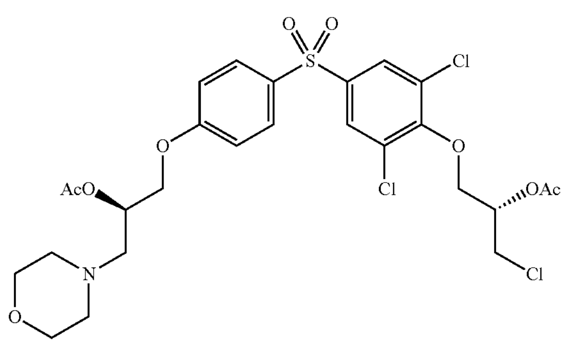 [SMILES: CC(=O)O[C@H](CCl)COc1c(Cl)cc(S(=O)(=O)c2ccc(OC[C@@H](CN3CCOCC3)OC(C)=O)cc2)cc1Cl] | (R)-1-(4-((4-((S)-2-acetoxy-3-chloropropoxy)-3,5-dichlorophenyl)sulfonyl)phenoxy)-3-morpholinopropan-2-yl acetate |
| A47b | 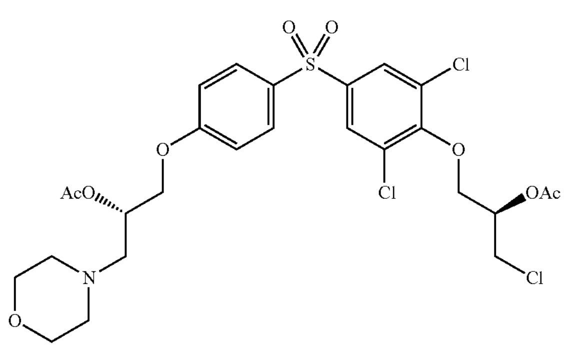 [SMILES: CC(=O)O[C@H](COc1ccc(S(=O)(=O)c2cc(Cl)c(OC[C@H](CCl)OC(C)=O)c(Cl)c2)cc1)CN1CCOCC1] | (S)-1-(4-((4-((R)-2-acetoxy-3-chloropropoxy)-3,5-dichlorophenyl)sulfonyl)phenoxy)-3-morpholinopropan-2-yl acetate |

TABLE 4-continued

| No. | Structure | Name |
|---|---|---|
| A47c | 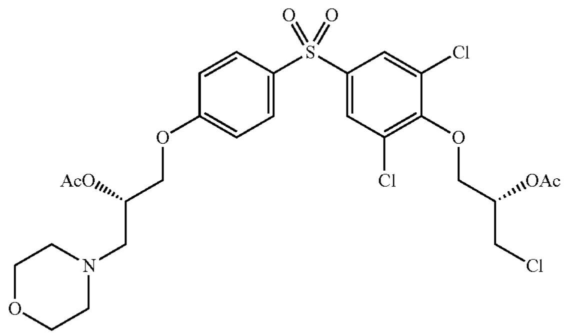 [SMILES: CC(=O)O[C@H](CCl)COc1c(Cl)cc(S(=O)(=O)c2ccc(OC[C@H](CN3CCOCC3)OC(C)=O)cc2)cc1Cl] | (S)-1-(4-((4-((S)-2-acetoxy-3-chloropropoxy)-3,5-dichlorophenyl)sulfonyl)phenoxy)-3-morpholinopropan-2-yl acetate |
| A47d | 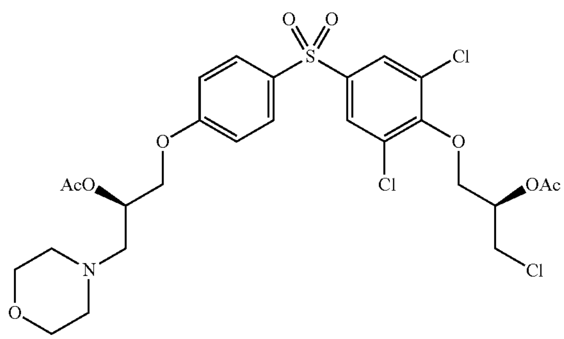 [SMILES: CC(=O)O[C@@H](CCl)COc1c(Cl)cc(S(=O)(=O)c2ccc(OC[C@@H](CN3CCOCC3)OC(C)=O)cc2)cc1Cl] | (R)-1-(4-((4-((R)-2-acetoxy-3-chloropropoxy)-3,5-dichlorophenyl)sulfonyl)phenoxy)-3-morpholinopropan-2-yl acetate |
| A48 | 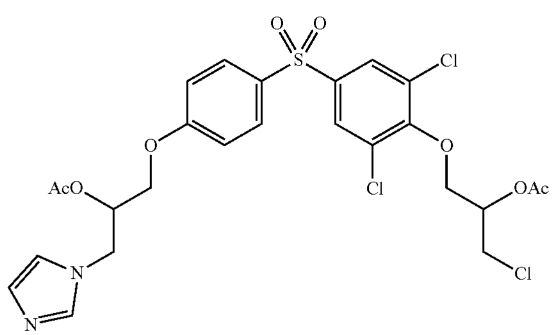 [SMILES: CC(=O)OC(CCl)COc1c(Cl)cc(S(=O)(=O)c2ccc(OCC(Cn3ccnc3)OC(C)=O)cc2)cc1Cl] | 1-(4-((4-(2-acetoxy-3-(1H-imidazol-1-yl)propoxy)phenyl)sulfonyl)-2,6-dichlorophenoxy)-3-chloropropan-2-yl acetate |
| A48a | 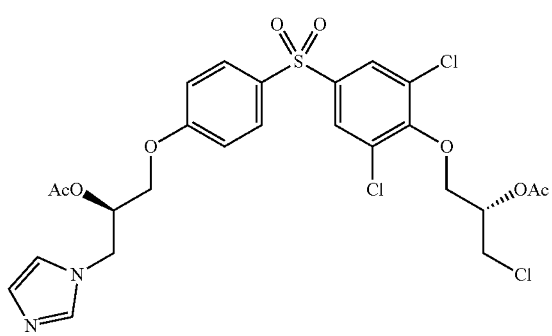 [SMILES: CC(=O)O[C@H](CCl)COc1c(Cl)cc(S(=O)(=O)c2ccc(OC[C@@H](Cn3ccnc3)OC(C)=O)cc2)cc1Cl] | (S)-1-(4-((4-((R)-2-acetoxy-3-(1H-imidazol-1-yl)propoxy)phenyl)sulfonyl)-2,6-dichlorophenoxy)-3-chloropropan-2-yl acetate |

TABLE 4-continued

| No. | Structure | Name |
| --- | --- | --- |
| A48b | 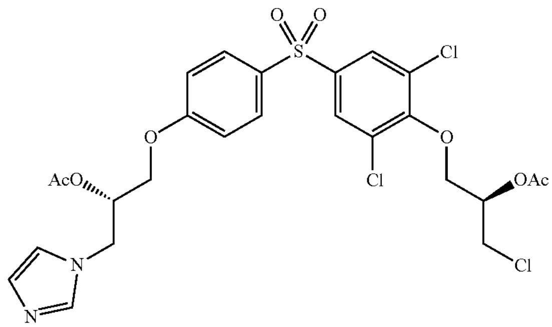 [SMILES: CC(=O)O[C@H](COc1ccc(S(=O)(=O)c2cc(Cl)c(OC[C@H](CCl)OC(C)=O)c(Cl)c2)cc1)Cn1ccnc1] | (R)-1-(4-((4-((S)-2-acetoxy-3-(1H-imidazol-1-yl)propoxy)phenyl)sulfonyl)-2,6-dichlorophenoxy)-3-chloropropan-2-yl acetate |
| A48c | 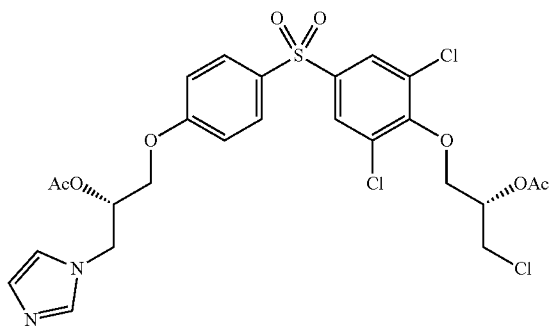 [SMILES: CC(=O)O[C@H](CCl)COc1c(Cl)cc(S(=O)(=O)c2ccc(OC[C@H](Cn3ccnc3)OC(C)=O)cc2)cc1Cl] | (S)-1-(4-((4-((S)-2-acetoxy-3-(1H-imidazol-1-yl)propoxy)phenyl)sulfonyl)-2,6-dichlorophenoxy)-3-chloropropan-2-yl acetate |
| A48d | 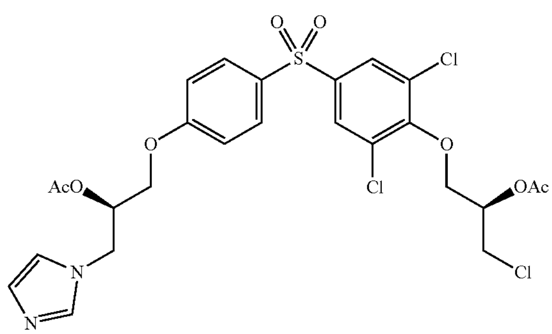 [SMILES: CC(=O)O[C@@H](CCl)COc1c(Cl)cc(S(=O)(=O)c2ccc(OC[C@@H](Cn3ccnc3)OC(C)=O)cc2)cc1Cl] | (R)-1-(4-((4-((R)-2-acetoxy-3-(1H-imidazol-1-yl)propoxy)phenyl)sulfonyl)-2,6-dichlorophenoxy)-3-chloropropan-2-yl acetate |
| A49 | 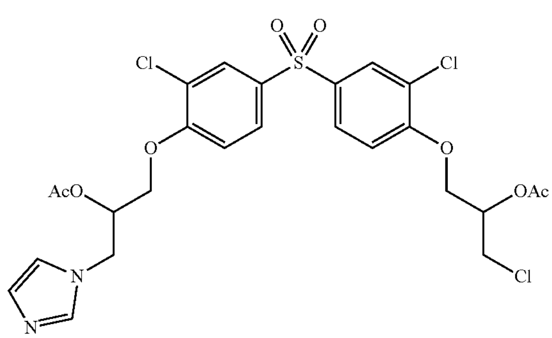 [SMILES: CC(=O)OC(CCl)COc1ccc(S(=O)(=O)c2ccc(OCC(Cn3ccnc3)OC(C)=O)c(Cl)c2)cc1Cl] | 1-(4-((4-(2-acetoxy-3-(1H-imidazol-1-yl)propoxy)-3-chlorophenyl)sulfonyl)-2-chlorophenoxy)-3-chloropropan-2-yl acetate |

TABLE 4-continued

| No. | Structure | Name |
|---|---|---|
| A49a | 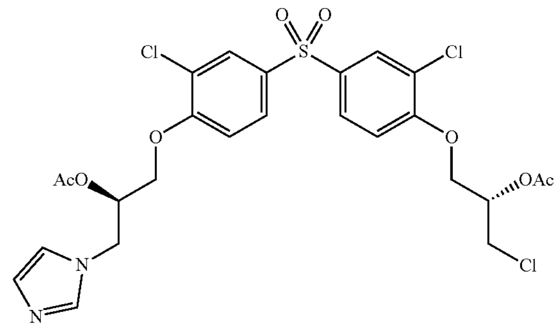 [SMILES: CC(=O)O[C@H](CCl)COc1ccc(S(=O)(=O)c2ccc(OC[C@@H](Cn3ccnc3)OC(C)=O)c(Cl)c2)cc1Cl] | (S)-1-(4-((4-((R)-2-acetoxy-3-(1H-imidazol-1-yl)propoxy)-3-chlorophenyl)sulfonyl)-2-chlorophenoxy)-3-chloropropan-2-yl acetate |
| A49b | 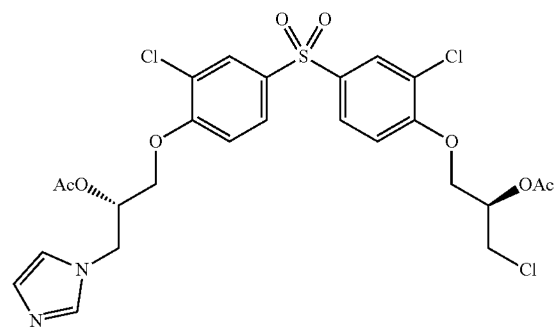 [SMILES: CC(=O)O[C@H](COc1ccc(S(=O)(=O)c2ccc(OC[C@H](CCl)OC(C)=O)c(Cl)c2)cc1Cl)Cn1ccnc1] | (R)-1-(4-((4-((S)-2-acetoxy-3-(1H-imidazol-1-yl)propoxy)-3-chlorophenyl)sulfonyl)-2-chlorophenoxy)-3-chloropropan-2-yl acetate |
| A49c | 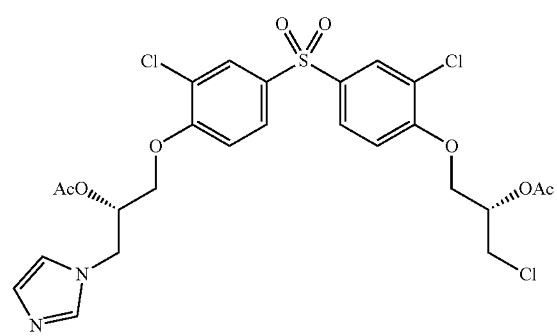 [SMILES: CC(=O)O[C@H](CCl)COc1ccc(S(=O)(=O)c2ccc(OC[C@H](Cn3ccnc3)OC(C)=O)c(Cl)c2)cc1Cl] | (S)-1-(4-((4-((S)-2-acetoxy-3-(1H-imidazol-1-yl)propoxy)-3-chlorophenyl)sulfonyl)-2-chlorophenoxy)-3-chloropropan-2-yl acetate |
| A49d | 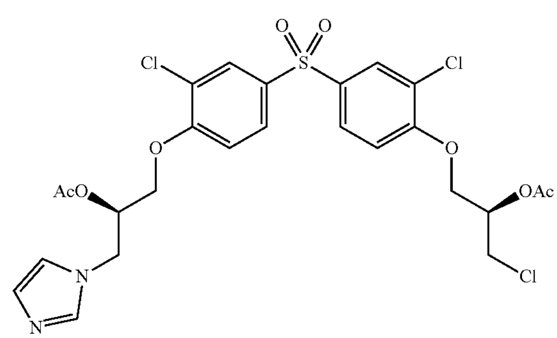 [SMILES: CC(=O)O[C@@H](CCl)COc1ccc(S(=O)(=O)c2ccc(OC[C@@H](Cn3ccnc3)OC(C)=O)c(Cl)c2)cc1Cl] | (R)-1-(4-((4-((R)-2-acetoxy-3-(1H-imidazol-1-yl)propoxy)-3-chlorophenyl)sulfonyl)-2-chlorophenoxy)-3-chloropropan-2-yl acetate |

TABLE 4-continued

Compounds

| No. | Structure | Name |
|---|---|---|
| A50 | 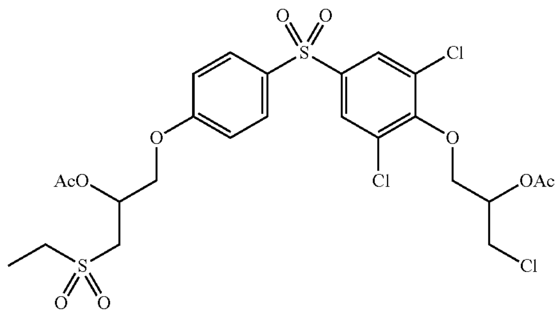 [SMILES: CCS(=O)(=O)CC(COc1ccc(S(=O)(=O)c2cc(Cl)c(OCC(CCl)OC(C)=O)c(Cl)c2)cc1)OC(C)=O] | 1-(4-((4-(2-acetoxy-3-(ethylsulfonyl)propoxy)phenyl)sulfonyl)-2,6-dichlorophenoxy)-3-chloropropan-2-yl acetate |
| A50a | 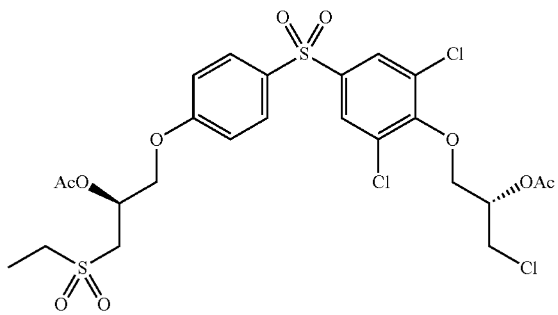 [SMILES: CCS(=O)(=O)C[C@H](COc1ccc(S(=O)(=O)c2cc(Cl)c(OC[C@@H](CCl)OC(C)=O)c(Cl)c2)cc1)OC(C)=O] | (S)-1-(4-((4-((S)-2-acetoxy-3-(ethylsulfonyl)propoxy)phenyl)sulfonyl)-2,6-dichlorophenoxy)-3-chloropropan-2-yl acetate |
| A50b | 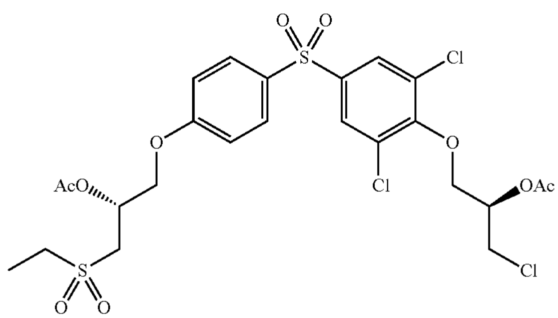 [SMILES: CCS(=O)(=O)C[C@@H](COc1ccc(S(=O)(=O)c2cc(Cl)c(OC[C@H](CCl)OC(C)=O)c(Cl)c2)cc1)OC(C)=O] | (R)-1-(4-((4-((R)-2-acetoxy-3-(ethylsulfonyl)propoxy)phenyl)sulfonyl)-2,6-dichlorophenoxy)-3-chloropropan-2-yl acetate |
| A50c | 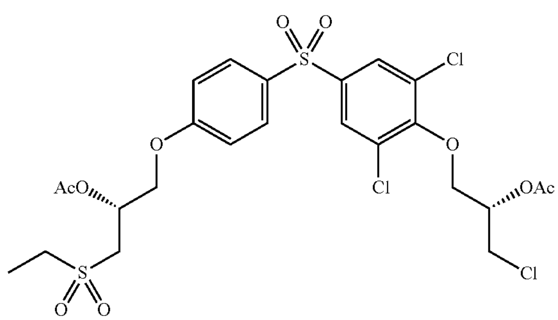 [SMILES: CCS(=O)(=O)C[C@@H](COc1ccc(S(=O)(=O)c2cc(Cl)c(OC[C@@H](CCl)OC(C)=O)c(Cl)c2)cc1)OC(C)=O] | (S)-1-(4-((4-((R)-2-acetoxy-3-(ethylsulfonyl)propoxy)phenyl)sulfonyl)-2,6-dichlorophenoxy)-3-chloropropan-2-yl acetate |
| A50d | 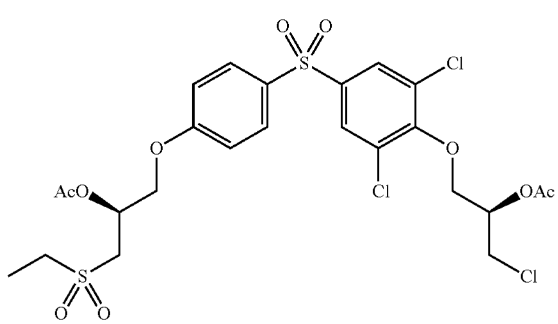 [SMILES: CCS(=O)(=O)C[C@H](COc1ccc(S(=O)(=O)c2cc(Cl)c(OC[C@H](CCl)OC(C)=O)c(Cl)c2)cc1)OC(C)=O] | (R)-1-(4-((4-((S)-2-acetoxy-3-(ethylsulfonyl)propoxy)phenyl)sulfonyl)-2,6-dichlorophenoxy)-3-chloropropan-2-yl acetate |

TABLE 4-continued

| No. | Structure | Name |
|---|---|---|
| A51 | 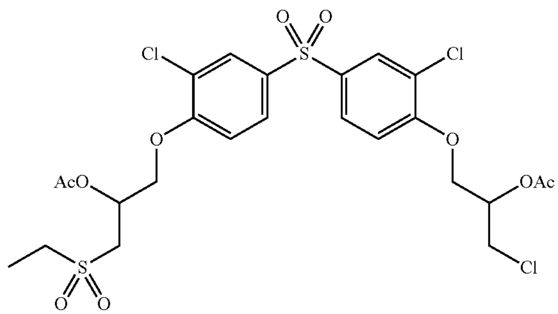 [SMILES: CCS(=O)(=O)CC(COc1ccc(S(=O)(=O)c2ccc(OCC(CCl)OC(C)=O)c(Cl)c2)cc1Cl)OC(C)=O] | 1-(4-((4-(2-acetoxy-3-(ethylsulfonyl)propoxy)-3-chlorophenyl)sulfonyl)-2-chlorophenoxy)-3-chloropropan-2-yl acetate |
| A51a | 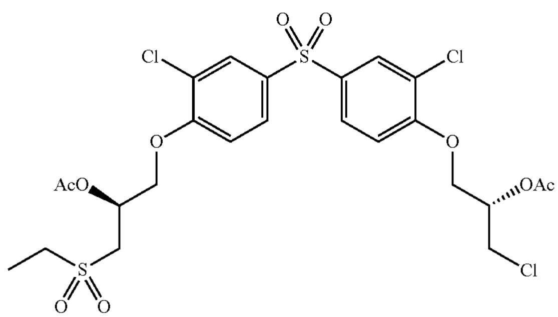 [SMILES: CCS(=O)(=O)C[C@H](COc1ccc(S(=O)(=O)c2ccc(OC[C@@H](CCl)OC(C)=O)c(Cl)c2)cc1Cl)OC(C)=O] | (S)-1-(4-((4-((S)-2-acetoxy-3-(ethylsulfonyl)propoxy)-3-chlorophenyl)sulfonyl)-2-chlorophenoxy)-3-chloropropan-2-yl acetate |
| A51b | 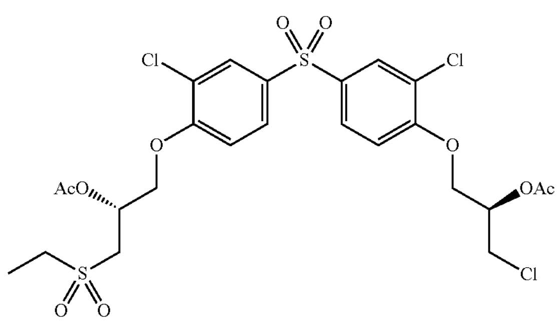 [SMILES: CCS(=O)(=O)C[C@@H](COc1ccc(S(=O)(=O)c2ccc(OC[C@H](CCl)OC(C)=O)c(Cl)c2)cc1Cl)OC(C)=O] | (R)-1-(4-((4-((R)-2-acetoxy-3-(ethylsulfonyl)propoxy)-3-chlorophenyl)sulfonyl)-2-chlorophenoxy)-3-chloropropan-2-yl acetate |
| A51c | 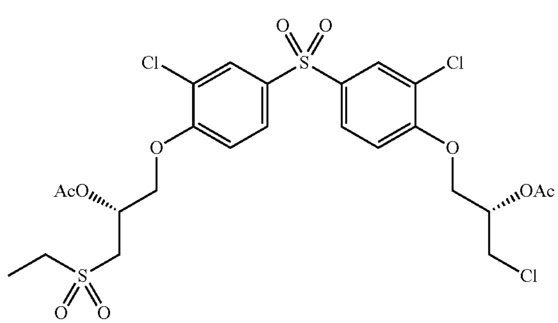 [SMILES: CCS(=O)(=O)C[C@@H](COc1ccc(S(=O)(=O)c2ccc(OC[C@@H](CCl)OC(C)=O)c(Cl)c2)cc1Cl)OC(C)=O] | (S)-1-(4-((4-((R)-2-acetoxy-3-(ethylsulfonyl)propoxy)-3-chlorophenyl)sulfonyl)-2-chlorophenoxy)-3-chloropropan-2-yl acetate |

TABLE 4-continued

| No. | Structure | Name |
|---|---|---|
| A51d | 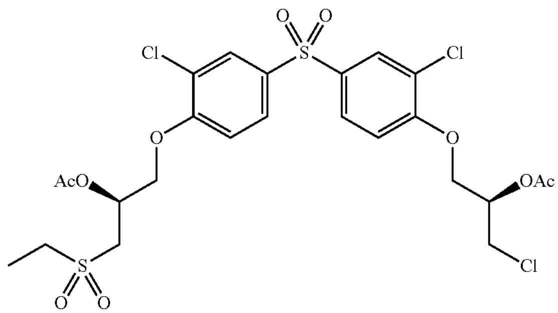 [SMILES: CCS(=O)(=O)C[C@H](COc1ccc(S(=O)(=O)c2ccc(OC[C@H](CCl)OC(C)=O)c(Cl)c2)cc1Cl)OC(C)=O] | (R)-1-(4-((4-((S)-2-acetoxy-3-(ethylsulfonyl)propoxy)-3-chlorophenyl)sulfonyl)-2-chlorophenoxy)-3-chloropropan-2-yl acetate |
| A52 | 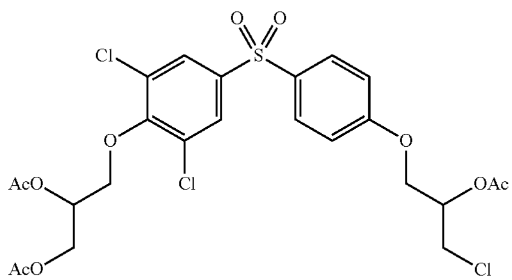 [SMILES: CC(=O)OCC(COc1c(Cl)cc(S(=O)(=O)c2ccc(OCC(CCl)OC(C)=O)cc2)cc1Cl)OC(C)=O] | 3-(4-((4-(2-acetoxy-3-chloropropoxy)phenyl)sulfonyl)-2,6-dichlorophenoxy)propane-1,2-diyl diacetate |
| A52a | 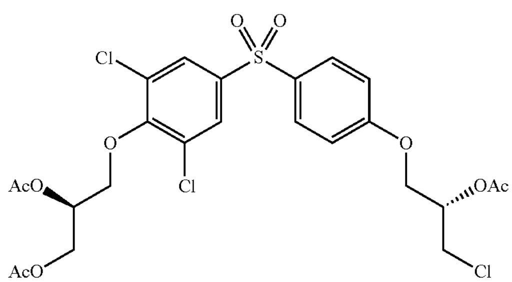 [SMILES: CC(=O)OC[C@H](COc1c(Cl)cc(S(=O)(=O)c2ccc(OC[C@@H](CCl)OC(C)=O)cc2)cc1Cl)OC(C)=O] | (S)-3-(4-((4-((S)-2-acetoxy-3-chloropropoxy)phenyl)sulfonyl)-2,6-dichlorophenoxy)propane-1,2-diyl diacetate |
| A52b | 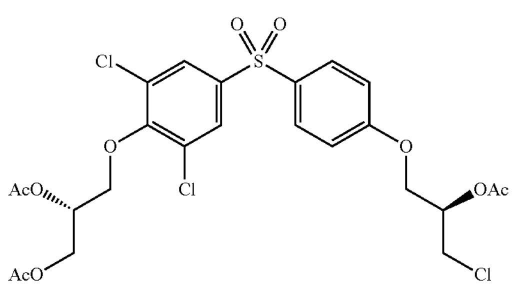 [SMILES: CC(=O)OC[C@@H](COc1c(Cl)cc(S(=O)(=O)c2ccc(OC[C@H](CCl)OC(C)=O)cc2)cc1Cl)OC(C)=O] | (R)-3-(4-((4-((R)-2-acetoxy-3-chloropropoxy)phenyl)sulfonyl)-2,6-dichlorophenoxy)propane-1,2-diyl diacetate |
| A52c | 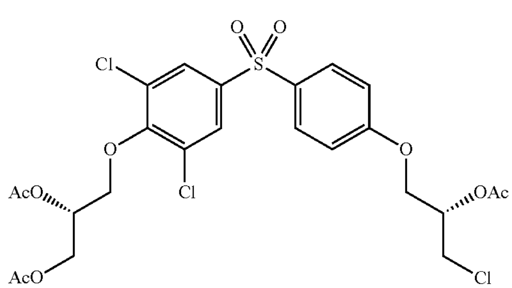 [SMILES: CC(=O)OC[C@@H](COc1c(Cl)cc(S(=O)(=O)c2ccc(OC[C@@H](CCl)OC(C)=O)cc2)cc1Cl)OC(C)=O] | (R)-3-(4-((4-((S)-2-acetoxy-3-chloropropoxy)phenyl)sulfonyl)-2,6-dichlorophenoxy)propane-1,2-diyl diacetate |

TABLE 4-continued

| No. | Structure | Name |
|---|---|---|
| A52d | 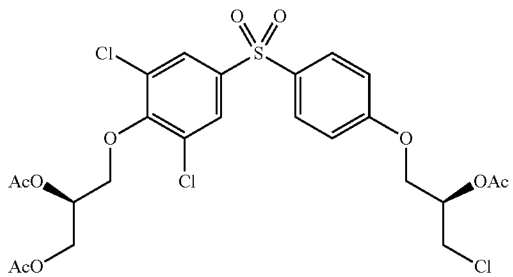 [SMILES: CC(=O)OC[C@H](COc1c(Cl)cc(S(=O)(=O)c2ccc(OC[C@H](CCl)OC(C)=O)cc2)cc1Cl)OC(C)=O] | (S)-3-(4-((4-((R)-2-acetoxy-3-chloropropoxy)phenyl)sulfonyl)-2,6-dichlorophenoxy)propane-1,2-diyl diacetate |
| A53 | 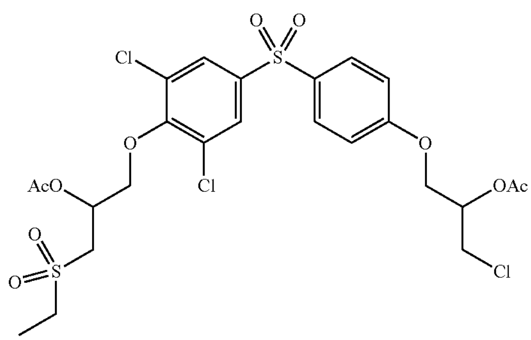 [SMILES: CCS(=O)(=O)CC(COc1c(Cl)cc(S(=O)(=O)c2ccc(OCC(CCl)OC(C)=O)cc2)cc1Cl)OC(C)=O] | 1-(4-((4-(2-acetoxy-3-(ethylsulfonyl)propoxy)-3,5-dichlorophenyl)sulfonyl)phenoxy)-3-chloropropan-2-yl acetate |
| A53a | 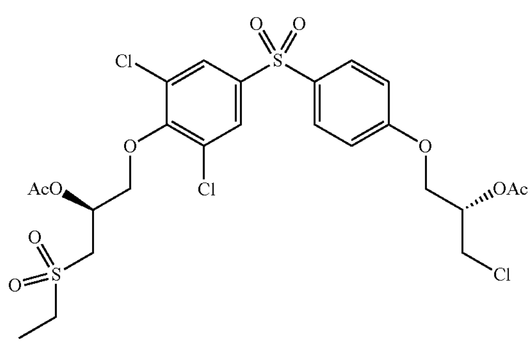 [SMILES: CCS(=O)(=O)C[C@H](COc1c(Cl)cc(S(=O)(=O)c2ccc(OC[C@@H](CCl)OC(C)=O)cc2)cc1Cl)OC(C)=O] | (S)-1-(4-((4-((S)-2-acetoxy-3-(ethylsulfonyl)propoxy)-3,5-dichlorophenyl)sulfonyl)phenoxy)-3-chloropropan-2-yl acetate |
| A53b | 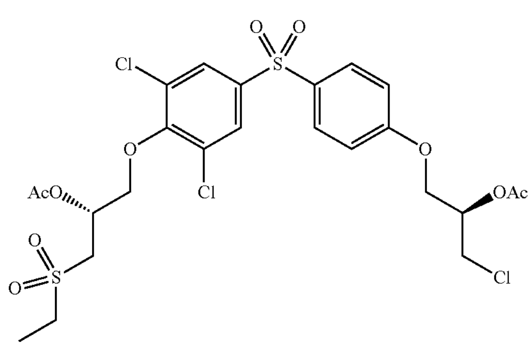 [SMILES: CCS(=O)(=O)C[C@@H](COc1c(Cl)cc(S(=O)(=O)c2ccc(OC[C@H](CCl)OC(C)=O)cc2)cc1Cl)OC(C)=O] | (R)-1-(4-((4-((R)-2-acetoxy-3-(ethylsulfonyl)propoxy)-3,5-dichlorophenyl)sulfonyl)phenoxy)-3-chloropropan-2-yl acetate |

TABLE 4-continued

Compounds

| No. | Structure | Name |
|---|---|---|
| A53c | 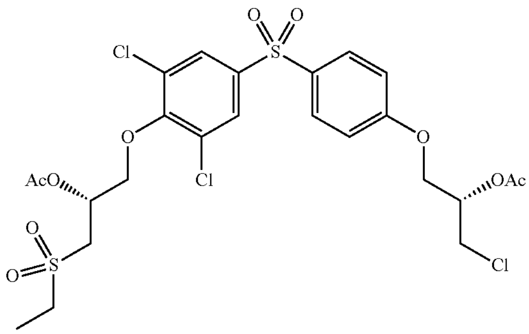 [SMILES: CCS(=O)(=O)C[C@@H](COc1c(Cl)cc(S(=O)(=O)c2ccc(OC[C@@H](CCl)OC(C)=O)cc2)cc1Cl)OC(C)=O] | (S)-1-(4-((4-((R)-2-acetoxy-3-(ethylsulfonyl)propoxy)-3,5-dichlorophenyl)sulfonyl)phenoxy)-3-chloropropan-2-yl acetate |
| A53d | 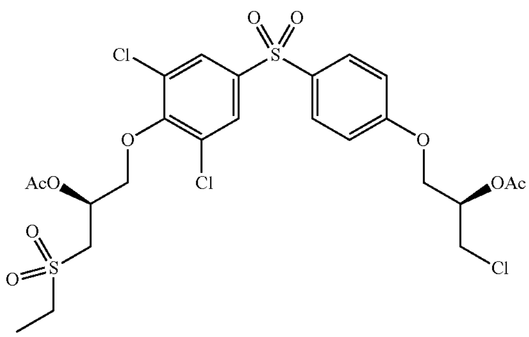 [SMILES: CCS(=O)(=O)C[C@H](COc1c(Cl)cc(S(=O)(=O)c2ccc(OC[C@H](CCl)OC(C)=O)cc2)cc1Cl)OC(C)=O] | (R)-1-(4-((4-((S)-2-acetoxy-3-(ethylsulfonyl)propoxy)-3,5-dichlorophenyl)sulfonyl)phenoxy)-3-chloropropan-2-yl acetate |
| A54 | 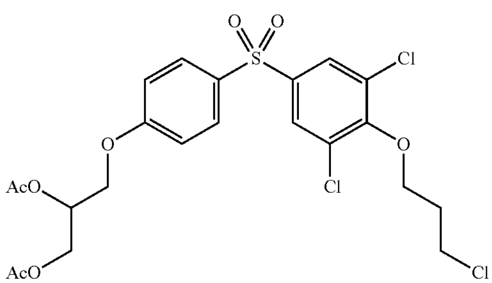 [SMILES: CC(=O)OCC(COc1ccc(S(=O)(=O)c2cc(Cl)c(OCCCCl)c(Cl)c2)cc1)OC(C)=O] | 3-(4-((3,5-dichloro-4-(3-chloropropoxy)phenyl)sulfonyl)phenoxy)propane-1,2-diyl diacetate |
| A54a | 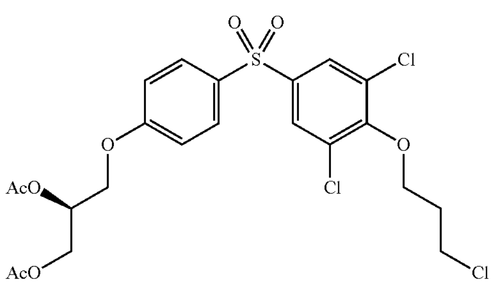 [SMILES: CC(=O)OC[C@H](COc1ccc(S(=O)(=O)c2cc(Cl)c(OCCCCl)c(Cl)c2)cc1)OC(C)=O] | (S)-3-(4-((3,5-dichloro-4-(3-chloropropoxy)phenyl)sulfonyl)phenoxy)propane-1,2-diyl diacetate |
| A54b | 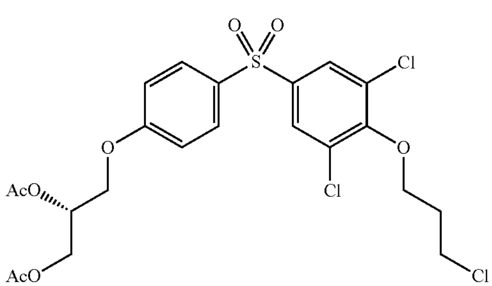 [SMILES: CC(=O)OC[C@@H](COc1ccc(S(=O)(=O)c2cc(Cl)c(OCCCCl)c(Cl)c2)cc1)OC(C)=O] | (R)-3-(4-((3,5-dichloro-4-(3-chloropropoxy)phenyl)sulfonyl)phenoxy)propane-1,2-diyl diacetate |

TABLE 4-continued

Compounds

| No. | Structure | Name |
|---|---|---|
| A55 | 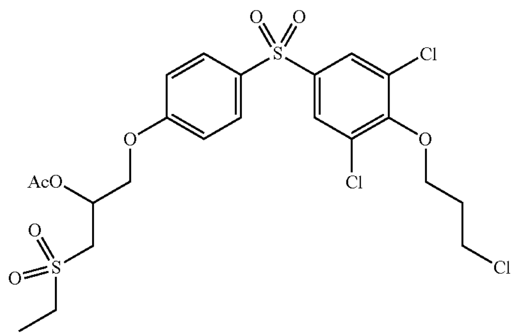 [SMILES: CCS(=O)(=O)CC(COc1ccc(S(=O)(=O)c2cc(Cl)c(OCCCCl)c(Cl)c2)cc1)OC(C)=O] | 1-(4-((3,5-dichloro-4-(3-chloropropoxy)phenyl)sulfonyl)phenoxy)-3-(ethylsulfonyl)propan-2-yl acetate |
| A55a | 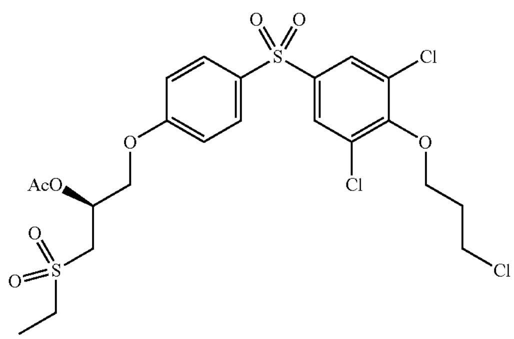 [SMILES: CCS(=O)(=O)C[C@H](COc1ccc(S(=O)(=O)c2cc(Cl)c(OCCCCl)c(Cl)c2)cc1)OC(C)=O] | (S)-1-(4-((3,5-dichloro-4-(3-chloropropoxy)phenyl)sulfonyl)phenoxy)-3-(ethylsulfonyl)propan-2-yl acetate |
| A55b | 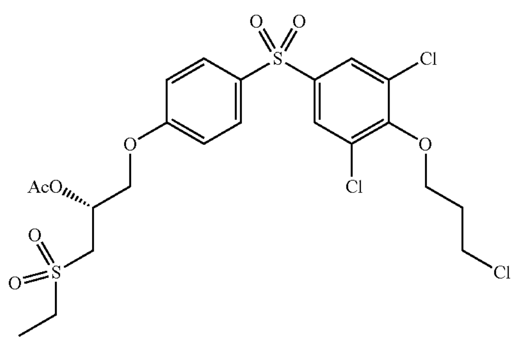 [SMILES: CCS(=O)(=O)C[C@@H](COc1ccc(S(=O)(=O)c2cc(Cl)c(OCCCCl)c(Cl)c2)cc1)OC(C)=O] | (R)-1-(4-((3,5-dichloro-4-(3-chloropropoxy)phenyl)sulfonyl)phenoxy)-3-(ethylsulfonyl)propan-2-yl acetate |
| A56 | 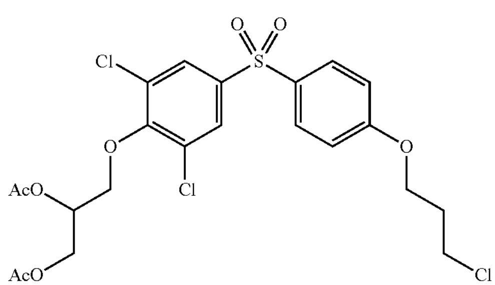 [SMILES: CC(=O)OCC(COc1c(Cl)cc(S(=O)(=O)c2ccc(OCCCCl)cc2)cc1Cl)OC(C)=O] | 3-(2,6-dichloro-4-((4-(3-chloropropoxy)phenyl)sulfonyl)phenoxy)propane-1,2-diyl diacetate |
| A56a | 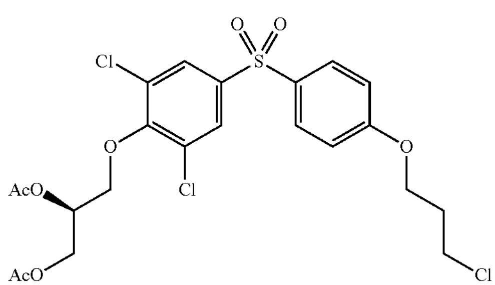 [SMILES: CC(=O)OC[C@H](COc1c(Cl)cc(S(=O)(=O)c2ccc(OCCCCl)cc2)cc1Cl)OC(C)=O] | (S)-3-(2,6-dichloro-4-((4-(3-chloropropoxy)phenyl)sulfonyl)phenoxy)propane-1,2-diyl diacetate |

TABLE 4-continued

Compounds

| No. | Structure | Name |
|---|---|---|
| A56b | 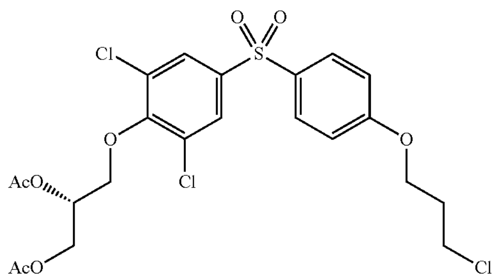 [SMILES: CC(=O)OC[C@@H](COc1c(Cl)cc(S(=O)(=O)c2ccc(OCCCCl)cc2)cc1Cl)OC(C)=O] | (R)-3-(2,6-dichloro-4-((4-(3-chloropropoxy)phenyl)sulfonyl)phenoxy)propane-1,2-diyl diacetate |
| A57 | 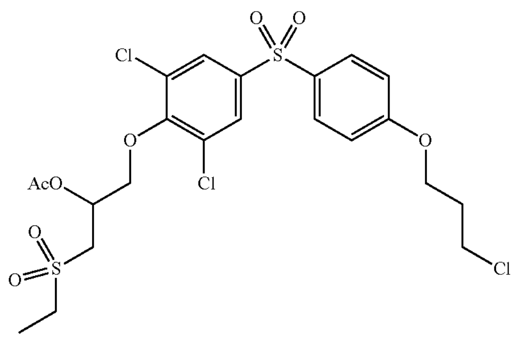 [SMILES: CCS(=O)(=O)CC(COc1c(Cl)cc(S(=O)(=O)c2ccc(OCCCCl)cc2)cc1Cl)OC(C)=O] | 1-(2,6-dichloro-4-((4-(3-chloropropoxy)phenyl)sulfonyl)phenoxy)-3-(ethylsulfonyl)propan-2-yl acetate |
| A57a | 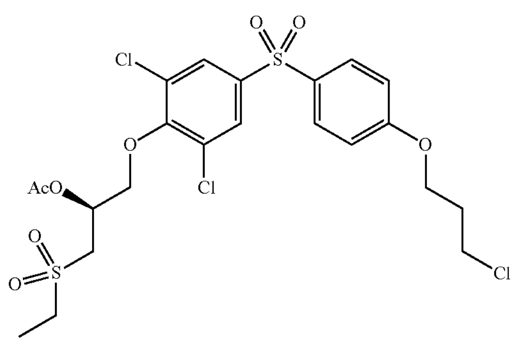 [SMILES: CCS(=O)(=O)C[C@H](COc1c(Cl)cc(S(=O)(=O)c2ccc(OCCCCl)cc2)cc1Cl)OC(C)=O] | (S)-1-(2,6-dichloro-4-((4-(3-chloropropoxy)phenyl)sulfonyl)phenoxy)-3-(ethylsulfonyl)propan-2-yl acetate |
| A57b | 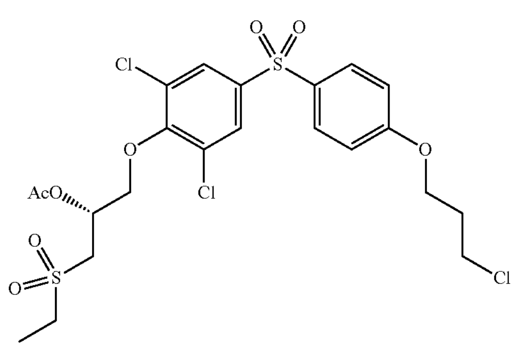 [SMILES: CCS(=O)(=O)C[C@@H](COc1c(Cl)cc(S(=O)(=O)c2ccc(OCCCCl)cc2)cc1Cl)OC(C)=O] | (R)-1-(2,6-dichloro-4-((4-(3-chloropropoxy)phenyl)sulfonyl)phenoxy)-3-(ethylsulfonyl)propan-2-yl acetate |

In some embodiments of the compound of Formula I, the compound has one of the following structures from Tables 1, 2, 3, or 4, or a pharmaceutically acceptable salt, tautomer, or stereoisomer thereof.

The present invention includes all compounds which have the above described properties (i.e., binding to androgen receptor (AR)). In one embodiment, the present invention is directed to a compound having a structure of Formula II:

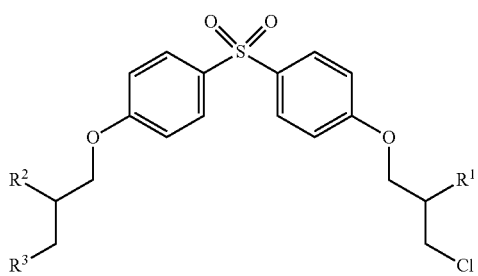
(II)

or a pharmaceutically acceptable salt, tautomer or stereoisomer thereof, wherein:

$R^1$ is H, hydroxyl or —OC(=O)$R^{13}$;

$R^2$ is hydroxyl or —OC(=O)$R^{13}$;

$R^3$ is halo, —OH, —O$R^4$, —OC(=O)$R^{13}$, —$NH_2$, —NHC(=O)$R^{13}$, —N(C(=O)$R^{13})_2$, —NHS(O)$_n R^5$, —N(C(=O)$R^{13}$)(S(O)$_n R^5$), —N($C_1$-$C_6$ alkyl)(S(O)$_n R^5$), —S(O)$_n R^5$, —$N_3$, aryl, carbocyclyl, heteroaryl or heterocyclyl which are optionally substituted with one or more $R^6$;

$R^4$ is $C_1$-$C_6$ alkyl, $C_2$-$C_6$ alkenyl, $C_2$-$C_6$ alkynyl, aryl, carbocyclyl, heteroaryl or heterocyclyl which are optionally substituted with one or more $R^6$;

$R^5$ is each independently $C_1$-$C_6$ alkyl or aryl which are optionally substituted with one or more $R^6$;

$R^6$ is each independently selected from the group consisting of H, F, Cl, Br, I, $^{123}$I, hydroxyl, oxo, $C_1$-$C_6$ alkyl, $C_2$-$C_6$ alkenyl, $C_2$-$C_6$ alkynyl, $C_1$-$C_6$ alkoxy, $C_6$-$C_{12}$ aryl, wherein each $R^6$ is optionally substituted with one or more of halogen, $^{123}$I, $^{18}$F, hydroxyl, —OS(O)$_2$-aryl, $C_1$-$C_6$ alkyl, $C_2$-$C_6$ alkenyl, or $C_2$-$C_6$ alkynyl;

$R^{13}$ is $C_1$-$C_6$ alkyl; and n is 0, 1, or 2.

In various embodiments, different stereoisomers of the compound of structure (II) are provided, for example in some embodiments the compound has one of the following structures (IIa), (IIb), (IIc) or (IId):

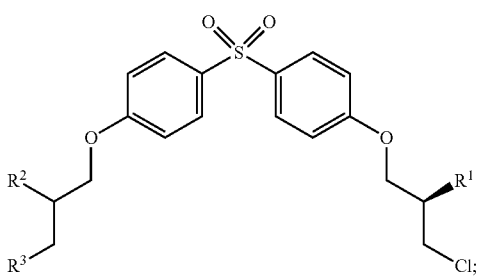
(IIa)

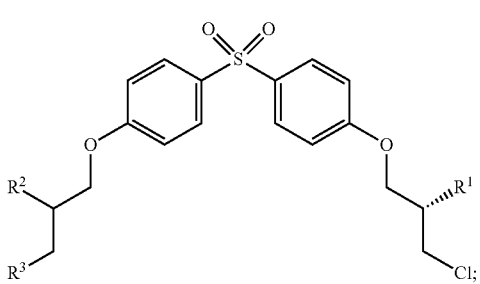
(IIb)

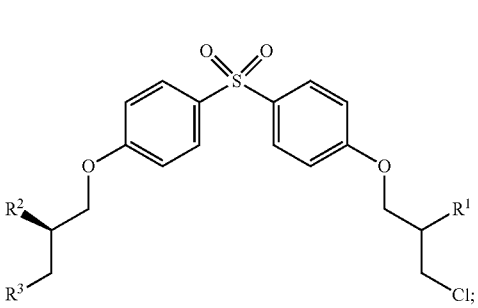
(IIc); or

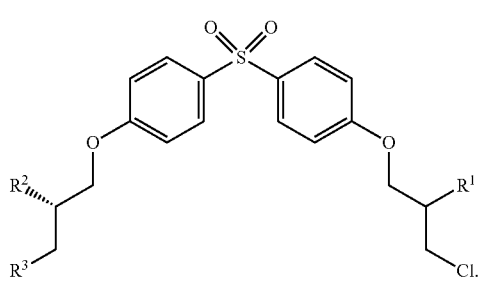
(IId)

In still other embodiments, the compound has one of the following structures (IIe), (IIf), (IIg) or (IIh):

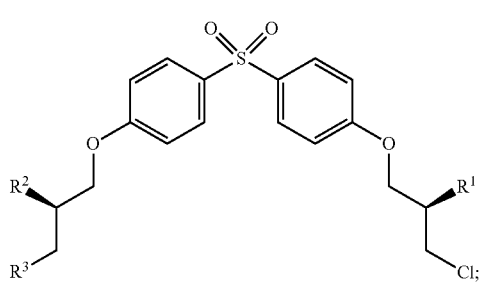
(IIe)

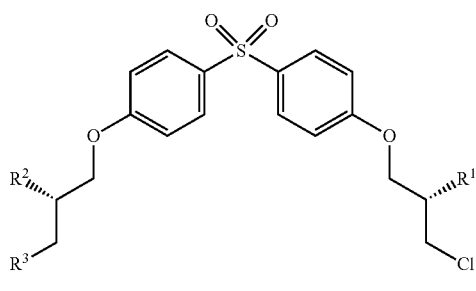
(IIf)

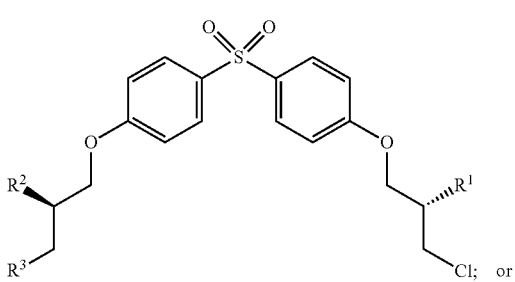
(IIg) or

235

-continued

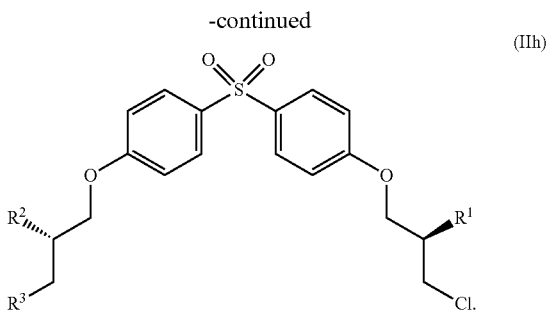

(IIh)

In one embodiment, $R^1$ is hydroxyl. In another embodiment, $R^1$ is —OC(=O)$R^{13}$. In some embodiments, $R^1$ is —OC(=O)$R^{13}$, wherein $R^{13}$ is $C_1$-$C_4$ alkyl. In other embodiments, $R^1$ is —OC(=O)$R^{13}$, wherein $R^{13}$ is methyl. In one embodiment, $R^1$ is H.

In one embodiment, $R^2$ is hydroxyl. In another embodiment, $R^2$ is —OC(=O)$R^{13}$. In some embodiments, $R^2$ is —OC(=O)$R^{13}$, wherein $R^{13}$ is $C_1$-$C_4$ alkyl. In other embodiments, $R^2$ is —OC(=O)$R^{13}$, wherein $R^{13}$ is methyl.

In one embodiment, $R^3$ is —OH. In another embodiment, $R^3$ is —OC(=O)$R^{13}$. In some embodiments, $R^3$ is —OC(=O)$R^{13}$, wherein $R^{13}$ is $C_1$-$C_4$ alkyl. In other embodiments, $R^3$ is —OC(=O)$R^{13}$, wherein $R^{13}$ is methyl.

In some embodiments, at least one of $R^1$, $R^2$, or $R^3$ is —OH. In another embodiment, at least one of $R^1$, $R^2$, or $R^3$ is —OH. In some embodiments, at least two of $R^1$, $R^2$, or $R^3$ are each —OH. In another embodiment, $R^1$ and $R^2$ are each —OH. In one embodiment, $R^1$, $R^2$, or $R^3$ are each —OH.

In some embodiments, at least one of $R^1$, $R^2$, or $R^3$ is —OC(=O)$R^{13}$, wherein $R^{13}$ is $C_1$-$C_4$ alkyl. In another embodiment, at least one of $R^1$, $R^2$, or $R^3$ is —OC(=O)$R^{13}$, wherein $R^{13}$ is methyl. In some embodiments, at least two of $R^1$, $R^2$, or $R^3$ are each —OC(=O)$R^{13}$, wherein $R^{13}$ is $C_1$-$C_4$ alkyl. In another embodiment, at least two of $R^1$, $R^2$, or $R^3$ are each —OC(=O)$R^{13}$, wherein $R^{13}$ is methyl.

In some embodiments, one of $R^1$, $R^2$, or $R^3$ is —OC(=O)$R^{13}$, wherein $R^{13}$ is $C_1$-$C_4$ alkyl. In another embodiment, one of $R^1$, $R^2$, or $R^3$ is —OC(=O)$R^{13}$, wherein $R^{13}$ is methyl. In some embodiments, two of $R^1$, $R^2$, or $R^3$ are each —OC(=O)$R^{13}$, wherein $R^{13}$ is $C_1$-$C_4$ alkyl. In another embodiment, two of $R^1$, $R^2$, or $R^3$ are each —OC(=O)$R^{13}$, wherein $R^{13}$ is methyl. In some embodiments, $R^1$, $R^2$, or $R^3$ are each —OC(=O)$R^{13}$, wherein $R^{13}$ is $C_1$-$C_4$ alkyl. In another embodiment, $R^1$, $R^2$, or $R^3$ are each —OC(=O)$R^{13}$, wherein $R^{13}$ is methyl.

In other embodiments, $R^3$ is —O$R^4$. In one embodiment, $R^3$ is —O$R^4$, wherein $R^4$ is $C_1$-$C_6$ alkyl. In another embodiment, $R^3$ is —O$R^4$, wherein $R^4$ is $C_1$-$C_3$ alkyl. In one embodiment, $R^3$ is —O$R^4$, wherein $R^4$ is $C_1$ alkyl. In another embodiment, $R^3$ is —O$R^4$, wherein $R^4$ is isopropyl.

In other embodiments, $R^3$ is a halogen. In one embodiment, $R^3$ is F.

In other embodiments, $R^3$ is —NH$_2$, —NHC(=O)$R^{13}$, —N(C(=O)$R^{13}$)$_2$, —NHS(O)$_n$$R^5$, —N(C(=O)$R^{13}$)(S(O)$_n$$R^5$), or —N($C_1$-$C_6$ alkyl)(S(O)$_n$$R^5$). In one embodiment, $R^3$ is a —NH$_2$. In one embodiment, $R^3$ is a —NHC(=O)$R^{13}$. In one embodiment, $R^3$ is a —N(C(=O)$R^{13}$)$_2$. In another embodiment, $R^3$ is a —NHS(O)$_n$$R^5$. In some embodiments, $R^3$ is a —NHS(O)$_2$$R^5$. In other embodiments, $R^3$ is a —NHS(O)$_2$$R^5$, wherein $R^5$ is $C_1$-$C_3$ alkyl. In one embodiment, $R^3$ is a —NHS(O)$_2$$R^5$, wherein $R^5$ is methyl. In one embodiment, $R^3$ is a —N(C(=O)$R^{13}$)(S(O)$_n$$R^5$). In one embodiment, $R^3$ is a —N($C_1$-$C_6$ alkyl)S(O)$_n$$R^5$.

236

In other embodiments, $R^3$ is —NH$_2$, —NHC(=O)($C_1$-$C_4$ alkyl), —N[(C(=O)($C_1$-$C_4$ alkyl)]$_2$, —NHS(O)$_n$($C_1$-$C_3$ alkyl), —N[C(=O)($C_1$-$C_4$ alkyl)][(S(O)$_n$($C_1$-$C_3$ alkyl)], or —N[$C_1$-$C_6$ alkyl][S(O)$_n$($C_1$-$C_3$ alkyl)]. In some embodiments, $R^3$ is —NH(C(=O)CH$_3$) or —N(C(=O)CH$_3$)$_2$. In other embodiments, $R^3$ is —NHS(O)$_2$CH$_3$. In other embodiments, $R^3$ is —N(C(=O)CH$_3$) (S(O)$_2$CH$_3$).

In another embodiment, $R^3$ is a —S(O)$_n$$R^5$. In one embodiment, $R^3$ is a —S(O)$_2$$R^5$. In another embodiment, $R^3$ is a —S(O)$_2$($C_1$-$C_3$ alkyl). In other embodiments, $R^3$ is a —S(O)$_2$CH$_3$. In other embodiments, $R^3$ is a —S(O)$_2$CH$_2$CH$_3$.

In another embodiment, $R^3$ is a —S(O)$_n$$R^5$. In one embodiment, $R^3$ is a —S(O)$_2$$R^5$. In some embodiments, $R^3$ is a —S(O)$_2$$R^5$, wherein $R^5$ is $C_1$-$C_3$ alkyl. In other embodiments, $R^3$ is a —S(O)$_2$$R^5$, wherein $R^5$ is $C_1$ alkyl.

In some embodiments, $R^3$ is an optionally substituted 5 or 6 membered heteroaryl or an optionally substituted 3 to 7 membered heterocyclyl, wherein said heteroaryl or said heterocyclyl respectively comprises at least one N atom in the ring. In one embodiment, $R^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine. In a certain embodiment, $R^3$ is

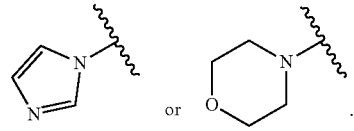 [SMILES: *n1ccnc1 ; *N1CCOCC1]

In some embodiments, $R^{13}$ is $C_1$-$C_4$ alkyl. In other embodiments, $R^{13}$ is methyl, ethyl, n-propyl, i-propyl, n-butyl, i-butyl, t-butyl, or sec-butyl. In one embodiment, $R^{13}$ is a methyl.

In one embodiment, n is 0. In another embodiment n is 1. In some embodiments, n is 2.

The compounds for use in the imaging and treatment methods described herein. In some embodiments, the compounds comprise one F, Cl, Br, I, or $^{123}$I substitution.

In another embodiment, the compound comprise one or more of F, Cl, Br, I or $^{123}$I substitutions for $R^3$. In one embodiment, the compound comprise one or more of I or $^{123}$I substitutions for $R^3$.

In some embodiments, the compound comprises at least one $R^6$ substituent on $R^3$, wherein at least one $R^6$ is further substituted with at least one of F, Cl, Br, I or $^{123}$I. In another embodiment, $R^6$ substituent on $R^3$ is further substituted with at least one of I or $^{123}$I.

In some more specific embodiments of the compound of Formula II, the compound has one of the following structures from Table 5, or a pharmaceutically acceptable salt, tautomer, or stereoisomer thereof:

TABLE 5

| No. | Structure | Name |
|-----|-----------|------|
| 80 | 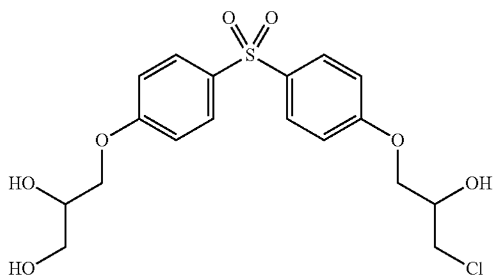 [SMILES: O=S(=O)(c1ccc(OCC(O)CO)cc1)c1ccc(OCC(O)CCl)cc1] | 3-(4-((4-(3-chloro-2-hydroxypropoxy)phenyl)sulfonyl)phenoxy)propane-1,2-diol |
| 80a | 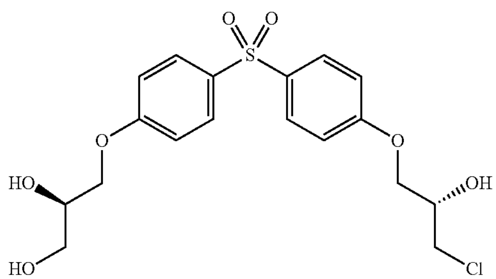 [SMILES: O=S(=O)(c1ccc(OC[C@H](O)CO)cc1)c1ccc(OC[C@H](O)CCl)cc1] | (R)-3-(4-((4-((S)-3-chloro-2-hydroxypropoxy)phenyl)sulfonyl)phenoxy)propane-1,2-diol |
| 80b | 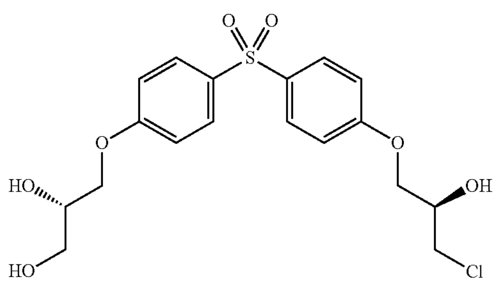 [SMILES: O=S(=O)(c1ccc(OC[C@@H](O)CO)cc1)c1ccc(OC[C@@H](O)CCl)cc1] | (S)-3-(4-((4-((R)-3-chloro-2-hydroxypropoxy)phenyl)sulfonyl)phenoxy)propane-1,2-diol |
| 80c | 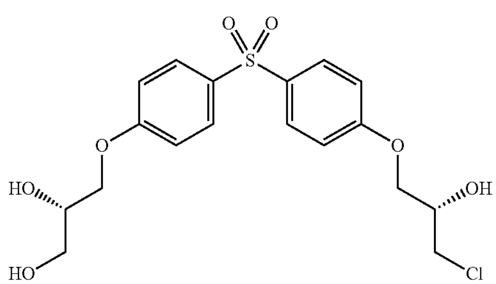 [SMILES: O=S(=O)(c1ccc(OC[C@H](O)CCl)cc1)c1ccc(OC[C@@H](O)CO)cc1] | (S)-3-(4-((4-((S)-3-chloro-2-hydroxypropoxy)phenyl)sulfonyl)phenoxy)propane-1,2-diol |
| 80d | 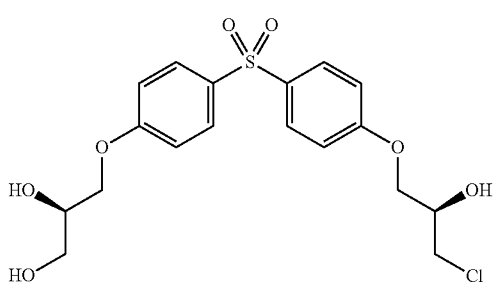 [SMILES: O=S(=O)(c1ccc(OC[C@H](O)CO)cc1)c1ccc(OC[C@@H](O)CCl)cc1] | (R)-3-(4-((4-((R)-3-chloro-2-hydroxypropoxy)phenyl)sulfonyl)phenoxy)propane-1,2-diol |

TABLE 5-continued

Compounds

| No. | Structure | Name |
|---|---|---|
| A80 | 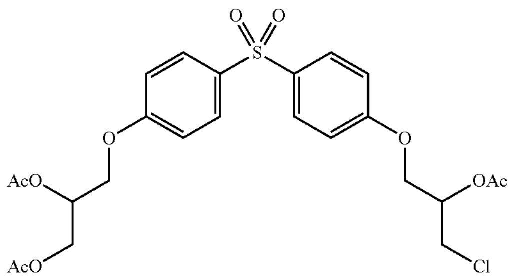 [SMILES: CC(=O)OCC(COc1ccc(S(=O)(=O)c2ccc(OCC(CCl)OC(C)=O)cc2)cc1)OC(C)=O] | 3-(4-((4-(2-acetoxy-3-chloropropoxy)phenyl)sulfonyl)phenoxy)propane-1,2-diyl diacetate |
| A80a | 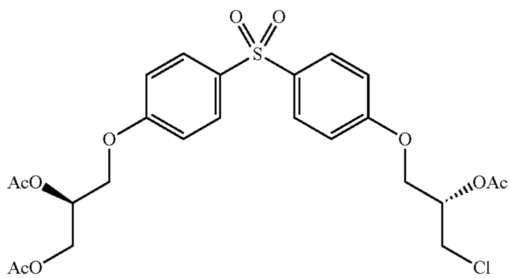 [SMILES: CC(=O)OC[C@H](COc1ccc(S(=O)(=O)c2ccc(OC[C@@H](CCl)OC(C)=O)cc2)cc1)OC(C)=O] | (S)-3-(4-((4-((S)-2-acetoxy-3-chloropropoxy)phenyl)sulfonyl)phenoxy)propane-1,2-diyl diacetate |
| A80b | 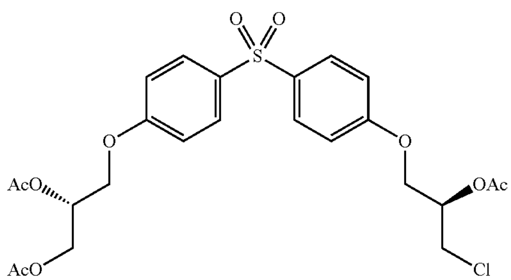 [SMILES: CC(=O)OC[C@@H](COc1ccc(S(=O)(=O)c2ccc(OC[C@H](CCl)OC(C)=O)cc2)cc1)OC(C)=O] | (R)-3-(4-((4-((R)-2-acetoxy-3-chloropropoxy)phenyl)sulfonyl)phenoxy)propane-1,2-diyl diacetate |
| A80c | 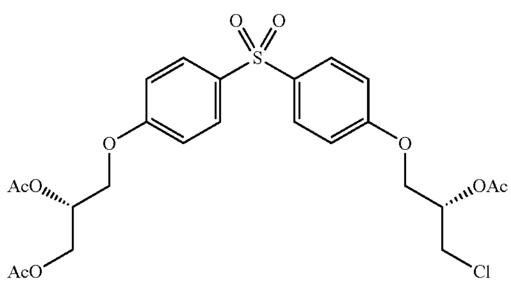 [SMILES: CC(=O)OC[C@@H](COc1ccc(S(=O)(=O)c2ccc(OC[C@@H](CCl)OC(C)=O)cc2)cc1)OC(C)=O] | (R)-3-(4-((4-((S)-2-acetoxy-3-chloropropoxy)phenyl)sulfonyl)phenoxy)propane-1,2-diyl diacetate |
| A80d | 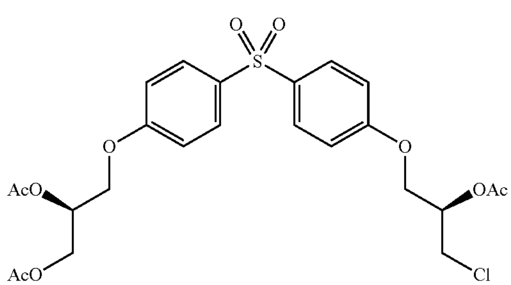 [SMILES: CC(=O)OC[C@H](COc1ccc(S(=O)(=O)c2ccc(OC[C@H](CCl)OC(C)=O)cc2)cc1)OC(C)=O] | (S)-3-(4-((4-((R)-2-acetoxy-3-chloropropoxy)phenyl)sulfonyl)phenoxy)propane-1,2-diyl diacetate |

In one embodiment, the present invention is directed to a pharmaceutical composition, comprising a compound of Formula I or Formula II, or a pharmaceutically acceptable salt, tautomer or stereoisomer thereof, as described herein.

In one embodiment, the present invention is directed to a pharmaceutical composition, comprising a compound of Formula I or Formula II, or a pharmaceutically acceptable salt or stereoisomer thereof, as described herein.

In some embodiment, the pharmaceutical composition comprising a compound having a structure of Formula I or Formula II, or a pharmaceutically acceptable salt, tautomer or stereoisomer thereof, further comprises a pharmaceutically acceptable carrier. In another embodiment, the pharmaceutical composition comprising a compound having a structure of Formula I or Formula II, or a pharmaceutically acceptable salt, tautomer or stereoisomer thereof, further comprises an additional therapeutic agent. In one embodiment, the pharmaceutical composition comprising a compound having a structure of Formula I or Formula II, or a pharmaceutically acceptable salt, tautomer or stereoisomer thereof, further comprises a pharmaceutically acceptable carrier and an additional therapeutic agent.

In another embodiment, the pharmaceutical composition comprising a compound having a structure of Formula I or Formula II, or a pharmaceutically acceptable salt, tautomer or stereoisomer thereof, further comprises an additional therapeutic agent which is for treating prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

Accordingly, one embodiment comprises the use of the disclosed compounds in combination therapy with one or more currently-used or experimental pharmacological therapies which are utilized for treating the above disease states irrespective of the biological mechanism of action of such pharmacological therapies, including without limitation pharmacological therapies which directly or indirectly inhibit the androgen receptor, pharmacological therapies which are cytotoxic in nature, and pharmacological therapies which interfere with the biological production or function of androgen (hereinafter, an "additional therapeutic agent"). By "combination therapy" is meant the administration of any one or more of a compound of Formula I or Formula II, or a pharmaceutically acceptable salt, tautomer or stereoisomer thereof, with one or more of another therapeutic agent to the same patient such that their pharmacological effects are contemporaneous with one another, or if not contemporaneous, that their effects are synergistic with one another even though dosed sequentially rather than contemporaneously.

Such administration includes without limitation dosing of one or more of a compound of Formula I or Formula II, or a pharmaceutically acceptable salt, tautomer or stereoisomer thereof, and one or more of the additional therapeutic agent(s) as separate agents without any comingling prior to dosing, as well as formulations which include one or more other androgen-blocking therapeutic agents mixed with one or more compound of Formula I or Formula II, or a pharmaceutically acceptable salt, tautomer or stereoisomer thereof, as a pre-mixed formulation. Administration of the compound(s) of Formula I or Formula II, or a pharmaceutically acceptable salt, tautomer or stereoisomer thereof, in combination with the additional therapeutic agents for treatment of the above disease states also includes dosing by any dosing method including without limitation, intravenous delivery (IV), oral delivery, intra-peritoneal delivery, intramuscular delivery, or intra-tumoral delivery.

In another aspect of the present disclosure, the one or more of the additional therapeutic agents can be administered to the patient before administration of the compound(s) of Formula I or Formula II, or a pharmaceutically acceptable salt, tautomer or stereoisomer thereof. In another embodiment, the compound(s) of Formula I can be co-administered with one or more of the additional therapeutic agents. In yet another aspect, the one or more additional therapeutic agents can be administered to the patient after administration of the compound(s) of Formula I or Formula II, or a pharmaceutically acceptable salt, tautomer or stereoisomer thereof.

The ratio of the doses of compound(s) of Formula I or Formula II, or a pharmaceutically acceptable salt, tautomer or stereoisomer thereof, to that of the one or more additional therapeutic agents can be about 1:1 or can vary, e.g., about 2:1, about 3:1, about 4:1, about 5:1, about 6:1, about 7:1, about 8:1, about 9:1, about 10:1, about 1:2, about 1:3, about 1:4, about 1:5, about 1:6, about 1:7, about 1:8, about 1:9, about 1:10, and can be varied accordingly to achieve the optimal therapeutic benefit.

The compound(s) of Formula I or Formula II, or a pharmaceutically acceptable salt, tautomer or stereoisomer thereof, that are combined with the one or more additional therapeutic agents for improved treatment of the above disease states can comprise, but are not limited to any compound having a structure of Formula I or Formula II, or a pharmaceutically acceptable salt, tautomer or stereoisomer thereof, including those compounds shown in Tables 1, 2, 3, 4, or 5.

The additional therapeutic agents include without limitation any pharmacological agent which is currently approved by the FDA in the U.S. (or elsewhere by any other regulatory body) for use as pharmacological treatment of any of the above disease states, or which is currently being used experimentally as part of a clinical trial program that relates to the above disease states. Non-limiting examples of the Other Pharmacological Agents comprise, without limitation: the chemical entity known as ODM-201 (also known as BAY1841788) and related compounds, which appears to bind to the AR and blocks its cellular function, and is currently in clinical development as a treatment for prostate cancer); the chemical entity known as ODM-204 and related compounds, which appears to be a dual inhibitor of AR and CYP17A1 and can be useful for treatment of prostate cancer; the chemical entity known as enzalutamide (4-(3-(4-cyano-3-(trifluoromethyl)phenyl)-5,5-dimethyl-4-oxo-2-thioxoimidazolidin-1-yl)-2-fluoro-N-methylbenzamide) and related compounds, which appears to be a blocker of the androgen receptor (AR) LBD and a FDA-approved treatment for prostate cancer; the chemical entity known as Galeterone and related compounds which appears to be a blocker of the androgen receptor (AR) LBD, and a CYP17 lyase inhibitor, and also appears to decrease overall androgen receptor levels in prostate cancer cells. Galeterone is currently in development as a treatment for prostate cancer; the chemical entity known as ARN-509 or apalutamide (4-[7-[6-cyano-5-(trifluoromethyl)pyridin-3-yl]-8-oxo-6-sulfanylidene-5,7-diazaspiro[3.4]octan-5-yl]-2-fluoro-A-methylbenzamide) and related compounds which appears to be a blocker of the androgen receptor (AR) LBD and is currently in development as a treatment for prostate cancer; the chemical entity known as abiraterone (or CB-7630; (3S,8R,9S,10R,13S,14S)-10,13-dimethyl-17-(pyridin-3-yl) 2,3,4,7,8,9,10,11,12,13,14,15-dodecahydro-1H-cyclopenta [a]phenanthren-3-ol), and related molecules, which appears to block the production of androgen and FDA-approved treatment for prostate cancer; the chemical entity known as bicalutamide (N-[4-cyano-3-(trifluoromethyl)phenyl]-3-[(4-fluorophenyl)sulfonyl]-2-hydroxy-2-methylpropanamide) and related compounds, which appears to be a blocker of the androgen receptor (AR) LBD and which is currently used to treat prostate cancer, the chemical entity known as nilutamide (5,5-dimethyl-3-[4-nitro-3-(trifluoromethyl)phenyl] imidazolidine-2,4-dione) and related compounds, which appears to be a blocker of the AR LBD and which is currently used to treat prostate cancer, the chemical entity known as flutamide (2-methyl-A-[4-nitro-3-(trifluoromethyl)phenyl]-propanamide) and related compounds, which appears to be a blocker of the androgen receptor (AR) LBD and which is currently used to treat prostate cancer, the chemical entities known as cyproterone acetate (6-chloro-1β,2β-dihydro-17-hydroxy-3'H-cyclopropa[1,2]pregna-4,6-diene-3,20-dione) and related compounds, which appears to be a blocker of the androgen receptor (AR) LBD and which is currently used to treat prostate cancer, the chemical entity known as docetaxel (Taxotere; 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) and related compounds, which appears to be a cytotoxic antimicrotubule agent and is currently used in combination with prednisone to treat prostate cancer, the chemical entity known as Bevacizumab (Avastin), a monoclonal antibody that recognizes and blocks vascular endothelial growth factor A (VEGF-A) and can be used to treat prostate cancer, the chemical entity known as OSU-HDAC42 ((S)-(+)-N-hydroxy-4-(3-methyl-2-phenylbutyrylamino)-benzamide), and related compounds, which appears to act as a histone deacetylase inhibitor, and is currently being developed as a treatment for prostate cancer, the chemical entity known as VITAXIN which appears to be a monoclonal antibody against the vascular integrin αvβ3 to prevent angiogenesis, and which can be used to treat prostate cancer, the chemical entity known as sunitumib (N-(2-diethylaminoethyl)-5-[(Z)-(5-fluoro-2-oxo-ln-indol-3-ylidene)methyl]-2,4-dimethyl-ln-pyrrole-3-carboxamide) and related compounds, which appears to inhibit multiple receptor tyrosine kinases (RTKs) and can be used for treatment of prostate cancer, the chemical entity known as ZD-4054 (N-(3-Methoxy-5-methylpyrazin-2-yl)-2-[4-(1,3,4-oxadiazol-2-yl)phenyl]pyridin-3-sulfonamid) and related compounds, which appears to block the edta receptor and which can be used for treatment of prostate cancer; the chemical entity known as Cabazitaxel (XRP-6258), and related compounds, which appears to be a cytotoxic microtubule inhibitor, and which is currently used to treat prostate cancer; the chemical entity known as MDX-010 (Ipilimumab), a fully human monoclonal antibody that binds to and blocks the activity of CTLA-4 which is currently in development as an immunotherapeutic agent for treatment of prostate cancer; the chemical entity known as OGX 427 which appears to target HSP27 as an antisense agent, and which is currently in development for treatment of prostate cancer; the chemical entity known as OGX 011 which appears to target clusterin as an antisense agent, and which is currently in development as a treatment for prostate cancer; the chemical entity known as finasteride (Proscar, Propecia; N-(1,1-dimethylethyl)-3-oxo-(5α, 17β)-4-azaandrost-1-ene-17-carboxamide), and related compounds, which appears to be a 5-alpha reductase inhibitor that reduces levels of dihydrotestosterone, and can be used to treat prostate cancer; the chemical entity known as dutasteride (Avodart; 5α, 17β)-N-{2,5 bis(trifluoromethyl) phenyl}-3-oxo-4-azaandrost-1-ene-17-carboxamide) and related molecules, which appears to be a 5-alpha reductase inhibitor that reduces levels of dihydrotestosterone, and can be used in the treatment of prostate cancer; the chemical entity known as turosteride ((4aR,4bS,6aS,7S,9aS,9bS,11aR)-1,4a,6a-trimethyl-2-oxo-N-(propan-2-yl)-N-(propan-2-ylcarbamoyl)hexadecahydro-1H-indeno[5,4-f]quinoline-7-carboxamide), and related molecules, which appears to be a 5-alpha reductase inhibitor that reduces levels of dihydrotestosterone and can be used in the treatment of prostate cancer; the chemical entity known as bexlosteride (LY-191,704; (4aS,10bR)-8-chloro-4-methyl-1,2,4a,5,6,10b-hexahydrobenzo[f]quinolin-3-one), and related compounds, which appears to be a 5-alpha reductase inhibitor that reduces levels of dihydrotestosterone and can be used in the treatment of prostate cancer; the chemical entity known as izonsteride (LY-320,236; (4aR,10bR)-8-[(4-ethyl-1,3-benzothiazol-2-yl)sulfanyl]-4,1 Ob-dimethyl-1,4,4a, 5,6,10b-hexahydrobenzo[f]quinolin-3(2H)-one) and related compounds, which appears to be a 5-alpha reductase inhibitor that reduces levels of dihydrotestosterone and can be used for the treatment of prostate cancer; the chemical entity known as FCE 28260 and related compounds, which appears to be a 5-alpha reductase inhibitor that reduces levels of dihydrotestosterone and can be used for the treatment of prostate cancer; the chemical entity known as SKF105,111, and related compounds, which appears to be a 5-alpha reductase inhibitor that reduces levels of dihydrotestosterone and can be used for treatment of prostate cancer. The chemical entity known as niclosamide (4.5-Chloro-N-(2-chloro-4-nitrophenyl)-2-hydroxybenzamide) and related compounds, which appears to be an antihelminitic that is an AR-V7 inhibitor and can be used for treatment of prostate cancer. The chemical entity known as ARV-330 (Arvinas, Inc.) and related compounds, which appears to degrade androgen receptor in LNCaP and VCaP cells and can be useful for treatment of prostate cancer. The chemical entity known as VPC-14449 (4-(4-(4,5-bromo-ln-imidazol-1-yl) thiazol-2-yl)morpholine) and related compounds, which appears to target the DNA-binding domain of full-length AR and can be useful for treatment of prostate cancer. The chemical entity known as TAS3681 appears to be an AR antagonist with AR downregulating activity and can be useful for treatment of prostate cancer. The chemical entity known as sintokamides (e.g., sintokamide A also known as N-[(2R,4S)-5,5,5-trichloro-1-[(2 S)-2-[(2 S)-3,3-dichloro-2-methy 1 propyl]-3-methoxy-5-oxo-2H-pyrrol-1-yl]-4-methyl-1-oxopentan-2-yl]propanamide) and related compounds, which appears to be an AR antagonist and can be useful for treating prostate cancer.

Accordingly, in some embodiments, the pharmaceutical composition comprising a compound having a structure of Formula I or Formula II, or a pharmaceutically acceptable salt, tautomer or stereoisomer thereof, further comprises an additional therapeutic agent selected form the group consisting of enzalutamide, galeterone, abiraterone, bicalutamide, nilutamide, flutamide, cyproterone acetate, docetaxel, bevacizumab (Avastin), OSU-HDAC42, VITAXIN, sunitumib, ZD-4054, Cabazitaxel (XRP-6258), MDX-010 (Ipilimumab), OGX427, OGX Oil, finasteride, dutasteride, turosteride, bexlosteride, izonsteride, FCE 28260, SKF105,111, ODM-201, ODM-204, radium 233, niclosamide, apalutamide, ARV-330, VPC-14449, TAS3681, 3E10-AR441bsAb, sintokamide or related compounds thereof.

In some embodiments, compounds of Formula I or Formula II, or a pharmaceutically acceptable salt, tautomer or stereoisomer thereof, which result in unstable structures and/or unsatisfied valences are not included within the scope of the invention.

In another embodiment, the present disclosure provides a pharmaceutical composition comprising any of the foregoing compounds of Formula I or Formula II, or a pharmaceutically acceptable salt, tautomer or stereoisomer thereof, and a pharmaceutically acceptable carrier.

Compounds as described herein can be in the free form or in the form of a salt thereof. In some embodiments, compounds as described herein can be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt can be, for example, formed as a pharmaceutically acceptable salt. Compounds containing one or more basic functional groups can be capable of forming a pharmaceutically acceptable salt with, for example, a pharmaceutically acceptable organic or inorganic acid. Pharmaceutically acceptable salts can be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups can be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts can be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethyl ammonium compounds, pyridine, N,N-di methyl aniline, N-methylpiperidine, morpholine, N-methylmorpholine, A-ethyl morpholine, dicyclohexylamine, dibenzylamine, N,N-dibenzylphenethylamine, 1-ephenamine, N,N'-dibenzyl ethylenediamine or polyamine resins. In some embodiments, compounds as described herein can contain both acidic and basic groups and can be in the form of inner salts or zwitterions, for example, and without limitation, betaines. Salts as described herein can be prepared by conventional processes known to a person skilled in the art, for example, and without limitation, by reacting the free form with an organic acid or inorganic acid or base, or by anion exchange or cation exchange from other salts.

Those skilled in the art will appreciate that preparation of salts can occur in situ during isolation and purification of the compounds or preparation of salts can occur by separately reacting an isolated and purified compound.

In some embodiments, compounds and all different forms thereof (e.g. free forms, salts, polymorphs, isomeric forms) as described herein can be in the solvent addition form, for example, solvates. Solvates contain either stoichiometric or non-stoichiometric amounts of a solvent in physical association the compound or salt thereof. The solvent can be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein can include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature can cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

III. Methods

The present compounds find use in any number of methods. For example, in some embodiments the compounds are useful in methods for modulating androgen receptor (AR). Accordingly, in one embodiment, the present disclosure provides the use of any one of the foregoing compounds of Formula I for modulating androgen receptor (AR) activity. For example in some embodiments, modulating androgen receptor (AR) activity is in a mammalian cell. Modulating androgen receptor (AR) can be in a subject in need thereof (e.g., a mammalian subject) and for treatment of any of the described conditions or diseases.

In other embodiments, modulating androgen receptor (AR) activity is for treatment of at least one indication selected from the group consisting of: prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, age related macular degeneration, and combinations thereof. For example in some embodiments, the indication is prostate cancer. In other embodiments, the prostate cancer is primary/localized prostate cancer, locally advanced prostate cancer, recurrent prostate cancer, metastatic prostate cancer, advanced prostate cancer, or metastatic castration-resistant prostate cancer (CRPC), or hormone-sensitive prostate cancer. While in other embodiments, the prostate cancer is androgen dependent prostate cancer. In other embodiments, the spinal and bulbar muscular atrophy is Kennedy's disease.

In some embodiments, compounds as described herein can be administered to a subject. In one embodiment, the present invention is directed to a method of treating primary/localized prostate cancer comprising administering a pharmaceutical composition comprising a compound having a structure of Formula I or Formula II, or a pharmaceutically acceptable salt, tautomer or stereoisomer thereof. In some embodiments, the present invention is directed to a method of treating locally advanced prostate cancer comprising administering a pharmaceutical composition comprising a compound having a structure of Formula I or Formula II, or a pharmaceutically acceptable salt, tautomer or stereoisomer thereof. In other embodiments, the present invention is directed to a method of treating recurrent prostate cancer comprising administering a pharmaceutical composition comprising a compound having a structure of Formula I or Formula II, or a pharmaceutically acceptable salt, tautomer or stereoisomer thereof. In other embodiments, the present invention is directed to a method of treating metastatic prostate cancer comprising administering a pharmaceutical composition comprising a compound having a structure of Formula I or Formula II, or a pharmaceutically acceptable salt, tautomer or stereoisomer thereof. In other embodiments, the present invention is directed to a method of treating advanced prostate cancer comprising administering a pharmaceutical composition comprising a compound having a structure of Formula I or Formula II, or a pharmaceutically acceptable salt, tautomer or stereoisomer thereof. In other embodiments, the present invention is directed to a method of treating metastatic castration-resistant prostate cancer (CRPC) comprising administering a pharmaceutical composition comprising a compound having a structure of Formula I or Formula II, or a pharmaceutically acceptable salt, tautomer or stereoisomer thereof. In other embodiments, the present invention is directed to a method of treating hormone-sensitive prostate cancer comprising administering a pharmaceutical composition comprising a compound having a structure of Formula I or Formula II, or a pharmaceutically acceptable salt, tautomer or stereoisomer thereof.

In other embodiments, the present disclosure provides a method of modulating androgen receptor (AR) activity, the method comprising administering any one of the foregoing compounds of Formula I or Formula II, or a pharmaceutically acceptable salt, tautomer or stereoisomer thereof, or pharmaceutical composition of Formula I or Formula II, or a pharmaceutically acceptable salt, tautomer or stereoisomer thereof, as described herein (including compositions comprising a compound of Formula I or Formula II, or a pharmaceutically acceptable salt, tautomer or stereoisomer thereof, and an additional therapeutic agent), to a subject (e.g., mammal) in need thereof. In some embodiments, modulating androgen receptor (AR) activity is in a mammalian cell. In other embodiments, modulating androgen receptor (AR) activity is in a mammal. In one embodiment, modulating androgen receptor (AR) activity is in a human.

The modulating androgen receptor (AR) activity can be for inhibiting AR N-terminal domain activity. The modulating androgen receptor (AR) activity can be for inhibiting androgen receptor (AR) activity. The modulating can be in vivo. The modulating androgen receptor (AR) activity can be for treatment of at least one indication selected from the group consisting of: prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), and age related macular degeneration. The indication can be prostate cancer. The prostate cancer can be castration-resistant prostate cancer. In one embodiment, the prostate cancer is primary/localized prostate cancer, locally advanced prostate cancer, recurrent prostate cancer, metastatic prostate cancer, advanced prostate cancer, or metastatic castration-resistant prostate cancer (CRPC), or hormone-sensitive prostate cancer. The prostate cancer can be CRPC.

In accordance with another embodiment, there is provided a use of the compounds of Formula I or Formula II, or a pharmaceutically acceptable salt, tautomer or stereoisomer thereof, or pharmaceutical composition of Formula I or Formula II, or a pharmaceutically acceptable salt, tautomer or stereoisomer thereof, as described herein for preparation of a medicament for modulating androgen receptor (AR).

Alternatively, in one embodiment, a method of modulating androgen receptor activity, comprising administering Formula I or Formula II, or a pharmaceutically acceptable salt, tautomer or stereoisomer thereof, or pharmaceutical composition of Formula I or Formula II, or a pharmaceutically acceptable salt, tautomer or stereoisomer thereof, as described herein, is provided. In some embodiments, the administration can be to a mammal. In other embodiments, the administering can be to a mammal in need thereof and in an effective amount for the treatment of at least one indication selected from the group consisting of: prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), age related macular degeneration, and combinations thereof.

As noted above, the presently disclosed compounds can find utility in a number of medical imaging applications, including imaging of the prostate. Many currently available imaging agents tend to accumulate in the bladder, which decreases their effectiveness as imaging tools specifically for the prostate. While not wishing to be bound by theory, the present applicants believe the disclosed compounds are unexpectedly effective for imaging of the prostate due to their ability to accumulate in the prostate, rather than the bladder, allowing the prostate gland to be seen. Accordingly, the compounds can be used in methods for imaging the prostate, for example to image benign prostate diseases. In other embodiments, the compounds can be used in methods to image cancerous prostate diseases, such as tumors of the prostate.

Androgen ablation therapy causes a temporary reduction in prostate cancer tumor burden, but the malignancy will begin to grow again in the absence of testicular androgens to form castrate resistant prostate cancer (CRPC). A rising titer of serum prostate-specific antigen (PSA) after androgen ablation therapy indicates biochemical failure, the emergence of CRPC, and re-initiation of an androgen receptor (AR) transcription program. Most patients succumb to CRPC within two years of biochemical failure.

In one embodiment, the method identifies the presence of a tumor that expresses AR (both full-length and truncated AR lacking LBD) and then treats the tumor by radiotherapy. In another embodiment, the imaging methods provide information to determine if a tumor expresses AR species.

AR is a transcription factor and a validated target for prostate cancer therapy. Current therapies include androgen ablation and administration of antiandrogens. Most CRPC is suspected to be AR-dependent. AR has distinct functional domains that include the C-terminus ligand-binding domain (LBD), a DNA-binding domain (DBD), and an amino-terminal domain (NTD). AR NTD contains activation function-1 (AF-1) that contributes most of the transcriptional activity to the AR. Recently, splice variants of the AR that lack the LBD have been reported in prostate cancer cell lines (VCaP, LNCaP95 and 22Rv1), and in CRPC tissues. To date more than 20 splice variants of AR have been detected. Splice variants V7 and V567es are clinically relevant with levels of expression correlated to poor survival and CRPC. AR V567es is solely expressed in 20% of metastases. Abiraterone resistance is associated with expression of AR splice variants. Enzalutamide also increases levels of expression of these constitutively active AR splice variants. These splice variants lack LBD and thereby would not be inhibited by current therapies that target the AR LBD such as antiandrogens or androgen ablation therapy. A single patient with advanced prostate cancer can have many lesions throughout the body and skeleton and each tumor can have differing levels of expression of AR.

Biopsy of metastatic tumors in a patient to determine AR species is neither widely accessible nor feasible to sample tumors in a patient that can have multiple metastases. Thus it is essential to develop approaches to detect the expression of all AR species for the molecular classification of tumors based on the level and extent of expression of AR splice variants, or other AR species that cannot be detected using an imaging agent that interacts with the LBD, to identify patients with potentially aggressive disease and poor prognosis, or to identify patients that will not respond to hormone therapies that target the AR LBD. Accordingly, certain embodiments of the present invention provide an AR NTD-targeted molecular imaging probe (e.g., compound of formula I) which can be used to monitor response to therapy and provide insight into the role of AR in resistance mechanisms.

One current approach to image AR in prostate cancer uses positron emission tomography (PET) with 16β-[$^{18}$F]-fluoro-5α dihydrotestosterone ($^{18}$F-FDHT) that binds to AR LBD. Unfortunately this imaging agent cannot detect splice variants lacking LBD. In some embodiments, the invention employs sequential imaging with $^{18}$F-FDHT to detect full-length AR and gamma radiation emitting probes to specifically detect the AR NTD which would be the sum of both full-length AR and variant AR. In other embodiments, the invention employs sequential imaging with two different PET imaging agents to detects only full-length AR and another to specifically detect the AR NTD which would be the sum of both full-length AR and variant AR. Together these data reveal patients with tumors that express variant AR (NTD of variant plus full-length AR detected with NTD isotope minus full-length AR detected with $^{18}$F-FDHT). By using sequential imaging, a discordant distribution or discordant level of uptake between $^{18}$F-FDHT and a radiolabeled compound of this invention (i.e., compound of Formula I) indicates the presence of overexpression of splice variants lacking the LBD.

As described above, radioactive $^{18}$F labeled compounds have found use as imaging agents not only to image AR in prostate cancer but for imaging various organs and various tumors. Similarly, radioactive $^{123}$I labeled compounds have been known for the use as imaging agents. In one embodiment, the compounds of the present disclosure comprise at least one $^{123}$I.

In one embodiment, the present invention is directed to a method of imaging cancer by administering a compound having a structure of Formula I or Formula II, or a pharmaceutically acceptable salt, tautomer or stereoisomer thereof, to a subject. In another embodiment, the present invention is directed to a method of imaging cancer by administering a pharmaceutical composition comprising a compound having a structure of Formula I or Formula II, or a pharmaceutically acceptable salt, tautomer or stereoisomer thereof, to a subject.

In some embodiment, the method of imaging cancer by administering a compound having a structure of Formula I or Formula II, or a pharmaceutically acceptable salt, tautomer or stereoisomer thereof, or a pharmaceutical composition comprising Formula I or Formula II, or a pharmaceutically acceptable salt, tautomer or stereoisomer thereof, to a subject and detecting the presence or absence of cancer by use of SPECT or PET. In other embodiments, the method of imaging cancer by administering a compound having a structure of Formula I or Formula II, or a pharmaceutically acceptable salt, tautomer or stereoisomer thereof, to a subject and the method identifies the presence or absence of a tumor. In one embodiment, the method of imaging cancer by administering a compound having a structure of Formula I or Formula II, or a pharmaceutically acceptable salt, tautomer or stereoisomer thereof, to a subject and the method identifies the location of a tumor. In one embodiment, the method of imaging cancer by administering a compound having a structure of Formula I or Formula II, or a pharmaceutically acceptable salt, tautomer or stereoisomer thereof, to a subject and the method identifies a presence of a prostate cancer. In other embodiments, the prostate cancer is androgen-dependent prostate cancer. In some embodiments, the subject is a mammal such as a human.

In some other embodiments, the method is useful for detecting the presence of AR splice variants or other AR species that cannot be detected by imaging agents that interact with the AR LBD (i.e., mutations, truncations). Without wishing to be bound by any particular theory, since the present compounds bind to the AR N-terminal domain (NTD), even mutants or variants which lack the AR LBD can be imaged employing the present compounds. Thus, the present methods can be useful for detecting AR species, including mutants and variants, which lack the LBD or have LBD mutations, but do comprise the AR NTD. In other embodiments the method detects the presence or overexpression of AR splice variants lacking the ligand-binding domain. For example, the method can include sequential imaging with $^{18}$F-FDHT and a compound of the invention and a discordant distribution or discordant level of uptake between $^{18}$F-FDHT and the compound of the invention indicates the presence or overexpression of splice variants lacking the ligand-binding domain.

In other embodiments, the compounds of the invention are used in single photon emission computed tomography methods to monitor a patient's response to therapy. In other embodiments, the methods comprise use of a compound of the invention to detect the AR NTD.

In accordance with a further embodiment, the method of imaging a cancer is by administering a compound as described anywhere herein. In one embodiment, the method of imaging a cancer is by administering a compound of Formula I or Formula II, or a pharmaceutically acceptable salt, tautomer or stereoisomer thereof, wherein said compound comprises at least one $^{123}$I.

The administering and imaging can be to a mammal in need of diagnosis of at least one indication selected from the group consisting of: prostate cancer, breast cancer, ovarian cancer, bladder cancer, pancreatic cancer, hepatocellular cancer, endometrial cancer, salivary gland carcinoma, benign prostatic hyperplasia, hair loss, acne, hirsutism, ovarian cysts, polycystic ovary disease, precocious puberty, spinal and bulbar muscular atrophy (e.g., Kennedy's disease), and age-related macular degeneration. The imaging can be for imaging AR splice variants, mutants or other AR species which contain AR NTD.

In some embodiments, the compounds as described herein or pharmaceutically acceptable salts thereof can be used for imaging and diagnosis of at least one indication selected from the group consisting of: prostate cancer, breast cancer, ovarian cancer, bladder cancer, pancreatic cancer, hepatocellular cancer, endometrial cancer, salivary gland carcinoma, benign prostatic hyperplasia, hair loss, acne, hirsutism, ovarian cysts, polycystic ovary disease, precocious puberty, spinal and bulbar muscular atrophy, and age-related macular degeneration. In some embodiments, the compounds as described herein or acceptable salts thereof above can be used in the preparation of a medicament or a composition for imaging the prostate, for example for imaging benign prostate conditions or for imaging prostate cancer in a subject in need of such imaging (for example for diagnosis and/or location of prostate tumors).

In some embodiments, pharmaceutical compositions useful in modulating androgen receptor (AR) activity or useful for imaging, in accordance with this invention can comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents are those known in the art for use in such modes of administration.

In one embodiment, the imaging method disclosed herein is directed to imaging prostate cancer. In some embodiments, the prostate cancer is primary/localized prostate cancer, locally advanced prostate cancer, recurrent prostate cancer, metastatic prostate cancer, advanced prostate cancer, or metastatic castration-resistant prostate cancer (CRPC), and hormone-sensitive prostate cancer. In some embodiments the prostate cancer is CRPC. In other embodiments, the imaging is for imaging benign prostate conditions such as benign prostatic hyperplasia. Methods of imaging and/or treating any of the indications described herein are also provided. Such methods may include administering a compound as described herein or a composition of a compound as described herein, or an effective amount of a compound as described herein or composition of a compound as described herein to a subject in need thereof. In one embodiment, a pharmaceutical composition suitable for imaging is administered intravenously.

Suitable pharmaceutical compositions can be formulated by means known in the art and their mode of administration and dose determined by the skilled practitioner. For parenteral administration, a compound can be dissolved in sterile water or saline or a pharmaceutically acceptable vehicle used for administration of non-water soluble compounds such as those used for vitamin K. For enteral administration, the compound can be administered in a tablet, capsule or dissolved in liquid form. The tablet or capsule can be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant can be employed to provide release over a prolonged period of time. Many techniques known to one of skill in the art are described in Remington: the Science &Practice of Pharmacy by Alfonso Gennaro, 20$^{th}$ ed., Lippencott Williams & Wilkins, (2000). Formulations for parenteral administration can, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers can be used to control the release of the compounds. Other potentially useful parenteral delivery systems for modulatory compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate and deoxycholate, or can be oily solutions for administration in the form of nasal drops, or as a gel.

In another aspect, the present disclosure provides a pharmaceutical composition comprising a compound as described herein, and an additional therapeutic agent and/or a pharmaceutically acceptable carrier. In some embodiments, the additional therapeutic agent is for treating prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy or age related macular degeneration. In other embodiments, the additional therapeutic agent is enzalutamide, galeterone, ODN-201 abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX427, OGX Oil, finasteride, dutasteride, turosteride, bexlosteride, izonsteride, FCE 28260, SKF105,111, ODM-201 ODM-204, niclosamide, apalutamide, ARV-330, VPC-14449, TAS3681, 3E10-AR441bsAb, sintokamide, or related compounds thereof.

Compounds described herein can also be used in assays and for research purposes. Definitions used include ligand dependent activation of the androgen receptor (AR) by androgens such as dihydrotestosterone (DHT) or the synthetic androgen (R1881) used for research purposes. Ligand-independent activation of the androgen receptor (AR) refers to transactivation of the full-length androgen receptor (AR) in the absence of androgen (ligand) by, for examples, stimulation of the cAMP dependent protein kinase (PKA) pathway or the interleukin-6 (IL6)/STAT3 pathway. Such compounds should block a mechanism that is common to both ligand-dependent and ligand-independent activation of the androgen receptor (AR), as well as constitutively active splice variants of the androgen receptor (AR) that lack ligand-binding domain. This could involve any step in activation of the androgen receptor (AR) including dissociation of heatshock proteins, essential posttranslational modifications (e.g., acetylation, phosphorylation), nuclear translocation, protein-protein interactions, formation of the transcriptional complex, release of co repressors, and/or increased degradation. Numerous disorders in addition to prostate cancer involve the androgen axis (e.g., acne, hirsutism, alopecia, benign prostatic hyperplasia) and compounds interfering with this mechanism can be used to treat such conditions.

Compounds or pharmaceutical compositions in accordance with this invention or for use in this invention can be administered by means of a medical device or appliance such as an implant, graft, prosthesis, stent, etc. Also, implants can be devised which are intended to contain and release such compounds or compositions. An example would be an implant made of a polymeric material adapted to release the compound over a period of time.

It is to be noted that dosage values can vary with the exact imaging protocol. For any particular subject, specific dosage regimens can be adjusted over time according to the individual need and the professional judgment of the person administering or supervising the administration of the compositions. Dosage ranges set forth herein are exemplary only and do not limit the dosage ranges that can be selected by medical practitioners. The amount of active compound(s) in the composition can vary according to factors such as the disease state, age, sex, and weight of the subject. Dosage regimens can be adjusted to provide the optimum imaging result. For example, a single bolus can be administered, several divided doses can be administered over time or the dose can be proportionally reduced or increased as indicated by the imaging results. It can be advantageous to formulate parenteral compositions in dosage unit form for ease of administration and uniformity of dosage.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances, such as in severe disease conditions, substantial excesses of the compositions can be administered for therapeutic effects. Some compounds of this invention can be toxic at some concentrations. Titration studies can be used to determine toxic and non-toxic concentrations. Toxicity can be evaluated by examining a particular compound's or composition's specificity across cell lines using PC3 or DU145 cells as possible negative controls since these cells do not express functional AR. Animal studies can be used to provide an indication if the compound has any effects on other tissues. Systemic therapy that targets the AR will not likely cause major problems to other tissues since castration, antiandrogens and androgen insensitivity syndrome are not fatal.

Compounds for use in the present invention can be obtained from medical sources or modified using known methodologies from naturally occurring compounds. In addition, methods of preparing or synthesizing compounds of the present invention will be understood by a person of skill in the art having reference to known chemical synthesis principles. For example, Auzou et al 1974 *European Journal of Medicinal Chemistry* 9(5), 548-554 describes suitable synthetic procedures that can be considered and suitably adapted for preparing compounds of any one of the compounds of structure (I) as set out above. Other references that can be helpful include: Debasish Das, Jyh-Fu Lee and Soofin Cheng "Sulfonic acid functionalized mesoporous MCM-41 silica as a convenient catalyst for Bisphenol-A synthesis" *Chemical Communications*, (2001) 2178-2179; U.S. Pat. No. 2,571,217 Davis, Orris L.; Knight, Horace S.; Skinner, John R. (Shell Development Co.) "Halohydrin ethers of phenols." (1951); and Rokicki, G.; Pawlicki, J.; Kuran, W. "Reactions of 4-chloromethyl-1,3-dioxolan-2-one with phenols as a new route to polyols and cyclic carbonates." Journal fuer Praktische Chemie (Leipzig) (1985) 327, 718-722.

In some embodiments, compounds and all different forms thereof as described herein can be used, for example, and without limitation, in combination with other treatment methods for at least one indication selected from the group consisting of: prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, and age related macular degeneration. For example, compounds and all their different forms as described herein can be used as neoadjuvant (prior), adjunctive (during), and/or adjuvant (after) therapy with surgery, radiation (brachytherapy or external beam), or other therapies (eg. HIFU), and in combination with chemotherapies, androgen ablation, antiandrogens or any other therapeutic approach.

In an exemplary embodiment for imaging the prostate, a dose of the disclosed compounds in solution (typically 5 to 10 millicuries or 200 to 400 MBq) is typically injected rapidly into a saline drip running into a vein, in a patient. Then, the patient is placed in the SPECT for a series of one or more scans which can take from 20 minutes to as long as an hour (often, only about one quarter of the body length can be imaged at a time). Methods for SPECT scanning are well known in the art.

The compounds described herein can be used for in vivo or in vitro research uses (i.e. non-clinical) to investigate the mechanisms of orphan and nuclear receptors (including steroid receptors such as androgen receptor (AR)). Furthermore, these compounds can be used individually or as part of a kit for in vivo or in vitro research to investigate signal transduction pathways and/or the activation of orphan and nuclear receptors using recombinant proteins, cells maintained in culture, and/or animal models.

For example, exemplary compounds of the present invention can be prepared with reference to the following General Reaction Scheme I:

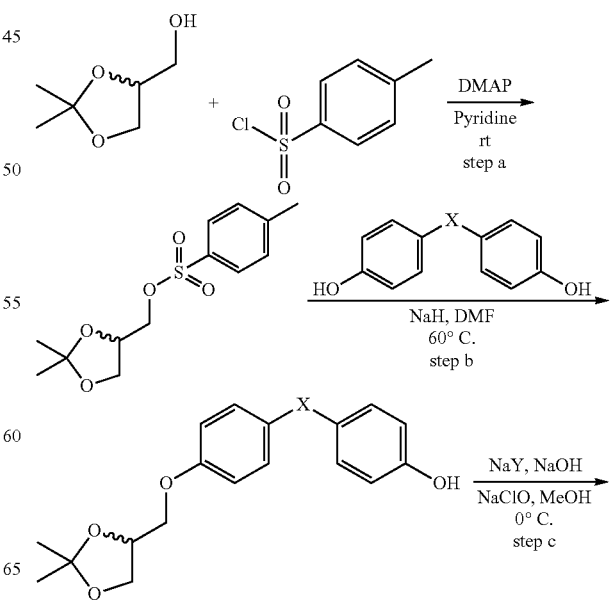

-continued

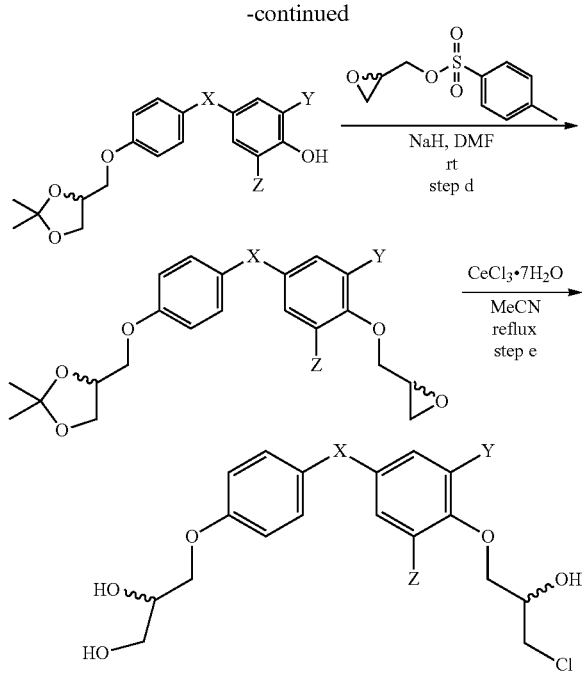

It should be noted that, although General Reaction Scheme I depicts a racemic synthesis, one skilled in the art would recognize that different stereoisomers and diastereomers can be synthesized by using starting materials of different stereochemistry, e.g., stereospecific (2,2-dimethyl-1,3-dioxolan-4-yl)methanol and/or stereospecific oxiran-2-ylmethyl 4-methylbenzenesulfonate.

Referring to General Reaction Scheme I, (2,2-dimethyl-1,3-dioxolan-4-yl)methanol is toslyated under basic conditions as shown in step a. In step b, tosly group (p-toulenesulfonate) is displaced with bisphenol derivatives under basic conditions (X can be —S(O)$_n$- where n=0, 1, or 2, or divalent linear or branched $C_1$-$C_6$ alkyl). Optionally, in step c, the bisphenol derivative is halogenated on the phenyl ring (e.g., Y and Z can be Cl or Br). In step d, the unreacted phenol portion undergoes another elimination reaction to afford a bisphenol derivative with an epoxide on one side and a protected diol on the other. In step e, epoxide is opened using $CeCl_3 \cdot 7H_2O$ and the diol is deprotected in situ.

One skilled in the art will recognize that variations to the order of the steps and reagents discussed in reference to the above General Synthetic Schemes I are possible.

In addition, protecting group strategies can be employed for preparation of the compounds disclosed herein. Such strategies are well known to those of skill in the art. Exemplary protecting groups and related strategies are disclosed in Greene's Protective Groups in Organic Synthesis, Wiley-InterScience; 4 edition (Oct. 30, 2006), which is hereby incorporated by reference in its entirety. In certain embodiments, a protecting group is used to mask an alcohol moiety while performing other chemical transformations. After removal of the protecting group, the free hydroxyl is obtained. Such protecting groups and strategies are well known in the art.

Various alternative embodiments and examples of the invention are described herein. These embodiments and examples are illustrative and should not be construed as limiting the scope of the invention. The following examples are provided for purposes of illustration, not limitation.

EXAMPLES

All non-aqueous reactions were performed in flame-dried round bottomed flasks. The flasks were fitted with rubber septa and reactions were conducted under a positive pressure of argon unless otherwise specified. Stainless steel syringes were used to transfer air- and moisture-sensitive liquids. Flash column chromatography was performed as described by Still et al. (Still, W. C.; Kahn, M.; Mitra, A. *J. Org. Chem.* 1978, 43, 2923) using 230-400 mesh silica gel. Thin-layer chromatography was performed using aluminum plates pre-coated with 0.25 mm 230-400 mesh silica gel impregnated with a fluorescent indicator (254 nm). Thin-layer chromatography plates were visualized by exposure to ultraviolet light and a "Seebach" staining solution (700 mL water, 10.5 g Cerium (IV) sulphate tetrahydrate, 15.0 g molybdato phosphoric acid, 17.5 g sulphuric acid) followed by heating (~1 min) with a heating gun (~250° C.). Organic solutions were concentrated on Büchi R-114 rotatory evaporators at reduced pressure (15-30 torr, house vacuum) at 25-40° C. Commercial regents and solvents were used as received. All solvents used for extraction and chromatography were HPLC grade. Normal-phase Si gel Sep Paks™ were purchased from waters, Inc. Thin-layer chromatography plates were Kieselgel 60F$_{254}$. All synthetic reagents were purchased from Sigma Aldrich and Fisher Scientific Canada.

Example 1: Synthesis of (R)-3-(4-(2-(3,5-dichloro-4-((S)-3-chloro-2-hydroxypropoxy)phenyl)propan-2-yl)phenoxy)propane-1,2-diol (Compound 1a)

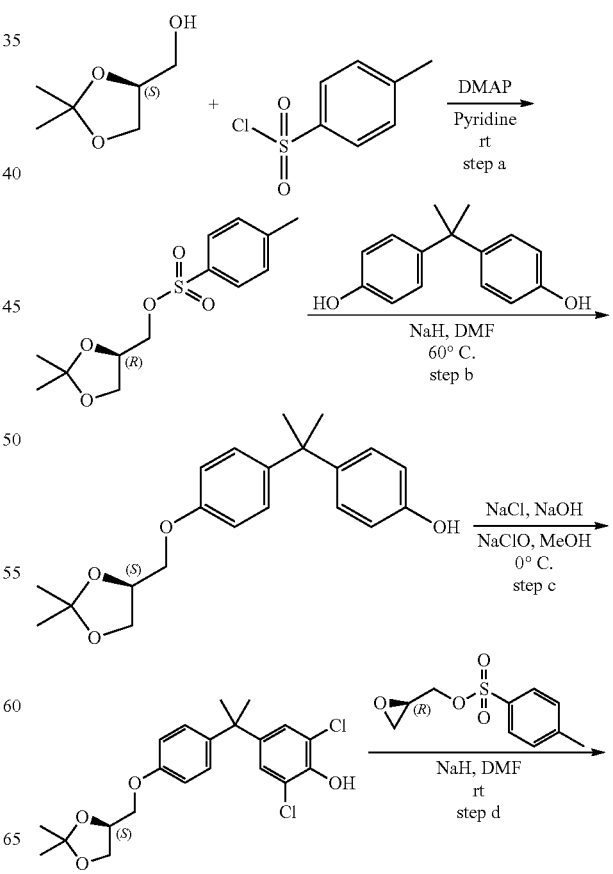

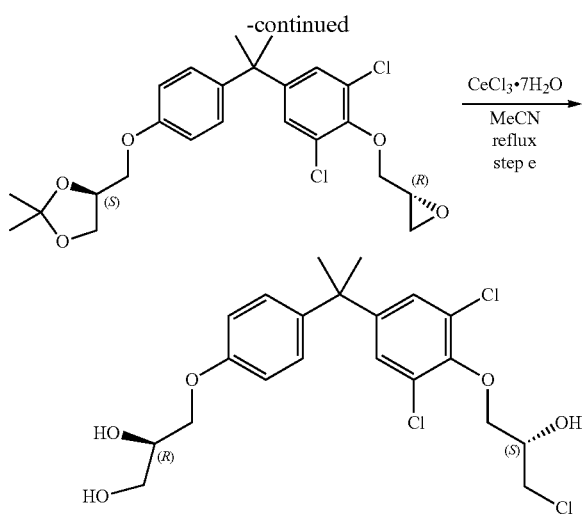

Steps a and b: Synthesis of (S)-4-(2-(4-((2,2-dimethyl-1,3-dioxolan-4-yl)methoxy)phenyl)propan-2-yl)phenol The titled compound was synthesized as previously reported. See, WO 2014/179867.

Step c: (S)-2,6-dichloro-4-(2-(4-((2,2-dimethyl-1,3-dioxolan-4-yl)methoxy)phenyl)propan-2-yl)phenol To a solution of (S)-4-(2-(4-((2,2-dimethyl-1,3-dioxolan-4-yl)methoxy)phenyl)propan-2-yl)phenol (500 mg, 1.46 mmol, 1.0 equiv) in MeOH (12 mL) was added NaCl (256 mg, 4.38 mmol, 3.0 equiv) and NaOH (87.6 mg, 2.19 mmol, 1.5 equiv). Aqueous sodium hypochlorite (6035 mg, 5.4% in $H_2O$, 4.38 mmol, 3.0 equiv) was then added dropwise over 2 min at 0° C. After 2 hours, the mixture was extracted with ethyl acetate (2×30 mL). The organic layer was washed with deionized water (2×30 mL), dried over anhydrous magnesium sulfate, filtered, and concentrated under reduced pressure. The resulting residue was purified by gradient flash Si gel column chromatography (elution: 10% ethyl acetate in hexane to 20% ethyl acetate in hexane) to provide the tile compound (454 mg, 75.6%) as a sticky oil. $^1$H NMR (600 MHz, DMSO-$D_6$) δ (ppm)=9.92 (s, 1H), 7.11 (d, J=9.0 Hz, 2H), 7.07 (s, 2H), 6.84 (d, J=8.4 Hz, 2H), 4.38-4.34 (m, 1H), 4.08-4.05 (m, 1H), 3.97-3.91 (m, 2H), 3.74-3.70 (m, 1H), 1.55 (s, 6H), 1.33 (s, 3H), 1.28 (s, 3H). $^{13}$C NMR (150 MHz, DMSO-$D_6$) δ (ppm)=156.33, 146.75, 143.77, 141.55, 127.47, 126.58, 121.78, 114.03, 108.79, 73.69, 68.60, 65.78, 41.36, 30.23, 26.59, 25.37.

Step d: (S)-4-((4-(2-(3,5-dichloro-4-(((R)-oxiran-2-yl)methoxy)phenyl)propan-2-yl)phenoxy)methyl)-2,2-dimethyl-1,3-dioxolane Sodium hydride (60% dispersion in mineral oil, 63.6 mg, 1.59 mmol, 1.5 equiv) was added slowly to a stirred solution of (S)-2,6-dichloro-4-(2-(4-((2,2-dimethyl-1,3-dioxolan-4-yl)methoxy)phenyl)propan-2-yl)phenol (434 mg, 1.06 mmol, 1.0 equiv) in anhydrous DMF (8 mL) at room temperature and the contents were stirred under an atmosphere of argon for 10 min. A solution of (2R)-(−)-glycidyl tosylate (363 mg, 1.59 mmol, 1.5 equiv) in anhydrous DMF (4 mL) was added via syringe and the mixture was allowed to react at 60° C. for 16 h. The reaction was quenched by the addition of a saturated solution of ammonium chloride (1 mL), and the mixture was extracted with ethyl acetate (60 mL). The organic layer was washed with deionized water (2×30 mL), dried over anhydrous magnesium sulfate, filtered, and concentrated under reduced pressure. The resulting residue was purified by gradient flash Si gel column chromatography (elution: 10% ethyl acetate in hexane to 20% ethyl acetate in hexane) to provide the titled compound (476 mg, 96.1%) as a sticky oil. $^1$H NMR (600 MHz, DMSO-$D_6$) δ (ppm)=7.20 (s, 2H), 7.13 (d, J=9.0 Hz, 2H), 6.86 (d, J=9.0 Hz, 2H), 4.38-4.34 (m, 1H), 4.25-4.22 (m, 1H), 4.07-4.05 (m, 1H), 3.98-3.91 (m, 2H), 3.82-3.80 (m, 1H), 3.74-3.70 (m, 1H), 3.35-3.32 (m, 1H), 2.79-2.77 (m, 1H), 2.62-2.60 (m, 1H), 1.58 (s, 6H), 1.32 (s, 3H), 1.28 (s, 3H). $^{13}$C NMR (150 MHz, DMSO-$D_6$) δ (ppm)=156.46, 149.15, 148.21, 141.01, 127.77, 127.54, 127.24, 114.10, 108.80, 75.01, 73.68, 68.61, 65.77, 49.88, 43.42, 41.80, 30.08, 26.59, 25.37.

Step e: Synthesis of (R)-3-(4-(2-(3,5-dichloro-4-((S)-3-chloro-2-hydroxypropoxy)phenyl)propan-2-yl)phenoxy)propane-1,2-diol (Compound 1a)

To a solution of (S)-4-((4-(2-(3,5-dichloro-4-(((R)-oxiran-2-yl)methoxy)phenyl)propan-2-yl)phenoxy)methyl)-2,2-dimethyl-1,3-dioxolane (560 mg, 1.2 mmol, 1.0 equiv) in MeCN (12 mL) was added $CeCl_3 \cdot 7H_2O$ (1118 mg, 3.0 mmol, 2.5 equiv) and the mixture was heated to reflux for 16 h. The resulting white paste was collected by filtration and washed with ethyl acetate and the clear suspension was concentrated under reduced pressure. The resulting residue was purified by column chromatography to provide the titled compound (512 mg, 92%) as a sticky oil. $^1$H NMR (600 MHz, $CDCl_3$) δ (ppm)=7.15-7.12 (m, 4H), 6.86 (d, J=9.0 Hz, 2H), 4.26-4.23 (m, 1H), 4.21-4.15 (m, 2H), 4.15-4.11 (m, 1H), 4.08-4.03 (m, 2H), 3.86 (dd, J=4.8 Hz, 10.8 Hz, 2H), 3.78 (dd, J=6.6 Hz, 12.6 Hz, 2H), 1.64 (s, 6H); $^{13}$C NMR (150 MHz, $CDCl_3$) δ (ppm)=156.76, 149.30, 148.26, 141.84, 128.52, 127.87, 127.67, 114.35, 73.69, 70.48, 69.26, 63.78, 45.55, 42.34, 30.79; ESI-LRMS calcd for $[M+Na]^+$ 485.1, found 485.4.

Example 2: Synthesis of (R)-3-(4-(2-(3,5-dibromo-4-((S)-3-chloro-2-hydroxypropoxy)phenyl)propan-2-yl)phenoxy)propane-1,2-diol (Compound 3a)

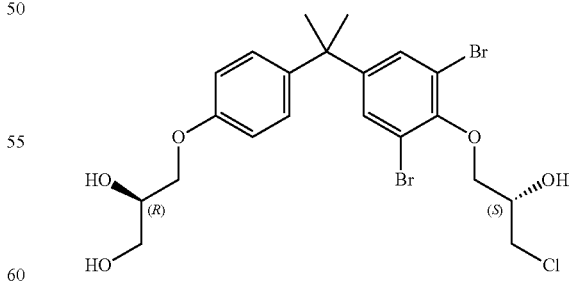

Compound 3a was synthesized according to Example 1 by suing NaBr instead of NaCl in step c. $^1$H NMR (400 MHz, DMSO-$D_6$) δ (ppm)=7.39 (s, 1H), 7.30 (dd, J=2.0 Hz, 34.4 Hz, 1H), 7.15 (d, J=8.8 Hz, 2H), 6.86 (d, J=8.8 Hz, 2H), 5.57-5.54 (m, 1H), 4.91 (d, J=4.8 Hz, 1H), 4.64 (t, J=5.6 Hz, 1H), 4.10-4.08 (m, 1H), 3.98-3.92 (m, 3H), 3.86-3.81 (m, 2H), 3.79-3.76 (m, 1H), 3.71 (dd, J=5.6 Hz, 11.2 Hz, 1H), 3.45-3.42 (m, 2H), 1.60 (s, 6H). $^{13}$C NMR spectrum of Compound 3a as synthesized is shown in FIG. 1.

Example 3: Synthesis of (S)-1-chloro-3-(2,6-dichloro-4-(2-(4-((R)-2-hydroxy-3-methoxypropoxy)phenyl)propan-2-yl)phenoxy)propan-2-ol (Compound 5a)

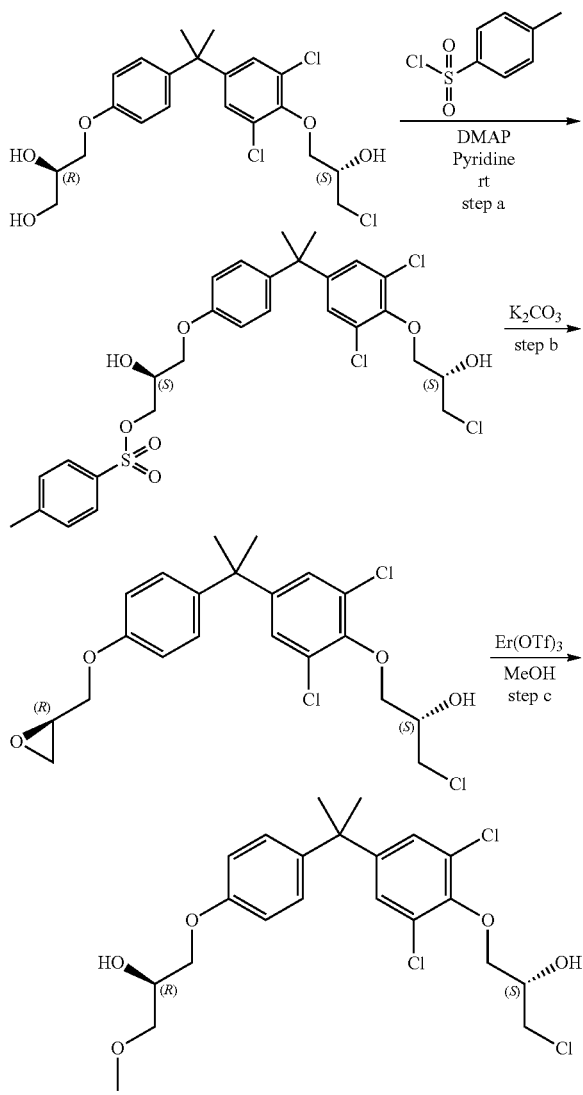

Step a: Synthesis of (S)-3-(4-(2-(3,5-dichloro-4-((S)-3-chloro-2-hydroxypropoxy)phenyl)propan-2-yl)phenoxy)-2-hydroxypropyl 4-methylbenzenesulfonate The titled compound was synthesized by tosylation of Compound 1a under basic conditions according to commonly known protocol, such as the protocol referenced for step a in Example 1.

Step b: Synthesis of (S)-1-chloro-3-(2,6-dichloro-4-(2-(4-(((R)-oxiran-2-yl)methoxy)phenyl)propan-2-yl)phenoxy)propan-2-ol The titled compound was synthesized via epoxidation reaction commonly known in the art under basic conditions. $^{1}$H NMR (400 MHz, CDCl$_3$) δ (ppm)=7.13-7.10 (m, 4H), 6.86 (d, J=6.8 Hz, 2H), 4.24-4.12 (m, 4H), 3.99-3.94 (m, 1H), 3.85 (dd, J=5.2 Hz, 11.2 Hz, 1H), 3.77 (dd, J=5.6 Hz, 11.2 Hz, 1H), 3.38-3.33 (m, 1H), 2.93-2.89 (m, 1H), 2.76 (dd, J=2.4 Hz, 4.8 Hz, 1H), 1.62 (s, 6H).

Step c: Synthesis of (S)-1-chloro-3-(2,6-dichloro-4-(2-(4-((R)-2-hydroxy-3-methoxypropoxy)phenyl)propan-2-yl)phenoxy)propan-2-ol (Compound 5a)

To a solution of (S)-1-chloro-3-(2,6-dichloro-4-(2-(4-(((R)-oxiran-2-yl)methoxy)phenyl)propan-2-yl)phenoxy)propan-2-ol (15 mg, 0.034 mmol, 1.0 equiv) in anhydrous methanol (2 mL) was added Erbium (III) trifluoromethanesulfonate (2.1 mg, 0.0034 mmol, 0.1 equiv) and the mixture was stirred at room temperature for 40 h. The reaction was quenched by the addition of a saturated solution of ammonium chloride (0.5 ml) and the mixture was extracted with ethyl acetate (2×10 ml). The organic layer was washed with deionized water (2×10 ml), dried over anhydrous magnesium sulfate, filtered, and concentrated under reduced pressure. The resulting residue was purified by gradient flash column chromatography on silica gel (elution: 30% ethyl acetate in hexane to 50% ethyl acetate in hexane) to provide Compound 5a (12.5 mg, 77.1%) as a colorless oil. $^{1}$H NMR (600 MHz, CDCl$_3$) δ (ppm)=7.14-7.10 (m, 4H), 6.87 (d, J=6.0 Hz, 2H), 4.26-4.22 (m, 1H), 4.21-4.15 (m, 3H), 4.06-4.01 (m, 2H), 3.87 (dd, J=6.0 Hz, 11.4 Hz, 1H), 3.79 (dd, J=5.4 Hz, 11.4 Hz, 1H), 3.61 (dd, J=4.2 Hz, 9.6 Hz, 1H), 3.57 (dd, J=6.0 Hz, 9.6 Hz, 1H), 3.44 (s, 3H), 1.64 (s, 6H); $^{13}$C NMR (150 MHz, CDCl$_3$) δ (ppm)=156.37, 148.81, 147.69, 141.04, 127.95, 127.25, 127.05, 113.81, 73.13, 73.00, 69.93, 68.58, 68.44, 58.88, 45.00, 41.78, 30.25.

Example 4: Synthesis of (S)-1-chloro-3-(2,6-dichloro-4-(2-(4-((R)-2-hydroxy-3-isopropoxypropoxy)phenyl)propan-2-yl)phenoxy)propan-2-ol (Compound 7a)

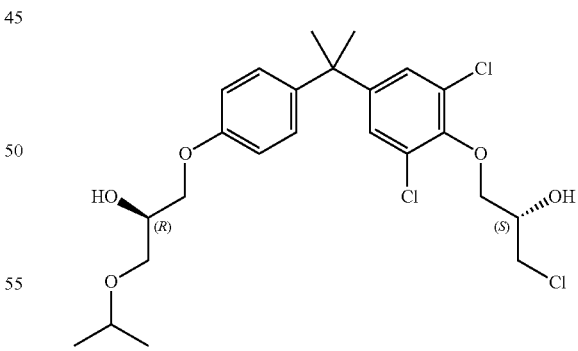

Compound 7a was synthesized according to Example 2 by using isopropanol in step c instead of methanol. $^{1}$H NMR (400 MHz, CDCl$_3$) δ (ppm)=7.13-7.10 (m, 4H), 6.86 (d, J=8.8 Hz, 2H), 4.25-4.12 (m, 4H), 4.03-3.98 (m, 2H), 3.85 (dd, J=5.2 Hz, 10.8 Hz, 1H), 3.77 (dd, J=5.6 Hz, 11.2 Hz, 1H), 3.67-3.53 (m, 3H), 2.83 (s, 1H), 2.57 (s, 1H), 1.62 (s, 6H), 1.18 (d, J=6.0 Hz, 6H).

Example 5: Synthesis of (S)-1-chloro-3-(2,6-di-chloro-4-(2-(4-((S)-3-fluoro-2-hydroxypropoxy)phenyl)propan-2-yl)phenoxy)propan-2-ol (Compound 8a)

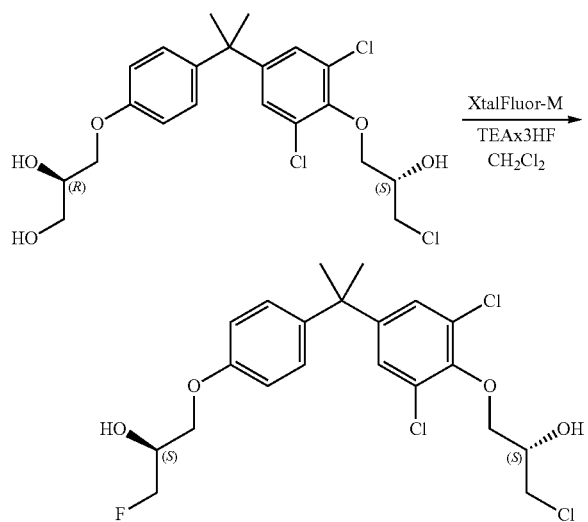

To a solution of Compound 1a (1 equiv; synthesized according to Example 1) in dichloromethane were successively added triethylamine trihydrofluoride (2 equiv) and XtalFluor-M (2 equiv). After 3 h, the reaction mixture was quenched at room temperature with a 5% aqueous sodium bicarbonate solution and stirred for 15 min, and the resulting mixture was extracted twice with dichloromethane. The organic phases were combined, dried over anhydrous magnesium sulfate, and filtered. Solvents were evaporated, and the resulting crude material was purified by silica gel chromatography to provide Compound 8a. $^1$H NMR (600 MHz, CDCl$_3$) δ (ppm)=7.16-7.14 (m, 4H), 6.87 (d, J=8.4 Hz, 2H), 4.69-4.56 (m, 2H), 4.30-4.22 (m, 2H), 4.22-4.16 (m, 2H), 4.10-4.09 (m, 2H), 3.87 (dd, J=6.0 Hz, 11.4 Hz, 1H), 3.79 (dd, J=5.4 Hz, 10.8 Hz, 1H), 1.64 (s, 6H).

Example 6: Synthesis of (S)-1-chloro-3-(2,6-di-chloro-4-(2-(4-((R)-2-hydroxy-3-(1H-imidazol-1-yl)propoxy)phenyl)propan-2-yl)phenoxy)propan-2-ol (Compound 9a)

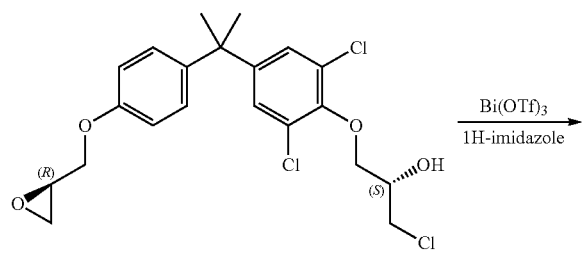

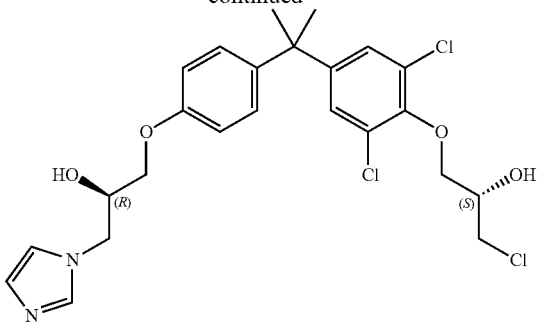

To a solution of (S)-1-chloro-3-(2,6-dichloro-4-(2-(4-(((R)-oxiran-2-yl)methoxy)phenyl)propan-2-yl)phenoxy)propan-2-ol (12.6 mg, 0.028 mmol, 1.0 equiv) in anhydrous MeCN (2 mL) was added Bismuth (III) trifluoromethanesulfonate (1.8 mg, 0.0028 mmol, 0.1 equiv) and the mixture was stirred at room temperature for 40 h. The reaction was quenched by the addition of a saturated solution of ammonium chloride (0.5 ml) and the mixture was extracted with ethyl acetate (2×10 ml). The organic layer was washed with deionized water (2×10 ml), dried over anhydrous magnesium sulfate, filtered, and concentrated under reduced pressure. The resulting residue was purified by flash column chromatography to provide Compound 9a (8.7 mg, 60.4%) as a colorless oil. $^1$H NMR (600 MHz, CDCl$_3$) δ (ppm)=7.56 (s, 1H), 7.16-7.14 (m, 4H), 7.04 (s, 1H), 7.01 (s, 1H), 6.86 (d, J=8.4 Hz, 2H), 4.29-4.23 (m, 3H), 4.22-4.13 (m, 3H), 3.98-3.92 (m, 2H), 3.87 (dd, J=6.0 Hz, 11.4 Hz, 1H), 3.79 (dd, J=4.8 Hz, 10.8 Hz, 1H), 1.65 (s, 6H).

Example 7: Synthesis of (S)-1-chloro-3-(2,6-di-chloro-4-(2-(4-((R)-2-hydroxy-3-morpholino-propoxy)phenyl)propan-2-yl)phenoxy)propan-2-ol (Compound 11a)

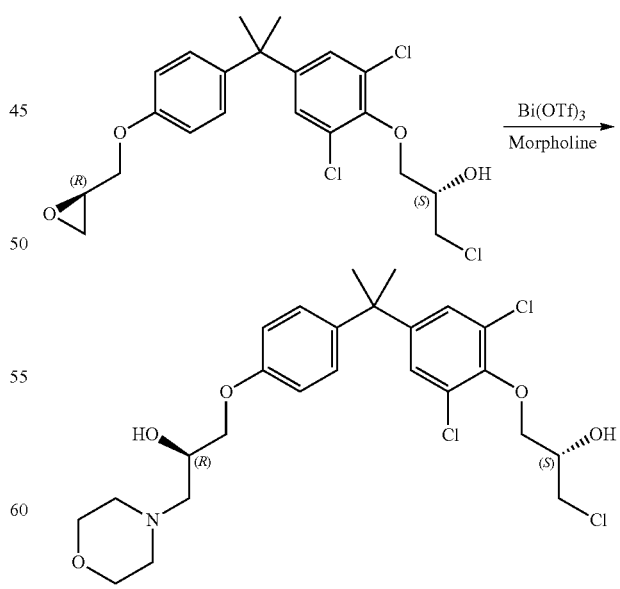

Compound 11a was synthesized according to Example 6 by using morpholine instead of 1H-imidazole. $^1$H NMR (400 MHz, CDCl$_3$) δ (ppm)=7.16-7.11 (m, 4H), 6.88 (d, J=8.8 Hz, 2H), 4.27-4.13 (m, 4H), 4.07-3.98 (m, 2H), 3.90-3.77 (m, 6H), 2.84-2.80 (m, 2H), 2.73-2.72 (m, 2H), 2.71-2.67 (m, 2H), 1.65 (s, 6H); ESI-LRMS calcd for [M+H]$^+$532.1, found 534.6.

Example 8: Synthesis of (R)-1-amino-3-(4-(2-(3,5-dichloro-4-((S)-3-chloro-2-hydroxypropoxy)phenyl)propan-2-yl)phenoxy)propan-2-ol (Compound 12a) and N-((R)-3-(4-(2-(3,5-dichloro-4-((S)-3-chloro-2-hydroxypropoxy)phenyl)propan-2-yl)phenoxy)-2-hydroxypropyl)methanesulfonamide (Compound 13a)

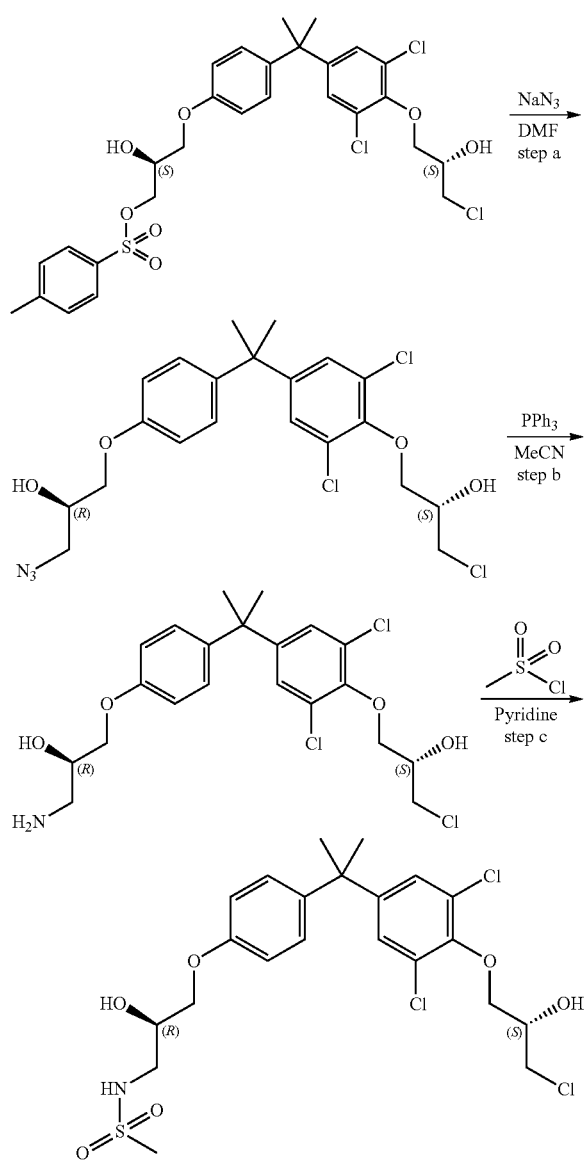

Step a: Synthesis of (R)-1-azido-3-(4-(2-(3,5-dichloro-4-((S)-3-chloro-2-hydroxypropoxy)phenyl)propan-2-yl)phenoxy)propan-2-ol To a solution of (S)-3-(4-(2-(3,5-dichloro-4-((S)-3-chloro-2-hydroxypropoxy)phenyl)propan-2-yl)phenoxy)-2-hydroxypropyl 4-methylbenzenesulfonate (90 mg, 0.146 mmol, 1.0 equiv) in anhydrous DMF (3 mL) was added sodium azide (9.5 mg, 0.146 mmol, 1.0 equiv) and the mixture was heated to 60-70° C. for 16 h. The reaction was quenched by the addition of a saturated solution of ammonium chloride (10 ml) and the mixture was extracted with ethyl acetate (2×30 ml). The organic layer was washed with deionized water (2×30 ml), dried over anhydrous magnesium sulfate, filtered, and concentrated under reduced pressure. The resulting residue was purified by gradient flash column chromatography on Si gel (elution: 20% ethyl acetate in hexane to 50% ethyl acetate in hexane) to provide the titled compound (57.4 mg, 80.1%) as a colorless oil. $^1$H NMR (600 MHz, CDCl$_3$) δ (ppm)=7.15-7.13 (m, 4H), 6.86 (d, J=9.0 Hz, 2H), 4.25-4.23 (m, 1H), 4.21-4.12 (m, 3H), 4.03-4.01 (m, 2H), 3.86 (dd, J=5.4 Hz, 10.8 Hz, 1H), 3.78 (dd, J=5.4 Hz, 11.4 Hz, 1H), 3.58-3.50 (m, 2H), 3.01 (s, 1H), 2.78 (s, 1H) 1.64 (s, 6H).

Step b: Synthesis of (R)-1-amino-3-(4-(2-(3,5-dichloro-4-((S)-3-chloro-2-hydroxypropoxy)phenyl)propan-2-yl)phenoxy)propan-2-ol (Compound 12a)

To a solution of (R)-1-azido-3-(4-(2-(3,5-dichloro-4-((S)-3-chloro-2-hydroxypropoxy)phenyl)propan-2-yl)phenoxy)propan-2-ol (57 mg, 0.117 mmol, 1.0 equiv) in MeCN (6 mL) was added triphenylphosphine (36.7 mg, 0.14 mmol, 1.2 equiv) and the mixture was heated to reflux for 16 h. The reaction was quenched by deionized water (2 ml) and the mixture was extracted with ethyl acetate (2×30 ml). The organic layer was washed with deionized water (2×30 ml), dried over anhydrous magnesium sulfate, filtered, and concentrated under reduced pressure. The resulting residue was purified by gradient flash column chromatography on Si gel (elution: 2% methanol in dichloromethane to 30% methanol in dichloromethane) to provide Compound 12a (24.3 mg, 44.9%) as a colorless oil. $^1$H NMR (400 MHz, CDCl$_3$) δ (ppm)=7.12-7.09 (m, 4H), 6.84 (d, J=8.4 Hz, 2H), 4.24-4.21 (m, 1H), 4.17-4.13 (m, 2H), 3.97 (m, 3H), 3.84 (dd, J=5.6 Hz, 11.2 Hz, 1H), 3.76 (dd, J=5.6 Hz, 11.2 Hz, 1H), 3.00-2.85 (m, 2H), 1.61 (s, 6H); $^{13}$C NMR (100 MHz, CDCl$_3$) δ (ppm)=157.00, 149.35, 148.31, 141.60, 128.52, 127.81, 127.61, 114.37, 73.78, 70.47, 70.42, 70.14, 45.65, 44.11, 42.34, 30.25; ESI-LRMS calcd for [M+H]$^+$462.1, found 463.9.

Step c: Synthesis of N-((R)-3-(4-(2-(3,5-dichloro-4-((S)-3-chloro-2-hydroxypropoxy)phenyl)propan-2-yl)phenoxy)-2-hydroxypropyl)methanesulfonamide (Compound 13a)

To a solution of (R)-1-azido-3-(4-(2-(3,5-dichloro-4-((S)-3-chloro-2-hydroxypropoxy)phenyl)propan-2-yl)phenoxy)propan-2-ol (14.3 mg, 0.031 mmol, 1.0 equiv) in anhydrous dichloromethane (3 mL) was treated triethylamine (12.5 mg, 0.124 mmol, 4.0 equiv) and methane sulfonyl chloride (3.6 mg, 0.031 mmol, 1.0 equiv) sequentially at 0° C. for 10 minutes. Then it was warmed to room temperature for 16 hours. The reaction was quenched by the addition of a saturated solution of ammonium chloride (2 ml) and the mixture was extracted with ethyl acetate (2×20 ml). The organic layer was washed with deionized water (2×20 ml), dried over anhydrous magnesium sulfate, filtered, and concentrated under reduced pressure. The resulting residue was purified by gradient flash column chromatography on silica gel (elution: 50% ethyl acetate in hexane to 75% ethyl acetate in hexane) to provide Compound 13a (9.7 mg, 57.9%) as a colorless oil. $^1$H NMR (600 MHz, CDCl$_3$) δ (ppm)=7.15-7.13 (m, 4H), 6.87 (d, J=5.4 Hz, 2H), 4.93-4.90 (m, 1H), 4.26-4.23 (m, 1H), 4.21-4.13 (m, 3H), 4.06-4.01 (m, 2H), 3.87 (dd, J=5.4 Hz, 11.4 Hz, 1H), 3.79 (dd, J=5.4 Hz, 10.8 Hz, 1H), 3.50-3.45 (m, 1H), 3.26-3.31 (m, 1H), 3.03 (s, 3H), 1.64 (s, 6H); $^{13}$C NMR (150 MHz, CDCl$_3$) δ (ppm)=155.94, 148.69, 147.73, 141.57, 127.99, 127.39, 127.05, 113.81, 73.14, 69.92, 68.85, 68.54, 45.19, 44.99, 41.81, 39.98, 30.22.

Example 9: Synthesis of (S)-1-chloro-3-(2,6-dichloro-4-(2-(4-((S)-3-(ethylsulfonyl)-2-hydroxypropoxy)phenyl)propan-2-yl)phenoxy)propan-2-ol (Compound 14a)

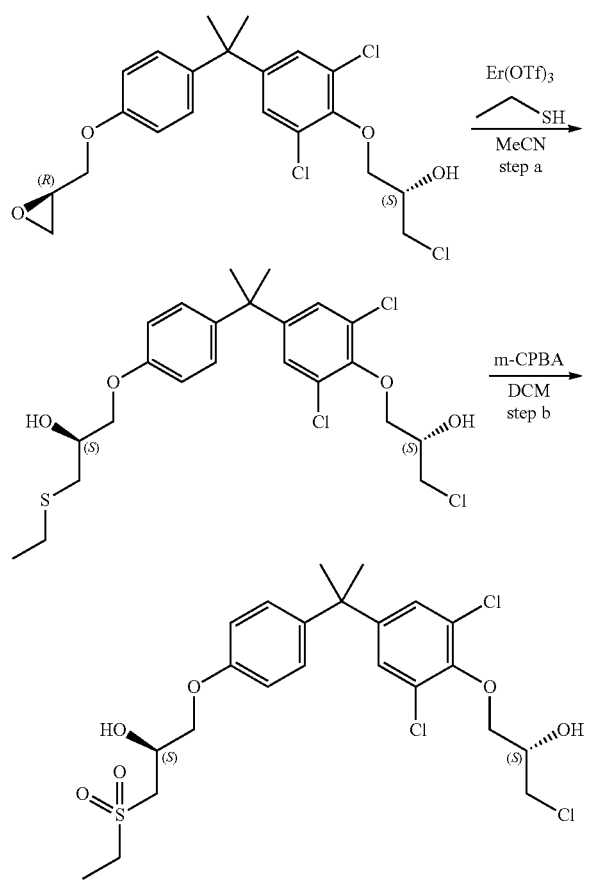

Step a: Synthesis of (S)-1-chloro-3-(2,6-dichloro-4-(2-(4-((S)-3-(ethylthio)-2-hydroxypropoxy)phenyl)propan-2-yl)phenoxy)propan-2-ol To a solution of (S)-1-chloro-3-(2,6-dichloro-4-(2-(4-(((R)-oxiran-2-yl)methoxy)phenyl)propan-2-yl)phenoxy)propan-2-ol (50 mg, 0.081 mmol, 1.0 equiv) in anhydrous DMF (3 mL) was added sodium ethanethiolate (6.8 mg, 0.081 mmol, 1.0 equiv) and the mixture was heated to 60-70° C. for 16 h. The reaction was quenched by the addition of a saturated solution of ammonium chloride (2 ml) and the mixture was extracted with ethyl acetate (2×30 ml). The organic layer was washed with deionized water (2×30 ml), dried over anhydrous magnesium sulfate, filtered, and concentrated under reduced pressure. The resulting residue was purified by gradient flash column chromatography on silica gel (elution: 20% ethyl acetate in hexane to 50% ethyl acetate in hexane) to provide the titled compound (16.4 mg, 39.5%) as a colorless oil.

Step b: Synthesis of (5)-1-chloro-3-(2,6-dichloro-4-(2-(4-((S)-3-(ethylsulfonyl)-2-hydroxypropoxy)phenyl)propan-2-yl)phenoxy)propan-2-ol (Compound 14a)

To a solution of (S)-1-chloro-3-(2,6-dichloro-4-(2-(4-((S)-3-(ethylthio)-2-hydroxypropoxy)phenyl)propan-2-yl)phenoxy)propan-2-ol (14.6 mg, 0.029 mmol, 1.0 equiv) in anhydrous dichloromethane (3 mL) was treated 3-chloroperbenzoic acid (14.0 mg, 0.081 mmol, 2.8 equiv) at 0° C. for 10 minutes. Then it was warmed to room temperature for 3 hours.

The reaction was quenched by the addition of a saturated solution of ammonium chloride (2 ml) and the mixture was extracted with ethyl acetate (2×20 ml). The organic layer was washed with saturated NaHCO$_3$ (20 ml), deionized water (2×20 ml), dried over anhydrous magnesium sulfate, filtered, and concentrated under reduced pressure. The resulting residue was purified by gradient flash column chromatography on Si gel (elution: 30% ethyl acetate in hexane to 75% ethyl acetate in hexane) to provide Compound 14a (4.7 mg, 31.0%) as a colorless oil. 1H NMR (400 MHz, CDCl$_3$) δ (ppm)=7.18-7.15 (m, 4H), 6.88 (d, J=8.8 Hz, 2H), 4.69-4.67 (m, 1H), 4.27-4.15 (m, 3H), 4.10-4.07 (m, 2H), 3.88 (dd, J=5.2 Hz, J=11.2 Hz, 1H), 3.80 (dd, J=5.2 Hz, J=10.8 Hz, 1H), 3.39-3.20 (m, 4H), 1.66 (s, 6H), 1.48 (t, J=7.2 Hz, 3H); ESI-LRMS calcd for [M+Na]$^+$561.1, found 561.5.

Example 10: Synthesis of (R)-3-(4-(2-(4-((S)-3-chloro-2-hydroxypropoxy)-3-methylphenyl)propan-2-yl)-2-methylphenoxy)propane-1,2-diol (Compound 22a)

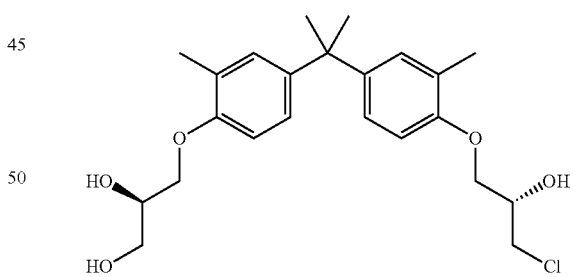

Compound 22a was synthesized according to Example 1 by using 4,4'-(Propane-2,2-diyl)bis(2-methylphenol) (commercially available) instead of 4,4'-(propane-2,2-diyl)diphenol and omitting step c. $^1$H NMR (400 MHz, DMSO-D$_6$) δ (ppm)=6.97-6.94 (m, 4H), 6.81-6.76 (m, 2H), 5.50 (d, J=4.8 Hz, 1H), 4.86 (s, 1H), 4.61 (s, 1H), 4.06-4.00 (m, 1H), 3.97-3.89 (m, 3H), 3.86-3.76 (m, 3H), 3.69 (dd, J=5.6 Hz, 11.2 Hz, 1H), 3.50-3.44 (m, 2H), 2.10 (s, 6H), 1.55 (s, 6H); $^{13}$C NMR (100 MHz, DMSO-D$_6$) δ (ppm)=155.14, 154.74, 143.23, 142.75, 129.32, 129.23, 125.66, 125.62, 125.22, 125.16, 111.28, 111.16, 70.67, 70.02, 69.48, 69.32, 63.43, 55.50, 47.53, 31.42, 16.86, 16.79.

Example 11: Synthesis of (R)-3-(4-((3-chloro-4-((S)-3-chloro-2-hydroxypropoxy)phenyl)sulfonyl)phenoxy)propane-1,2-diol (Compound 40a)

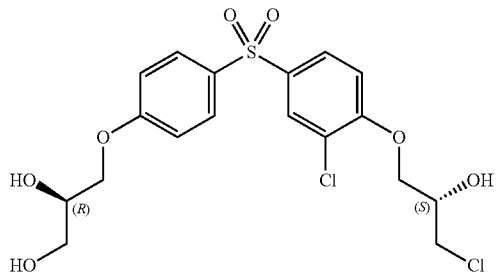

Compound 40a was synthesized according to Example 1 by using 4,4'-sulfonyldiphenol instead of 4,4'-(propane-2,2-diyl)diphenol and with only 1 equiv of NaCl in step c. $^1$H NMR (400 MHz, MeOD) δ (ppm)=7.92-7.82 (m, 4H), 7.26 (d, J=8.8 Hz, 1H), 7.13 (d, J=8.8 Hz, 2H), 4.23-4.12 (m, 4H), 4.08-4.03 (m, 1H), 4.00-3.96 (m, 1H), 3.81 (dd, J=4.8 Hz, 11.6 Hz, 1H), 3.72 (dd, J=5.2 Hz, 11.2 Hz, 1H), 3.68-3.61 (m, 2H); $^{13}$C NMR (100 MHz, MeOD) δ (ppm)=163.24, 157.96, 135.21, 133.24, 129.56, 128.90, 127.82, 123.46, 115.12, 113.49, 70.23, 70.16, 69.62, 69.30, 62.64, 45.28; ESI-LRMS calcd for [M+Na]$^+$473.0, found 472.8.

Example 12: Synthesis of (R)-3-(4-((3,5-dichloro-4-((S)-3-chloro-2-hydroxypropoxy)phenyl)sulfonyl)phenoxy)propane-1,2-diol (Compound 41a)

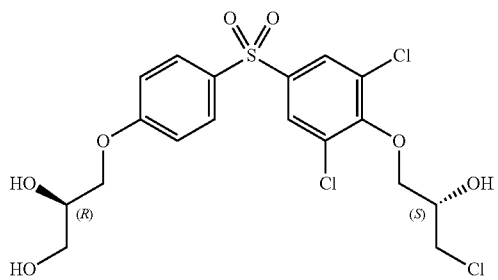

Compound 41a was synthesized according to Example 1 by using 4,4'-sulfonyldiphenol instead of 4,4'-(propane-2,2-diyl)diphenol. $^1$H NMR (400 MHz, MeOD) δ (ppm)=7.94-7.89 (m, 4H), 7.14 (d, J=8.8 Hz, 2H), 4.21-4.13 (m, 4H), 4.09-4.04 (m, 1H), 4.01-3.95 (m, 1H), 3.84 (dd, J=4.4 Hz, 11.6 Hz, 1H, 3.72 (dd, J=5.2 Hz, 11.2 Hz, 1H), 3.69-3.62 (m, 2H); $^{13}$C NMR (100 MHz, MeOD) δ (ppm)=165.08, 156.38, 141.20, 133.48, 131.65, 131.46, 129.37, 116.74, 75.60, 71.62, 71.46, 71.11, 64.06, 46.76; ESI-LRMS calcd for [M+Na]$^+$506.9, found 506.9.

Example 13: Synthesis of (S)-1-chloro-3-(2,6-dichloro-4-((4-((R)-2-hydroxy-3-methoxypropoxy)phenyl)sulfonyl)phenoxy)propan-2-ol (Compound 43a)

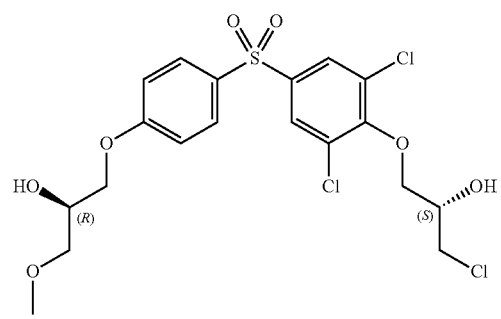

Compound 43a was synthesized according to Examples 3 by starting with Compound 41a. $^1$H NMR (600 MHz, CD$_3$Cl) δ (ppm)=7.91-7.85 (m, 4H), 7.06 (d, J=9.0 Hz, 2H), 4.27-4.16 (m, 4H), 4.13-4.07 (m, 2H), 3.85 (dd, J=4.8 Hz, 10.8 Hz, 1H), 3.79 (dd, J=5.4 Hz, 11.4 Hz, 1H), 3.62-3.54 (m, 2H), 3.43 (s, 3H); $^{13}$C NMR (150 MHz, CD$_3$Cl) δ (ppm)=163.22, 154.58, 139.94, 132.47, 130.56, 130.47, 128.37, 115.67, 74.18, 73.31, 70.42, 69.70, 69.01, 59.62, 45.56; ESI-LRMS calcd for [M+Na]$^+$521.0, found 520.9.

Example 14: Synthesis of (R)-1-amino-3-(4-((3,5-dichloro-4-((S)-3-chloro-2-hydroxypropoxy)phenyl)sulfonyl)phenoxy)propan-2-ol (Compound 45a)

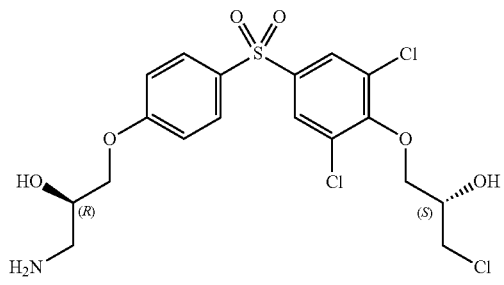

Compound 45a was synthesized according to Examples 3 and 8 by starting with Compound 41a. $^1$H NMR (400 MHz, MeOD) δ (ppm)=7.93-7.90 (m, 4H), 7.14 (d, J=9.2 Hz, 2H), 4.19-4.13 (m, 3H), 4.10-4.01 (m, 2H), 3.95-3.91 (m, 1H), 3.85-3.80 (m, 1H), 3.74-3.69 (m, 1H), 2.85 (dd, J=4.4 Hz, 13.2 Hz, 1H), 2.74 (dd, J=5.2 Hz, 13.2 Hz, 1H); $^{13}$C NMR (100 MHz, MeOD) δ (ppm)=165.08, 156.51, 141.32, 133.70, 131.76, 131.57, 129.46, 116.86, 75.71, 72.15, 71.73, 71.57, 46.83, 45.26; ESI-LRMS calcd for [M+Na]$^+$506.0, found 507.9.

Example 15: Synthesis of N-((R)-3-(4-((3,5-di-chloro-4-((S)-3-chloro-2-hydroxypropoxy)phenyl)sulfonyl)phenoxy)-2-hydroxypropyl)methanesulfonamide (Compound 46a)

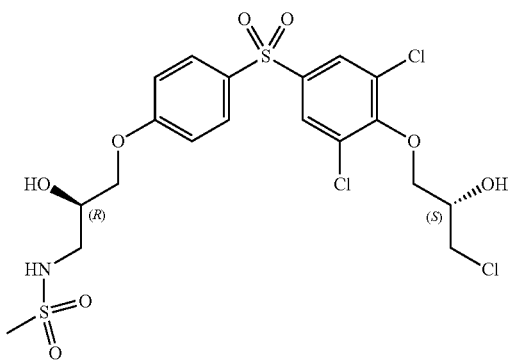

Compound 46a was synthesized according to Examples 3 and 8 by starting with Compound 41a. $^1$H NMR (600 MHz, MeOD) δ (ppm)=7.93-7.90 (m, 4H), 7.14 (d, J=9.0 Hz, 2H), 4.18-4.10 (m, 4H), 4.07-4.01 (m, 2H), 3.82 (dd, J=4.2 Hz, 11.4 Hz, 1H), 3.71 (dd, J=4.8 Hz, 10.8 Hz, 1H), 3.30-3.27 (m, 1H), 3.20 (dd, J=6.0 Hz, 13.2 Hz, 1H), 2.95 (s, 3H); $^{13}$C NMR (150 MHz, MeOD) δ (ppm)=165.01, 156.49, 141.31, 133.74, 131.75, 131.56, 129.46, 116.86, 75.68, 71.55, 71.47, 70.27, 46.81, 46.70, 40.22; ESI-LRMS calcd for [M+Na]$^+$ 584.0, found 584.0.

Example 16: Synthesis of (S)-1-chloro-3-(2,6-dichloro-4-((4-((R)-2-hydroxy-3-morpholinopropoxy)phenyl)sulfonyl)phenoxy)propan-2-ol (Compound 47a)

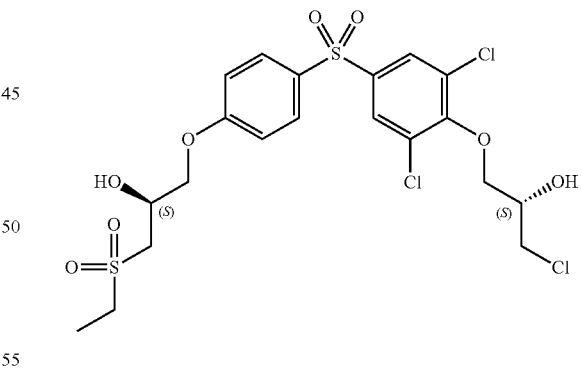

Compound 47a was synthesized according to Examples 3 and 7 by starting with Compound 41a. $^1$H NMR (600 MHz, CDCl$_3$) δ (ppm)=7.90-7.86 (m, 4H), 7.06 (d, J=9.0 Hz, 2H), 4.28-4.19 (m, 4H), 4.08-4.07 (m, 2H), 3.87-3.77 (m, 6H), 2.77-2.58 (m, 6H); $^{13}$C NMR (150 MHz, CDCl$_3$) δ (ppm)= 162.51, 153.88, 139.21, 131.79, 129.85, 129.75, 127.66, 114.97, 73.48, 70.03, 69.71, 66.14, 64.45, 60.50, 53.26, 44.85; ESI-LRMS calcd for [M+H]$^+$554.1, found 556.0.

Example 17: Synthesis of (S)-1-chloro-3-(2,6-dichloro-4-((4-((R)-2-hydroxy-3-(1H-imidazol-1-yl)propoxy)phenyl)sulfonyl)phenoxy)propan-2-ol (Compound 48a)

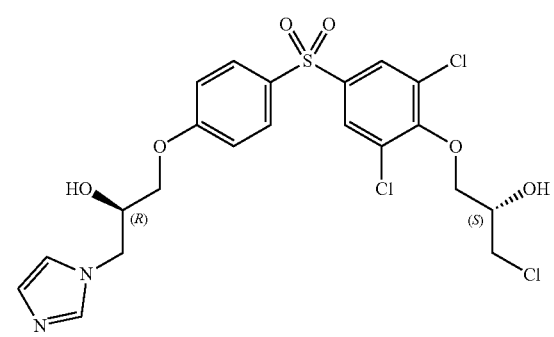

Compound 48a was synthesized according to Examples 3 and 6 by starting with Compound 41a. $^1$H NMR (400 MHz, CDCl$_3$) δ (ppm)=7.88-7.83 (m, 4H), 7.65 (s, 1H), 7.03-6.97 (m, 4H), 4.27-4.10 (m, 6H), 4.02 (dd, J=4.8 Hz, 9.6 Hz, 1H), 3.96-3.90 (m, 1H), 3.82 (dd, J=4.8 Hz, 11.2 Hz, 1H), 3.75 (dd, J=5.2 Hz, 11.2 Hz, 1H); $^{13}$C NMR (100 MHz, CDCl$_3$) δ (ppm)=162.53, 154.66, 139.49, 137.72, 132.85, 130.46, 130.40, 128.24, 128.00, 120.24, 115.50, 74.12, 70.14, 69.22, 68.64, 50.29, 45.48; ESI-LRMS calcd for [M+H]$^+$535.0, found 535.0.

Example 18: Synthesis of (S)-1-chloro-3-(2,6-dichloro-4-((4-((S)-3-(ethylsulfonyl)-2-hydroxypropoxy)phenyl)sulfonyl)phenoxy)propan-2-ol (Compound 50a)

Compound 50a was synthesized according to Examples 3 and 9 by starting with Compound 41a. $^1$H NMR (400 MHz, CDCl$_3$) δ (ppm)=7.89 (d, J=9.2 Hz, 2H), 7.85 (s, 2H), 7.04 (d, J=9.2 Hz, 2H), 4.72-4.66 (m, 1H), 4.26-4.19 (m, 3H), 4.14-4.09 (m, 2H), 3.83 (dd, J=5.2 Hz, 11.2 Hz, 1H), 3.77 (dd, J=4.8 Hz, 11.2 Hz, 1H), 3.35-3.14 (m, 4H), 1.45 (t, J=7.6 Hz, 3H); $^{13}$C NMR (100 MHz, CDCl$_3$) δ (ppm)= 162.37, 154.56, 139.59, 133.08, 130.46, 130.43, 128.27, 115.56, 74.08, 70.82, 70.29, 65.20, 54.87, 49.39, 45.41, 6.70; ESI-LRMS calcd for [M+Na]$^+$583.0, found 582.9.

Example 19: Synthesis of (R)-3-(4-((4-((S)-3-chloro-2-hydroxypropoxy)phenyl)sulfonyl)phenoxy)propane-1,2-diol (Compound 80a)

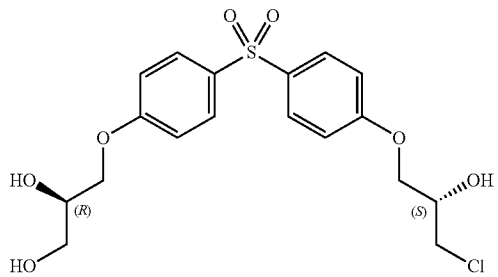

Compound 80a was synthesized according to Examples 1 by using 4,4'-sulfonyldiphenol instead of 4,4'-(propane-2,2-diyl)diphenol and omitting step c. $^1$H NMR (400 MHz, MeOD) δ (ppm)=7.84 (dd, J=2.8 Hz, 9.2 Hz, 4H), 7.09 (dd, J=2.0 Hz, 9.2 Hz, 4H), 4.15-4.08 (m, 4H), 4.05-4.01 (m, 1H), 3.99-3.93 (m, 1H), 3.76-3.71 (m, 1H), 3.70-3.60 (m, 3H); $^{13}$C NMR (100 MHz, MeOD) δ (ppm)=164.50, 164.17, 135.74, 135.40, 130.89, 130.87, 116.52, 71.78, 71.12, 70.97, 70.87, 64.19, 46.74; ESI-LRMS calcd for [M+Na]$^+$439.1, found 438.9.

Example 20: Synthesis (R)-1-(4-(2-(4-((R)-2-acetoxy-3-chloropropoxy)-3,5-dichlorophenyl)propan-2-yl)phenoxy)-3-methoxypropan-2-yl acetate (Compound A5d)

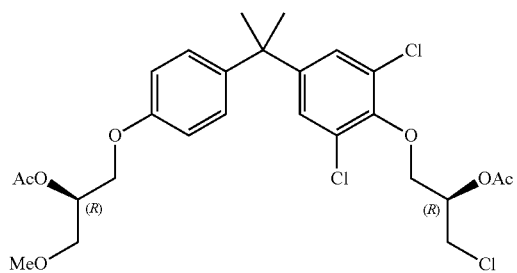

Ac$_2$O (128 mg, 1.26 mmol, 6.0 equiv.), Et3N (127 mg, 1.26 mmol, 6.0 equiv.) and DMAP (26 mg, 0.21 mmol, 1.0 equiv.) were added to a solution of Compound 5a (100 mg, 0.21 mmol, 1.0 equiv., see Example 3) in anhydrous DCM (5 mL) at room temperature and the resultant mixture was stirred at the same temperature overnight. The mixture was diluted with EtOAc (30 mL) and the organic layer was washed with water (15 mL) and brine (15 mL). The organic layer was further dried over anhydrous MgSO$_4$ and evaporated under reduced pressure. The crude was loaded onto a silica gel column and eluted with Hexane/EtOAc (13/1 to 6/1) to give 111 mg of the titled compound as colorless oil (yield: 95.0%).

$^1$H NMR (600 MHz, CHLOROFORM-d) δ 7.11-7.12 (m, 2H), 7.09-7.11 (m, 2H), 6.82-6.87 (m, 2H), 5.32-5.35 (m, 1H), 5.28-5.32 (m, 1H), 4.18-4.26 (m, 2H), 4.09-4.16 (m, 2H), 3.97 (dd, J=5.14, 11.74 Hz, 1H), 3.88 (dd, J=5.14, 11.74 Hz, 1H), 3.66 (dd, J=2.20, 4.40 Hz, 2H), 3.40 (s, 3H), 2.14 (s, 3H), 2.11 (s, 3H), 1.61 (s, 6H).

$^{13}$C NMR (151 MHz, CHLOROFORM-d) δ 170.8, 170.4, 156.9, 149.4, 148.4, 141.8, 128.7, 127.9, 127.7, 114.5, 71.9, 71.1, 70.9, 66.4, 59.6, 42.7, 42.4, 30.9, 21.4, 21.2.

Example 21: Synthesis (R)-1-(4-(2-(4-((S)-2-acetoxy-3-chloropropoxy)-3,5-dichlorophenyl)propan-2-yl)phenoxy)-3-methoxypropan-2-yl acetate (Compound A5a)

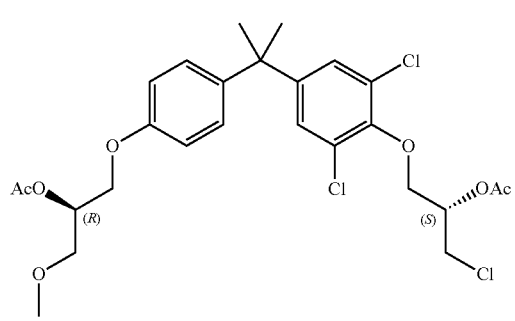

Acetic Anhydride (4.1 mg, 0.04 mmol, 4.0 equiv) was added to a solution of Compound 5a (5.0 mg, 0.01 mmol, 1.0 equiv, see Example 3), DMAP (0.1 mg, 0.001 mmol, 0.1 equiv) and Et$_3$N (4.1 mg, 0.04 mmol, 4.0 equiv) in anhydrous dichloromethane (1 mL). The resulting solution stirred overnight at room temperature. Dichloromethane was removed under reduced pressure and the residue was purified by column chromatography to afford the title compound as a colorless oil (5.8 mg, 98.6%). $^1$H NMR (400 MHz, CDCl$_3$) δ (ppm)=7.11-7.08 (m, 4H), 6.83 (d, J=8.8, 2H), 5.35-5.26 (m, 2H), 4.26-4.17 (m, 2H), 4.16-4.07 (m, 2H), 3.96 (dd, J=5.2 Hz, 11.6 Hz, 1H), 3.86 (dd, J=5.6 Hz, 11.6 Hz, 1H), 3.66-3.61 (m, 2H), 3.38 (s, 3H), 2.13 (s, 3H), 2.10 (s, 3H), 1.60 (s, 6H); $^{13}$C NMR (150 MHz, CDCl$_3$) δ (ppm)=170.80, 170.45, 156.96, 149.41, 148.39, 141.80, 128.69, 127.90, 127.70, 114.54, 71.91, 71.12, 70.54, 66.44, 59.62, 42.73, 42.43, 30.90, 21.38, 21.18; ESI-LRMS calcd for [M+H]$^+$561.1, found 561.1.

Example 22: Synthesis of (R)-1-(4-(2-(4-((S)-2-acetoxy-3-chloropropoxy)-3,5-dichlorophenyl)propan-2-yl)phenoxy)-3-isopropoxypropan-2-yl acetate (Compound A7a)

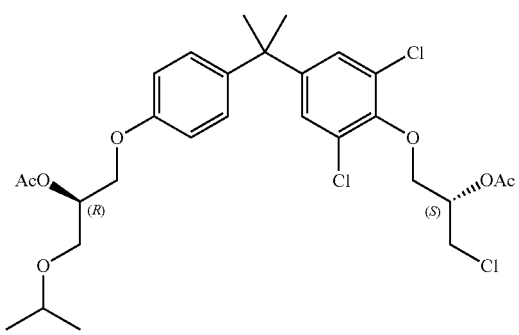

Compound A7a was synthesized according to Examples 21 by using Compound 7a prepared according to Example 4. Compound A7a was obtained as a colorless oil (6.4 mg, 96.2%). $^1$H NMR (400 MHz, CDCl$_3$) δ (ppm)=7.12-7.08 (m, 4H), 6.85 (d, J=8.8, 2H), 5.36-5.30 (m, 1H), 5.28-5.22 (m, 1H), 4.27-4.09 (m, 4H), 3.97 (dd, J=5.2 Hz, 11.6 Hz, 1H), 3.87 (dd, J=5.6 Hz, 11.6 Hz, 1H), 3.71-3.57 (m, 3H), 2.14 (s, 3H), 2.09 (s, 3H), 1.61 (s, 6H), 1.15 (dd, J=2.0 Hz, 6.0 Hz, 6H); $^{13}$C NMR (150 MHz, CDCl$_3$) δ (ppm)=170.16, 169.78, 156.42, 148.77, 147.72, 141.03, 128.02, 127.20, 127.03, 113.91, 71.97, 71.25, 70.98, 70.30, 66.01, 65.72, 42.06, 41.76, 30.24, 21.60, 21.54, 20.74, 20.52; ESI-LRMS calcd for [M+Na]$^+$611.1, found 611.1.

Example 23: Synthesis of (S)-1-(4-(2-(4-((S)-2-acetoxy-3-(ethylsulfonyl)propoxy)phenyl)propan-2-yl)-2,6-dichlorophenoxy)-3-chloropropan-2-yl acetate (Compound A14a)

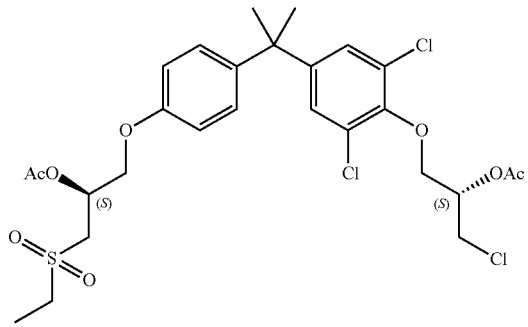

Compound A14a was synthesized according to Examples 21 by using Compound 14a prepared according to Example 9. Compound A14a was obtained as a colorless oil (3.4 mg, 97.3%). $^1$H NMR (400 MHz, CDCl$_3$) δ (ppm)=7.13-7.08 (m, 4H), 6.84 (d, J=8.8, 2H), 5.63-5.57 (m, 1H), 5.36-5.30 (m, 1H), 4.29-4.18 (m, 4H), 3.97 (dd, J=5.2 Hz, 12.0 Hz, 1H), 3.87 (dd, J=5.6 Hz, 11.6 Hz, 1H), 3.54-3.40 (m, 2H), 3.10 (q, J=7.2 Hz, 2H), 2.14 (s, 3H), 2.12 (s, 3H), 1.61 (s, 6H), 1.44 (t, J=7.2 Hz, 3H); $^{13}$C NMR (150 MHz, CDCl$_3$) δ (ppm)=170.41, 170.16, 158.50, 154.94, 142.86, 142.39, 128.70, 128.03, 127.66, 114.48, 71.87, 71.46, 67.79, 67.05, 52.48, 48.82, 42.69, 42.44, 30.86, 21.15, 20.90, 6.80; ESI-LRMS calcd for [M+Na]$^+$ 645.1, found 645.1.

Example 24: Synthesis of (R)-1-(4-(2-(4-((S)-2-acetoxy-3-chloropropoxy)-3,5-dichlorophenyl)propan-2-yl)phenoxy)-3-morpholinopropan-2-yl acetate (Compound A11a)

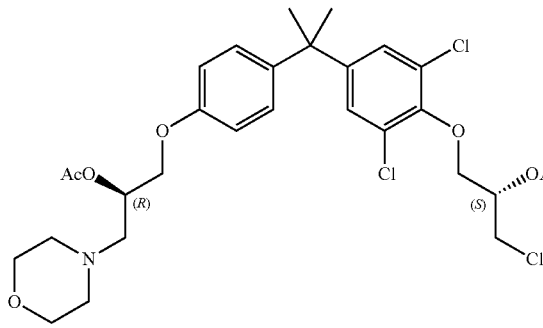

Compound A11a was synthesized according to Examples 21 by using Compound 11a prepared according to Example 7. Compound A11a was obtained as a colorless oil (6.8 mg, 97.6%). $^1$H NMR (400 MHz, CDCl$_3$) δ (ppm)=7.14-7.07 (m, 4H), 6.83 (d, J=8.8, 2H), 5.72-5.70 (m, 1H), 5.36-5.30 (m, 1H), 4.47-4.40 (m, 1H), 4.39-4.32 (m, 1H), 4.29-4.14 (m, 4H), 3.99-3.94 (m, 3H), 3.87 (dd, J=5.6 Hz, 11.6 Hz, 1H), 3.58-3.37 (m, 4H), 2.97 (m, 2H), 2.23 (s, 3H), 2.14 (s, 3H), 1.61 (s, 6H); $^{13}$C NMR (150 MHz, CDCl$_3$) δ (ppm)= 170.54, 170.37, 156.02, 149.12, 148.39, 142.61, 128.67, 128.06, 127.60, 114.34, 71.81, 70.90, 67.26, 65.89, 63.60, 58.52, 53.17, 52.58, 42.64, 42.40, 30.78, 29.87, 21.56, 21.11; ESI-LRMS calcd for [M+H]$^+$ 616.1, found 616.1.

Example 25: Synthesis of (S)-1-(4-(2-(4-((R)-2-acetoxy-3-(1H-imidazol-1-yl)propoxy)phenyl)propan-2-yl)-2,6-dichlorophenoxy)-3-chloropropan-2-yl acetate (Compound A9a)

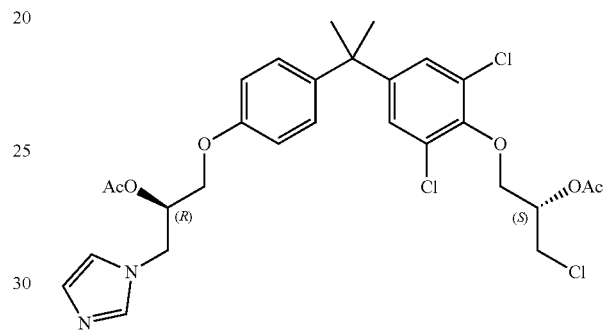

Compound A9a was synthesized according to Examples 21 by using Compound 9a prepared according to Example 6. Compound A9a was obtained as a colorless oil (5.6 mg, 93.6%). $^1$H NMR (400 MHz, CDCl$_3$) δ (ppm)=9.40 (s, 1H), 7.39 (s, 1H), 7.20 (s, 1H), 7.14-7.10 (m, 4H), 6.82 (d, J=8.4, 2H), 5.50 (m, 1H), 5.35-5.31 (m, 1H), 4.78-4.70 (m, 2H), 4.27-4.18 (m, 4H), 3.96 (dd, J=5.6 Hz, 11.6 Hz, 1H), 3.87 (dd, J=5.6 Hz, 11.6 Hz, 1H), 2.14 (s, 3H), 2.11 (s, 3H), 1.61 (s, 6H); $^{13}$C NMR (150 MHz, CDCl$_3$) δ (ppm)=170.21, 169.67, 155.72, 148.93, 142.61, 136.02, 128.53, 127.97, 127.46, 121.62, 120.13, 114.19, 71.66, 70.76, 69.72, 65.27, 49.70, 42.49, 42.26, 30.65, 20.96, 20.91; ESI-LRMS calcd for [M+H]$^+$597.1, found 597.1.

Example 26: Synthesis of (S)-1-(4-(2-(4-((R)-2-acetoxy-3-(N-(methylsulfonyl)acetamido)propoxy)phenyl)propan-2-yl)-2,6-dichlorophenoxy)-3-chloropropan-2-yl acetate (Compound A13a)

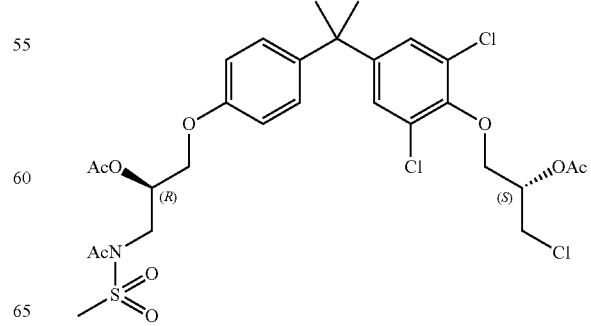

Compound A13a was synthesized according to Examples 21 by using Compound 13a prepared according to Example 8. Compound A13a was obtained as a colorless oil (6.0 mg, 100%). $^1$H NMR (400 MHz, CDCl$_3$) δ (ppm)=7.13-7.08 (m, 4H), 6.82 (d, J=8.4, 2H), 5.47-5.42 (m, 1H), 5.36-5.30 (m, 1H), 4.29-4.07 (m, 6H), 3.97 (dd, J=5.2 Hz, 11.6 Hz, 1H), 3.87 (dd, J=5.6 Hz, 11.6 Hz, 1H), 3.33 (s, 3H), 2.44 (s, 3H), 2.14 (s, 3H), 2.10 (s, 3H), 1.61 (s, 6H); $^{13}$C NMR (150 MHz, CDCl$_3$) δ (ppm)=171.33, 170.47, 170.29, 156.42, 149.13, 148.29, 142.17, 128.58, 127.88, 127.54, 114.33, 71.74, 70.82, 70.36, 67.19, 46.69, 42.66, 42.57, 42.31, 30.73, 24.49, 21.07, 20.03; ESI-LRMS calcd for [M+H]$^+$666.1, found 666.1.

Example 27: Synthesis of (S)-1-(4-(2-(4-((S)-2-acetoxy-3-chloropropoxy)-3,5-dichlorophenyl)propan-2-yl)phenoxy)-3-fluoropropan-2-yl acetate (Compound A8a)

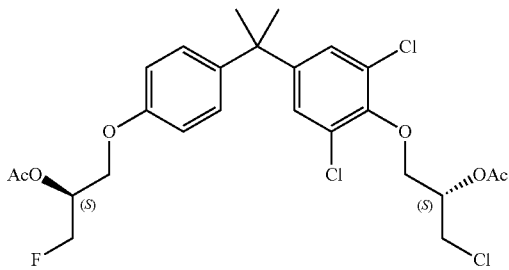

Compound A8a was synthesized according to Examples 21 by using Compound 8a prepared according to Example 5. Compound A8a was obtained as a colorless oil (5.8 mg, 95.9%). $^1$H NMR (400 MHz, CDCl$_3$) δ (ppm)=7.13-7.10 (m, 4H), 6.84 (d, J=8.8 Hz, 2H), 5.39-5.29 (m, 2H), 4.79-4.71 (m, 1H), 4.67-4.59 (m, 1H), 4.27-4.18 (m, 2H), 4.16-4.14 (m, 2H), 3.97 (dd, J=5.2 Hz, 11.6 Hz, 1H), 3.87 (dd, J=5.6 Hz, 11.6 Hz, 1H), 2.14 (s, 3H), 2.13 (s, 3H), 1.61 (s, 6H); $^{13}$C NMR (150 MHz, CDCl$_3$) δ (ppm)=170.58, 170.46, 156.65, 149.33, 148.43, 142.14, 128.73, 127.99, 127.70, 114.48, 82.13, 80.99 (d, J=513.0 Hz), 71.92, 70.98, 70.77, 70.64 (d, J=19.5 Hz), 65.19, 65.15 (d, J=6.0 Hz), 42.73, 42.46, 30.91, 21.22, 21.19; ESI-LRMS calcd for [M+H]$^+$ 549.1, found 549.1.

Example 28: Synthesis of (S)-3-(4-(2-(4-((S)-2-acetoxy-3-chloropropoxy)-3,5-dichlorophenyl)propan-2-yl)phenoxy)propane-1,2-diyl diacetate (Compound A1a)

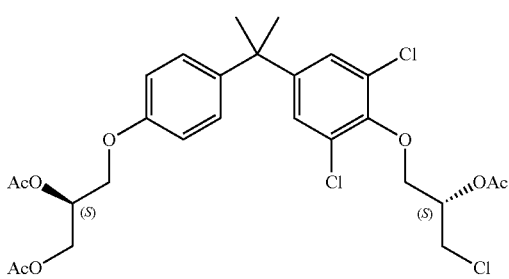

Compound A1a was synthesized according to Examples 21 by using Compound 1a prepared according to Example 1. Compound A1a was obtained as a colorless oil (63.0 mg, 97.1%). $^1$H NMR (600 MHz, CDCl$_3$) δ (ppm)=7.14-7.11 (m, 4H), 6.85 (d, J=12.0 Hz, 2H), 5.39-5.33 (m, 2H), 4.45 (dd, J=4.2 Hz, 12.0 Hz, 1H), 4.32 (dd, J=6.0 Hz, 12.0 Hz, 1H), 4.26 (dd, J=4.8 Hz, 10.2 Hz, 1H), 4.22 (dd, J=4.8 Hz, 10.2 Hz, 1H), 4.13-4.12 (m, 2H), 3.98 (dd, J=5.4 Hz, 12.0 Hz, 1H), 3.89 (dd, J=5.4 Hz, 12.0 Hz, 1H), 2.16 (s, 3H), 2.12 (s, 3H), 2.10 (s, 3H), 1.63 (s, 6H); $^{13}$C NMR (150 MHz, CDCl$_3$) δ (ppm)=170.21, 169.90, 169.77, 156.07, 148.66, 147.76, 141.40, 128.04, 127.28, 127.02, 113.88, 71.24, 70.31, 69.30, 65.55, 62.10, 42.05, 41.77, 30.23, 20.56, 20.50, 20.35; ESI-LRMS calcd for [M+Na]$^+$611.1, found 611.0.

Example 29: Compound Activity

Figure 2:
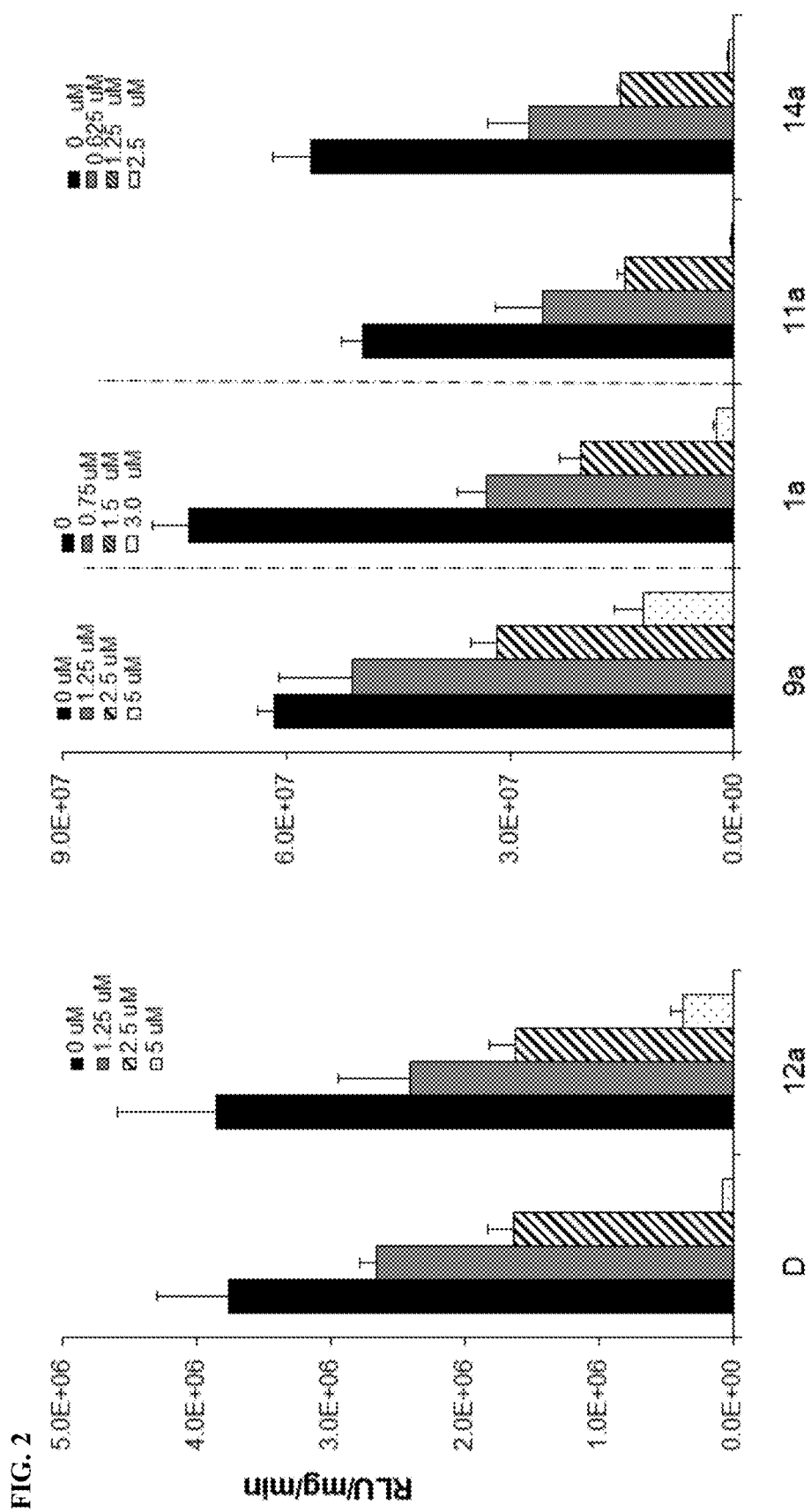
FIG. 2 shows a dose-response for selected compounds of the present disclosure in LNCaP cells transfected with the PSA (6.1 kb)-luciferase reporter and treated with androgen.

LNCaP cells (3×10$^4$) were seeded into 24-well plates overnight. Next day, LNCaP cells were transiently transfected with 0.25 µg/well of PSA (6.1 kb)-luciferase reporter plasmid prior to pre-treatment with compounds of the invention or reference compounds (e.g., compounds A, B, C, 1a, 5a, 9a, 11a, 12a, 13a, and 14a) ranging in concentration from 0 µM to 35 µM for 1 hour before the addition of vehicle, or synthetic androgen, R1881 (1 nM) to induce luciferase production. After 48 h of exposure, cells were harvested in Passive lysis buffer (Promega). Luciferase activities were measured and normalized to protein concentration determined by the Bradford assay. IC$_{50}$ calculations were done using OriginPro 8.1 Software (Northampton, MA, USA). Transfection experiments to determine IC$_{50}$ values were performed in at least 4 independent experiments ("trials") using triplicate wells. Dose responses of representative compounds are shown in FIG. 2. Luciferase activity is presented as the mean standard deviation of the technical replicates.

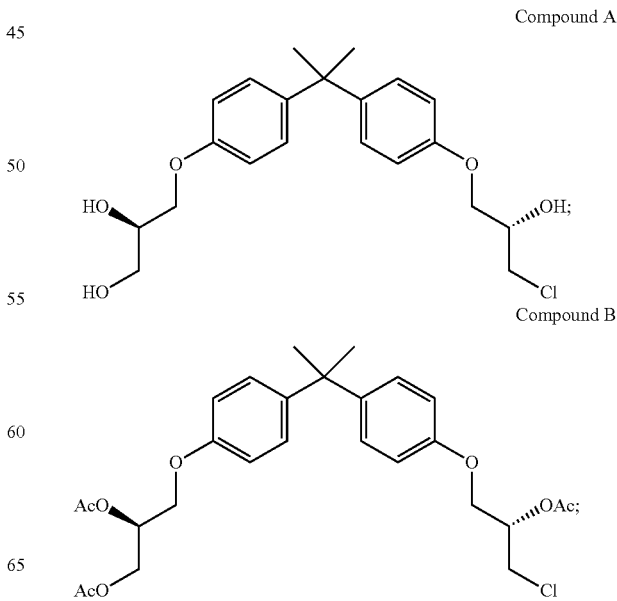

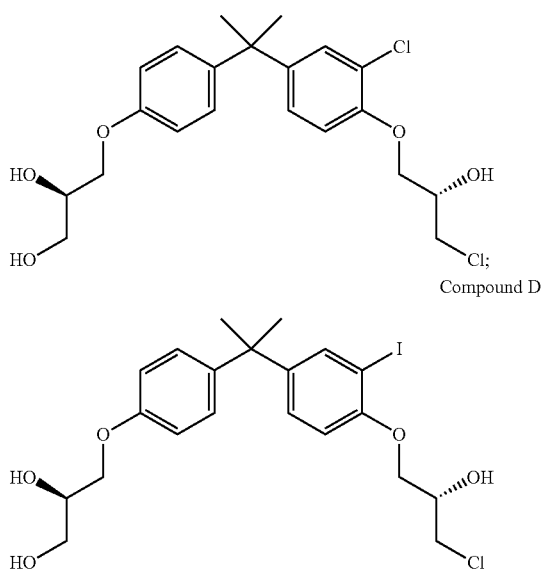

TABLE 6

IC$_{50}$ values for selected compounds (µM) with standard error

| Compound | Number of Trials | Average IC$_{50}$ |
|---|---|---|
| A | 12 | 13.9 ± 2.6 |
| B | 6 | 10.68 ± 1.04 |
| C | 4 | 2.47 ± 0.26 |
| 1a | 11 | 1.41 ± 0.27 |
| 5a | 6 | 1.03 ± 0.39 |
| 9a | 11 | 3.12 ± 0.68 |
| 11a | 10 | 1.05 ± 0.15 |
| 12a | 4 | 2.26 ± 0.24 |
| 13a | 6 | 1.00 ± 0.16 |
| 14a | 11 | 0.95 ± 0.21 |

Example 30: Compound 1a Treatment in LNCaP Xenograft Model

LNCaP Cell Preparation: LNCaP cells were passaged prior to seeding in T175flasks at a concentration of ~2-3×10$^7$/mL. The cells were grown for 7 days until 90% confluent. Cell preparations were then prepared in RPMI with 5% FBS/Matrigel (50/50, v/v) yielding a final concentration of 1×10$^8$/mL.

Tumor Induction and Treatment: Six to eight week old NOD-SCID mice were received from BC Cancer Research Centre's Animal Resource Centre and acclimated for 28 days. Tumors were initiated with sub-cutaneous back of each animal. Tumors were allowed to grow to an average size of approximately 100 mm$^3$. Mice were then castrated and the tumors allowed to adapt for a period of one week before first dose was administered. Tumor volume was measured as length×width×height in mm multiplied by 0.5236.

Compound Preparation and Treatment: Compound 1a was dissolved in 100% DMSO (ATCC Lot 61908420) to yield a stock solution of 157 mg/mL. Compound 1a was administered as an oral gavage once per day at dose levels of 10 and 30 mg/kg. Vehicle control animals were administered 1% CMC formulation as an oral gavage once daily. CMC (n=17 tumours); 10 mg/kg (n=15 tumours); 30 mg/kg (n=14 tumours). CMC (n=9 animals); 10 mg/kg (n=9 animals); 30 mg/kg (n=9 animals).

Oral treatment was initiated one week after castration. The start of treatment was designated "Day 1" and animals were treated once daily for a total of 24 doses. Two days after the last dose, the tumours were measured and harvested. Body weight was assessed daily throughout the treatment period. Tumor volume was measured on day −7 (castration day), and again on days 1, 4, 8, 12, 16, 20, 24 and 26.

Quantitative Real-Time Polymerase Chain Reaction (QPCR) Method: LNCaP xenografts were homogenized using TRIzol® reagent (Invitrogen™), and total RNA was extracted using PureLink RNA Mini Kit (Life Technologies). Amplification Grade DNase I treatment (Sigma-Aldrich) was applied to the RNA before RT-PCR using High Capacity RNA-to-DNA kit (Life Technologies) to generate cDNA. cDNA and gene-specific primers were combined with Platinum® SYBR® Green qPCRSuperMix-UDG with ROX (Invitrogen™). Transcripts were measured by quantitative real-time PCR (QPCR) using ABI PRISM 7900 Sequence Detection System (ABI PRISM®, Applied Biosystems by Life Technologies) in triplicates for each biological sample. Gene expression levels were normalized to housekeeping gene RPL13A. Primers for PSA have been previously described (Andersen R. J., et al. *Cancer Cell*. 2010; Myung J. K., et al. *J. Clin. Invest.* 2013).

Figure 3:
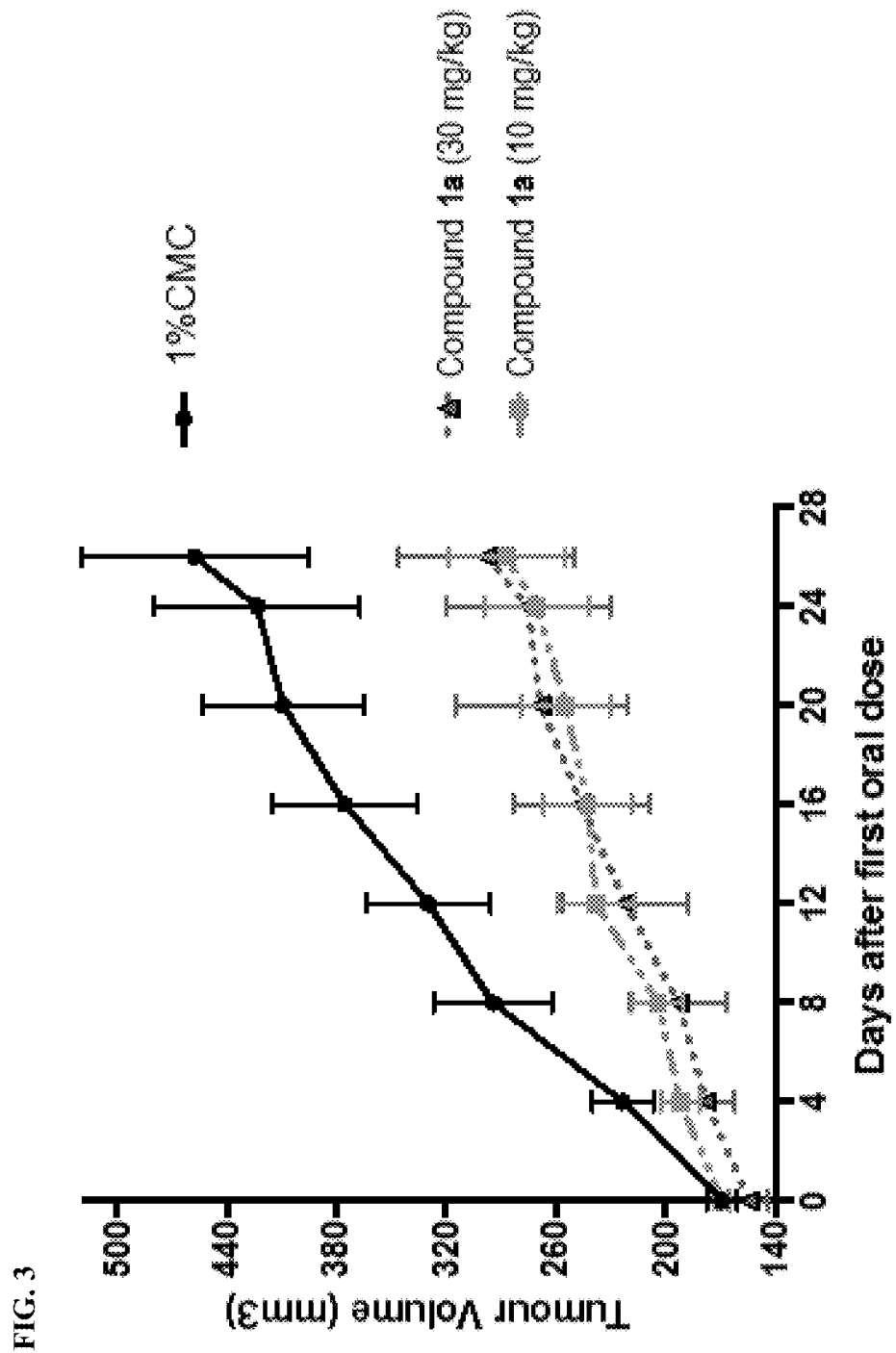
FIG. 3 shows tumor volume of LNCaP xenografts in SCID-NOD mice treated with Compound 1a or CMC-treated mice (control) in the course of 26 day treatment.
Figure 4:
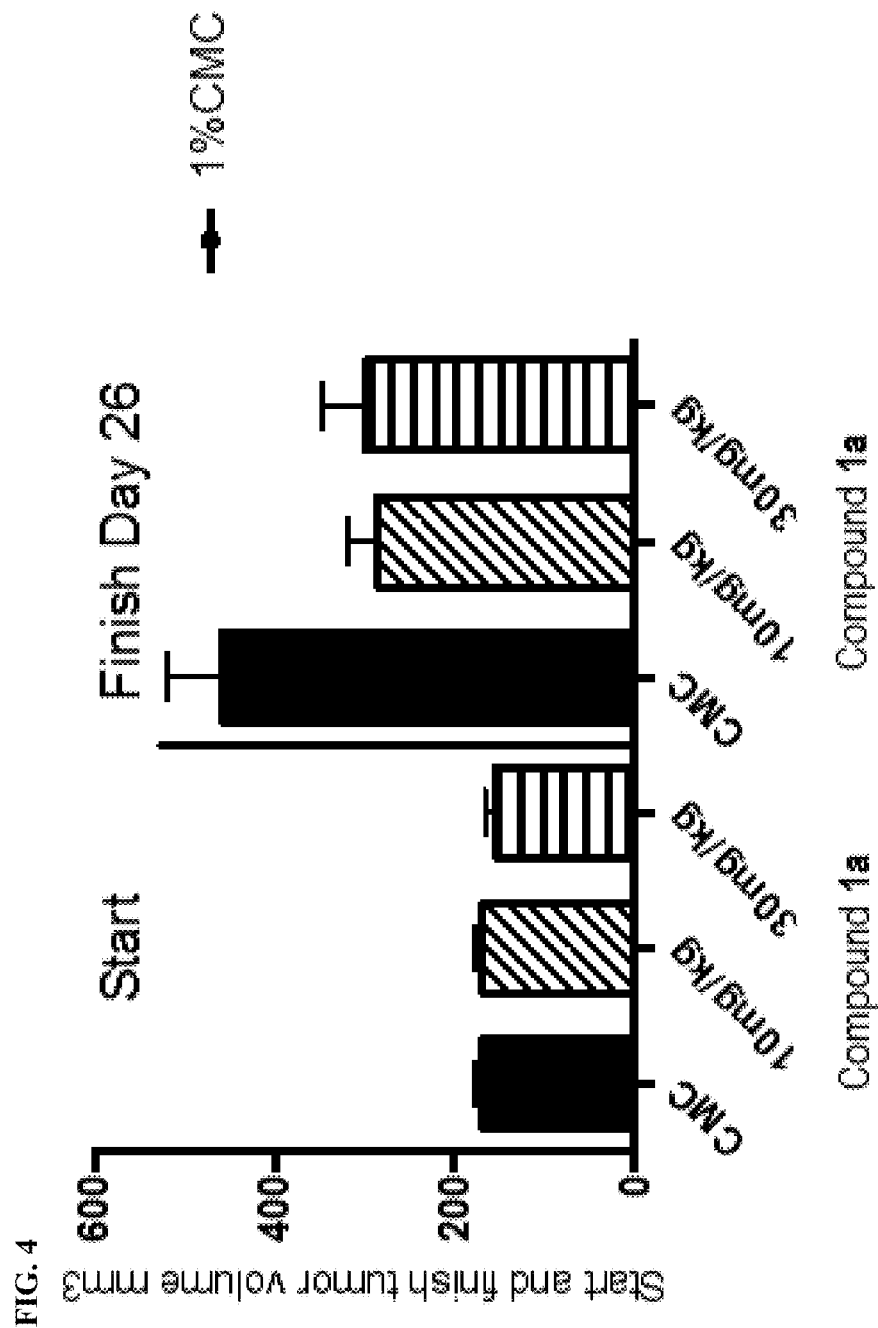
FIG. 4 shows tumor volume of LNCaP xenografts at the start and the finish (day 26) for Compound 1a treated mice and CMC-treated mice.
Figure 5:
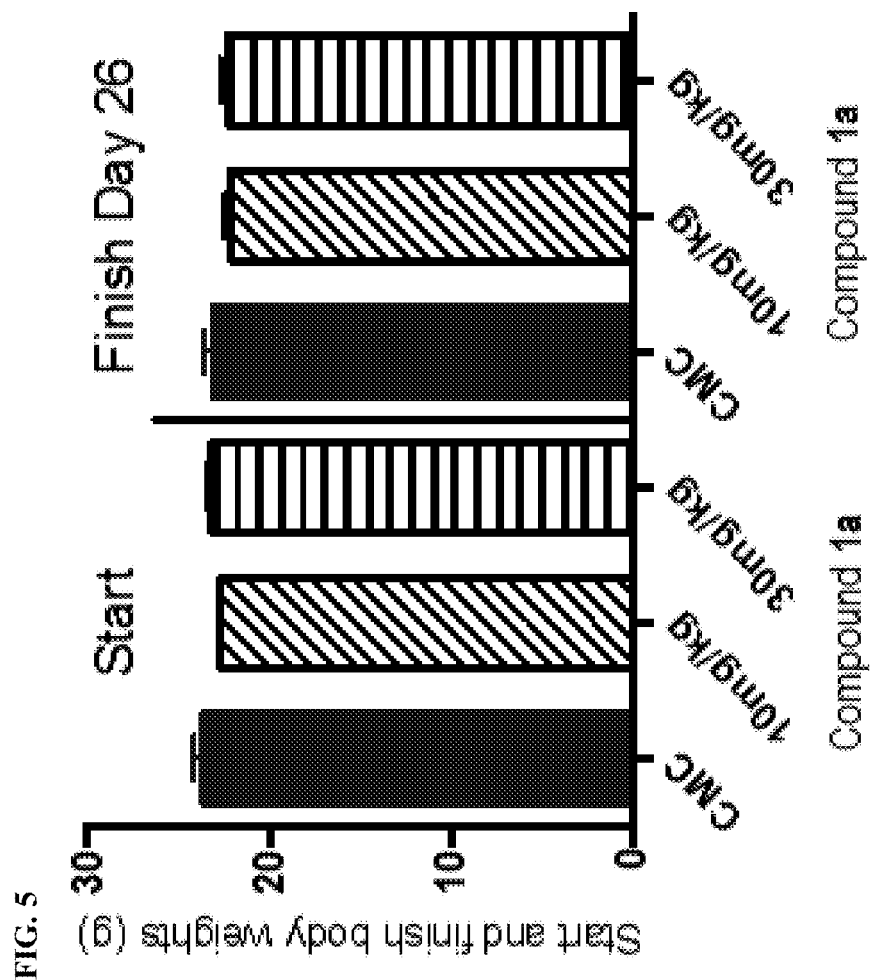
FIG. 5 shows body weight at the start and the finish (day 26) for Compound 1a treated mice and CMC-treated mice.
Figure 6:
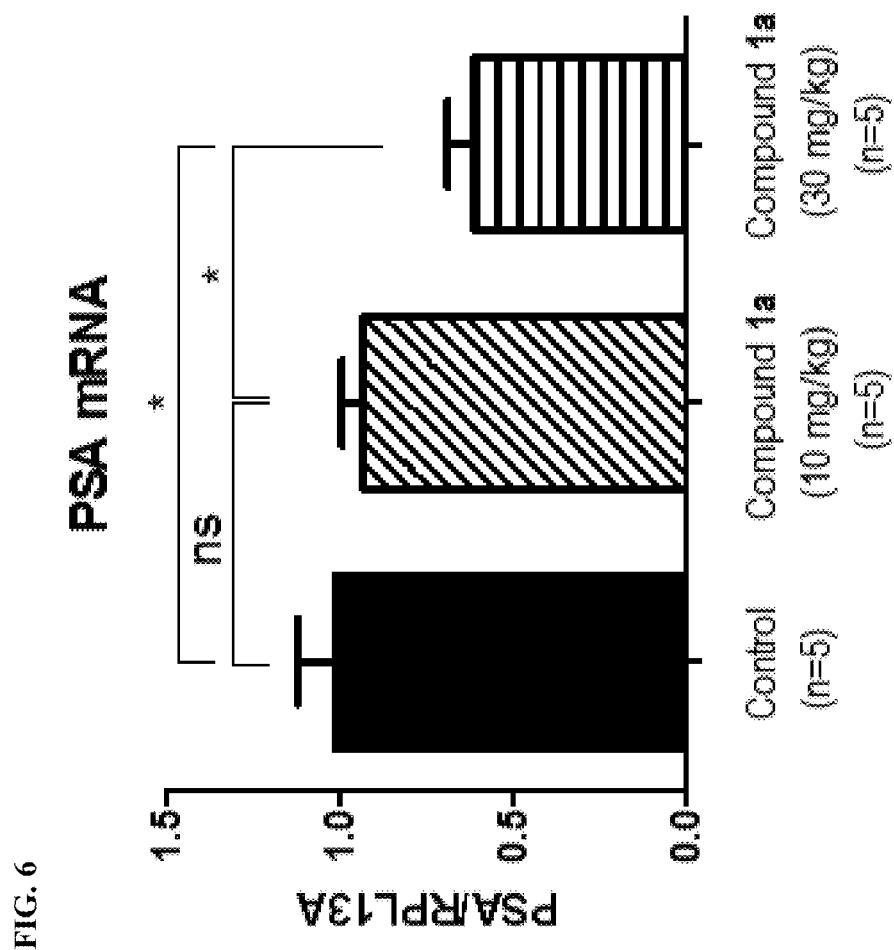
FIG. 6 shows tissues levels of PSA mRNA in five representative xenografts from each treatment group measured by QPCR.

Daily oral treatment of Compound 1a at 10 mg/kg or 30 mg/kg resulted in inhibition of tumor growth and significant reduction of tumor volume at the end of the treatment period (FIGS. 3 and 4). There was no statistical difference in the tumor volumes between the 10 mg/kg and 30 mg/kg doses of Compound 1a. There were no significant differences between the start and finish body weights for the mice treated with Compound 1a and mice treated with control (CMC formulation) (FIG. 5). Since androgen receptor transcriptionally regulates the expression of PSA, the mRNA levels of PSA in the tumors were measured and examined to confirm the in vivo on-target activity of Compound 1a (FIG. 6). Indeed, Compound 1a demonstrated a dose-dependent inhibition of the mRNA expression of PSA, as 30 mg/kg treatment of Compound 1a caused a significant reduction of PSA expression when compared to the 10 mg/kg dose and control treatment. Together, these data indicated that Compound 1a significantly reduced the castration-resistant growth of LNCaP tumors, while demonstrating on-target activity to block androgen receptor transcriptional activity.

In FIG. 6, bars represent mean±SEM with n=5 representative tumors from each treatment group. One-way ANOVA post-hoc Tukey's multiple comparisons test was performed for statistical analysis. *p<0.05; p<0.01; *p<0.001.

Although various embodiments of the invention are disclosed herein, many adaptations and modifications can be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method for prostate cancer comprising administering a compound having the following structure (I):

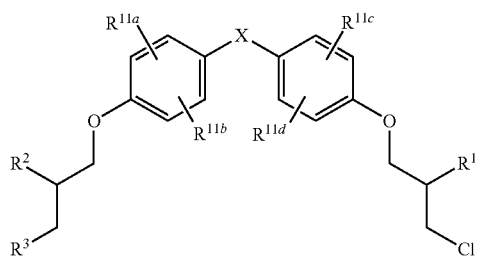

or a pharmaceutically acceptable salt, tautomer or stereoisomer thereof to a subject in need thereof, wherein:

X is —S(O)$_n$— or —C(R$^8$R$^9$)—;

R$^1$ is H, hydroxyl or —OC(=O)R$^{13}$;

R$^2$ is hydroxyl or —OC(=O)R$^{13}$;

R$^3$ is —NH$_2$, —NHC(=O)R$^{13}$, —N(C(=O)R$^{13}$)$_2$, —NHS(O)$_n$R$^5$, —N(C(=O)R$^{13}$)(S(O)$_n$R$_5$), —N(C$_1$-C$_6$ alkyl)(S(O)$_n$R$^5$), or —S(O)$_n$R$^5$, which are optionally substituted with one or more R$^6$;

R$^5$ is each independently C$_1$-C$_6$ alkyl which is optionally substituted with one or more R$^6$;

R$^6$ is each independently selected from the group consisting of H, F, Cl, Br, I, $^{123}$I, hydroxyl, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;

R$^8$ and R$^9$ are each independently H or C$_1$-C$_6$ alkyl;

R$^{11a}$, R$^{11b}$, R$^{11c}$ and R$^{11d}$ are each independently H, methyl, F, Cl, Br, I, or $^{123}$I;

R$^{13}$ is C$_1$-C$_6$ alkyl; and n is 0, 1, or 2;

wherein at least one of R$^{11a}$, R$^{11b}$, R$^{11c}$ and R$^{11d}$ is methyl F, Cl, Br, I, or $^{123}$I.

2. The method of claim 1, wherein the prostate cancer is primary or localized prostate cancer, locally advanced prostate cancer, recurrent prostate cancer, advanced prostate cancer, metastatic prostate cancer, metastatic castration-resistant prostate cancer (CRPC), or hormone-sensitive prostate cancer.

3. The method of claim 1, wherein at least two of R$^{11a}$, R$^{11b}$, R$^{11c}$ and R$^{11d}$ are methyl, F, Cl, Br, I, or $^{123}$I.

4. The method of claim 1, wherein R$^{11a}$ and R$^{11b}$ are each H; and R$^{11c}$ and R$^{11d}$ are each independently methyl, F, Cl, Br, I, or $^{123}$I.

5. The method of claim 4, wherein R$^{11c}$ and R$^{11d}$ are each Cl.

6. The method of claim 1, wherein R$^{11a}$ and R$^{11c}$ are each H; and R$^{11b}$ and R$^{11d}$ are each independently methyl, F, Cl, Br, I, or $^{123}$I.

7. The method of claim 6, wherein R$^{11b}$ and R$^{11d}$ are each Cl.

8. The method of claim 1, wherein X is —S(O)2—.

9. The method of claim 1, wherein X is —C(R$^8$R$^9$)— and R$^8$ and R$^9$ are each independently C$_1$-C$_3$ alkyl.

10. The method of claim 9, wherein R$^8$ an R$^9$ are each methyl.

11. The method of claim 1, wherein le and R$^2$ are each independently hydroxyl or —OC(=O)R$^{13}$.

12. The method of claim 11, wherein R$^1$ and R$^2$ are both hydroxyl.

13. The method of claim 11, wherein R$^1$ and R$^2$ are both —OC(=O)R$^{13}$.

14. The method of claim 1, wherein R$^1$ is H.

15. The method of claim 1, wherein R$^3$ is —NH$_2$, —NHC(=O)(C$_1$-C$_4$ alkyl), —NRC(=O)(C$_1$-C$_4$ alkyl)]$_2$, —NHS(O)$_n$(C$_1$-C$_3$ alkyl), —N[C(=O)(C$_1$-C$_4$ alkyl)][(S(O)$_n$(C$_1$-C$_3$ alkyl)], —N[C$_1$-C$_6$ alkyl][S(O)$_n$(C$_1$-C$_3$ alkyl)], or —S(O)$_n$(C$_1$-C$_3$ alkyl).

16. The compound of claim 1, wherein each R$^{13}$ is C$_1$-C$_4$ alkyl.

17. The method of claim 1, wherein the compound has one of the following structures:

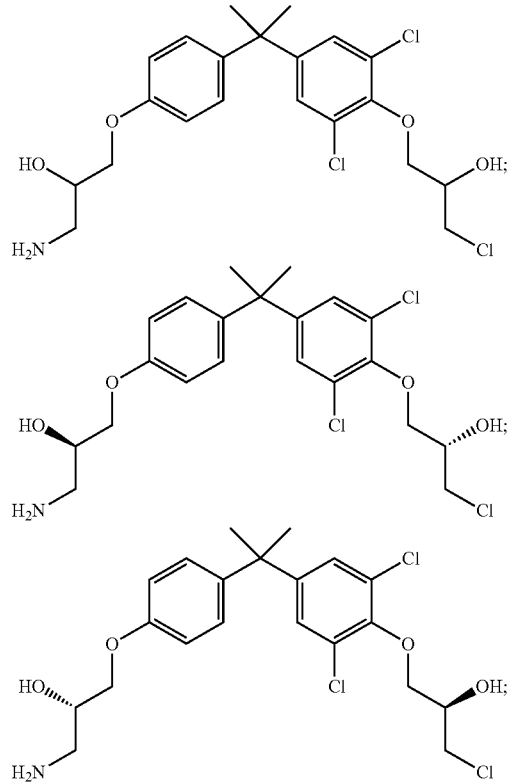

281
-continued
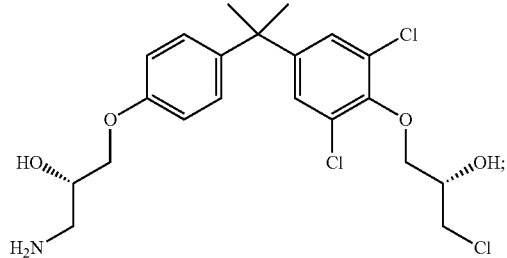
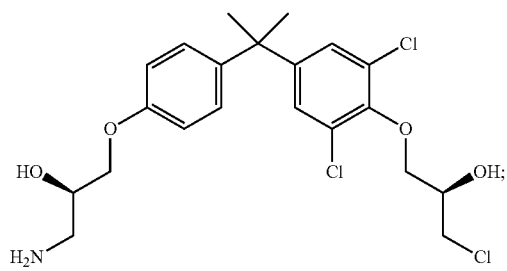
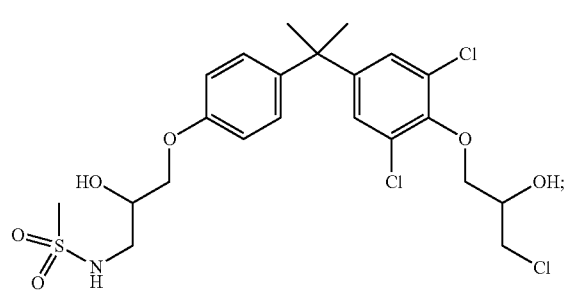 [SMILES: CC(C)(c1ccc(OCC(O)CNS(C)(=O)=O)cc1)c1cc(Cl)c(OCC(O)CCl)c(Cl)c1]
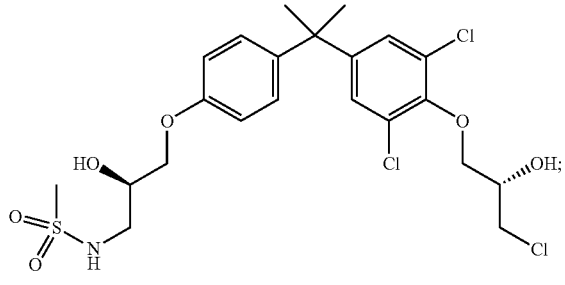 [SMILES: CC(C)(c1ccc(OC[C@H](O)CNS(C)(=O)=O)cc1)c1cc(Cl)c(OC[C@H](O)CCl)c(Cl)c1]
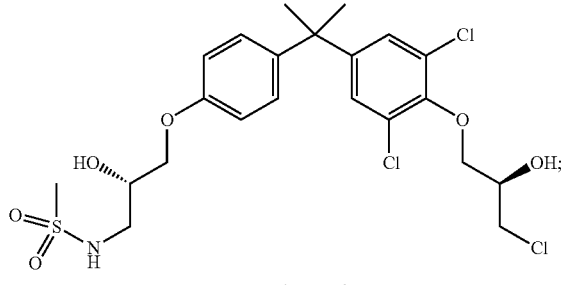
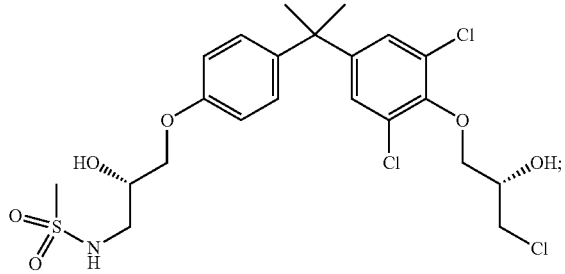
282
-continued
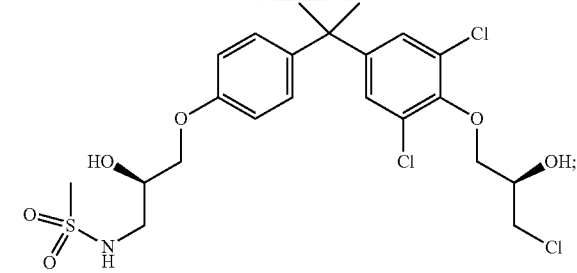
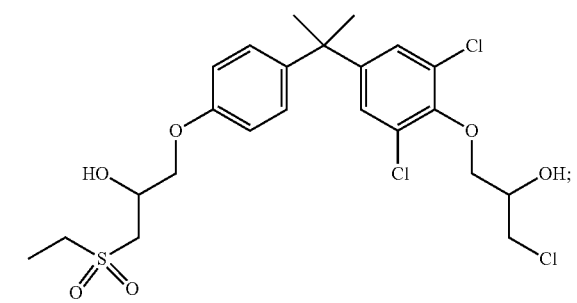
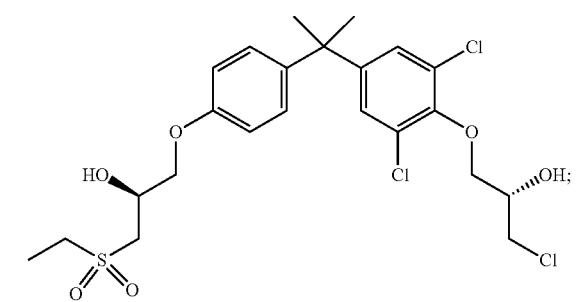
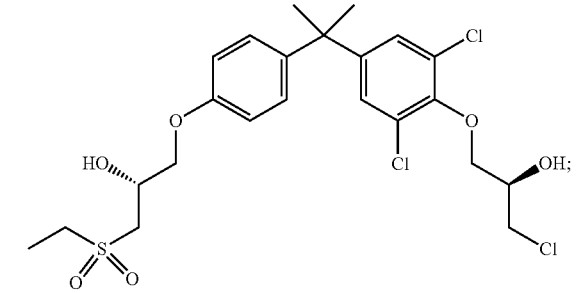
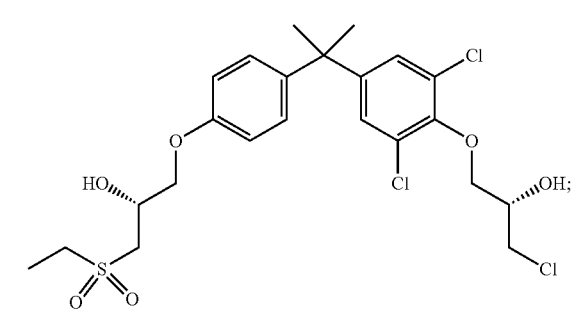

283
-continued
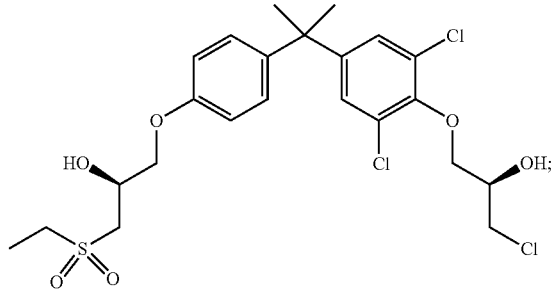
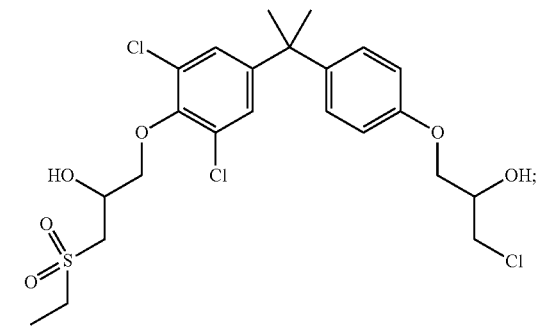
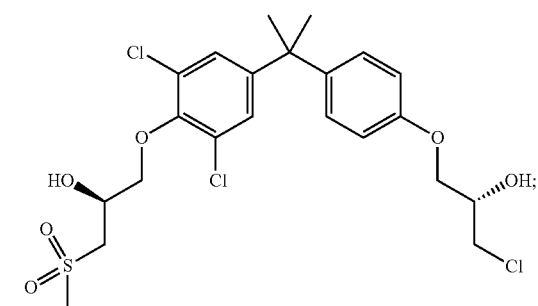
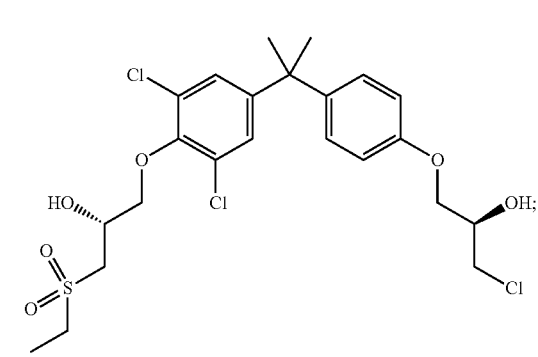
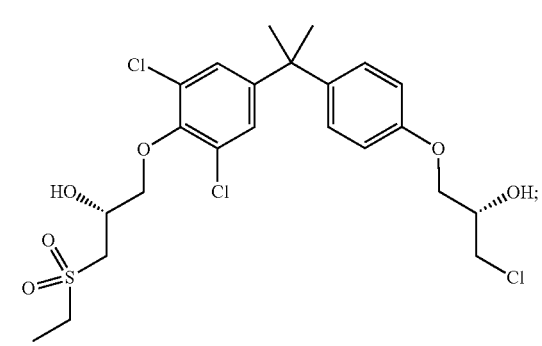
284
-continued
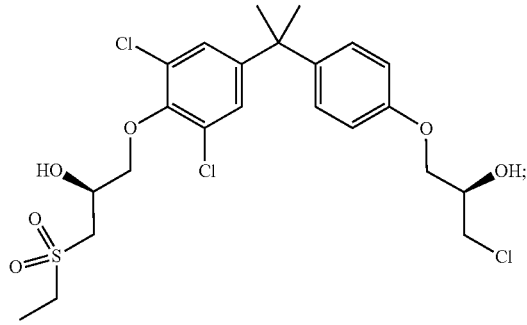
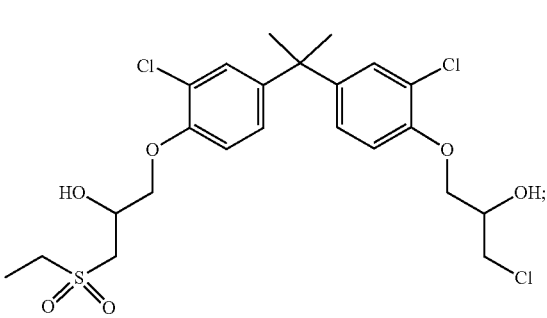
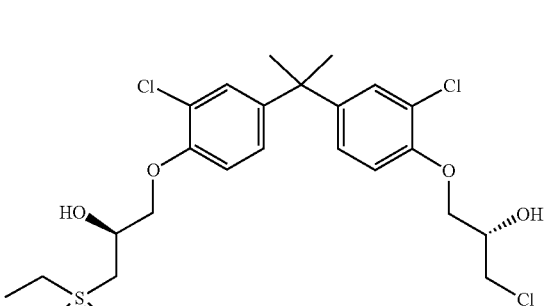
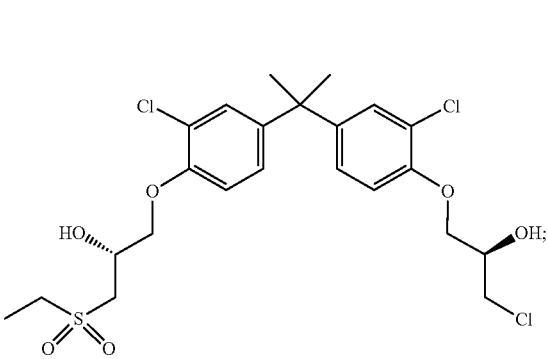
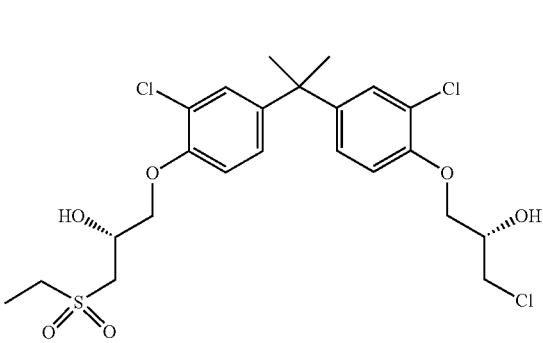

285
-continued
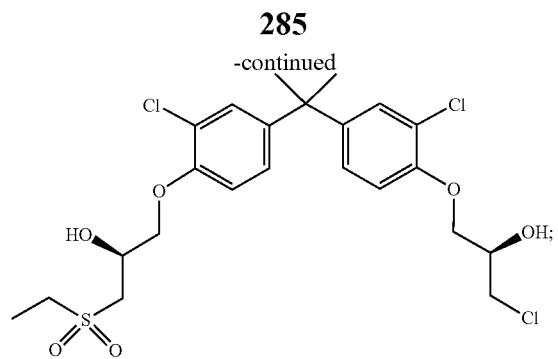
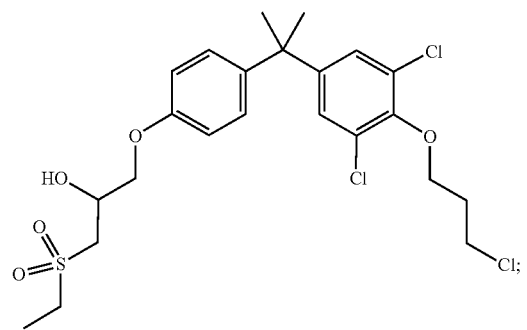
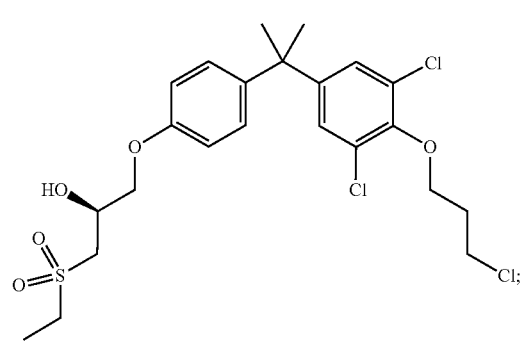
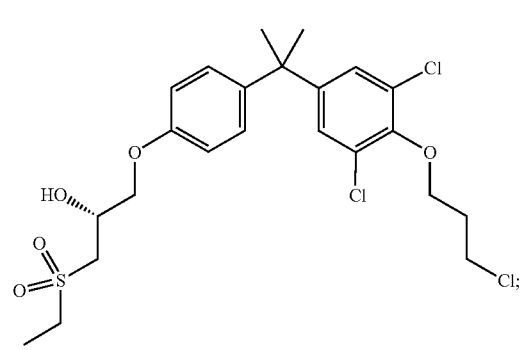
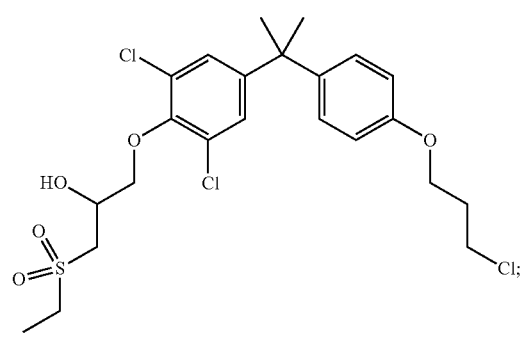
286
-continued
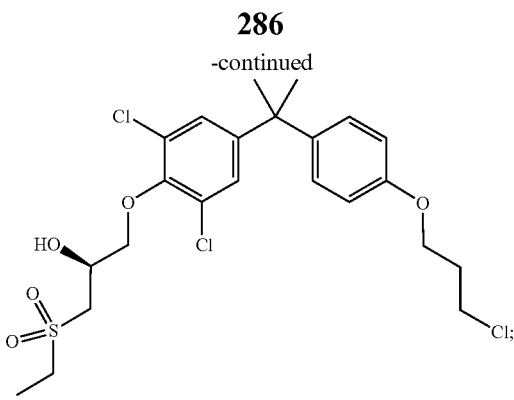
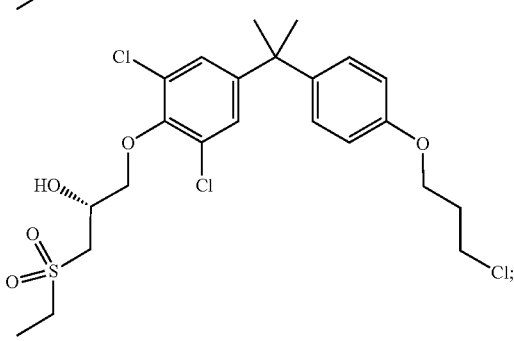
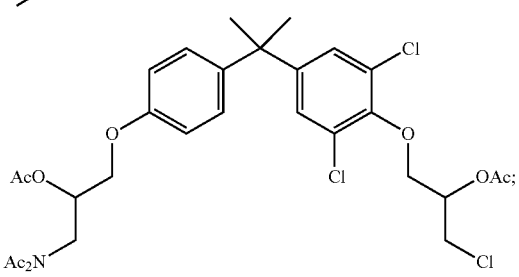
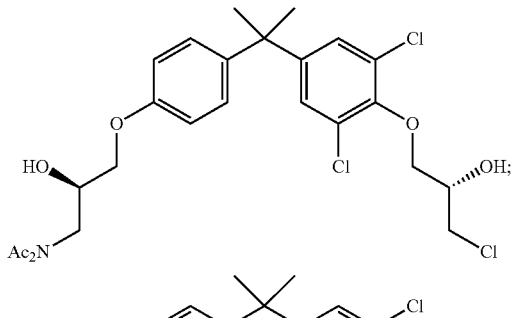
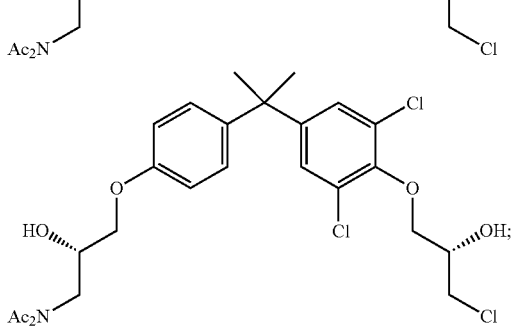

287
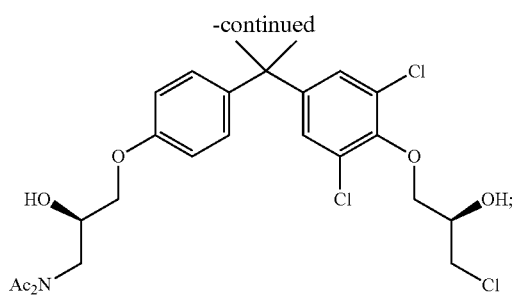
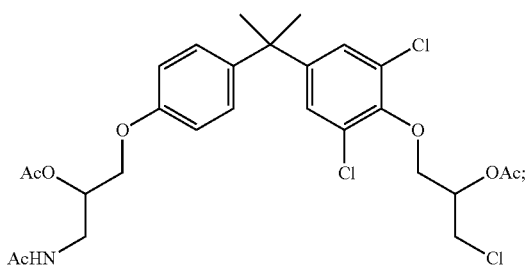
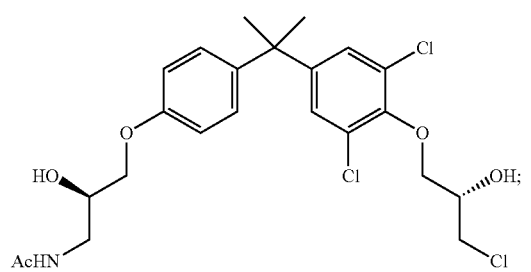
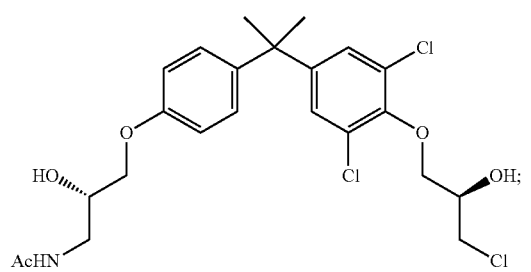
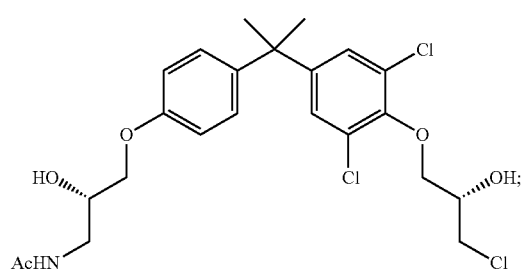
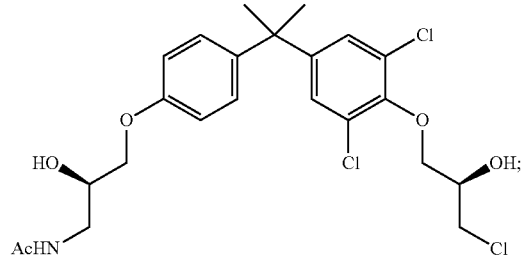
288
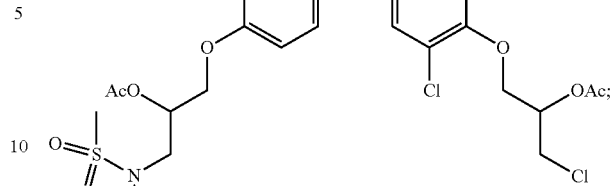
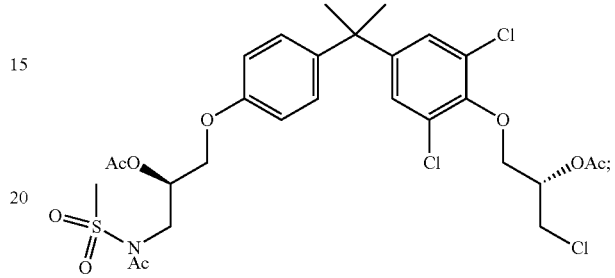
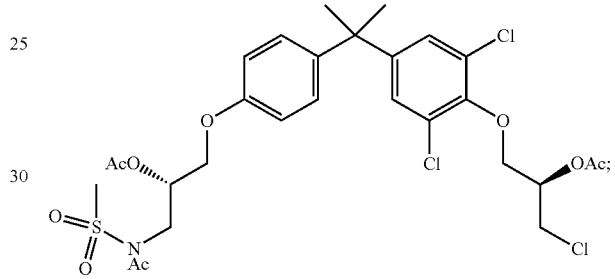
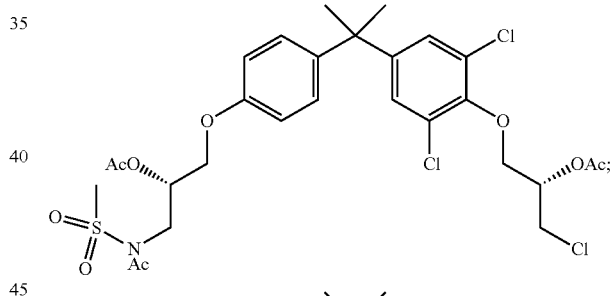
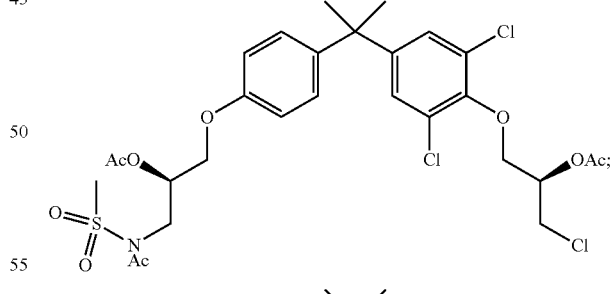
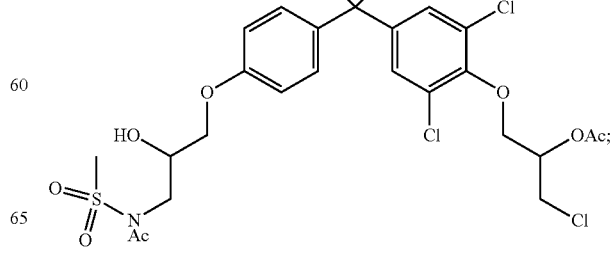

289
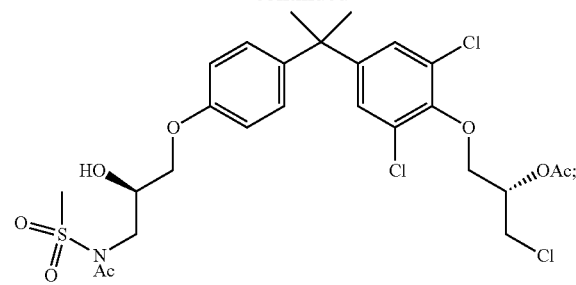
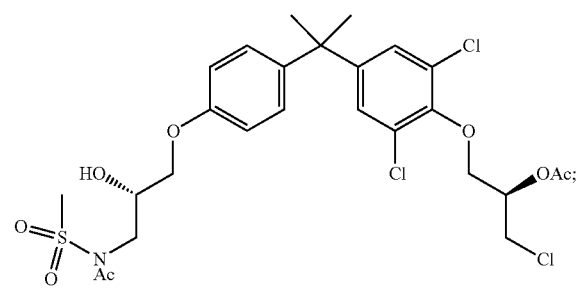
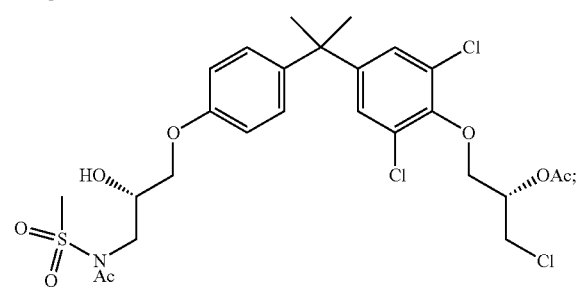
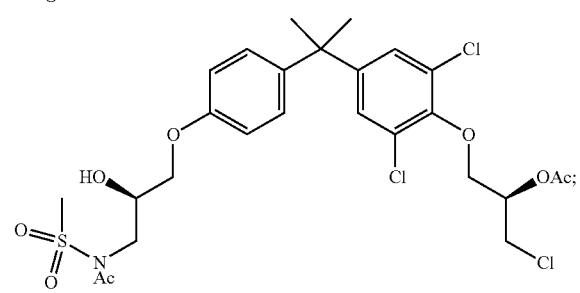
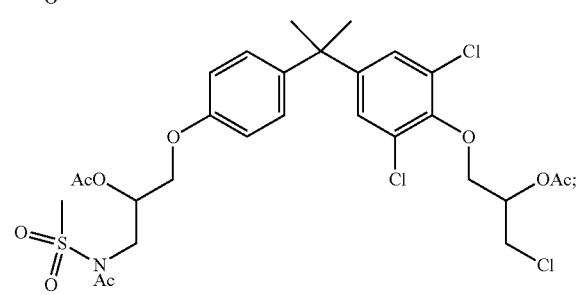
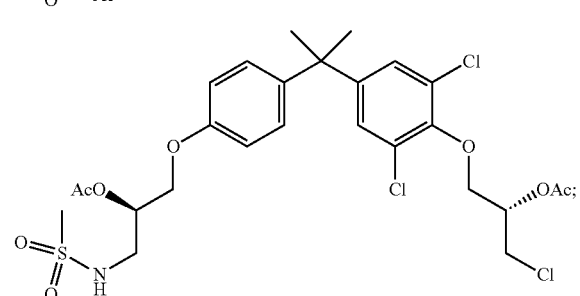
290
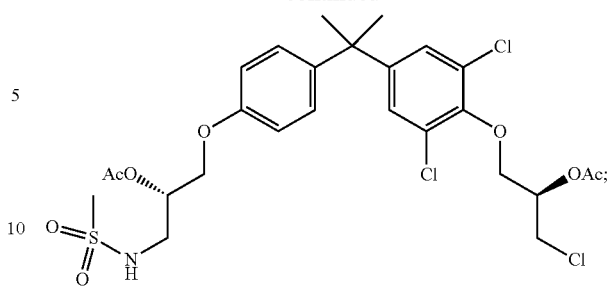
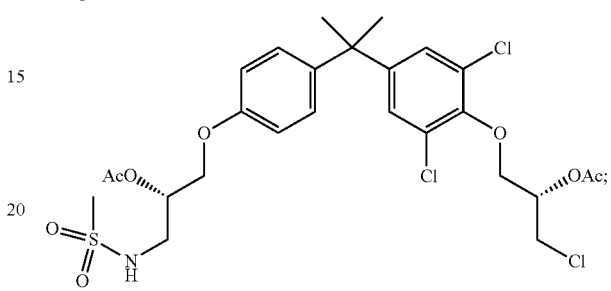
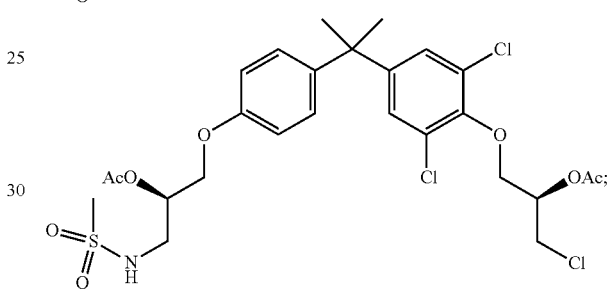
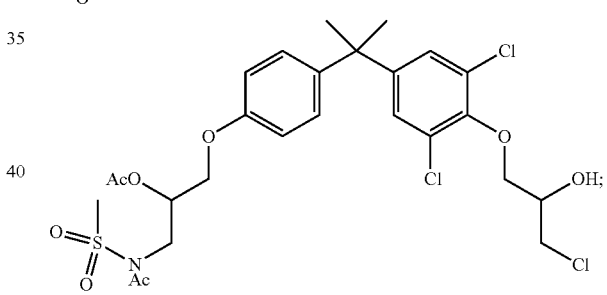
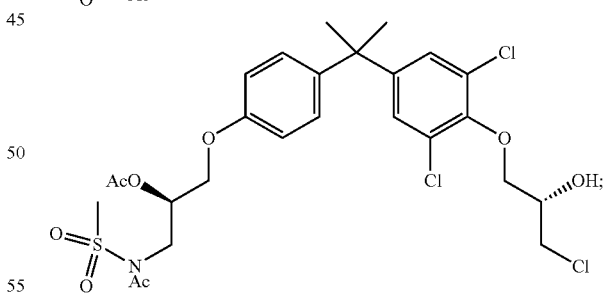
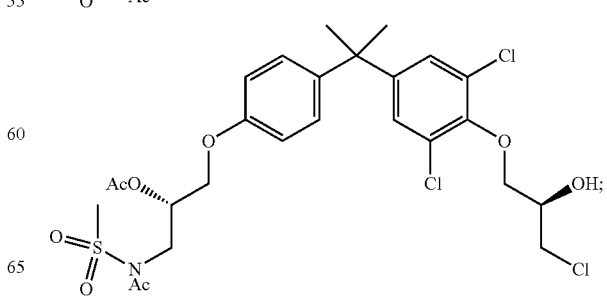

291
-continued
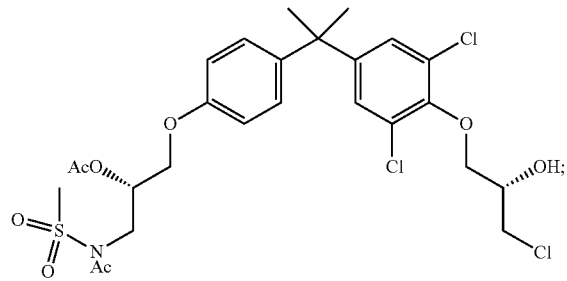
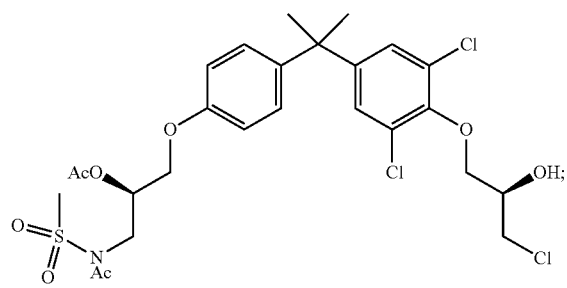
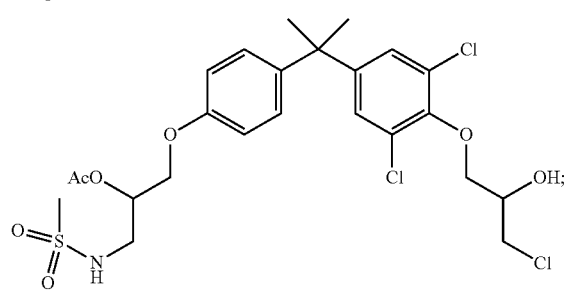
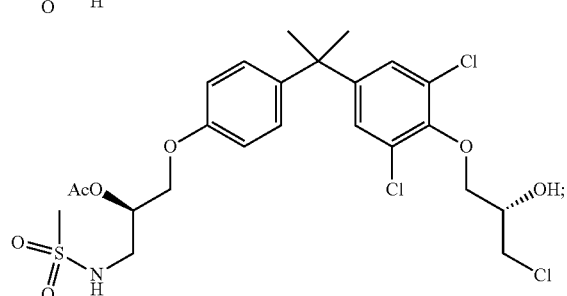
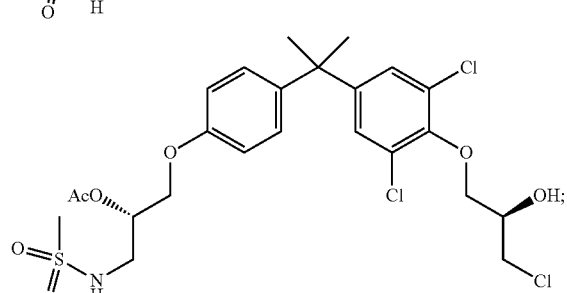
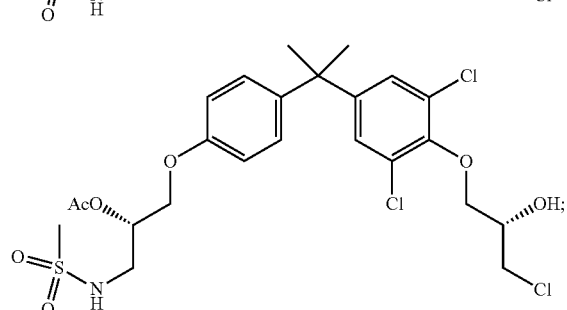
292
-continued
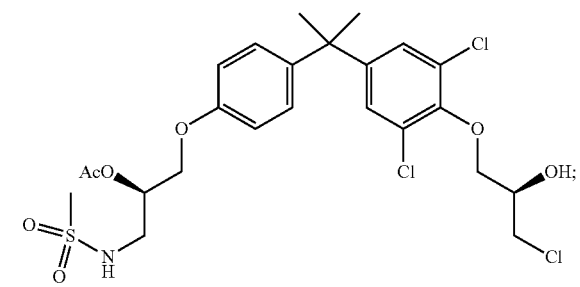
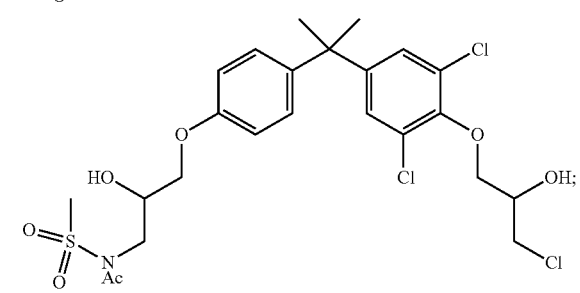
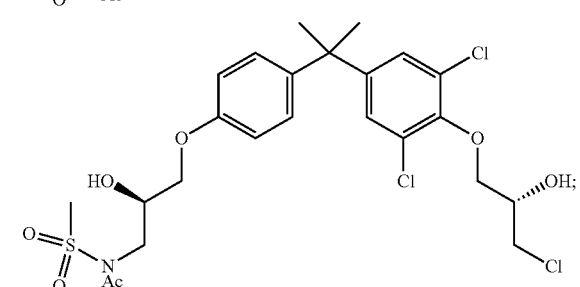
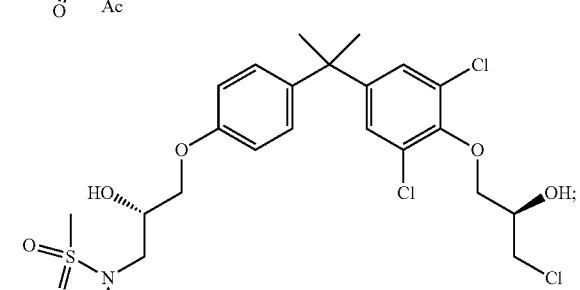
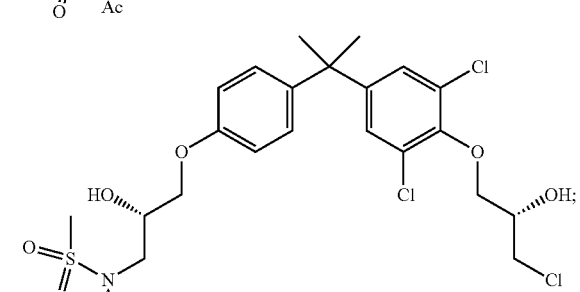
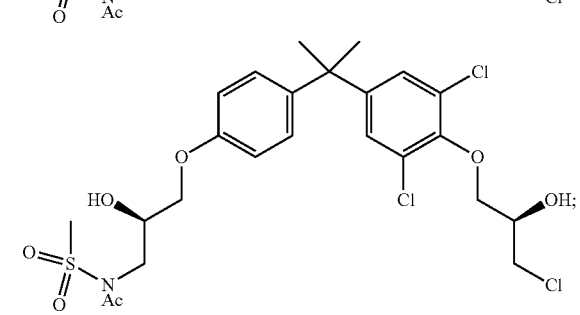

293
-continued
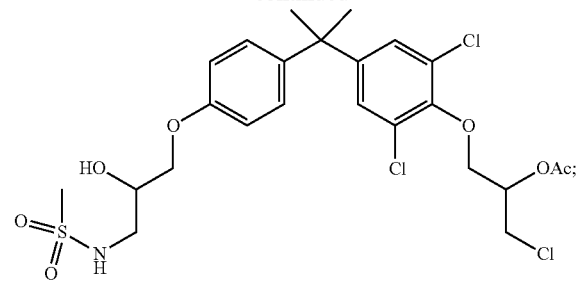
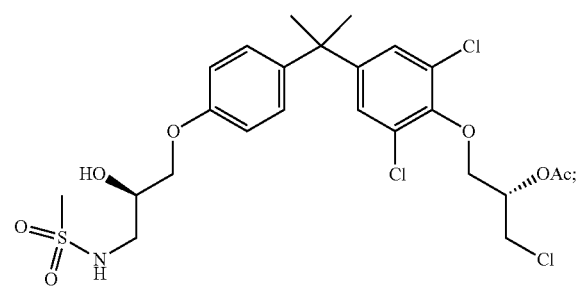
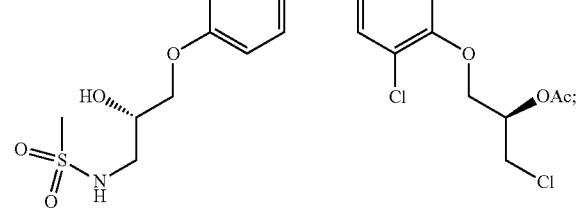
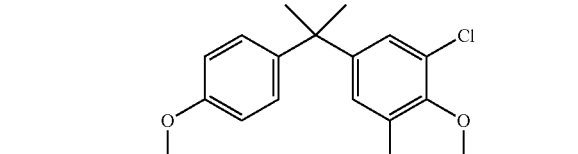
294
-continued
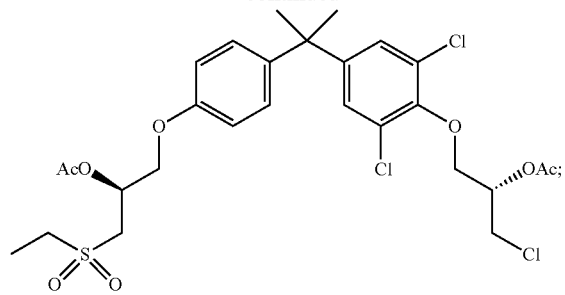
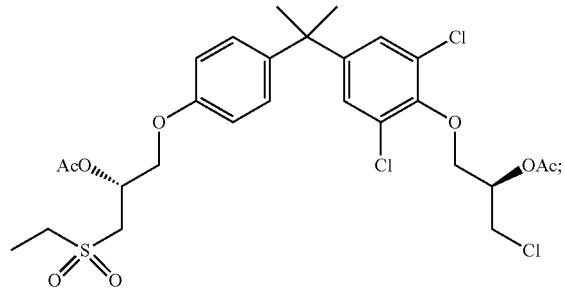
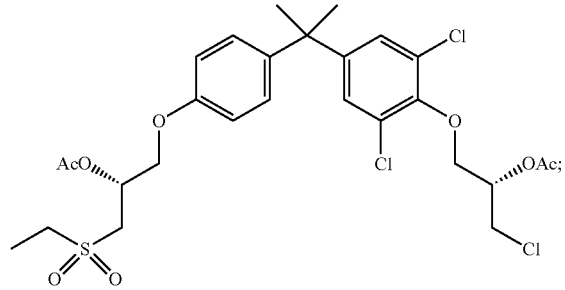
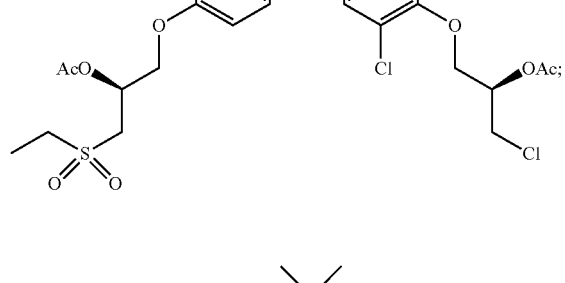
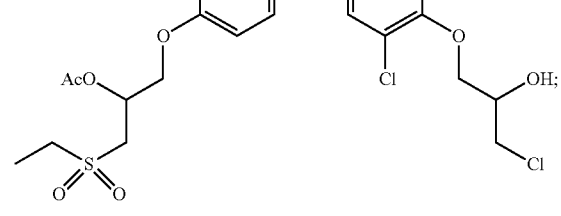

295
-continued
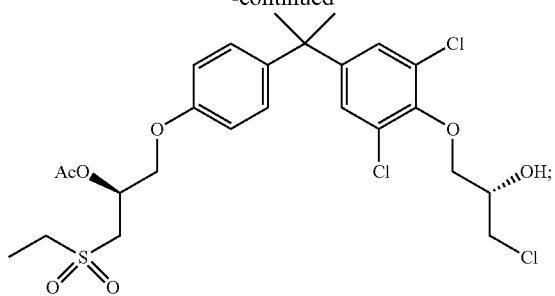
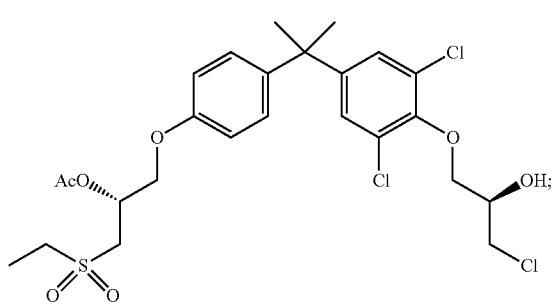
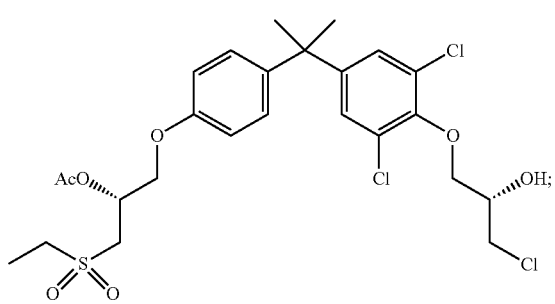
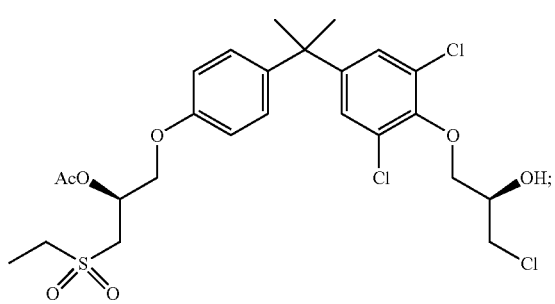
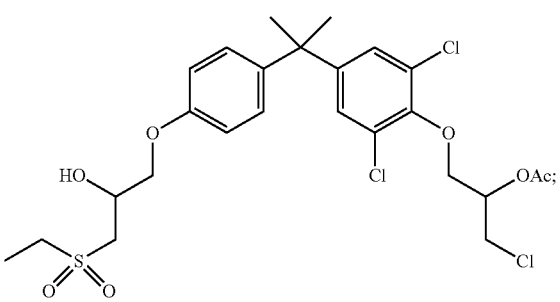
296
-continued
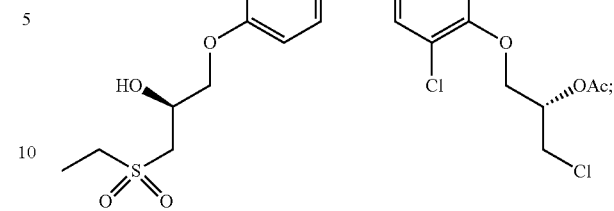
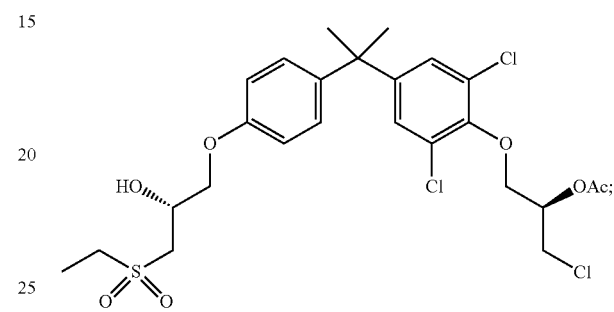
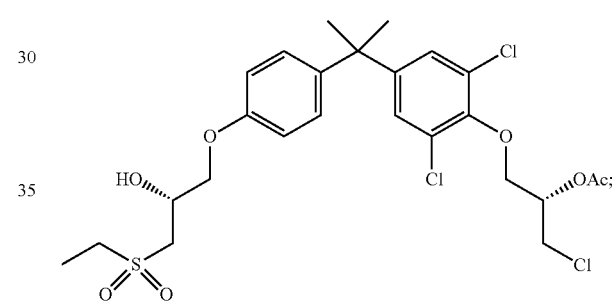
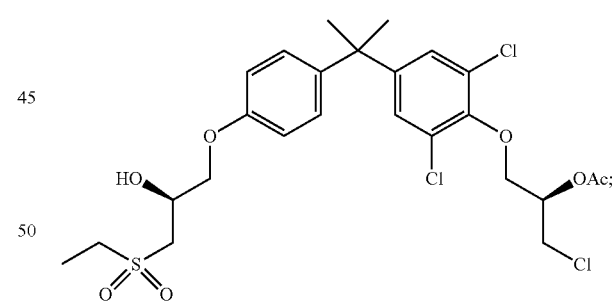
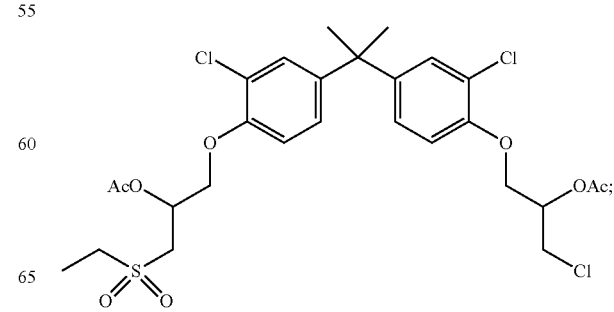

297
-continued
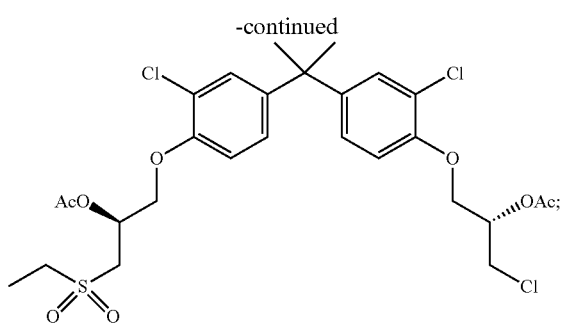
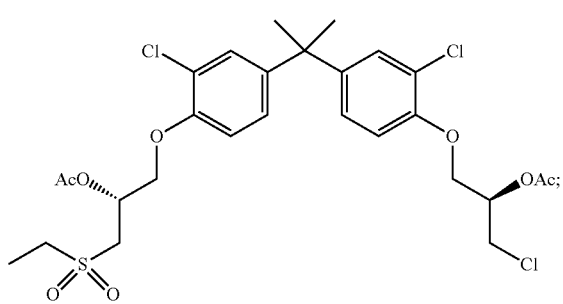
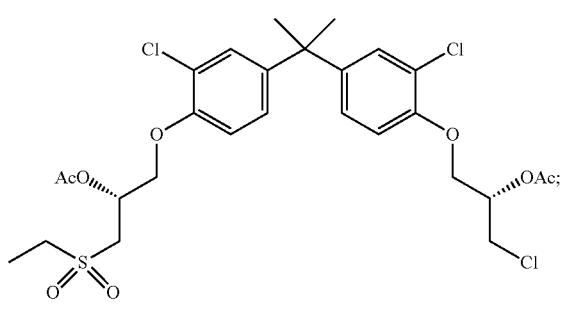
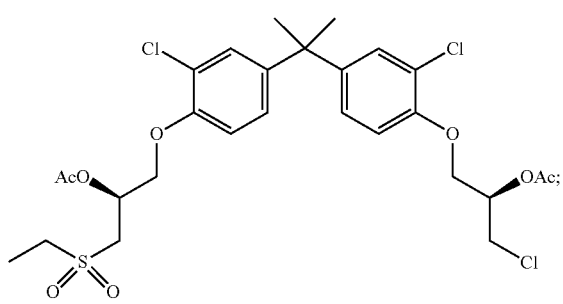
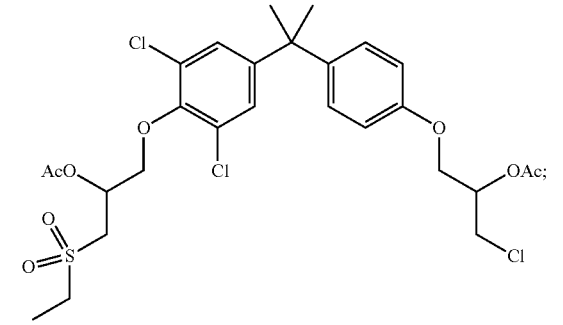
298
-continued
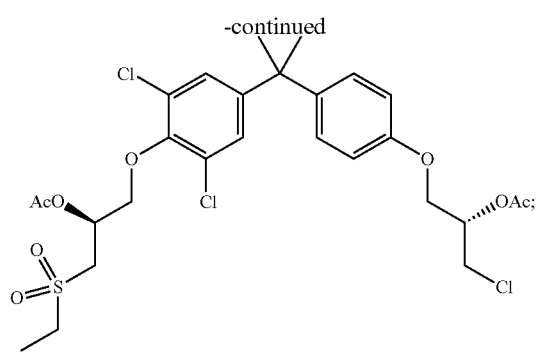
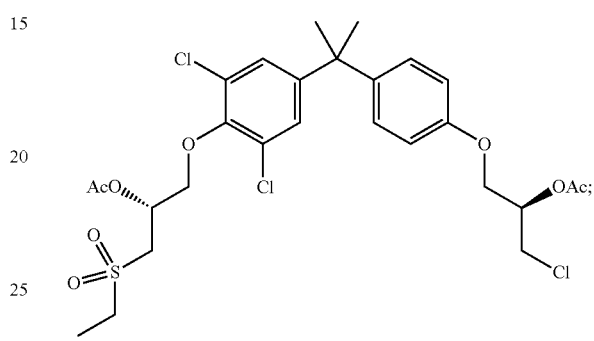
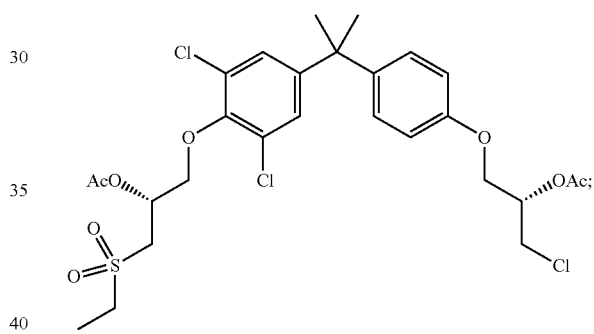
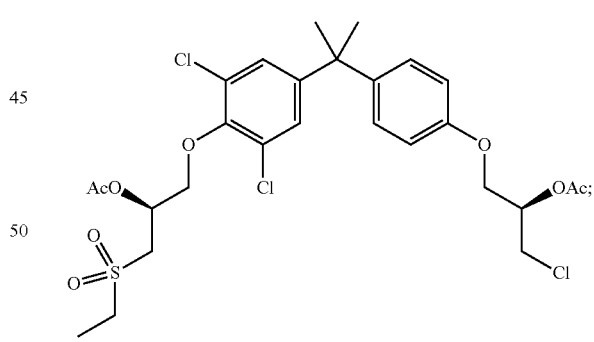
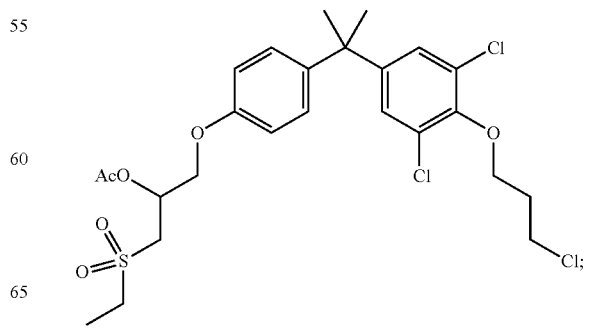

299
-continued
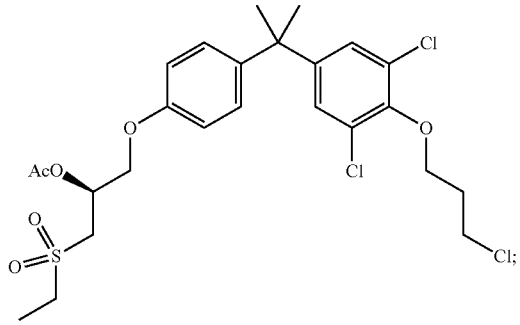
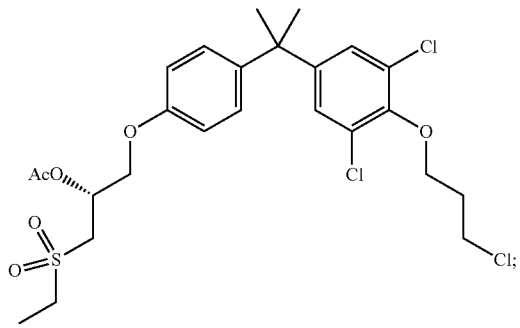
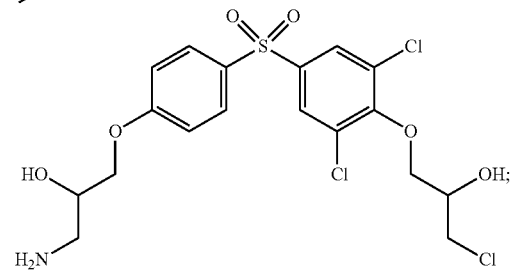
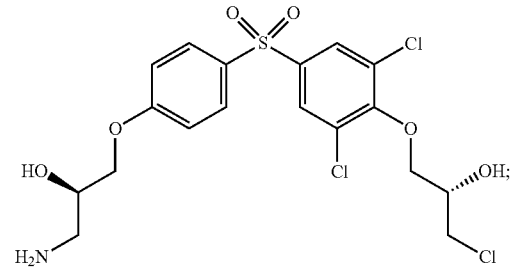
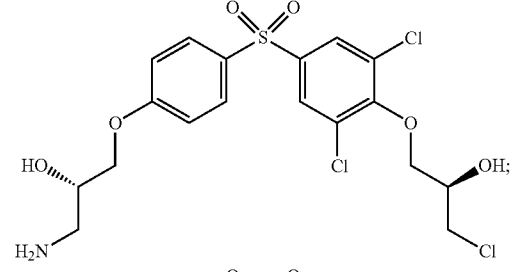
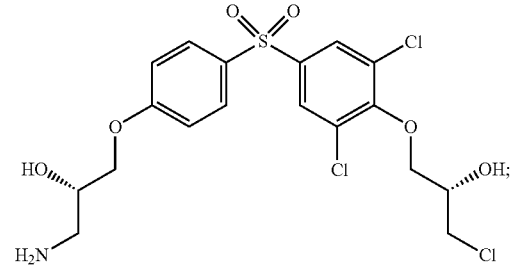
300
-continued
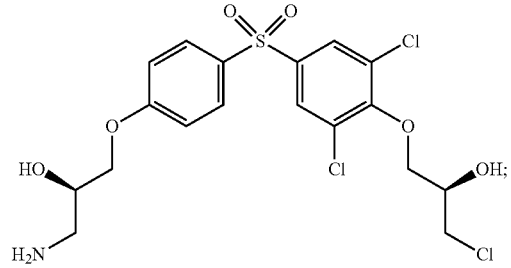
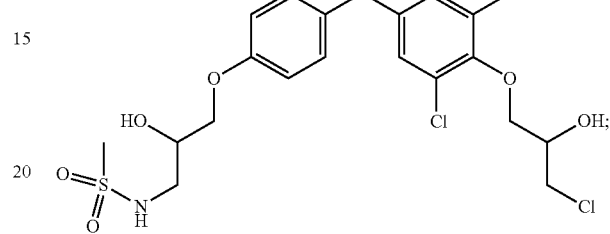
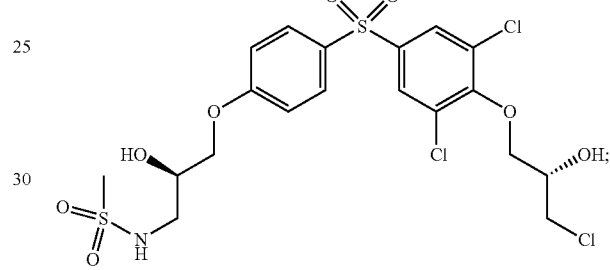
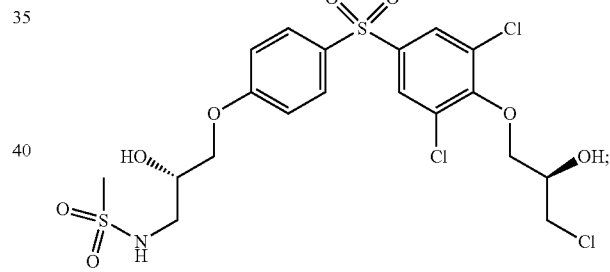
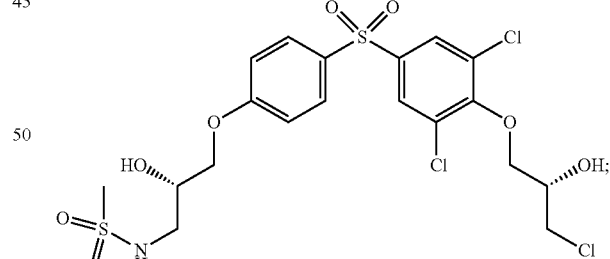
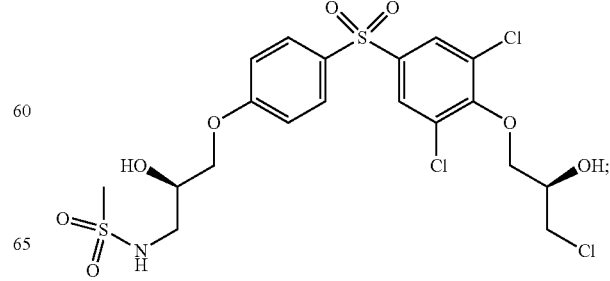

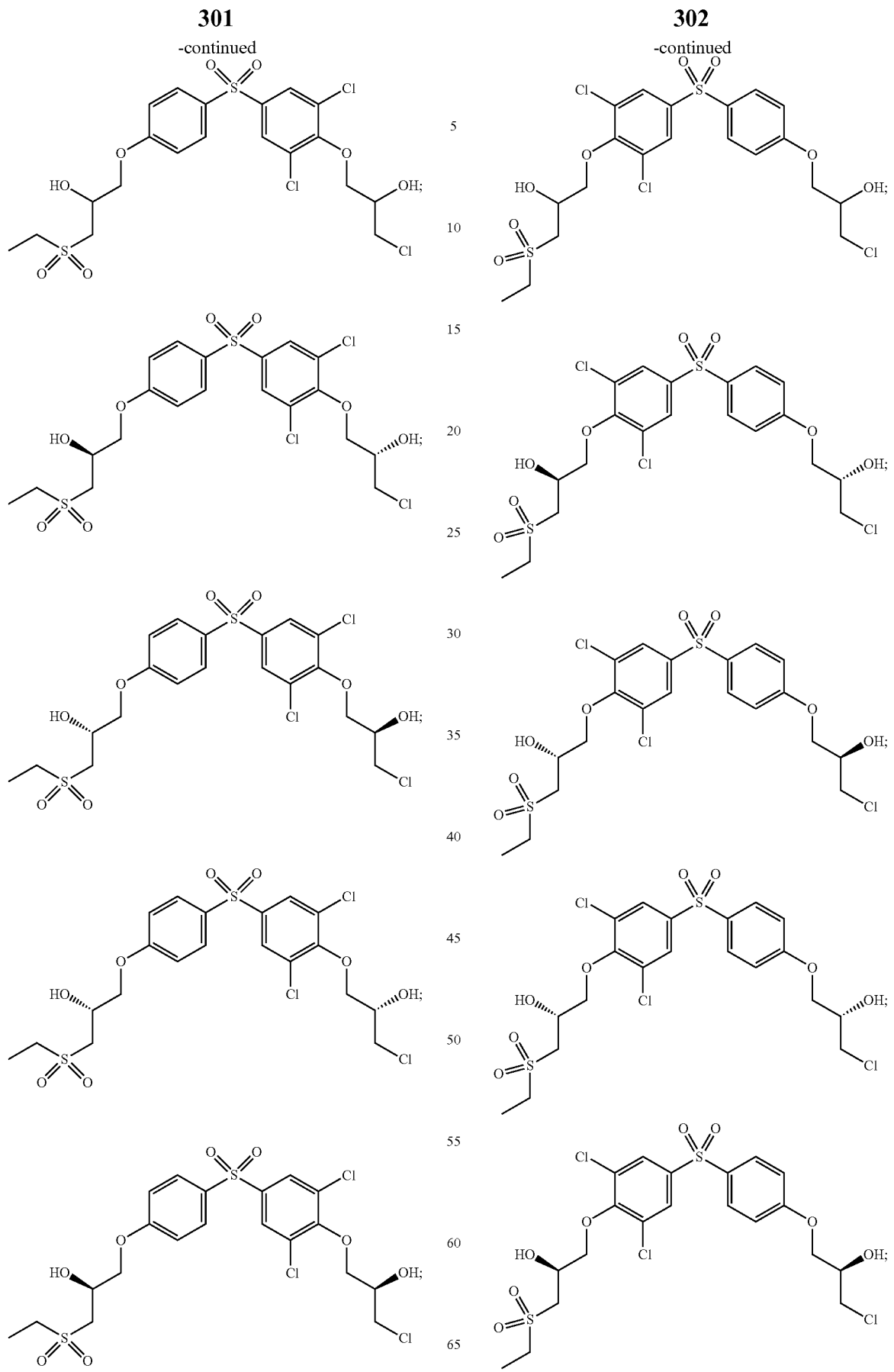

303
-continued
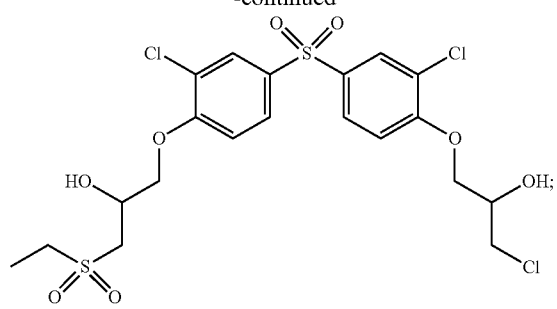
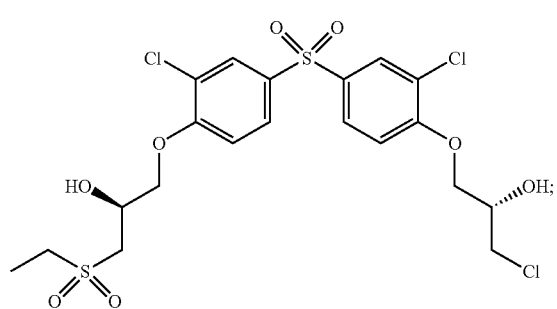
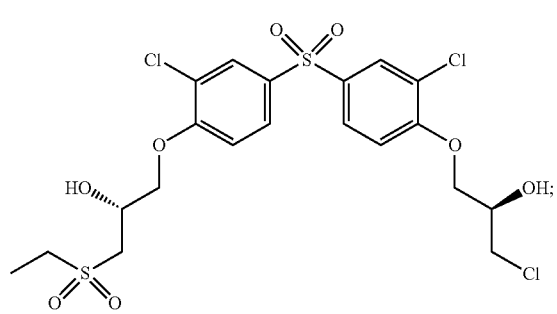
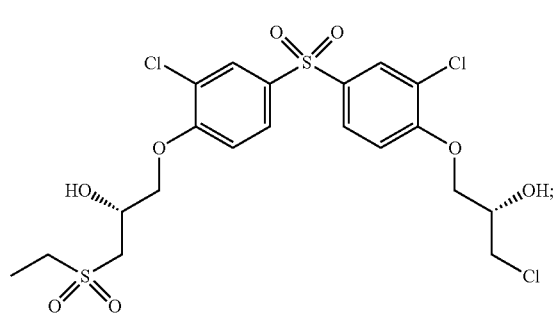
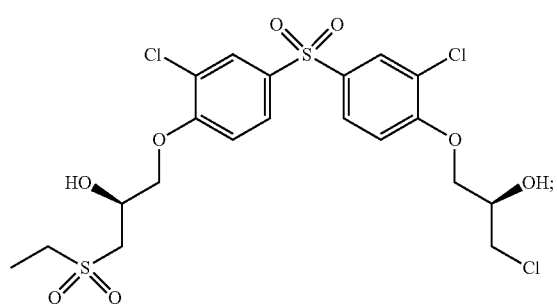
304
-continued
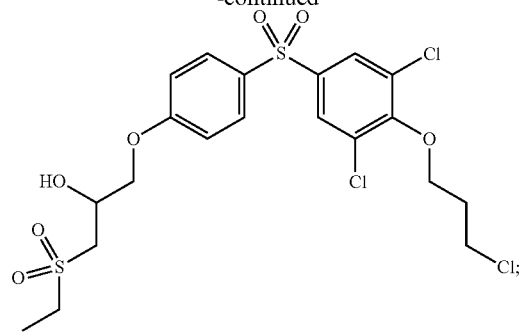
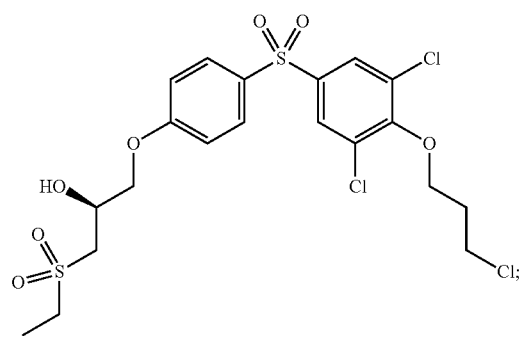
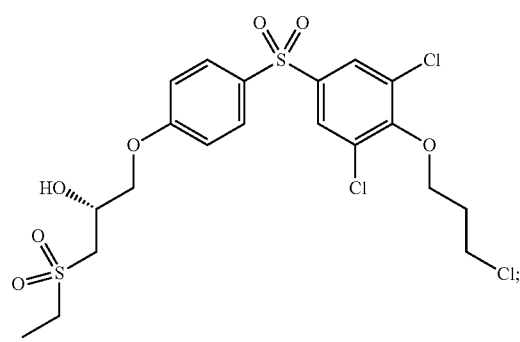
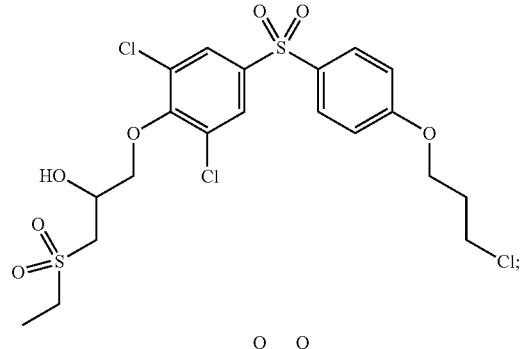
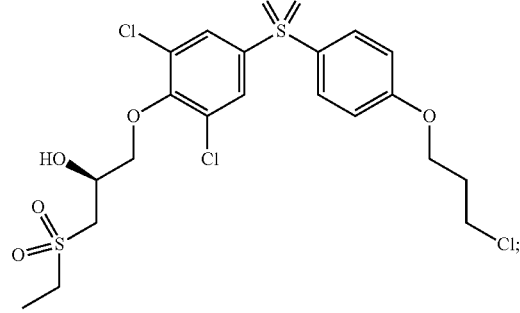

305
-continued
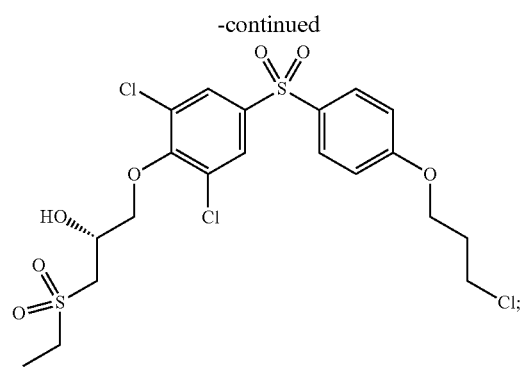
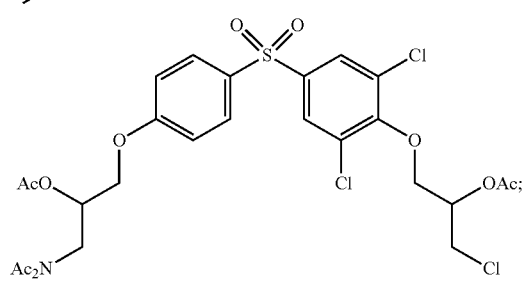
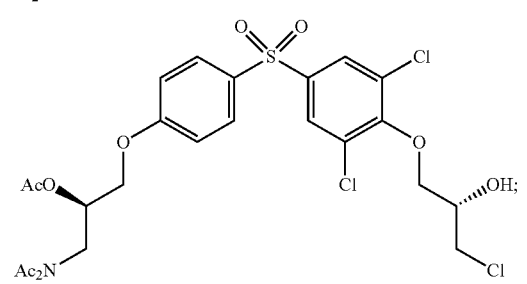
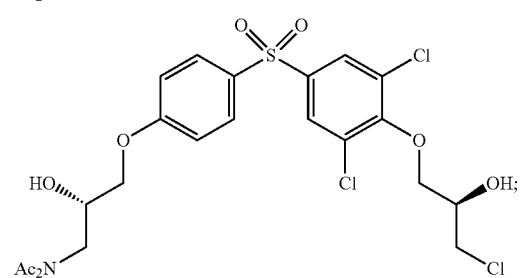
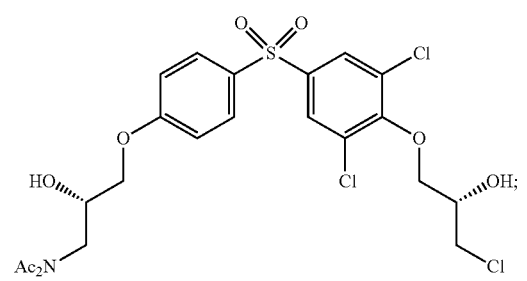
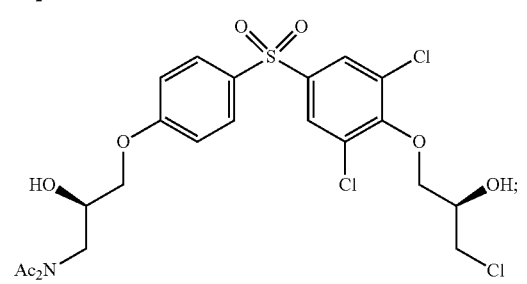
306
-continued
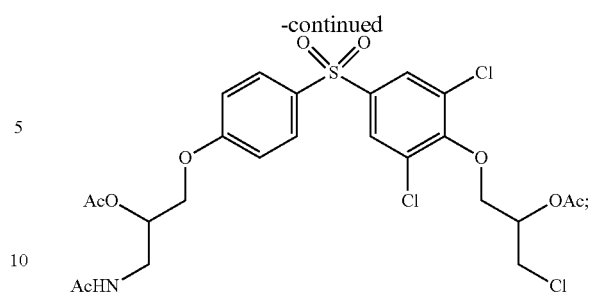
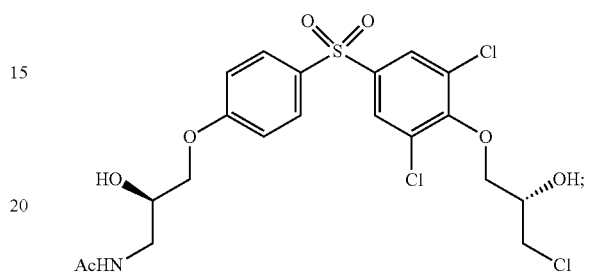
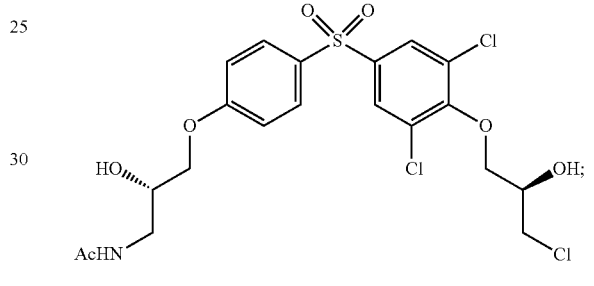
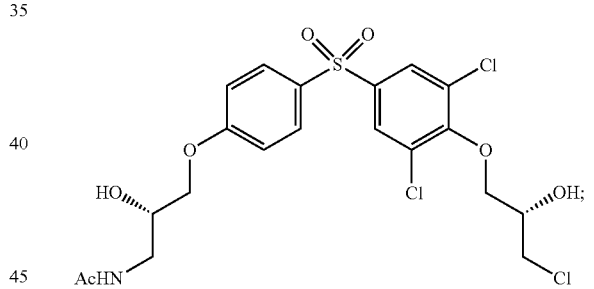
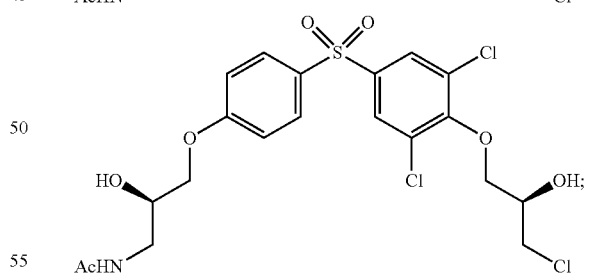
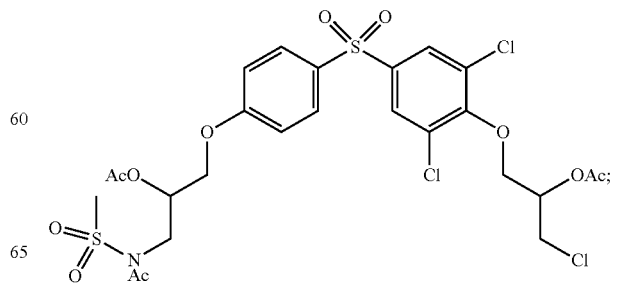

307
-continued
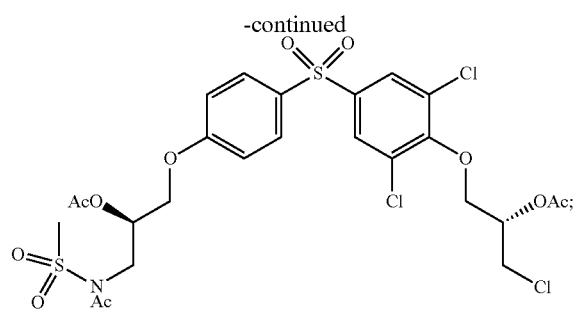
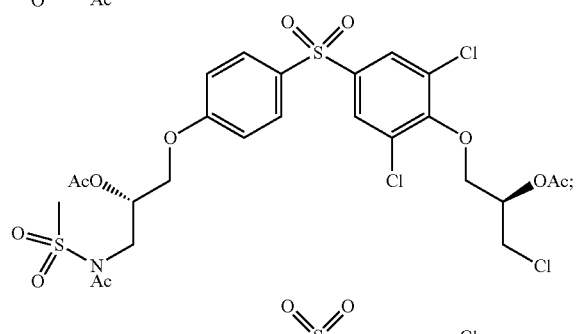
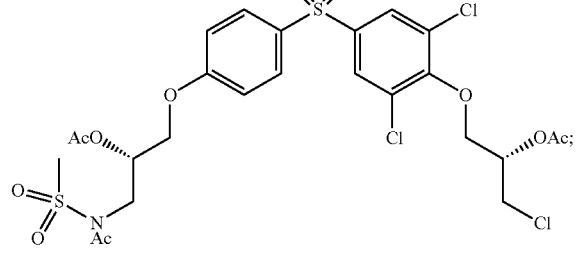
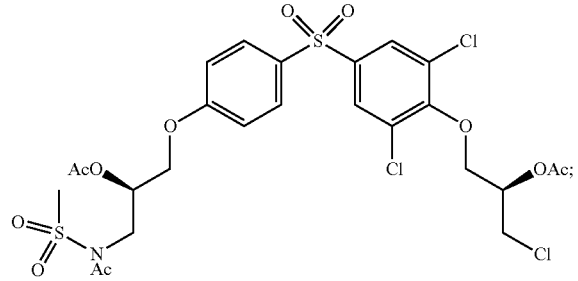
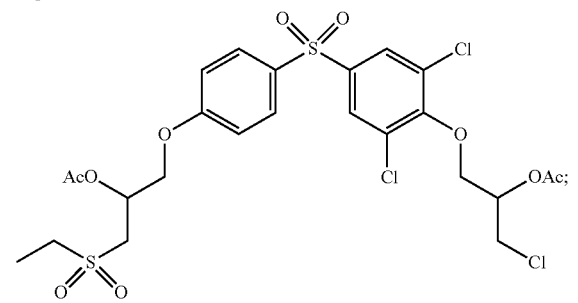
308
-continued
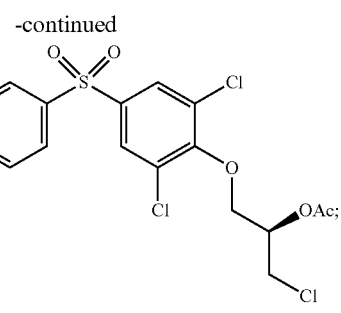
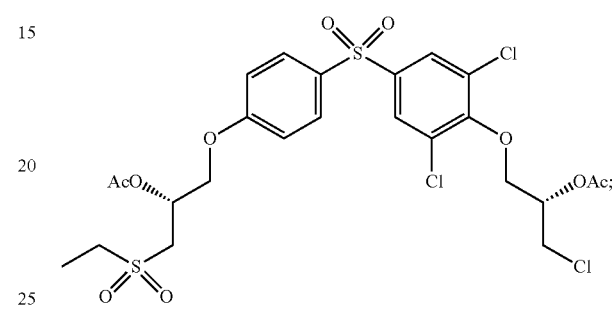
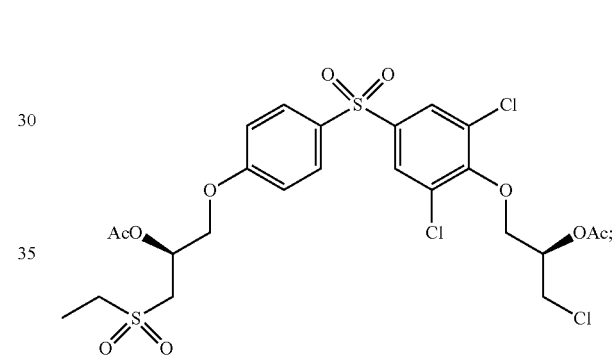
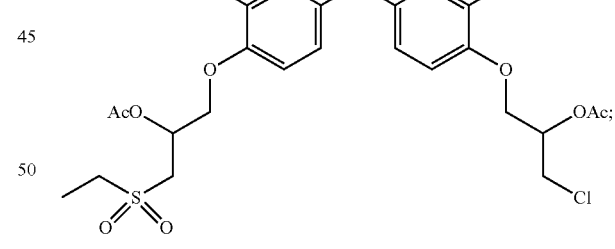
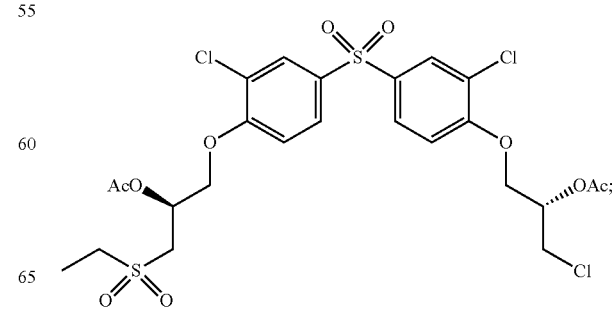

309
-continued
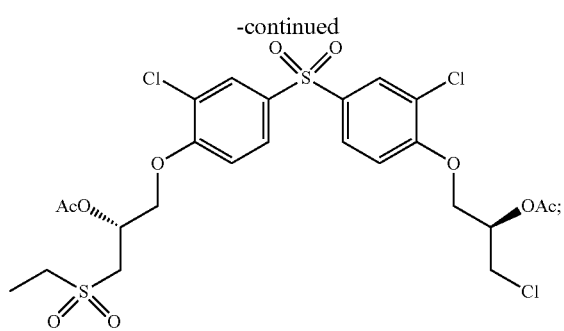
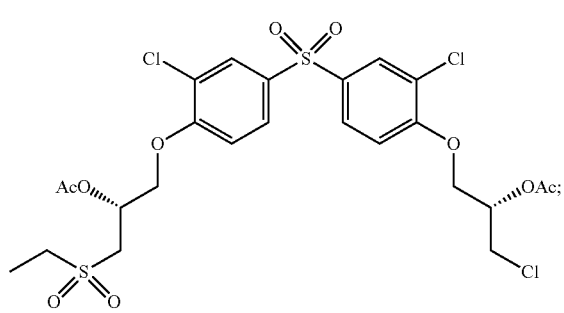
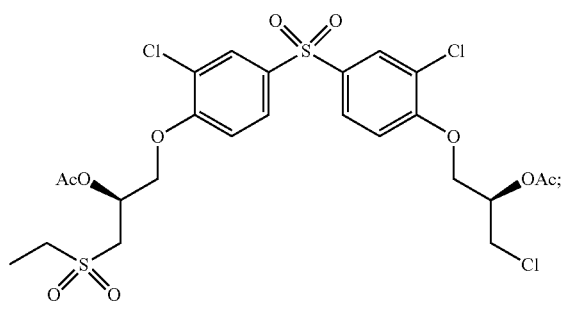
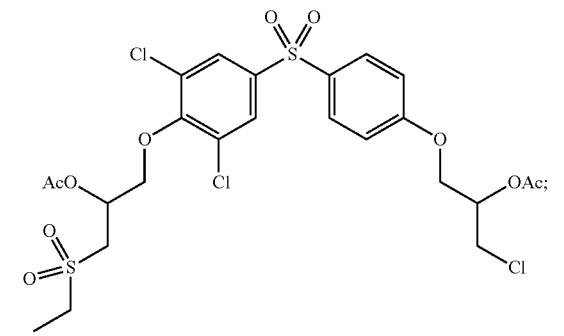
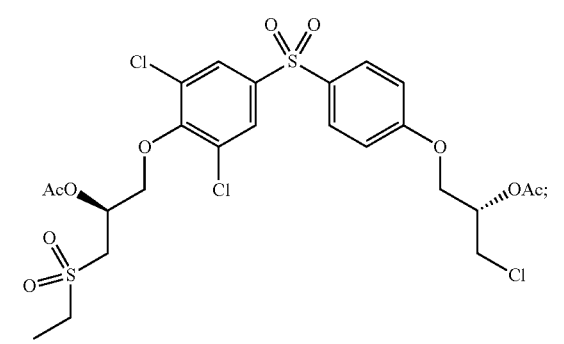
310
-continued
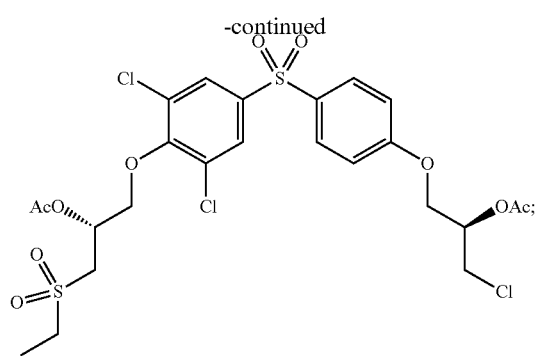
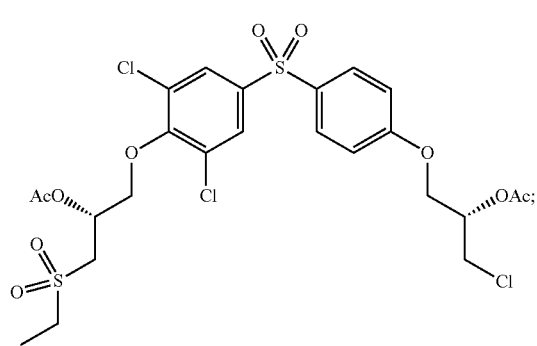
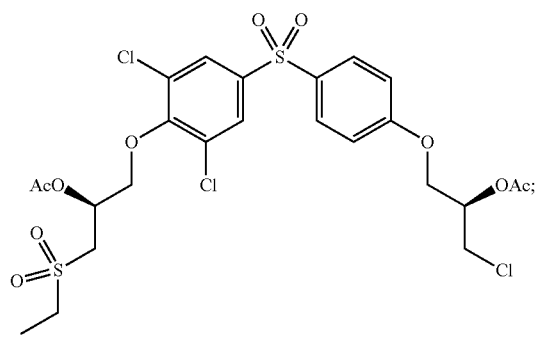
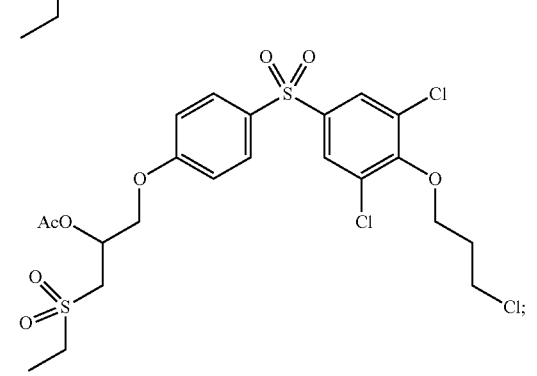
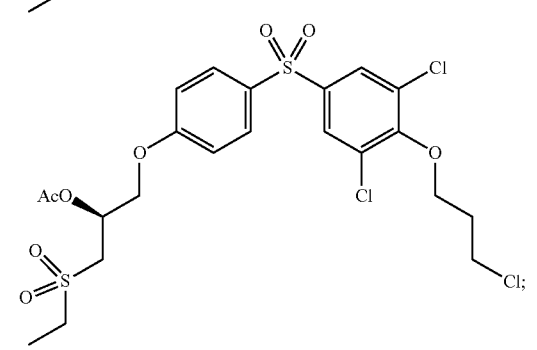

311
-continued
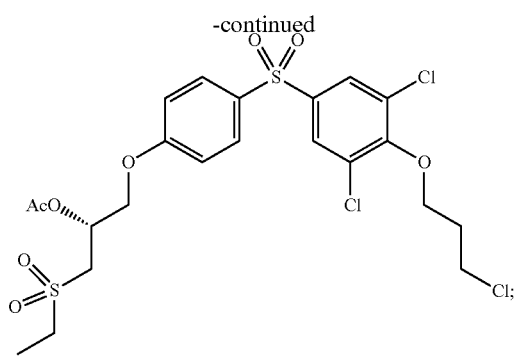
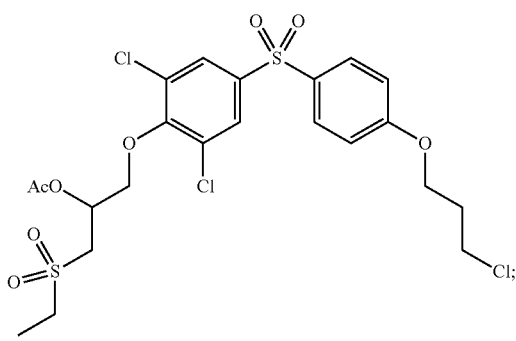
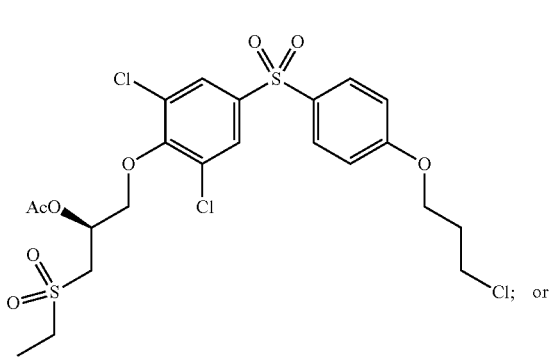
312
-continued
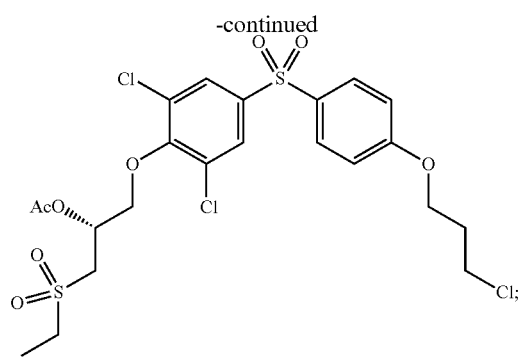
or a pharmaceutically acceptable salt thereof.
18. The method of claim 1 having the structure of
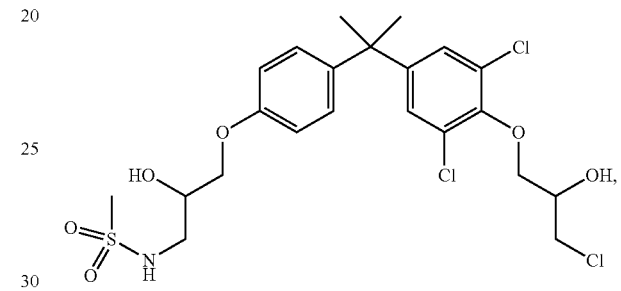
or a pharmaceutically acceptable salt or stereoisomer thereof.
19. The method of claim 1 having the structure of
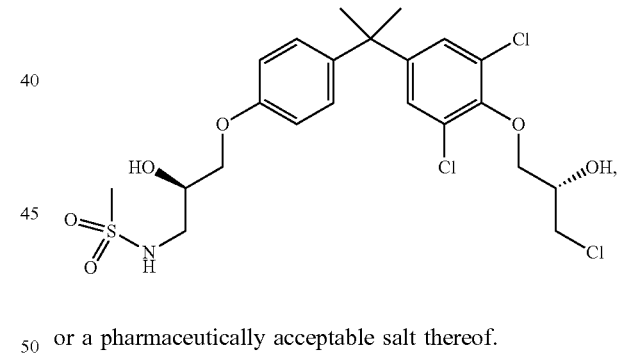
or a pharmaceutically acceptable salt thereof.
* * * * *

UNITED STATES PATENT AND TRADEMARK OFFICE
CERTIFICATE OF CORRECTION

PATENT NO. : 11,919,874 B2
APPLICATION NO. : 17/404589
DATED : March 5, 2024
INVENTOR(S) : Raymond J. Andersen et al.

It is certified that error appears in the above-identified patent and that said Letters Patent is hereby corrected as shown below:

In the Claims

At Column 279, Line 14:
"A method for prostate cancer comprising administering"
Should read:
-- A method for treating prostate cancer comprising administering --.

At Column 279, Line 40:
"$C_6$ alkyl)(S(O)$_n$R$^5$), or -S(O),R$^5$, which are optionally"
Should read:
-- $C_6$ alkyl)(S(O)$_n$R$^5$), or -S(O)$_n$R$^5$, which are optionally --.

At Column 279, Line 44:
"R$^6$is each independently selected from the group consist-"
Should read:
-- R$^6$ is each independently selected from the group consist- --.

At Column 279, Line 47:
"aryl, wherein each R$^6$is optionally substituted with one"
Should read:
-- aryl, wherein each R$^6$ is optionally substituted with one --.

At Column 280, Line 12:
"8. The method of claim 1, wherein X is -S(O)2-."
Should read:
-- 8. The method of claim 1, wherein X is -S(O)$_2$-. --.

At Column 280, Line 17:
"11. The method of claim 1, wherein le and R$^2$ are each"
Should read:

Signed and Sealed this
Fifteenth Day of October, 2024

Katherine Kelly Vidal
*Director of the United States Patent and Trademark Office*

CERTIFICATE OF CORRECTION (continued)

-- 11. The method of claim 1, wherein $R^1$ and $R^2$ are each --.

At Column 280, Lines 27-30:
"(=O)($C_1$-$C_4$ alkyl), -NRC(=O)($C_1$-$C_4$ alkyl)]$_2$, -NHS(O)$_n$($C_1$-$C_3$ alkyl), -N[C(=O)($C_1$-$C_4$ alkyl)][(S(O)$_n$,($C_1$-$C_3$ alkyl)], -N[$C_1$-$C_6$ alkyl][S(O)$_n$($C_1$-$C_3$ alkyl)], or -S(O),($C_1$-$C_3$ alkyl)."
Should read:
-- (=O)($C_1$-$C_4$ alkyl), -N[(C(=O)($C_1$-$C_4$ alkyl)]$_2$, -NHS(O)$_n$($C_1$-$C_3$ alkyl), -N[C(=O)($C_1$-$C_4$ alkyl)][(S(O)$_n$($C_1$-$C_3$ alkyl)], -N[$C_1$-$C_6$ alkyl][S(O)$_n$($C_1$-$C_3$ alkyl)], or -S(O)$_n$($C_1$-$C_3$ alkyl). --.

At Column 305, Lines 25-35:

"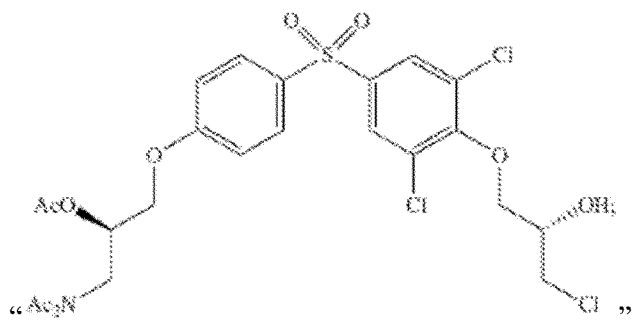"

Should read:

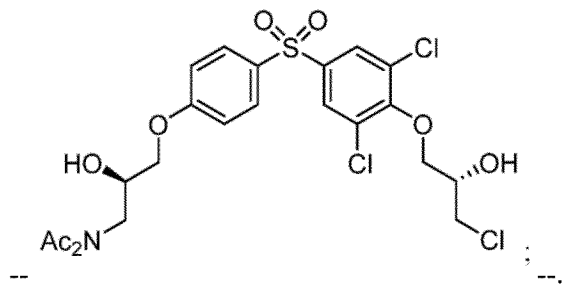

-- --.